United States Patent
Inoue et al.

(10) Patent No.: US 8,652,654 B2
(45) Date of Patent: Feb. 18, 2014

(54) BISCARBAZOLE DERIVATIVE, MATERIAL FOR ORGANIC ELECTROLUMINESCENCE DEVICE AND ORGANIC ELECTROLUMINESCENCE DEVICE USING THE SAME

(75) Inventors: Tetsuya Inoue, Sodegaura (JP); Mitsunori Ito, Sodegaura (JP); Kei Yoshida, Sodegaura (JP); Kumiko Hibino, Sodegaura (JP); Kazuki Nishimura, Sodegaura (JP); Toshinari Ogiwara, Sodegaura (JP); Kiyoshi Ikeda, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 13/091,036

(22) Filed: Apr. 20, 2011

(65) Prior Publication Data

US 2011/0279020 A1 Nov. 17, 2011

Related U.S. Application Data

(60) Provisional application No. 61/353,047, filed on Jun. 9, 2010, provisional application No. 61/433,084, filed on Jan. 14, 2011.

(30) Foreign Application Priority Data

Apr. 20, 2010 (JP) ................................. 2010-097317
Dec. 27, 2010 (JP) ................................. 2010-291138

(51) Int. Cl.
*H01L 51/54* (2006.01)
*C09K 11/06* (2006.01)
*C07D 403/00* (2006.01)

(52) U.S. Cl.
USPC ........... 428/690; 428/917; 313/504; 313/506; 257/E51.05; 544/283; 548/440

(58) Field of Classification Search
None
See application file for complete search history.

(56) References Cited

U.S. PATENT DOCUMENTS

| | | | |
|---|---|---|---|
| 6,645,645 B1 | 11/2003 | Adachi et al. | |
| 8,227,801 B2 * | 7/2012 | Xia et al. | 257/40 |
| 8,394,510 B2 | 3/2013 | Mizuki et al. | |
| 2004/0086745 A1 | 5/2004 | Iwakuma et al. | |
| 2006/0046172 A1 | 3/2006 | Vaitkeviciene et al. | |
| 2008/0124572 A1 | 5/2008 | Mizuki et al. | |
| 2009/0009065 A1 | 1/2009 | Nishimura et al. | |
| 2009/0009067 A1 | 1/2009 | Nishimura et al. | |
| 2009/0302742 A1 | 12/2009 | Komori et al. | |
| 2009/0302745 A1 | 12/2009 | Otsu et al. | |
| 2011/0278555 A1 | 11/2011 | Inoue et al. | |
| 2012/0068170 A1 | 3/2012 | Pflumm et al. | |
| 2012/0211736 A1 | 8/2012 | Kim et al. | |

FOREIGN PATENT DOCUMENTS

| | | |
|---|---|---|
| CN | 1701111 A | 11/2005 |
| CN | 101535256 A | 9/2009 |
| CN | 102597158 A | 7/2012 |
| JP | 3139321 B2 | 12/2000 |
| JP | 2001-171860 | 6/2001 |
| JP | 2003-151774 A | 5/2003 |
| JP | 2004-171860 A | 6/2004 |
| JP | 2007-194241 A | 8/2007 |
| JP | 2007-288035 | 11/2007 |
| JP | 2007-311460 | 11/2007 |
| JP | 2008-135498 A | 6/2008 |
| JP | 2008-205491 | 9/2008 |
| JP | 2008-214307 A | 9/2008 |
| JP | 2009-021336 A | 1/2009 |
| JP | 4357781 B2 | 8/2009 |
| JP | 2010-135467 | 6/2010 |
| JP | 2010-215759 | 9/2010 |
| JP | 2010-241801 A | 10/2010 |

(Continued)

OTHER PUBLICATIONS

Office Action in U.S. Appl. No. 13/372,943 dated Apr. 11, 2012.

(Continued)

*Primary Examiner* — Marie R. Yamnitzky
(74) *Attorney, Agent, or Firm* — Foley and Lardner LLP

(57) ABSTRACT

A biscarbazole derivative of the invention is represented by a formula (1) below.

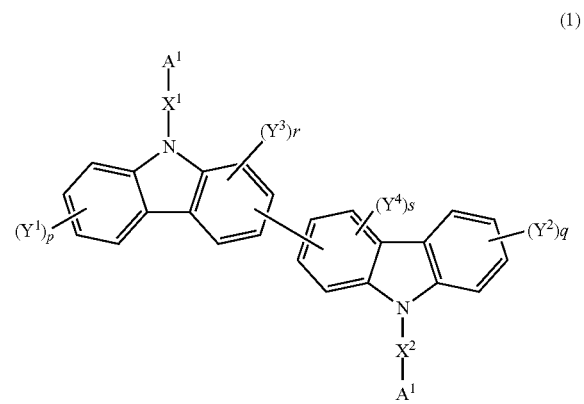

In the formula (1): $A^1$ represents a substituted or unsubstituted nitrogen-containing heterocyclic group having 1 to 30 ring carbon atoms; $A^2$ represents a substituted or unsubstituted aromatic hydrocarbon group having 6 to 30 ring carbon atoms, or substituted or unsubstituted nitrogen-containing heterocyclic group having 1 to 30 ring carbon atoms; $X^1$ and $X^2$ each are a linking group; $Y^1$ to $Y^4$ each represent a substituent; p and q represent an integer of 1 to 4; and r and s represent an integer of 1 to 3.

29 Claims, 2 Drawing Sheets

(56) References Cited

FOREIGN PATENT DOCUMENTS

| | | |
|---|---|---|
| JP | 2010-270245 A | 12/2010 |
| JP | 2011-008991 A | 1/2011 |
| JP | 2011-054931 | 3/2011 |
| JP | 2012-175025 | 9/2012 |
| JP | 05-074627 B2 | 11/2012 |
| JP | 2012-528088 A | 11/2012 |
| JP | 2013-510141 A | 3/2013 |
| TW | 200911959 A | 3/2009 |
| WO | WO 03/080760 A1 | 10/2003 |
| WO | WO 2004/018588 A1 | 3/2004 |
| WO | WO-2007/063754 A1 | 6/2007 |
| WO | WO 2007/119816 A1 | 10/2007 |
| WO | WO 2008/062636 A1 | 5/2008 |
| WO | WO 2008/149968 A1 | 12/2008 |
| WO | WO 2008/156105 A1 | 12/2008 |
| WO | WO-2009/008342 A1 | 1/2009 |
| WO | WO 2009/008360 A1 | 1/2009 |
| WO | WO 2009/008361 A1 | 1/2009 |
| WO | WO 2009/008364 A1 | 1/2009 |
| WO | WO 2009/020095 A1 | 2/2009 |
| WO | WO-2010/004877 A1 | 1/2010 |
| WO | WO-2010/044342 A1 | 4/2010 |
| WO | WO 2010/136109 A1 | 12/2010 |
| WO | WO 2011/019156 A1 | 2/2011 |
| WO | WO 2011/055934 A2 | 5/2011 |
| WO | WO-2012/029253 A1 | 3/2012 |
| WO | WO-2012/086170 A1 | 6/2012 |
| WO | WO-2012/090967 A1 | 7/2012 |
| WO | WO-2012/115034 A1 | 8/2012 |
| WO | WO-2012/121101 A1 | 9/2012 |
| WO | WO-2012/128298 A1 | 9/2012 |

OTHER PUBLICATIONS

Vaitkeviciene et al., "Well-defined [3,3']bicarbazolyl-based electroactive compounds for optoelectronics," Synthetic Metals, 2008, 158:383-390.

Supplementary European Search Report EP Application No. 11770992.3 dated Jan. 16, 2013.

Office Action dated Jan. 22, 2013 issued in connection with U.S. Appl. No. 13/372,954.

Office Action dated Dec. 20, 2012 issued in connection with U.S. Appl. No. 13/091,071.

Qin-De Liu et al., "Design and Synthesis of Phosphorescent Iridium Containing Dendrimers for Potential Applications in Organic Light-Emitting Diodes", Macromol. Chem. Phys., 2008, vol. 209, No. 18, pp. 1931-1941.

Non-Final Office Action U.S. Appl. No. 13/372,943 dated Apr. 5, 2013.

Feng et al., "Synthesis and Optical Properties of Starburst Carbazoles Based on 9-Phenylcarbazole Core," Synlett, 2006, No. 17, pp. 2841-2845.

Notice of Reason(s) of Rejection for Japanese Patent Application No. 2011-533888 dated Jul. 2, 2013.

First Notification of Examiner's Opinion Chinese Patent Application No. 201180002165.7 dated Mar. 29, 2013.

Office Action dated Oct. 3, 2013 received in Taiwanese Application No. 100113709.

\* cited by examiner

BISCARBAZOLE DERIVATIVE, MATERIAL FOR ORGANIC ELECTROLUMINESCENCE DEVICE AND ORGANIC ELECTROLUMINESCENCE DEVICE USING THE SAME

The entire disclosure of Japanese Patent Application No. 2010-097317, filed Apr. 20, 2010, Japanese Patent Application No. 2010-291138, filed Dec. 27, 2010, U.S. Provisional Application No. 61/353,047, filed Jun. 9, 2010, and U.S. Provisional Application No. 61/433,084, filed Jan. 14, 2011, is expressly incorporated by reference herein.

BACKGROUND OF THE INVENTION

1. Field of the Invention

The present invention relates to a biscarbazole derivative, a material for an organic electroluminescence device, and an organic electroluminescence device using those.

2. Description of Related Art

A known organic electroluminescence device includes an organic thin-film layer between an anode and a cathode, the organic thin-film layer including an emitting layer, and emits light using exciton energy generated by a recombination of holes and electrons injected into the emitting layer (see Patent Literature 1: WO2003-080760, Patent Literature 2: Japanese Patent No.: 3139321, Patent Literature 3: Japanese Patent No.: 4357781, Patent Literature 4: JP-A-2003-151774, Patent Literature 5: JP-A-2008-135498, Patent Literature 6: JP-A-2009-21336, Patent Literature 7: JP-A-2008-214307).

Such an organic EL device, which has the advantages as a self-emitting device, is expected to serve as an emitting device excellent in luminous efficiency, image quality, power consumption and thin design.

In forming the emitting layer, a doping method, according to which an emitting material (dopant) is doped to a host, has been known as a usable method.

The emitting layer formed by the doping method can efficiently generate excitons from electric charges injected into the host. With the exciton energy generated by the excitons being transferred to the dopant, the dopant can emit light with high efficiency.

Recently, in order to improve performance of the organic electroluminescence device (hereinafter, occasionally referred to as an organic EL device), a doping method has been further studied to find a suitable host material.

Such a host material is disclosed in, for instance, Patent Literatures 1 to 7. Patent Literatures 1 to 7 disclose a compound including a carbazole skeleton and a nitrogen-containing aromatic ring in the same molecule and a compound including a plurality of carbazole skeletons in the same molecule, as shown in the following compounds I to VIII.

The compounds I and II disclosed in Patent Literature 1 each have a structure in which a carbazole skeleton is bonded to a benzene ring and an electron-deficient nitrogen-containing hetero aromatic ring structure. A carbazole skeleton, which is represented by polyvinyl carbazole, has been known as a main skeleton of a hole transporting material. In contrast, the electron-deficient nitrogen-containing hetero aromatic ring structure has been known as a structure having a high electron transporting capability. In other words, the compounds I and II disclosed in Patent Literature 1 are materials for balancing charge transportation by combining a hole transporting skeleton and an electron transporting skeleton.

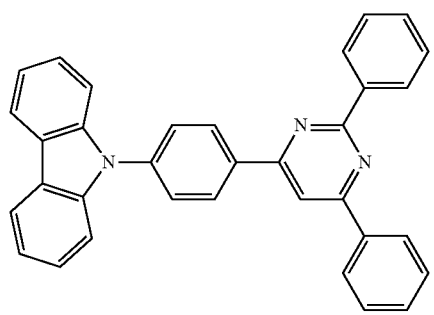

Compound I

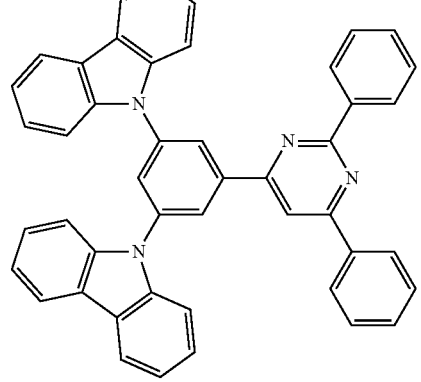

Compound II

-continued
Compound III
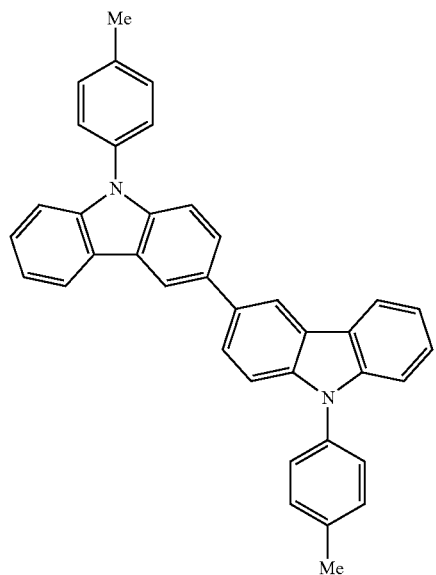
Compound IV
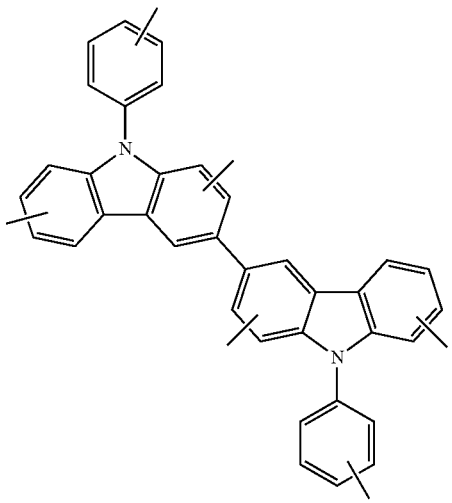
Compound V
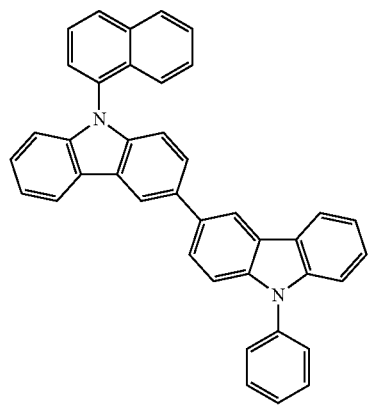
Compound VI
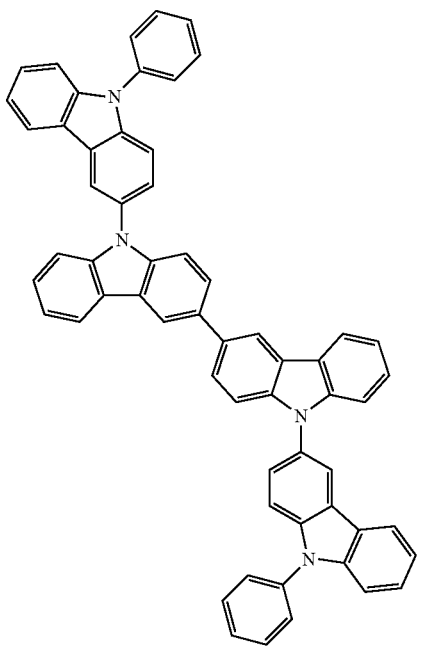

Compound VII

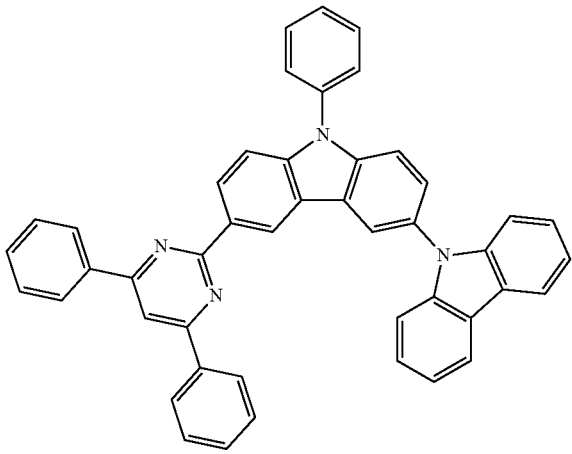

Compound VIII

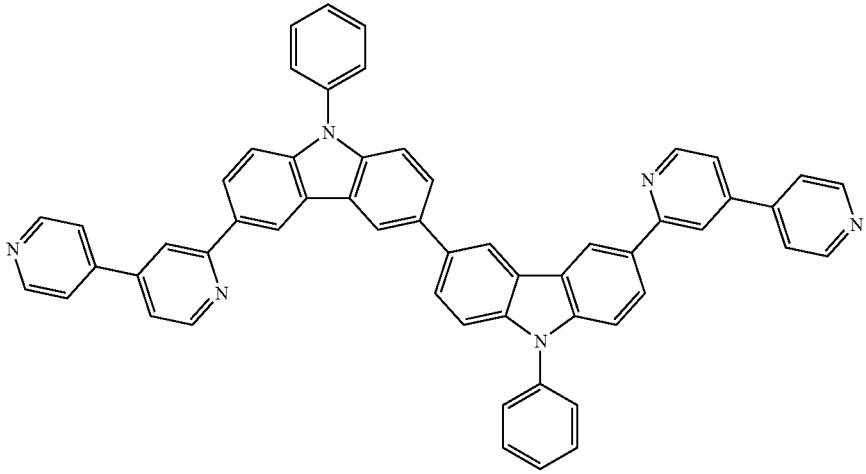

The compound I has only a single carbazole skeleton and lacks a hole transporting capability, so that a favorable luminescence property cannot be obtained. The compound II has two carbazolyl groups that are branched to left and right relative to a bond axis of a pyrimidine ring and a benzene ring (two conjugated aromatic ring). Accordingly, an overlapping margin of the carbazole skeleton between molecules is impaired, so that a hole transporting capability is insufficient and a re-bonding position of charges is likely to be closer to the anode. Consequently, favorable luminescence property and lifetime property cannot be obtained.

In order to enlarge the overlapping margin between the molecules and exhibit a sufficient hole transporting capability, it has been proposed to incorporate a structure in which carbazole skeletons are linked in the molecules. For instance, the compounds III to VI disclosed in Patent Literatures 2 to 5 have a structure in which two carbazole skeletons are linked. However, since none of the compounds III to VI has an electron-deficient nitrogen-containing hetero aromatic ring structure, adjustment of carrier balance between holes and electrons is difficult, so that a favorable luminescence property cannot be obtained.

The compound VII disclosed in Patent Literature 6 has an electron-deficient nitrogen-containing hetero aromatic ring structure and a carbazole-linking structure. However, two carbazole skeletons are bonded to a carbon atom at 3-position by a nitrogen atom. In this structure, the two carbazole skeletons are twisted to each other to lose flatness. Accordingly, the overlapping margin between the molecules becomes small and a hole transporting capability becomes insufficient, so that favorable luminescence property and lifetime property cannot be obtained.

The compound VIII disclosed in Patent Literature 7 has a structure in which a bipyridyl group (a nitrogen-containing aromatic heterocyclic group) is bonded to a benzene ring of a carbazole skeleton. The compound is not disclosed as a phosphorescent host material although being used as a material for an electron transporting layer. However, since the compound is considered to exhibit a high electron transporting capability, when used as a host material, the compound provides a poor carrier balance within the emitting layer and fails to exhibit a favorable luminescence property.

SUMMARY OF THE INVENTION

Accordingly, an object of the invention is to provide a novel biscarbazole derivative having a hole transporting capability and an electron transporting capability and exhibiting an excellent carrier balance, a material for an organic EL device (hereinafter, referred to as an organic-EL-device material) and a phosphorescent and long-life organic EL device using those.

After dedicated study to achieve the above object, the inventors found that a compound including two carbazolyl groups and a nitrogen-containing heterocyclic group effectively works for optimizing a carrier balance in the emitting layer of an organic EL device, and achieved the invention.

Specifically, a biscarbazole derivative according to an aspect of the invention is represented by a formula (1) below. Herein, "hydrogen" is meant to also include deuterium.

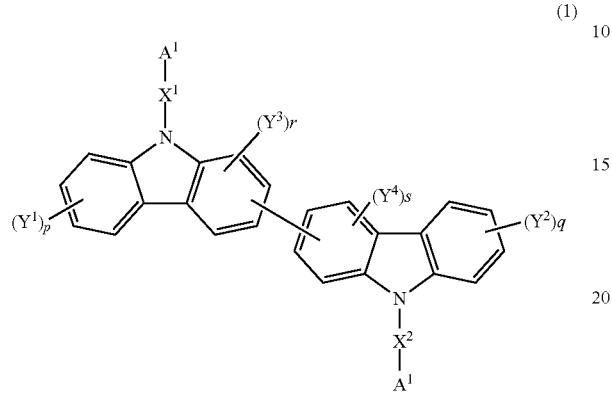

(1)

In the formula (1): $A^1$ represents a substituted or unsubstituted nitrogen-containing heterocyclic group having 1 to 30 carbon atoms forming a ring (hereinafter, referred to as ring carbon atoms);

$A^2$ represents a substituted or unsubstituted aromatic hydrocarbon group having 6 to 30 ring carbon atoms, or substituted or unsubstituted nitrogen-containing heterocyclic group having 1 to 30 ring carbon atoms;

$X^1$ and $X^2$ each are a linking group and independently represent a single bond, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms.

$Y^1$ to $Y^4$ independently represent a hydrogen atom, fluorine atom, cyano group, substituted or unsubstituted alkyl group having 1 to 20 carbon atoms, substituted or unsubstituted alkoxy group having 1 to 20 carbon atoms, substituted or unsubstituted haloalkyl group having 1 to 20 carbon atoms, substituted or unsubstituted haloalkoxy group having 1 to 20 carbon atoms, substituted or unsubstituted alkylsilyl having 1 to 10 carbon atoms, substituted or unsubstituted arylsilyl having 6 to 30 carbon atoms, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;

adjacent ones of $Y^1$ to $Y^4$ may be bonded to each other to form a ring structure;

p and q represent an integer of 1 to 4; r and s represent an integer of 1 to 3; and when p and q are an integer of 2 to 4 and r and s are an integer of 2 to 3, a plurality of $Y^1$ to $Y^4$ may be the same or different.

When $Y^1$ to $Y^4$ are bonded to each other to form a ring structure, the ring structure is exemplified by structures represented by the following formulae.

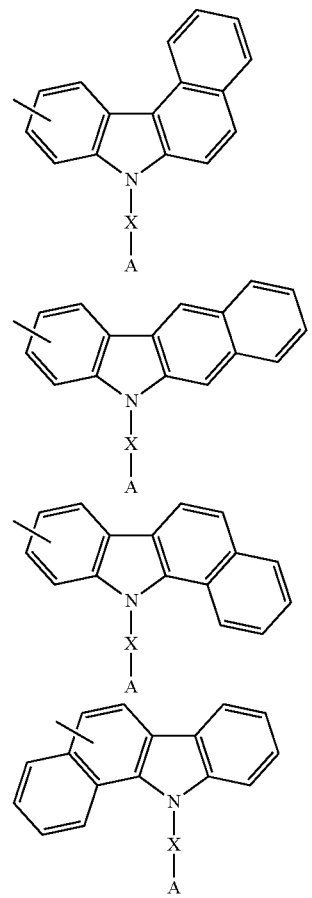

The biscarbazole derivative according to the aspect of the invention is preferably represented by a formula (2) below.

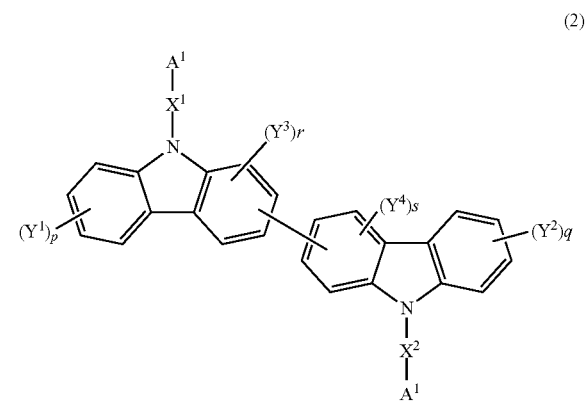

(2)

In the formula (2), $A^1$, $A^2$, $X^1$, $X^2$, $Y^1$ to $Y^4$, p, q, r and s represent the same as $A^1$, $A^2$, $X^1$, $X^2$, $Y^1$ to $Y^4$, p, q, r and s in the formula (1).

Moreover, in the biscarbazole derivative according to the above aspect of the invention, $A^1$ in the formula (1A) or (1B) is preferably selected from the group consisting of a substituted or unsubstituted pyridine ring, substituted or unsubstituted pyrimidine ring and substituted or unsubstituted triazine ring, more preferably selected from a substituted or unsubstituted pyrimidine ring or substituted or unsubstituted triazine ring, particularly preferably a substituted or unsubstituted pyrimidine ring.

The biscarbazole derivative according to the aspect of the invention is preferably represented by a formula (3) below in the formula (2)

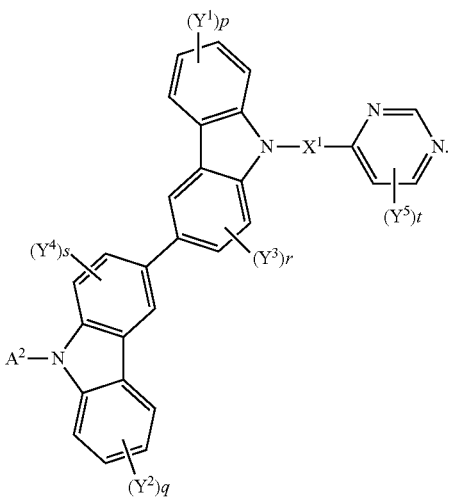

(3)

In the formula (3): $A^2$, $X^1$, $Y^1$ to $Y^4$, p, q, r and s represent the same as $A^2$, $X^1$, $Y^1$ to $Y^4$, p, q, r and s of the formula (1); $Y^5$ represent the same as $Y^1$ to $Y^4$ of the formula (1); t represents an integer from 1 to 3; and when t is an integer of 2 to 3, a plurality of $Y^5$ may be the same or different.

Moreover, in the biscarbazole derivative according to the aspect of the invention represented by the formula (1) or (2), $A^1$ is preferably a substituted or unsubstituted quinazoline ring.

The organic-EL-device material according to another aspect of the invention contains the above biscarbazole derivative.

The organic EL device according to still another aspect of the invention includes: a cathode; an anode; and a plurality of organic thin-film layers provided between the cathode and the anode, and the organic thin-film layer including an emitting layer, in which at least one layer of the organic thin-film layers contains the above-described organic-EL-device material.

In the organic EL device according to the above aspect of the invention, the emitting layer preferably contains the organic-EL-device material according to the aspect of the invention as a host material.

Also preferably in the organic EL device according to the above aspect of the invention, the emitting layer includes a phosphorescent material.

The phosphorescent material is preferably an ortho-metalated complex of a metal atom selected from iridium (Ir), osmium (Os) and platinum (Pt).

The organic EL device according to further aspect of the invention includes: a cathode; an anode; and a plurality of organic thin-film layers provided between a cathode and an anode, and the organic thin-film layer includes an emitting layer, in which at least one of the organic thin-film layers is the emitting layer containing a first host material, a second host material and a phosphorescent material providing phosphorescence, the first host material being a compound represented by a formula (4) below.

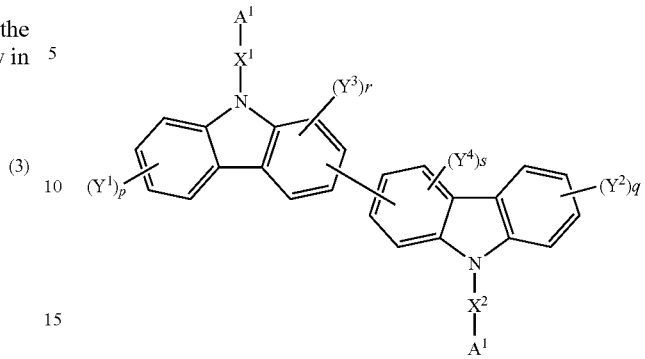

(4)

In the formula (4): $A^1$ represents a substituted or unsubstituted nitrogen-containing heterocyclic group having 1 to 30 ring carbon atoms;

$A^2$ represents a substituted or unsubstituted aromatic hydrocarbon group having 6 to 30 ring carbon atoms, or substituted or unsubstituted nitrogen-containing heterocyclic group having 1 to 30 ring carbon atoms;

$X^1$ and $X^2$ each are a linking group and independently represent a single bond, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;

$Y^1$ to $Y^4$ independently represent a hydrogen atom, fluorine atom, cyano group, substituted or unsubstituted alkyl group having 1 to 20 carbon atoms, substituted or unsubstituted alkoxy group having 1 to 20 carbon atoms, substituted or unsubstituted haloalkyl group having 1 to 20 carbon atoms, substituted or unsubstituted haloalkoxy group having 1 to 20 carbon atoms, substituted or unsubstituted alkylsilyl having 1 to 10 carbon atoms, substituted or unsubstituted arylsilyl having 6 to 30 carbon atoms, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;

adjacent ones of $Y^1$ to $Y^4$ may be bonded to each other to form a ring structure;

p and q represent an integer of 1 to 4; r and s represent an integer of 1 to 3; and when p and q are an integer of 2 to 4 and r and s are an integer of 2 to 3, a plurality of $Y^1$ to $Y^4$ may be the same or different.

When $Y^1$ to $Y^4$ are bonded to each other to form a ring structure, the ring structure is exemplified by the same structures as ones listed when $Y^1$ to $Y^4$ are bonded to each other to form a ring structure in the formula (1).

In the organic EL device according to the above aspect of the invention, the second host material is preferably represented by either one of a formula (5) or (6) below.

(5)

(6)

In the formula (5) or (6): Cz represents a substituted or unsubstituted arylcarbazolyl group or carbazolylaryl group;

$A^3$ represents a group represented by a formula (7A) or (7B) below; and a and b each represent an integer of 1 to 3.

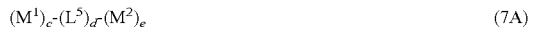  (7A)

In the formula (7A): $M^1$ and $M^2$ each independently represent a substituted or unsubstituted nitrogen-containing aromatic heterocyclic ring or nitrogen-containing fused aromatic heterocyclic ring having 2 to 40 ring carbon atoms; $M^1$ and $M^2$ may be the same or different;

$L^5$ represents a single bond, substituted or unsubstituted aromatic hydrocarbon group having 6 to 30 carbon atoms, substituted or unsubstituted fused aromatic hydrocarbon group having 6 to 30 carbon atoms, substituted or unsubstituted cycloalkylene group having 5 to 30 carbon atoms, substituted or unsubstituted aromatic heterocyclic group having 2 to 30 carbon atoms, or substituted or unsubstituted fused aromatic heterocyclic group having 2 to 30 carbon atoms;

c represents an integer of 0 to 2; d represents an integer of 1 to 2; e represents an integer of 0 to 2; and c+e represents 1 or more.

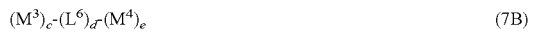  (7B)

In the formula (7B): $M^3$ and $M^4$ each independently represent a substituted or unsubstituted aromatic hydrocarbon group having 6 to 40 ring carbon atoms; $M^3$ and $M^4$ may be the same or different;

$L^6$ represents a single bond, substituted or unsubstituted aromatic hydrocarbon group having 6 to 30 carbon atoms, substituted or unsubstituted fused aromatic hydrocarbon group having 6 to 30 carbon atoms, or substituted or unsubstituted cycloalkylene group having 5 to 30 carbon atoms;

c represents an integer of 0 to 2; d represents an integer of 1 to 2; e represents an integer of 0 to 2; and c+e represents 1 or more.

In the organic EL device according to the above aspect of the invention, the second host material is preferably represented by a formula (8) below.

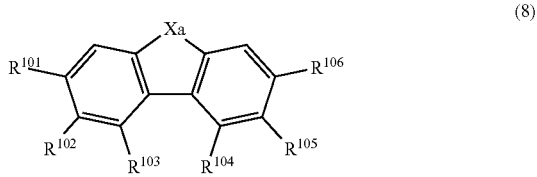  (8)

In the formula (8): $R^{101}$ to $R^{106}$ each independently represent a hydrogen atom, halogen atom, substituted or unsubstituted alkyl group having 1 to 40 carbon atoms, substituted or unsubstituted cycloalkyl group having 3 to 15 carbon atoms, substituted or unsubstituted heterocyclic group having 3 to 20 carbon atoms, substituted or unsubstituted alkoxy group having 1 to 40 carbon atoms, substituted or unsubstituted aryl group having 6 to 40 carbon atoms, substituted or unsubstituted aryloxy group having 6 to 20 carbon atoms, substituted or unsubstituted aralkyl group having 7 to 20 carbon atoms, substituted or unsubstituted arylamino group having 6 to 40 carbon atoms, substituted or unsubstituted alkylamino group having 1 to 40 carbon atoms, substituted or unsubstituted aralkylamino group having 7 to 60 carbon atoms, substituted or unsubstituted arylcarbonyl group having 7 to 40 carbon atoms, substituted or unsubstituted arylthio group having 6 to 20 carbon atoms, or substituted or unsubstituted halogenated alkyl group having 1 to 40 carbon atoms or cyano group;

at least one of $R^{101}$ to $R^{106}$ is a substituted or unsubstituted 9-carbazolyl group, substituted or unsubstituted azacarbazolyl group having 2 to 5 nitrogen atoms, or -L-9-carbazolyl group;

L represents a substituted or unsubstituted alkyl group having 1 to 40 carbon atoms, substituted or unsubstituted cycloalkyl group having 3 to 15 carbon atoms, substituted or unsubstituted heterocyclic group having 3 to 20 carbon atoms, substituted or unsubstituted alkoxy group having 1 to 40 carbon atoms, substituted or unsubstituted aryl group having 6 to 40 carbon atoms, substituted or unsubstituted aryloxy group having 6 to 20 carbon atoms, substituted or unsubstituted aralkyl group having 7 to 20 carbon atoms, substituted or unsubstituted arylamino group having 6 to 40 carbon atoms, substituted or unsubstituted alkylamino group having 1 to 40 carbon atoms, substituted or unsubstituted aralkylamino group having 7 to 60 carbon atoms, substituted or unsubstituted arylcarbonyl group having 7 to 40 carbon atoms, substituted or unsubstituted arylthio group having 6 to 20 carbon atoms, or substituted or unsubstituted halogenated alkyl group having 1 to 40 carbon atoms;

Xa represents a sulfur atom, oxygen atom or N—$R^{108}$; and $R^{108}$ represents the same as $R^{101}$ to $R^{106}$.

In the organic EL device according to the aspect of the invention, the second host material is preferably a compound selected from the group consisting of polycyclic aromatic compounds represented by formulae (9A), (9B) and (9C) below.

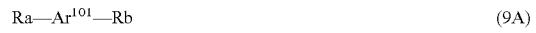  (9A)

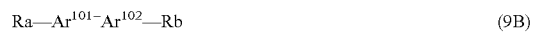  (9B)

  (9C)

In the formulae (9A) to (9C): $Ar^{101}$, $Ar^{102}$, $Ar^{103}$, Ra and Rb represent a polycyclic aromatic skeleton having 6 to 60 ring carbon atoms selected from a substituted or unsubstituted benzene ring, substituted or unsubstituted naphthalene ring, substituted or unsubstituted chrysene ring, substituted or unsubstituted fluoranthene ring, substituted or unsubstituted phenanthrene ring, substituted or unsubstituted benzophenanthrene ring, substituted or unsubstituted dibenzophenanthrene ring, substituted or unsubstituted triphenylene ring, substituted or unsubstituted benzo[a]triphenylene ring, substituted or unsubstituted benzochrysene ring, substituted or unsubstituted benzo[b]fluoranthene ring, substituted or unsubstituted fluorene ring and substituted or unsubstituted picene ring.

Moreover, in the organic EL device according to the aspect of the invention, in the formulae (9A) to (9C), either one or both of Ra and Rb are preferably selected from the group consisting of a substituted or unsubstituted phenanthrene ring, substituted or unsubstituted benzo[c]phenanthrene ring and substituted or unsubstituted fluoranthene ring.

In the organic EL device according to the above aspect of the invention, the second host material is preferably a monoamine derivative represented by any one of formulae (10) to (12) below.

  (10)

$Ar^{111}$, $Ar^{112}$ and $Ar^{113}$ are a substituted or unsubstituted aryl group or heteroaryl group.

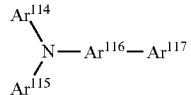 (11)

$Ar^{114}$, $Ar^{115}$ and $Ar^{117}$ are a substituted or unsubstituted aryl group or heteroaryl group.

$Ar^{116}$ is a substituted or unsubstituted arylene group or heteroarylene group.

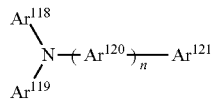 (12)

$Ar^{118}$, $R^{119}$ and $Ar^{121}$ are a substituted or unsubstituted aryl group or heteroaryl group.

$Ar^{120}$ is a substituted or unsubstituted arylene group or heteroarylene group.

n is an integer of 2 to 5: when n is 2 or more, $Ar^{120}$ may be the same or different.

In the organic EL device according to the aspect of the invention, the second host material is represented by a formula (13) or (14) below.

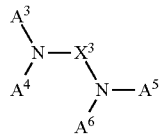 (13)

In the formula (14): $X^3$ represents a substituted or unsubstituted arylene group having 10 to 40 ring carbon atoms; and $A^3$ to $A^6$ represent a substituted or unsubstituted aryl group having 6 to 60 ring carbon atoms, or heteroaryl group having 6 to 60 ring atoms.

 (14)

In the formula (14), $A^7$ to $A^9$ represent a substituted or unsubstituted aryl group having 6 to 60 ring carbon atoms, or heteroaryl group having 6 to 60 ring atoms.

In the organic EL device according to the above aspect of the invention, the second host material is more preferably represented by any one of formulae (15) to (19) below.

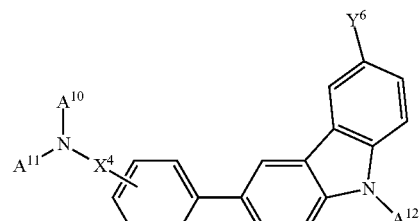 (15)

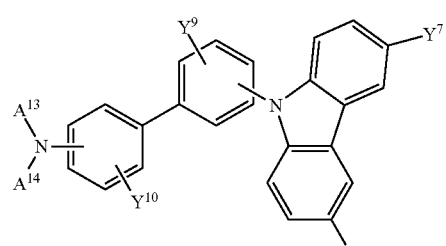 (16)

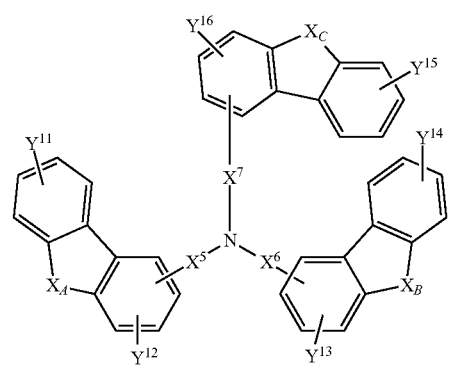 (17)

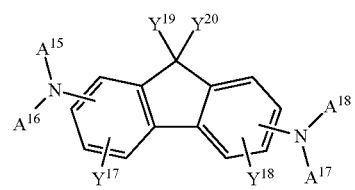 (18)

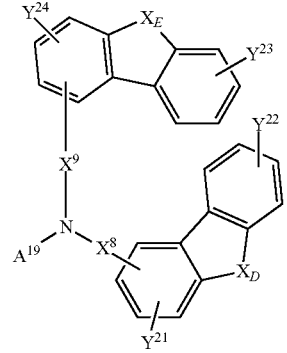 (19)

In the formulae (15) to (19): $A^{10}$ to $A^{19}$ each represent a substituted or unsubstituted aryl group having 6 to 40 carbon atoms, substituted or unsubstituted aromatic heterocyclic group having 2 to 40 carbon atoms, substituted or unsubstituted aryl group having 8 to 40 carbon atoms bonded with an aromatic amino group, or substituted or unsubstituted aryl group having 8 to 40 carbon atoms bonded with an aromatic heterocyclic group;

$A^{10}, A^{13}, A^{15}$ and $A^{17}$ are adapted to be respectively bonded to $A^{11}, A^{14}, A^{16}$ and $A^{18}$ to form a ring;

$X^4$ to $X^9$ represent a single bond or a linking group having 1 to 30 carbon atoms;

$Y^6$ to $Y^{24}$ represent a hydrogen atom, halogen atom, substituted or unsubstituted alkyl group having 1 to 40 carbon atoms, substituted or unsubstituted heterocyclic group having 3 to 20 carbon atoms, substituted or unsubstituted aryl group having 6 to 40 carbon atoms, substituted or unsubstituted aralkyl group having 7 to 20 carbon atoms, substituted or unsubstituted alkenyl group having 2 to 40 carbon atoms, substituted or unsubstituted alkylamino group having 1 to 40 carbon atoms, substituted or unsubstituted aralkylamino group having 7 to 60 carbon atoms, substituted or unsubstituted alkylsilyl group having 3 to 20 carbon atoms, substituted or unsubstituted arylsilyl group having 8 to 40 carbon atoms, substituted or unsubstituted aralkylsilyl group having 8 to 40 carbon atoms, or substituted or unsubstituted halogenated alkyl group having 1 to 40 carbon atoms; and $X_A, X_B, X_C, X_D, X_E$ each represent a sulfur atom, an oxygen atom or a monoaryl-substituted nitrogen atom.

In the organic EL device according to the above aspect of the invention, it is preferable that the emitting layer includes a host material and a phosphorescent material, the phosphorescent material being an ortho-metalated complex of a metal atom selected from iridium (Ir), osmium (Os) and platinum (Pt).

In the organic EL device according to the above aspect of the invention, it is preferable that an electron injecting layer is provided between the cathode and the emitting layer and includes a nitrogen-containing cyclic derivative.

In the organic EL device according to the above aspect of the invention, it is preferable that an electron transporting layer is provided between the cathode and the emitting layer and includes the above-described organic-EL-device material.

In the organic EL device according to the above aspect of the invention, it is preferable that a reduction-causing dopant is present at an interfacial region between the cathode and the organic thin-film layer.

The organic EL device according to the above aspect of the invention preferably includes a cathode, an anode, and an organic layer between the cathode and the anode, in which the organic layer include the biscarbazole derivative represented by the formulae (1) to (3).

In the organic electroluminescence device according to the above aspect of the invention, the organic layer preferably includes a phosphorescent material; the phosphorescent material being an ortho-metalated complex of a metal atom selected from iridium (Ir), osmium (Os) and platinum (Pt).

According to the above aspect of the invention, since the biscarbazole derivative is used as the organic-EL-device material, a long-life organic electroluminescence device can be provided. Moreover, the organic-EL-device material is effective as organic-electron-device material for an organic solar cell, an organic semiconductor laser, a sensor using an organic substance and an organic TFT.

DETAILED DESCRIPTION OF PREFERRED EMBODIMENT(S)

The invention will be described below in detail.

First Exemplary Embodiment

Arrangement of Organic EL Device

First of all, arrangement(s) of an organic EL device will be described below.

The followings are representative arrangement examples of an organic EL device:
(1) anode/emitting layer/cathode;
(2) anode/hole injecting layer/emitting layer/cathode;
(3) anode/emitting layer/electron injecting•transporting layer/cathode;
(4) anode/hole injecting layer/emitting layer/electron injecting•transporting layer/cathode;
(5) anode/organic semiconductor layer/emitting layer/cathode;
(6) anode/organic semiconductor layer/electron blocking layer/emitting layer/cathode;
(7) anode/organic semiconductor layer/emitting layer/adhesion improving layer/cathode;
(8) anode/hole injecting•transporting layer/emitting layer/electron injecting•transporting layer/cathode;
(9) anode/insulating layer/emitting layer/insulating layer/cathode;
(10) anode/inorganic semiconductor layer/insulating layer/emitting layer/insulating layer/cathode;
(11) anode/organic semiconductor layer/insulating layer/emitting layer/insulating layer/cathode;
(12) anode/insulating layer/hole injecting transporting layer/emitting layer/insulating layer/cathode; and
(13) anode/insulating layer/hole injecting•transporting layer/emitting layer/electron injecting transporting layer/cathode.

While the arrangement (8) is preferably used among the above, the arrangement of the invention is not limited to the above arrangements.

Figure 1:
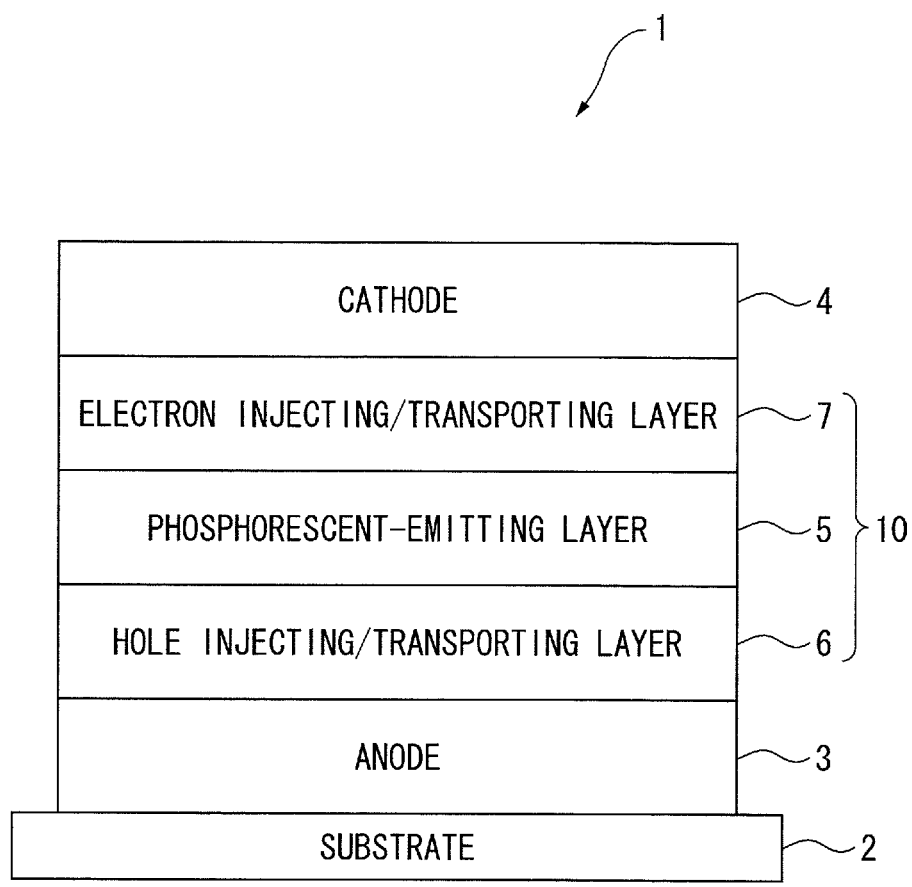
FIG. 1 schematically shows an exemplary arrangement of an organic electroluminescence device according to an exemplary embodiment of the invention.

FIG. 1 schematically shows an exemplary arrangement of an organic EL device according to a first exemplary embodiment of the invention.

The organic EL device 1 includes a transparent substrate 2, an anode 3, a cathode 4 and an organic thin-film layer 10 positioned between the anode 3 and the cathode 4.

The organic thin-film layer 10 includes a phosphorescent-emitting layer 5 containing a phosphorescent host (a host material) and a phosphorescent dopant (a phosphorescent material). A layer such as a hole injecting/transporting layer 6 may be provided between the phosphorescent-emitting layer 5 and the anode 3 while a layer such as an electron injecting/transporting layer 7 may be provided between the phosphorescent-emitting layer 5 and the cathode 4.

In addition, an electron blocking layer may be provided to the phosphorescent-emitting layer 5 adjacent to the anode 3 while a hole blocking layer may be provided to the phosphorescent-emitting layer 5 adjacent to the cathode 4.

With this arrangement, electrons and holes can be trapped in the phosphorescent-emitting layer 5, thereby enhancing probability of exciton generation in the phosphorescent-emitting layer 5.

It should be noted that a "fluorescent host" and a "phosphorescent host" herein respectively mean a host combined with a fluorescent dopant and a host combined with a phosphorescent dopant, and that a distinction between the fluorescent host and phosphorescent host is not unambiguously derived only from a molecular structure of the host in a limited manner.

In other words, the fluorescent host herein means a material for forming a fluorescent-emitting layer containing a fluorescent dopant, and does not mean a host that is only usable as a host of a fluorescent material.

Likewise, the phosphorescent host herein means a material for forming a phosphorescent-emitting layer containing a phosphorescent dopant, and does not mean a host that is only usable as a host of a phosphorescent material.

It should be noted that the "hole injecting/transporting layer" herein means "at least either one of a hole injecting layer and a hole transporting layer" while the "electron injecting/transporting layer" herein means "at least either one of an electron injecting layer and an electron transporting layer."

Transparent Substrate

The organic EL device according to this exemplary embodiment is formed on a light-transmissive substrate. The light-transmissive plate, which supports the organic EL device, is preferably a smoothly-shaped substrate that transmits 50% or more of light in a visible region of 400 nm to 700 nm.

Specifically, a glass plate, a polymer plate, and the like are preferable.

For the glass plate, materials such as soda-lime glass, barium/strontium-containing glass, lead glass, aluminosilicate glass, borosilicate glass, barium borosilicate glass and quartz can be used.

For the polymer plate, materials such as polycarbonate, acryl, polyethylene terephthalate, polyether sulfide and polysulfone can be used.

Anode and Cathode

The anode of the organic EL device is used for injecting holes into the hole injecting layer, the hole transporting layer or the emitting layer. It is effective that the anode has a work function of 4.5 eV or more.

Exemplary materials for the anode are alloys of indium-tin oxide (ITO), tin oxide (NESA), indium zinc oxide, gold, silver, platinum and copper.

The anode may be made by forming a thin film from these electrode materials through methods such as vapor deposition and sputtering.

When light from the emitting layer is to be emitted through the anode as in this embodiment, the anode preferably transmits more than 10% of the light in the visible region. Sheet resistance of the anode is preferably several hundreds IV square or lower. Although depending on the material of the anode, thickness of the anode is typically in a range of 10 nm to 1 μm, and preferably in a range of 10 to 200 nm.

The cathode is preferably formed of a material with smaller work function in order to inject electrons into the electron injecting layer, the electron transporting layer and the emitting layer.

Although a material for the cathode is subject to no specific limitation, examples of the material are indium, aluminum, magnesium, alloy of magnesium and indium, alloy of magnesium and aluminum, alloy of aluminum and lithium, alloy of aluminum, scandium and lithium, alloy of magnesium and silver and the like.

Like the anode, the cathode may be made by forming a thin film from the above materials through a method such as vapor deposition or sputtering. In addition, the light may be emitted through the cathode.

Emitting Layer

The emitting layer of the organic EL device is an organic thin-film layer having a function for providing conditions for recombination of the electrons and the holes to emit light.

Injectability of the holes may differ from that of the electrons and transporting capabilities of the hole and the electrons (represented by mobilities of the holes and the electrons) may differ from each other.

As a method of forming the emitting layer, known methods such as vapor deposition, spin coating and an LB method may be employed.

The emitting layer is preferably a molecular deposit film.

The molecular deposit film means a thin film formed by depositing a material compound in gas phase or a film formed by solidifying a material compound in a solution state or in liquid phase. The molecular deposit film is typically distinguished from a thin film formed by the LB method (molecular accumulation film) by differences in aggregation structures, higher order structures and functional differences arising therefrom.

As disclosed in JP-A-57-51781, the emitting layer can be formed from a thin film formed by spin coating or the like, the thin film being formed from a solution prepared by dissolving a binder (e.g. a resin) and a material compound in a solvent.

An organic EL device according to this exemplary embodiment includes: a cathode; an anode; and a single or a plurality of organic thin-film layers provided between the cathode and the anode, in which the organic thin-film layer(s) includes at least one emitting layer, and at least one of the organic thin-film layers includes at least one phosphorescent material and, as an organic-EL-device material, at least one biscarbazole derivative according to this exemplary embodiment (described later). It is also preferable that at least one emitting layer includes the biscarbazole derivative as the organic-EL-device material according to this exemplary embodiment and at least one phosphorescent material.

Biscarbazole Derivative

The biscarbazole derivative according to this exemplary embodiment is represented by a formula (1) below.

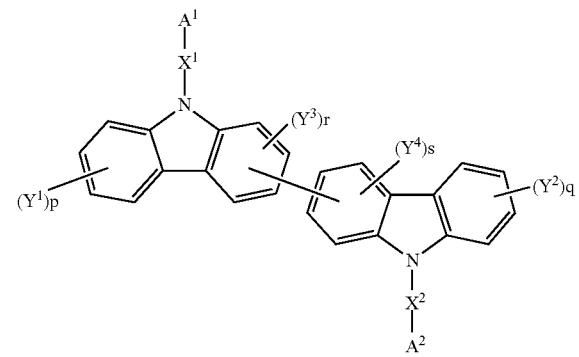

(1)

In the formula (1): $A^1$ represents a substituted or unsubstituted nitrogen-containing heterocyclic group having 1 to 30 ring carbon atoms;

$A^2$ represents a substituted or unsubstituted aromatic hydrocarbon group having 6 to 30 ring carbon atoms, or substituted or unsubstituted nitrogen-containing heterocyclic group having 1 to 30 ring carbon atoms;

$X^1$ and $X^2$ each are a linking group and independently represent a single bond, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;

$Y^1$ to $Y^4$ independently represent a hydrogen atom, fluorine atom, cyano group, substituted or unsubstituted alkyl group having 1 to 20 carbon atoms, substituted or unsubstituted alkoxy group having 1 to 20 carbon atoms, substituted or unsubstituted haloalkyl group having 1 to 20 carbon atoms, substituted or unsubstituted haloalkoxy group having 1 to 20 carbon atoms, substituted or unsubstituted alkylsilyl having 1 to 10 carbon atoms, substituted or unsubstituted arylsilyl having 6 to 30 carbon atoms, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;

adjacent ones of $Y^1$ to $Y^4$ may be bonded to each other to form a ring structure;

p and q represent an integer of 1 to 4; r and s represent an integer of 1 to 3; and when p and q are an integer of 2 to 4 and r and s are an integer of 2 to 3, a plurality of $Y^1$ to $Y^4$ may be the same or different.

When $Y^1$ to $Y^4$ are bonded to each other to form a ring structure, the ring structure is exemplified by structures represented by the following formulae.

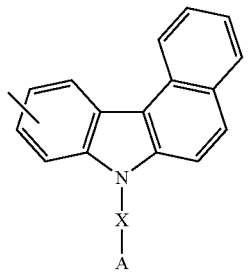

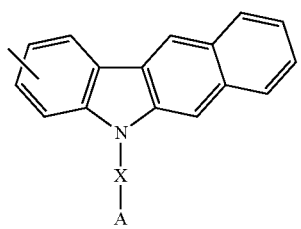

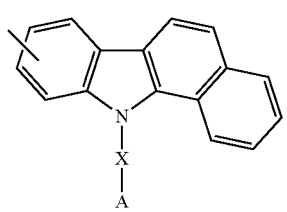

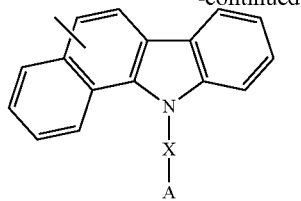

The biscarbazole derivative represented by the formula (1) is more preferably represented by a formula (2) below.

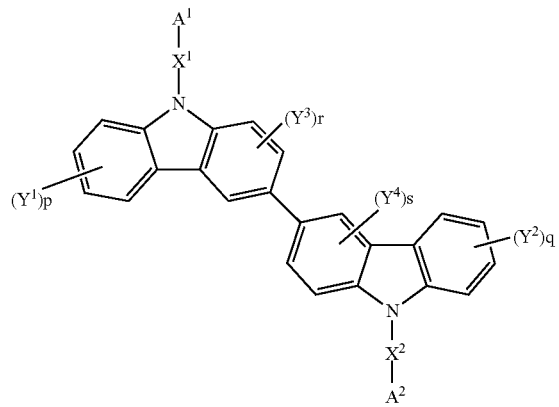

(2)

In the formula (2), $A^1$, $A^2$, $X^1$, $X^2$, $Y^1$ to $Y^4$, p, q, r and s are the same as those in the formula (1).

In the formula (2), $A^1$ and $A^2$ are preferably a nitrogen-containing heterocyclic group at the same time. More preferably, $A^1$ and $A^2$ are a substituted or unsubstituted aromatic heterocyclic group having 2 to 30 ring carbon atoms, or substituted or unsubstituted fused aromatic heterocyclic group having 2 to 30 ring carbon atoms.

Moreover, $A^1$ in the formula (2) is preferably selected from the group consisting of a substituted or unsubstituted pyridine ring, substituted or unsubstituted pyrimidine ring and substituted or unsubstituted triazine ring, more preferably selected from a substituted or unsubstituted pyrimidine ring or substituted or unsubstituted triazine ring.

$A^1$ in the formula (2) is further preferably a substituted or unsubstituted pyrimidine ring and is particularly preferably represented by a formula (3) below.

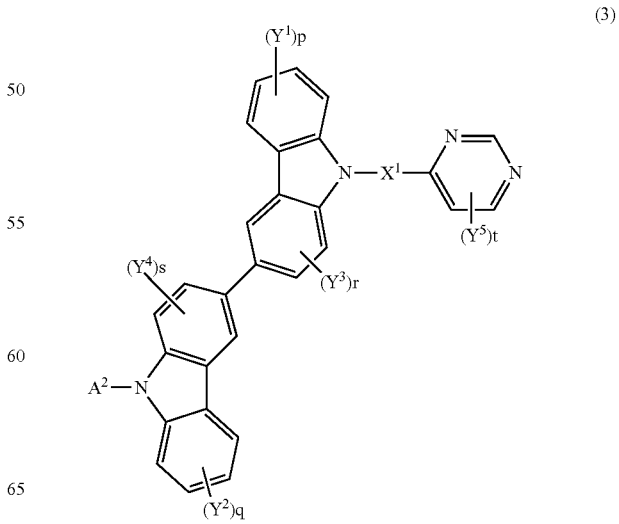

(3)

In the formula (3), $A^2$, $X^1$, $Y^1$ to $Y^4$, p, q, r and s are the same as those in the formula (1); $Y^5$ represents the same as $Y^1$ to $Y^4$ of the formula (1); t represents an integer from 1 to 3; and when t is an integer of 2 to 3, a plurality of $Y^5$ may be the same or different.

In the formula (3), $A^2$ is preferably a nitrogen-containing heterocyclic group. More preferably, $A^2$ is a substituted or unsubstituted aromatic heterocyclic group having 2 to 30 ring carbon atoms, or substituted or unsubstituted fused aromatic heterocyclic group having 2 to 30 ring carbon atoms.

In the formula (1) or (2), $A^1$ is preferably a substituted or unsubstituted quinazoline ring.

In the formulae (1) to (3), $X^1$ is preferably a single bond or a substituted or unsubstituted divalent aromatic hydrocarbon group having 6 to 30 ring carbon atoms, more preferably a substituted or unsubstituted divalent aromatic hydrocarbon group having 6 to 30 ring carbon atoms, particularly preferably a benzene ring or naphthalene ring.

When $X^1$ is a substituted or unsubstituted benzene ring in the formulae (1) to (3), $A^1$ and the carbazolyl group, which are bonded to $X^1$, are preferably in meta positions or para positions. Particularly preferably, $X^1$ is unsubstituted para-phenylene.

In the formulae (1) and (2), the pyridine ring, pyrimidine ring and triazine ring are more preferably represented by the following formulae. In the formulae, Y and Y' represent a substituent. Examples of the substituent are the same groups as those represented by $Y^1$ to $Y^4$ as described above. Y and Y' may be the same or different. Preferred examples thereof are the substituted or unsubstituted aromatic hydrocarbon group or fused aromatic hydrocarbon group having 6 to 30 ring carbon atoms, and the substituted or unsubstituted aromatic heterocyclic group or fused aromatic heterocyclic group having 2 to 30 ring carbon atoms. In the following formulae, * represents a bonding position to $X^1$ or $X^2$.

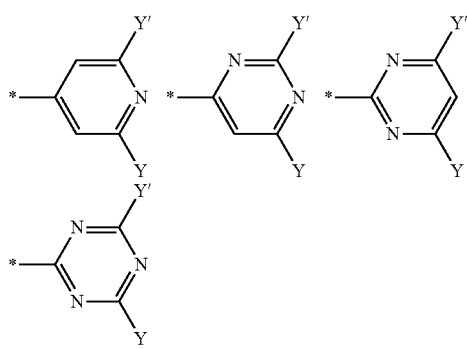

In the formulae (1) and (2), the quinazoline ring is represented by the following formula. Y represents a substituent. u represents an integer of 1 to 5. When u is an integer of 2 to 5, a plurality of Y may be the same or different. As the substituent Y, the same groups as those for the above $Y^1$ to $Y^4$ are usable, among which preferred examples thereof are the substituted or unsubstituted aromatic hydrocarbon group or fused aromatic hydrocarbon group having 6 to 30 ring carbon atoms, and the substituted or unsubstituted aromatic heterocyclic group or fused aromatic heterocyclic group having 2 to 30 ring carbon atoms. Also in the following formulae, * represents a bonding position to $X^1$ or $X^2$.

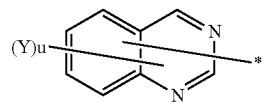

In the formulae (1) to (3), the alkyl group, alkoxy group, haloalkyl group, haloalkoxy group and alkylsilyl group, which are represented by $Y^1$ to $Y^5$, may be linear, branched or cyclic.

In the formulae (1) to (3), examples of the alkyl group having 1 to 20 carbon atoms are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, 1-methylpentyl group, 2-methylpentyl group, 1-pentylhexyl group, 1-butylpentyl group, 1-heptyloctyl group, 3-methylpentyl group, cyclopentyl group, cyclohexyl group, cycloheptyl group, cyclooctyl group and 3,5-tetramethylcyclohexyl group. Examples of the alkyl group having 1 to 10 carbon atoms are a methyl group, ethyl group, propyl group, isopropyl group, n-butyl group, s-butyl group, isobutyl group, t-butyl group, cyclopentyl group, cyclohexyl group and cycloheptyl group.

As the alkoxy group having 1 to 20 carbon atoms, an alkoxy group having 1 to 6 carbon atoms is preferable and specific examples thereof are a methoxy group, ethoxy group, propoxy group, butoxy group, pentyloxy group, and hexyloxy group.

The haloalkyl group having 1 to 20 carbon atoms is exemplified by an haloalkyl group provided by substituting the alkyl group having 1 to 20 carbon atoms with one or more halogen atoms. Preferred one of the halogen atoms is fluorine. The haloalkyl group is exemplified by a trifluoromethyl group and a 2,2,2-trifluoroethyl group.

The haloalkoxy group having 1 to 20 carbon atoms is exemplified by a haloalkoxy group provided by substituting the alkoxy group having 1 to 20 carbon atoms with one or more halogen atoms.

Examples of the alkylsilyl group having 1 to 10 carbon atoms are a trimethylsilyl group, triethylsilyl group, tributylsilyl group, dimethylethylsilyl group, dimethylisopropylsilyl group, dimethylpropylsilyl group, dimethylbutylsilyl group, dimethyl-tertiary-butylsilyl group and diethylisopropylsilyl group.

Examples of the arylsilyl group having 6 to 30 carbon atoms are a phenyldimethylsilyl group, diphenylmethylsilyl group, diphenyl-tertiary-butylsilyl group and triphenylsilyl group.

Examples of the aromatic heterocyclic group or fused aromatic heterocyclic group having 2 to 30 ring carbon atoms are a pyroryl group, pyrazinyl group, pyridinyl group, indolyl group, isoindolyl group, furyl group, benzofuranyl group, isobenzofuranyl group, dibenzofuranyl group, dibenzothiophenyl group, quinolyl group, isoquinolyl group, quinoxalinyl group, carbazolyl group, phenantridinyl group, acridinyl group, phenanthrolinyl group, thienyl group and a group formed from a pyridine ring, pyrazine ring, pyrimidine ring, pyridazine ring, triazine ring, indol ring, quinoline ring, acridine ring, pirrolidine ring, dioxane ring, piperidine ring, morpholine ring, piperadine ring, carbazole ring, furan ring, thiophene ring, oxazole ring, oxadiazole ring, benzooxazole ring, thiazole ring, thiadiazole ring, benzothiazole ring, triazole ring, imidazole ring, benzoimidazole ring, pyrane ring and dibenzofuran ring. Among the above, the aromatic heterocyclic group or fused aromatic heterocyclic group having 2 to 10 ring carbon atoms is preferable.

Examples of the aromatic hydrocarbon group or fused aromatic hydrocarbon group having 6 to 30 ring carbon atoms are a phenyl group, naphthyl group, phenanthryl group, biphenyl group, terphenyl group, quarterphenyl group, fluoranthenyl group, triphenylenyl group, phenanthrenyl group, pyrenyl group, chrysenyl group, fluorenyl group, and 9,9-dimethylfluorenyl group. Among the above, the aromatic hydrocarbon group or fused aromatic hydrocarbon group having 6 to 20 ring carbon atoms is preferable.

When $A^1$, $A^2$, $X^1$, $X^2$ and $Y^1$ to $Y^5$ of the formulae (1) to (3) each have one or more substituents, the substituents are preferably a linear, branched or cyclic alkyl group having 1 to 20 carbon atoms; linear, branched or cyclic alkoxy group having 1 to 20 carbon atoms; linear, branched or cyclic haloalkyl group having 1 to 20 carbon atoms; linear, branched or cyclic alkylsilyl group having 1 to 10 carbon atoms; arylsilyl group having 6 to 30 ring carbon atoms; cyano group; halogen atom; aromatic hydrocarbon group or fused aromatic hydrocarbon group having 6 to 30 ring carbon atoms; or aromatic heterocyclic group or fused aromatic heterocyclic group having 2 to 30 ring carbon atoms.

Examples of the linear, branched or cyclic alkyl group having 1 to 20 carbon atoms; linear, branched or cyclic alkoxy group having 1 to 20 carbon atoms; linear, branched or cyclic haloalkyl group having 1 to 20 carbon atoms; linear, branched or cyclic alkylsilyl group having 1 to 10 carbon atoms; arylsilyl group having 6 to 30 ring carbon atoms; aromatic hydrocarbon group or fused aromatic hydrocarbon group having 6 to 30 ring carbon atoms; and aromatic heterocyclic group or fused aromatic heterocyclic group having 2 to 30 ring carbon atoms are the above-described groups. The halogen atom is exemplified by a fluorine atom.

Examples of compounds for the biscarbazole derivative according to this exemplary embodiment represented by the formulae (1) to (3) are as follows.

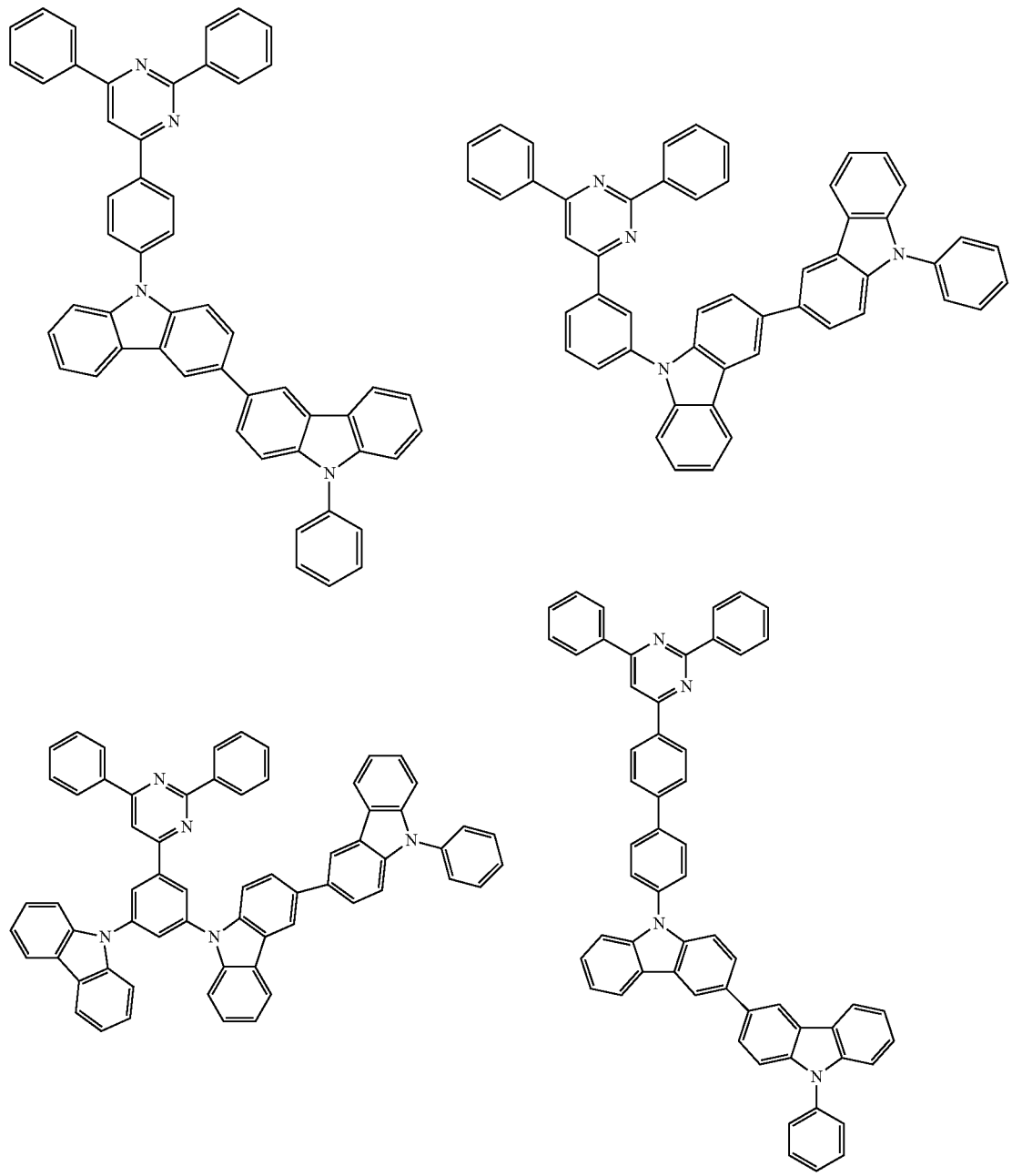

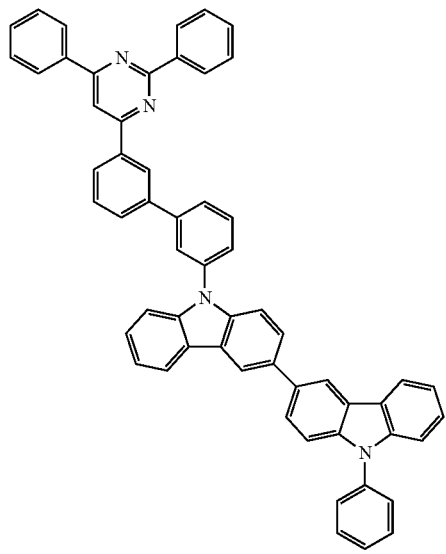
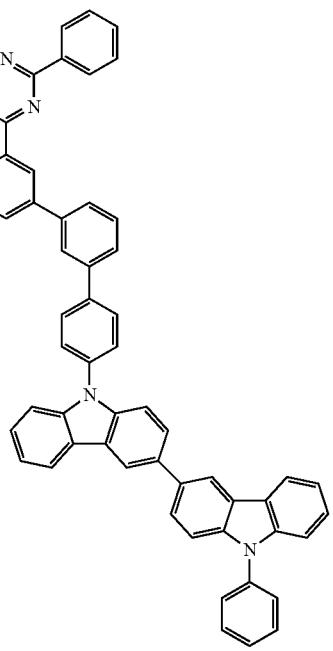
-continued
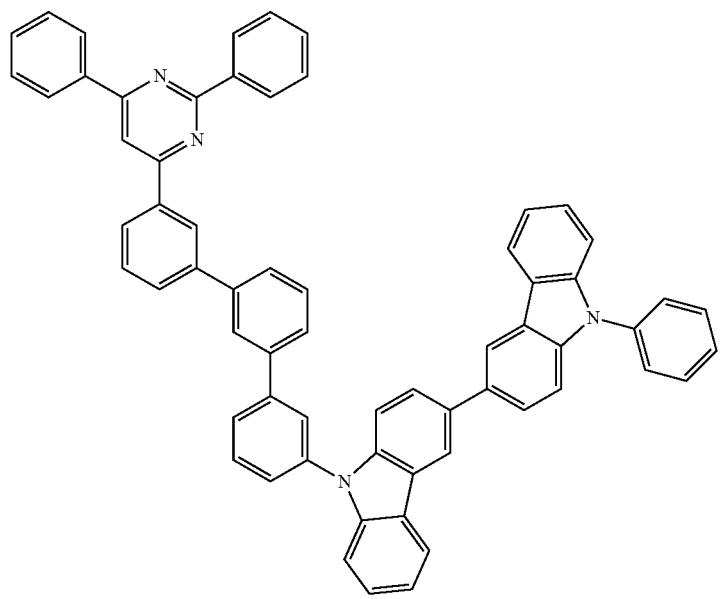

-continued
27
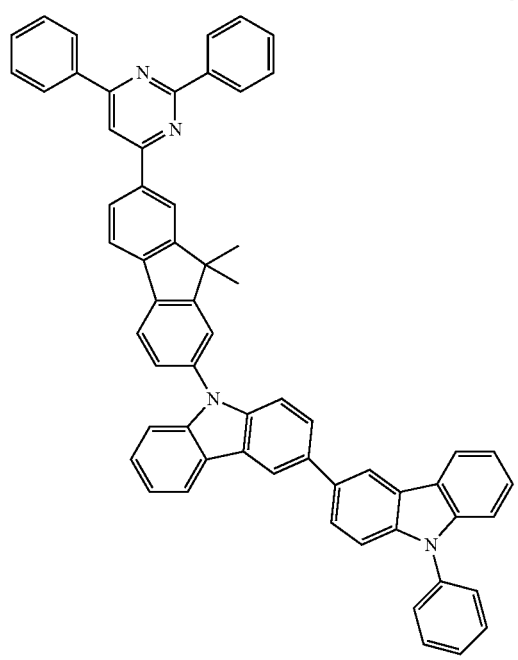
28
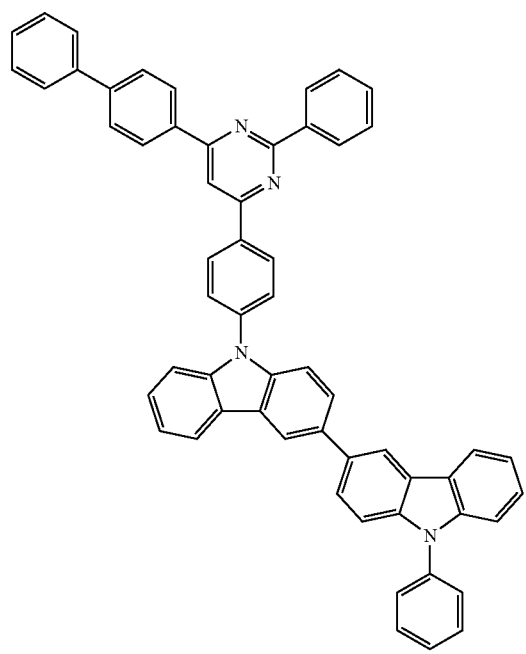
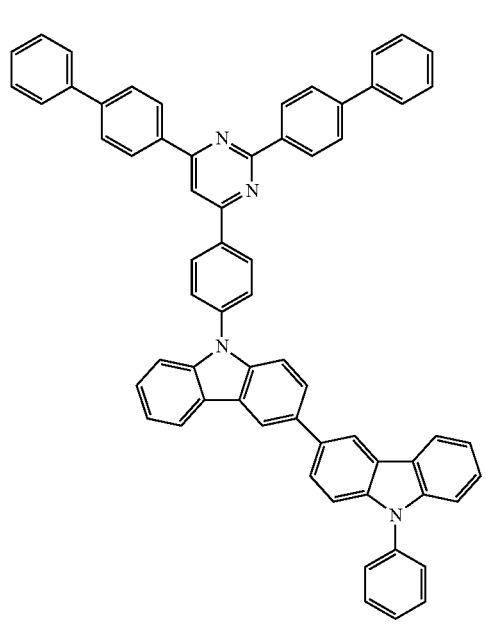
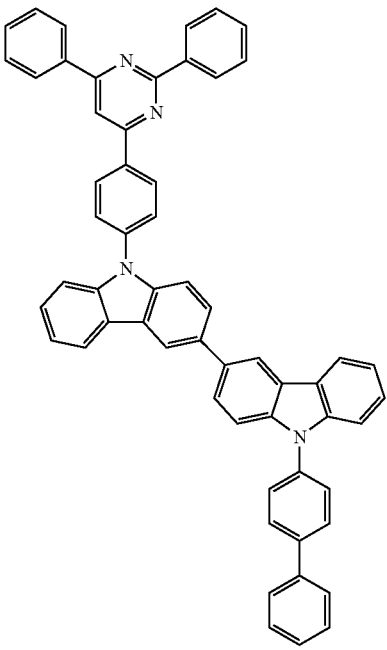

29
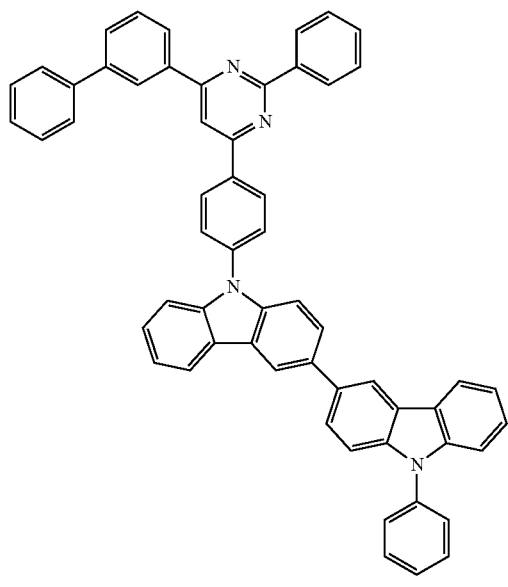
30
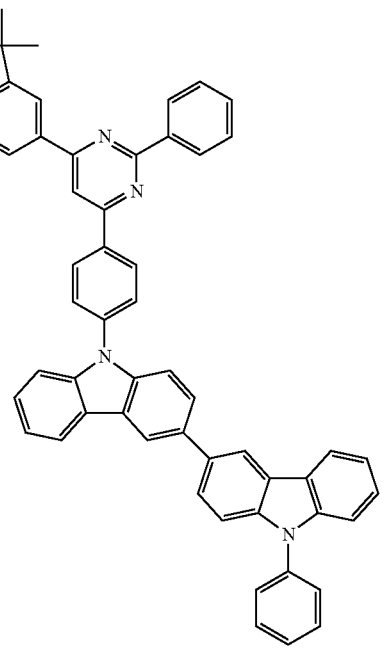
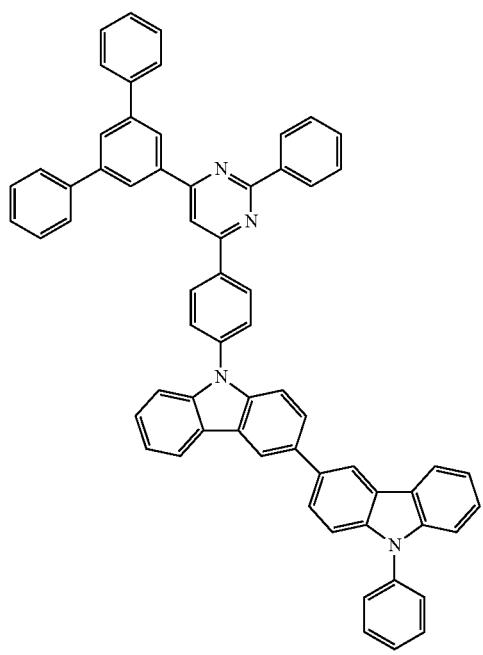
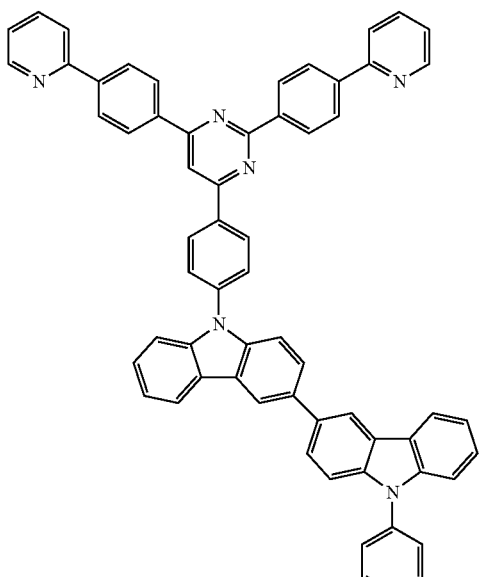

31
32
-continued
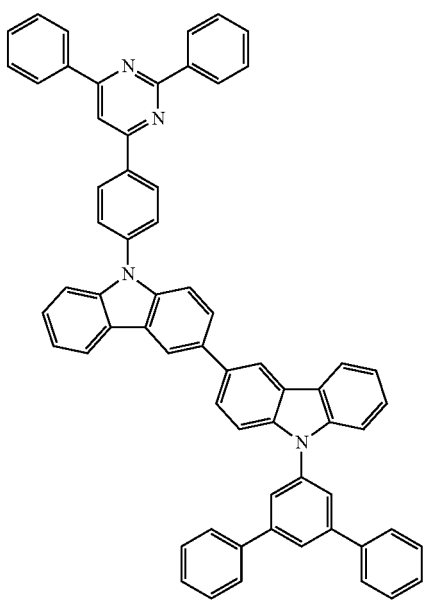
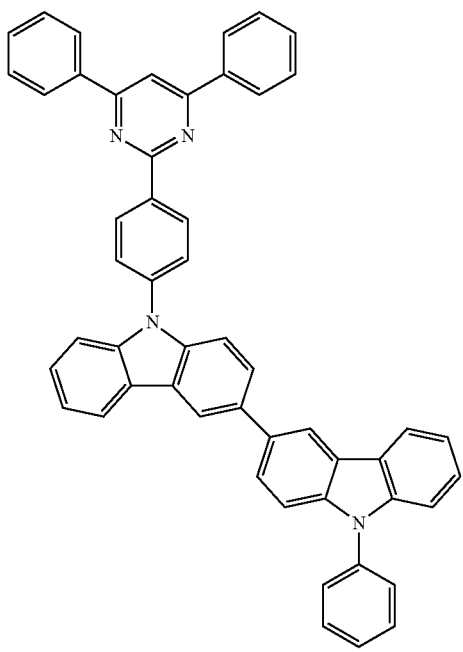
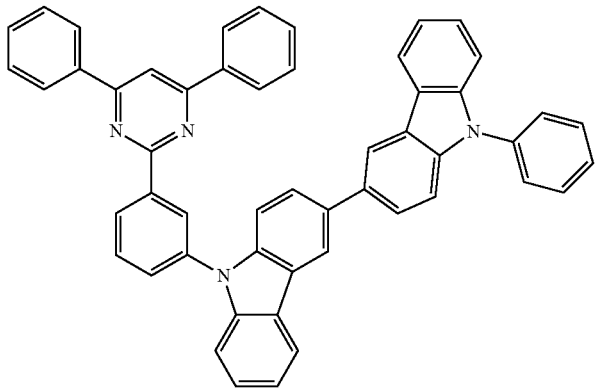

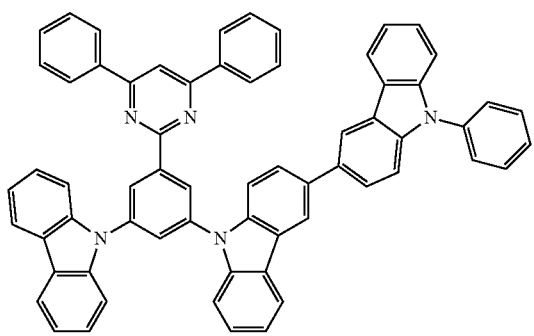
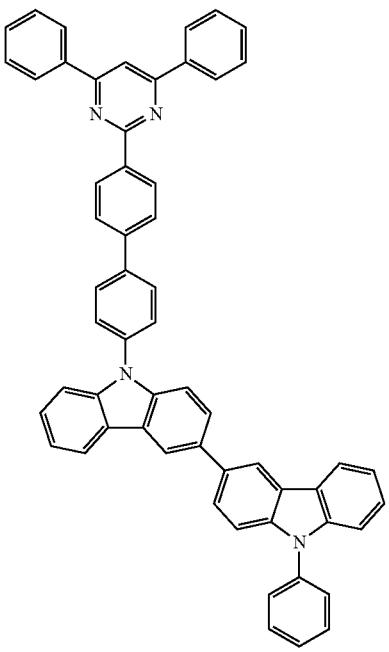
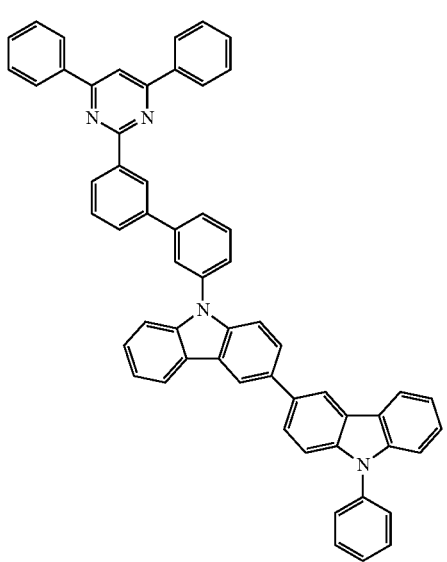
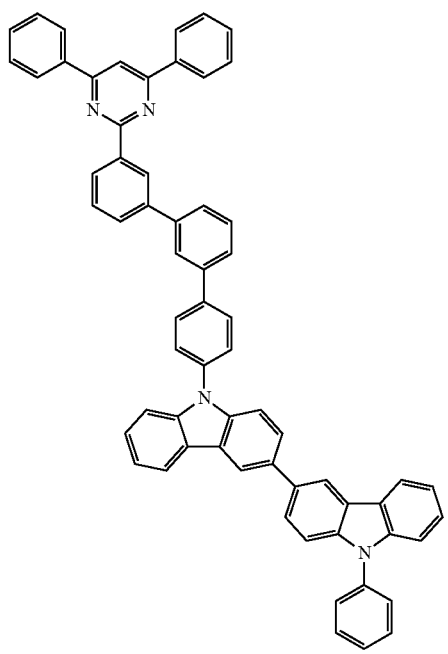

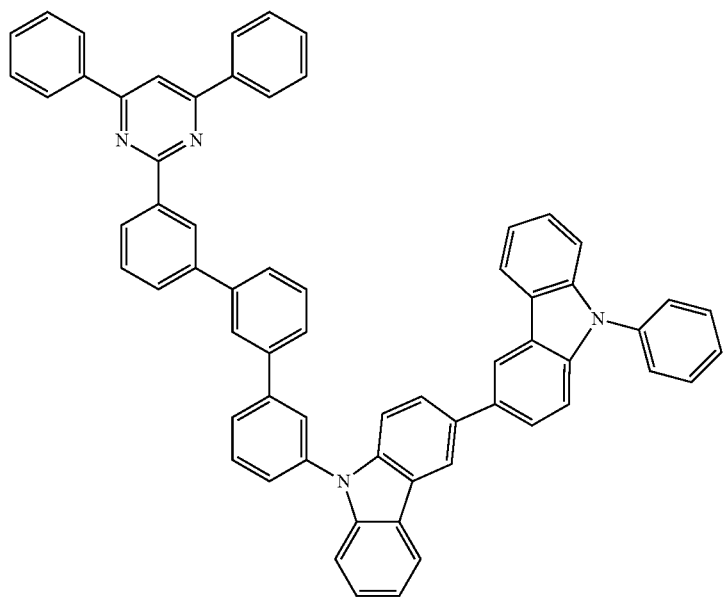
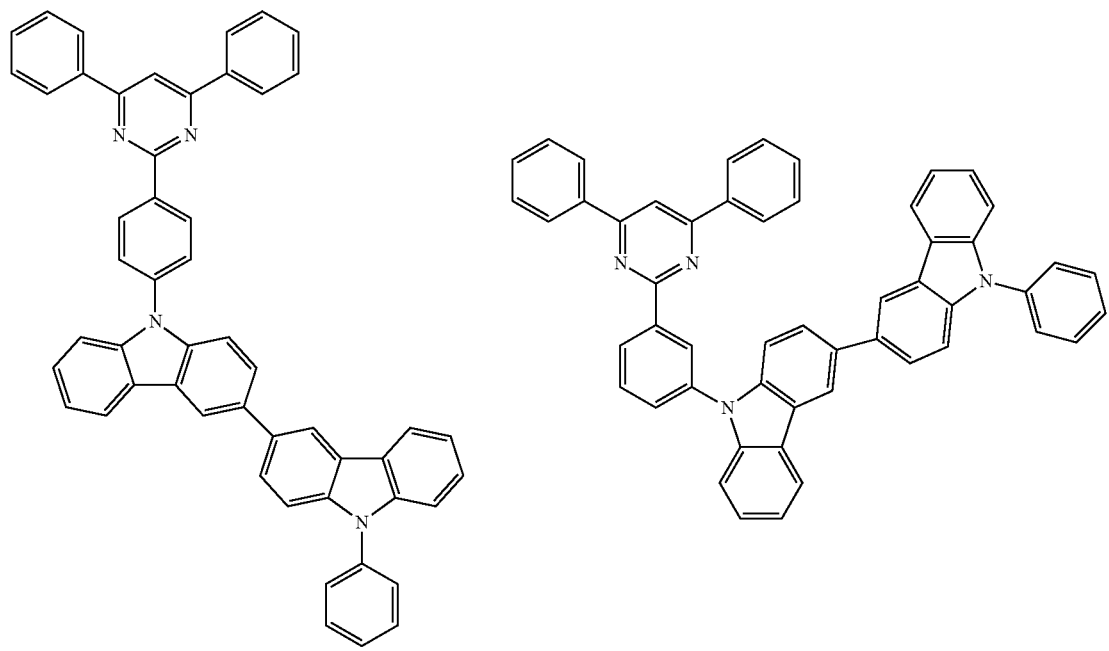

-continued
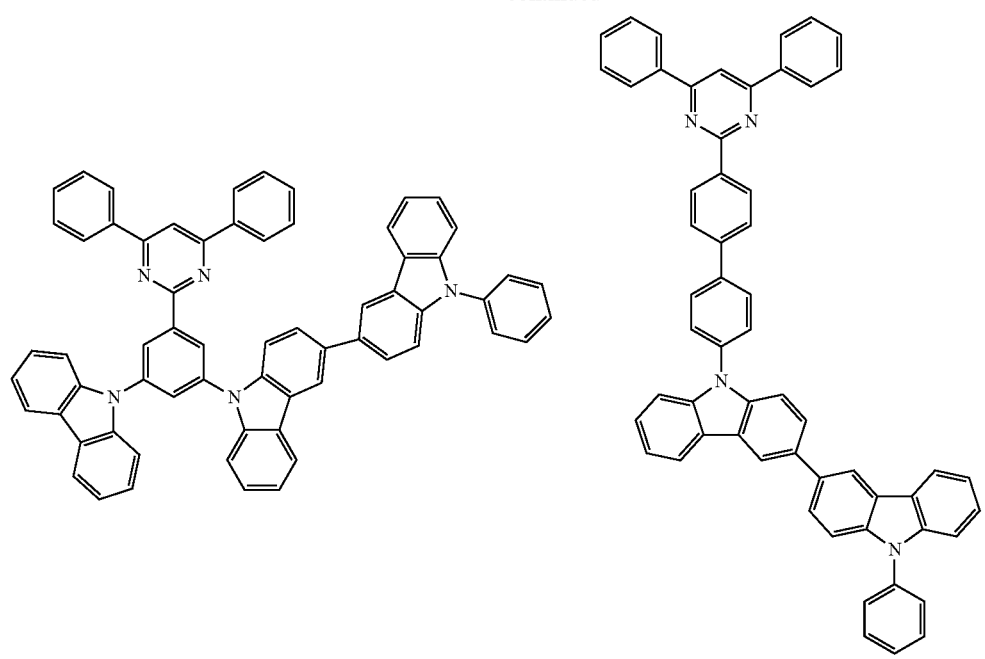
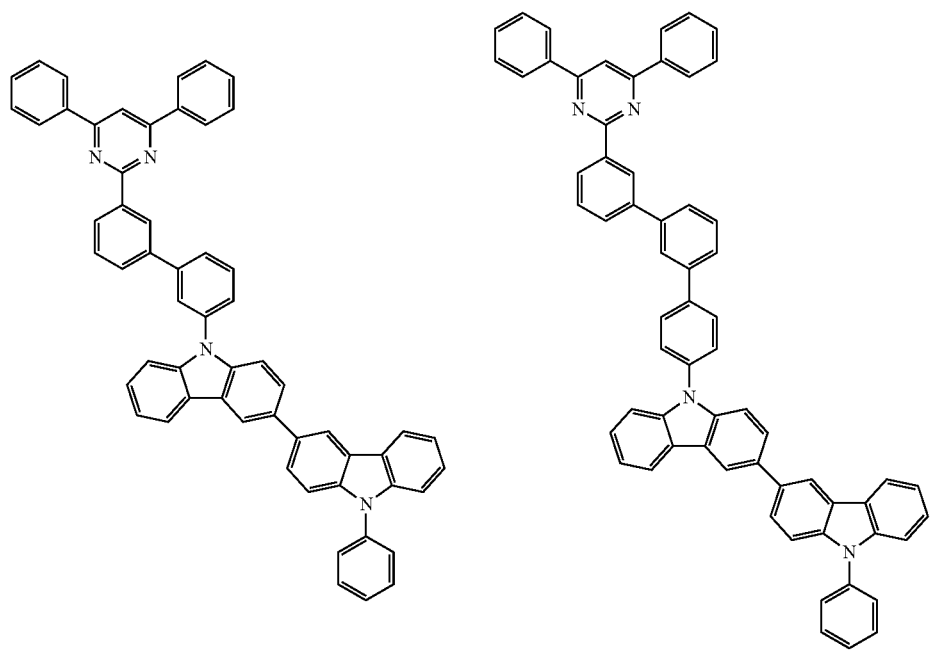 [SMILES: c1ccc(-c2cc(-c3cccc(-c4cccc(-n5c6ccccc6c6cc(-c7ccc8c(c7)c7ccccc7n8-c7ccccc7)ccc65)c4)c3)cc(-c3ccccc3)n2)cc1 ; c1ccc(-c2cc(-c3cccc(-c4cccc(-c5ccc(-n6c7ccccc7c7cc(-c8ccc9c(c8)c8ccccc8n9-c8ccccc8)ccc76)cc5)c4)c3)cc(-c3ccccc3)n2)cc1]

-continued
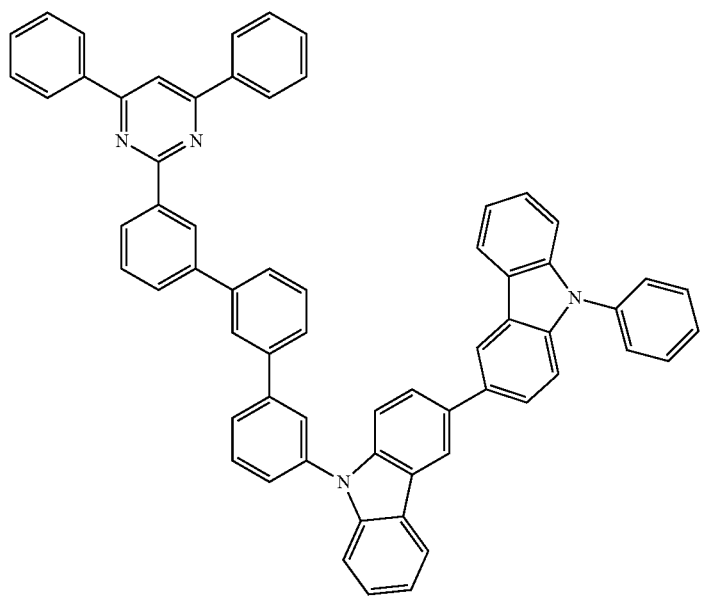
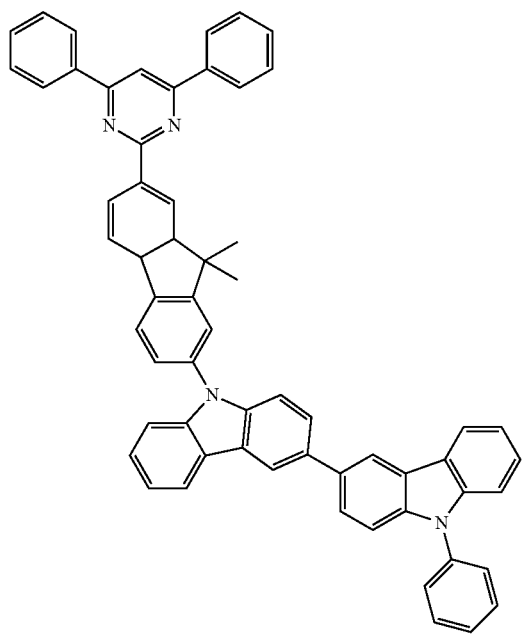
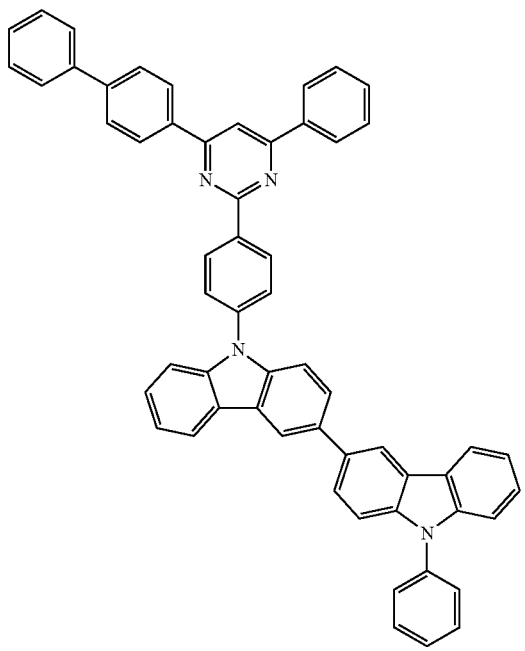

-continued
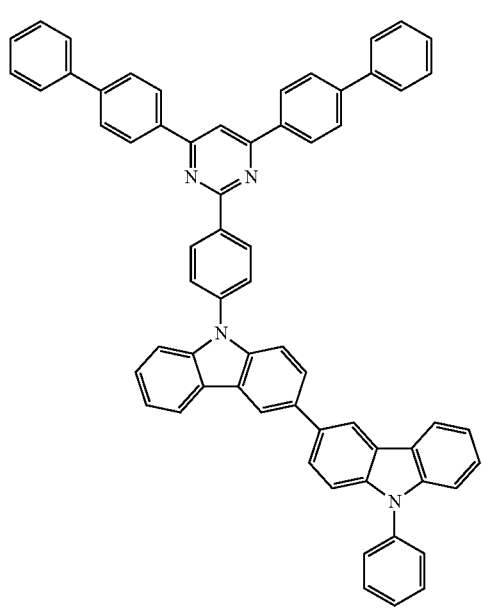
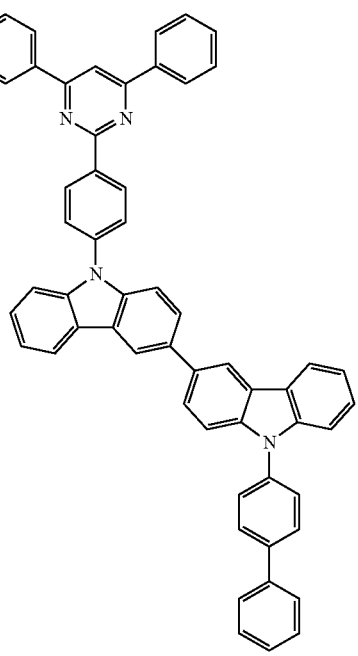
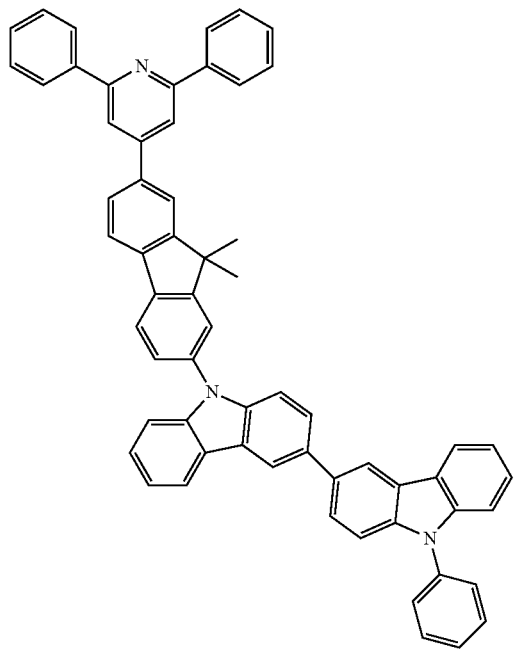
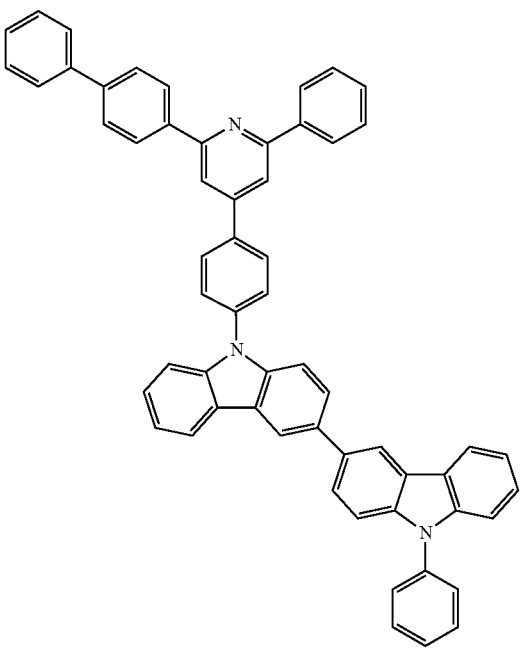

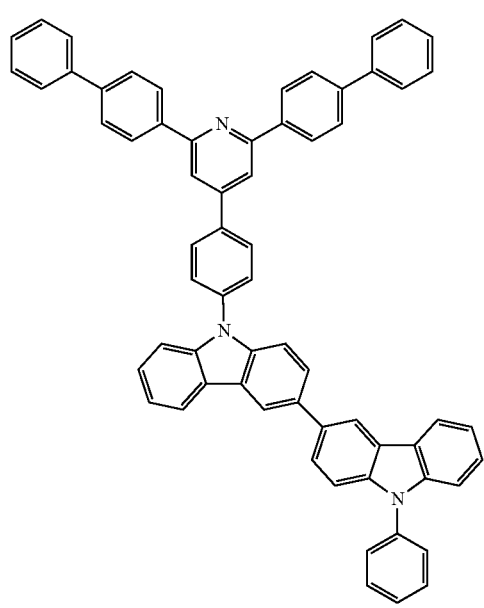
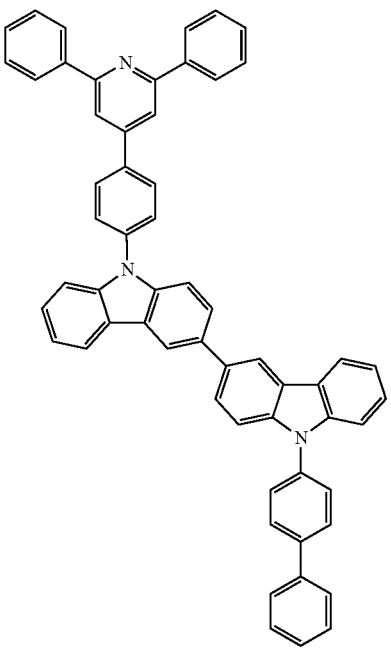
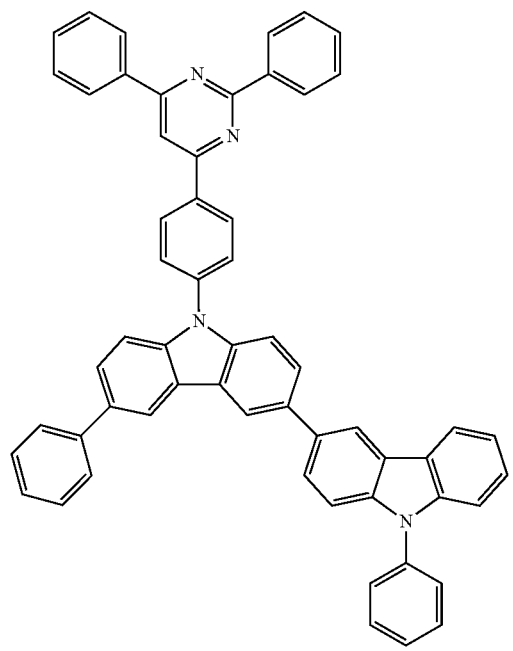
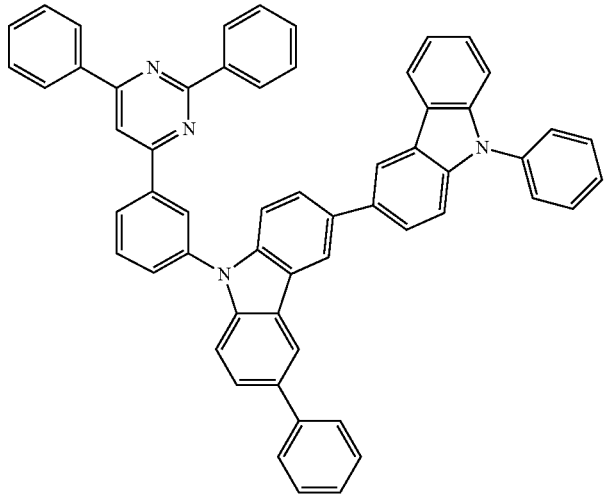

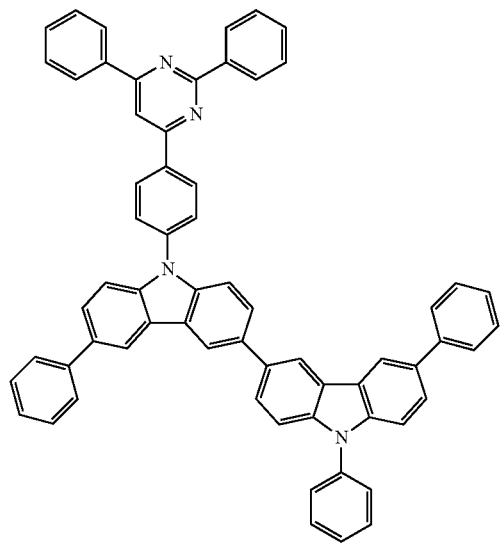
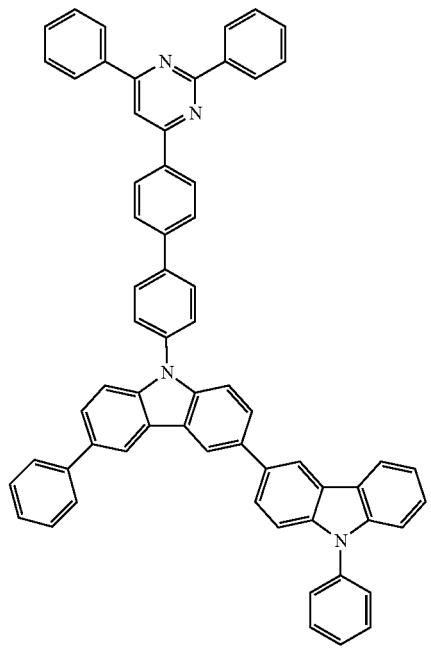
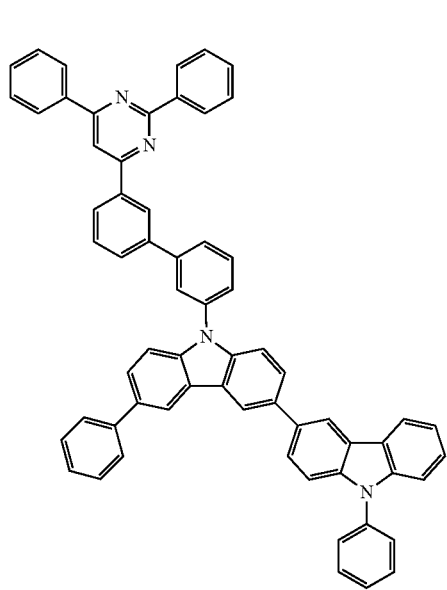
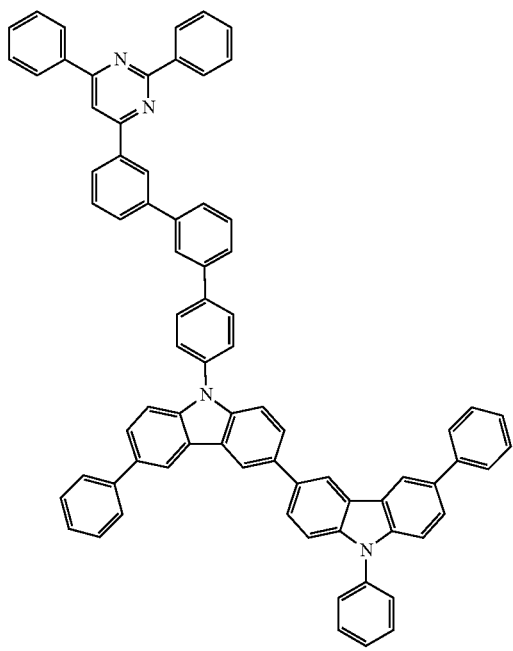

47
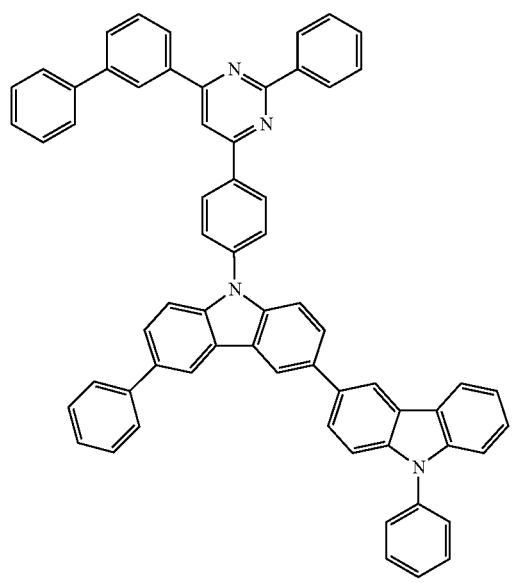
48
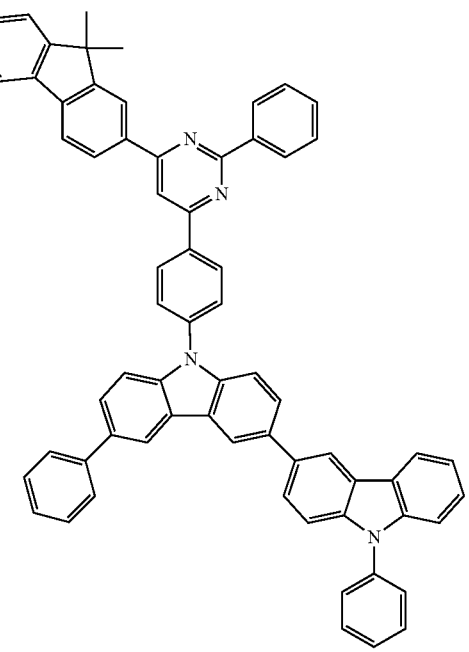
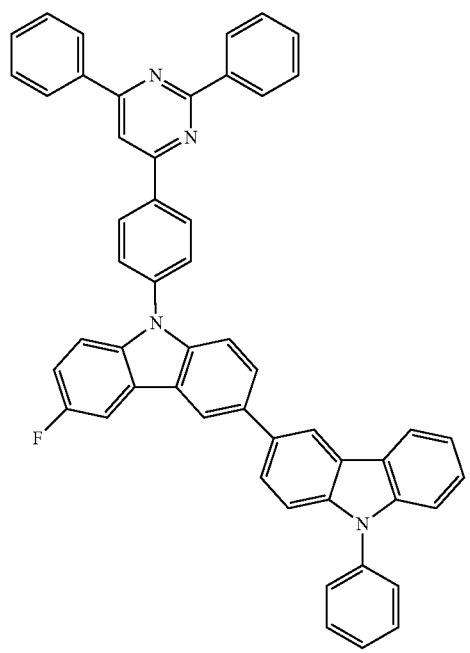
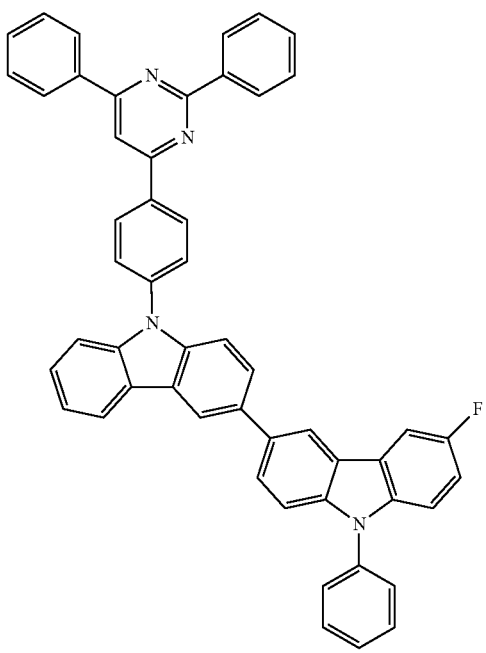

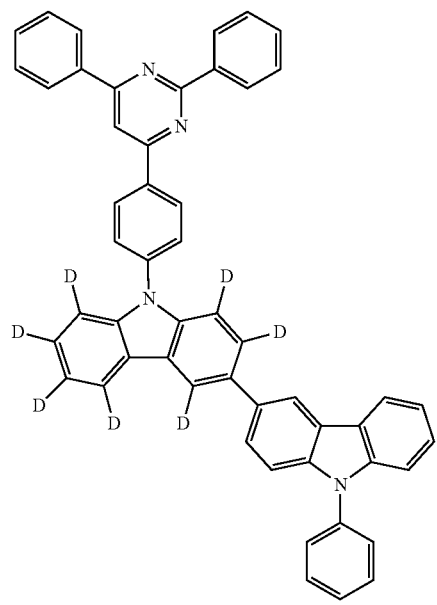
-continued
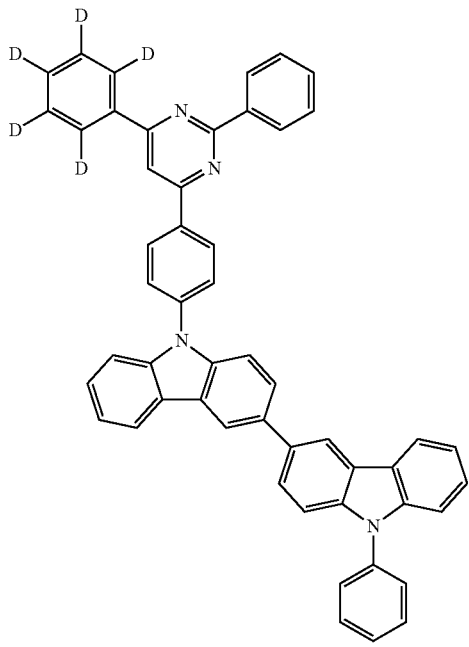
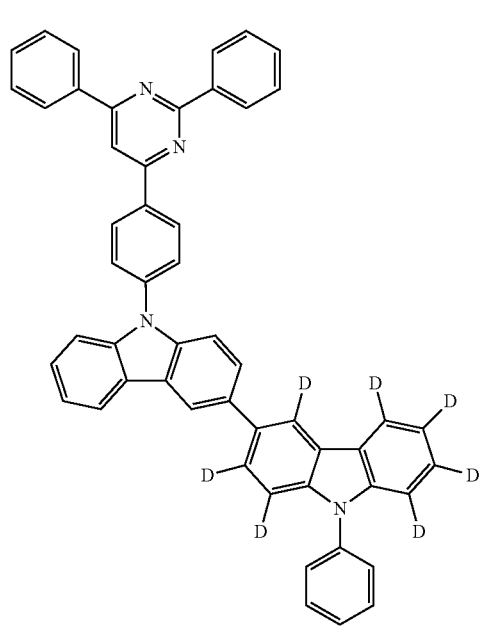
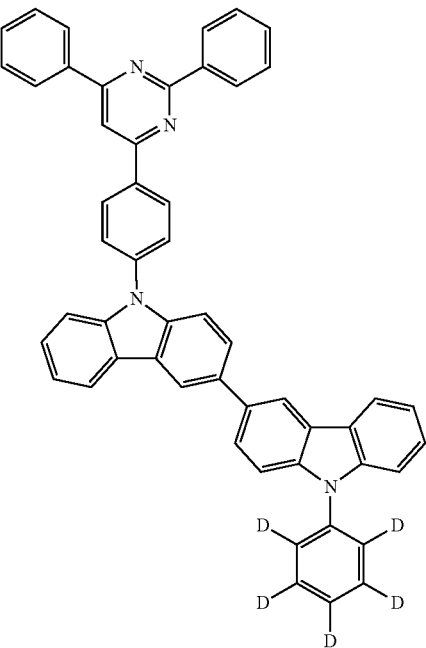

-continued
51
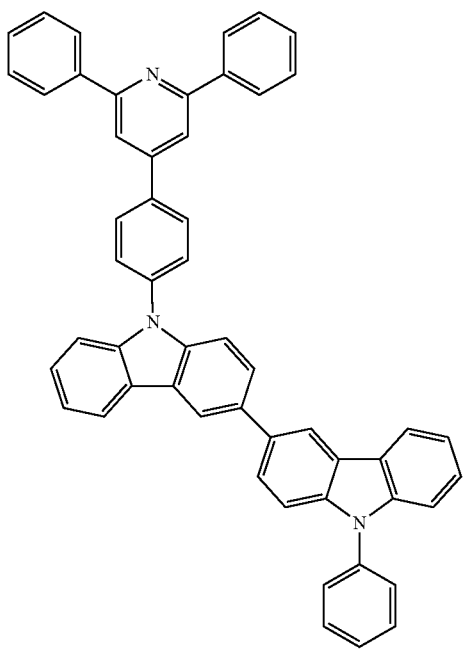
52
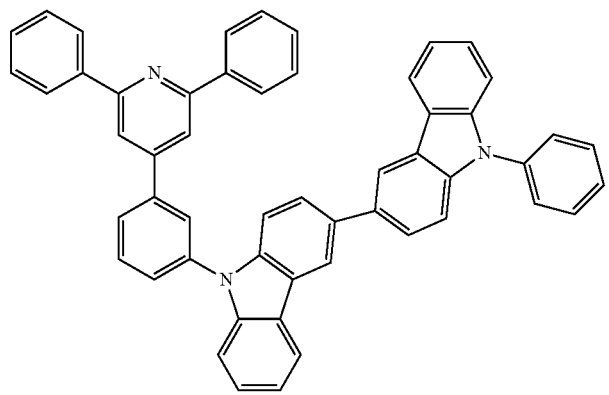
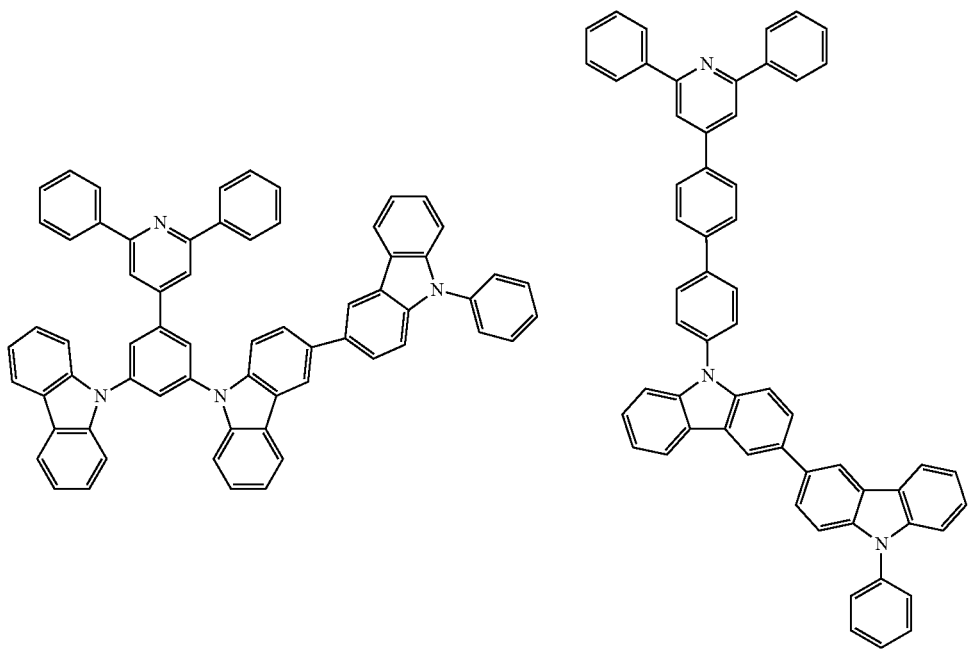

-continued
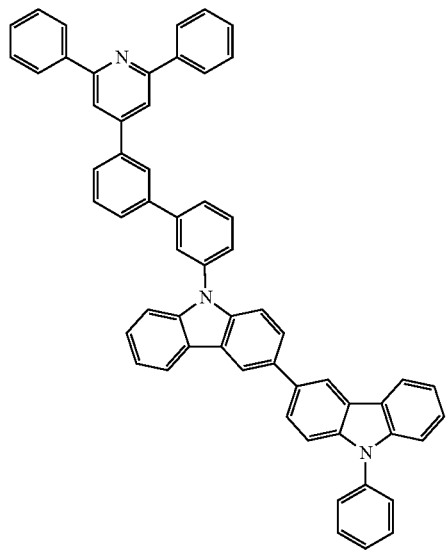
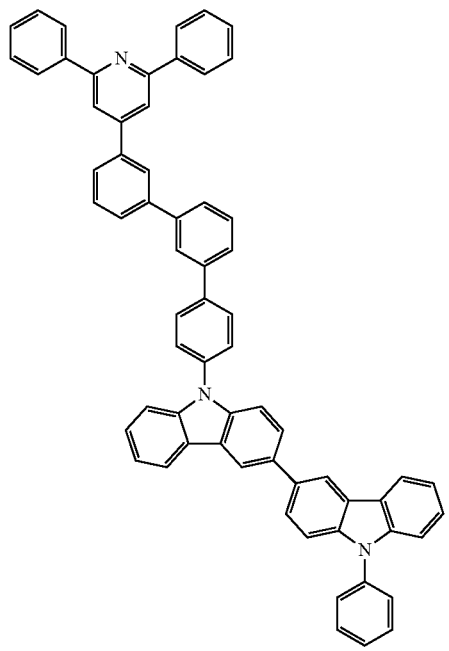
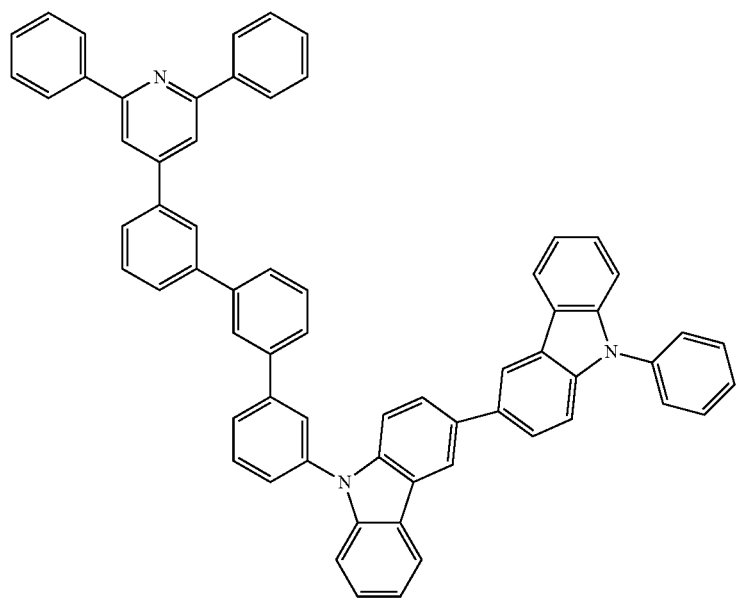

55
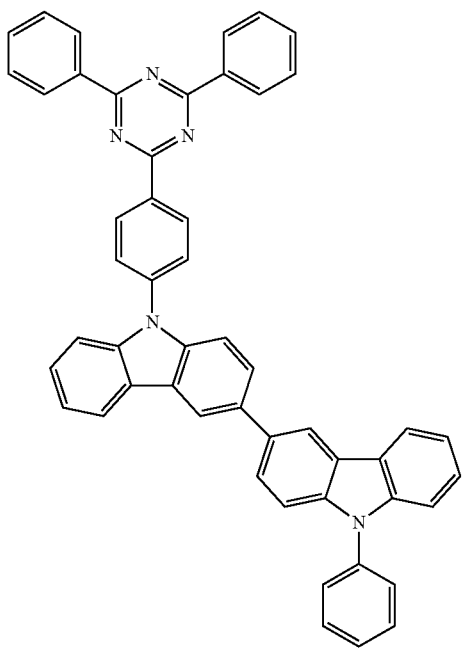
56
-continued
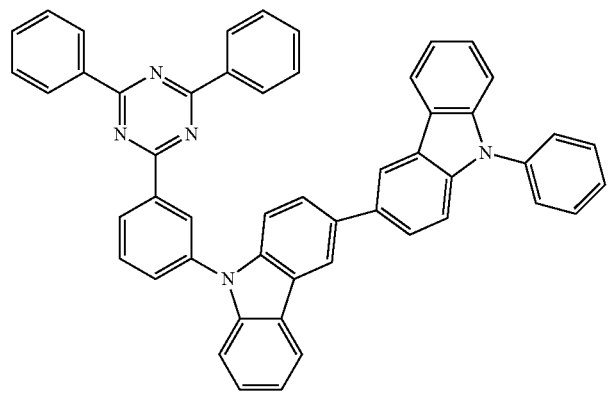
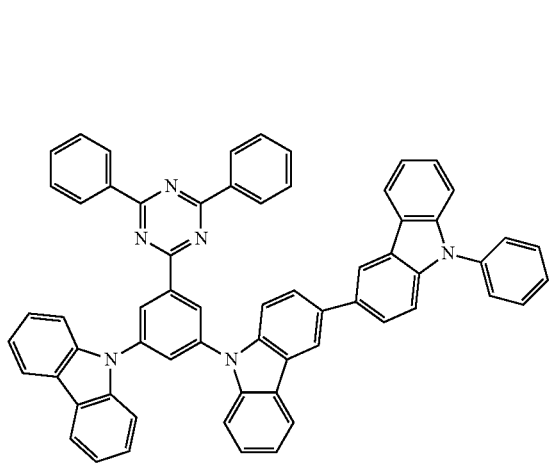
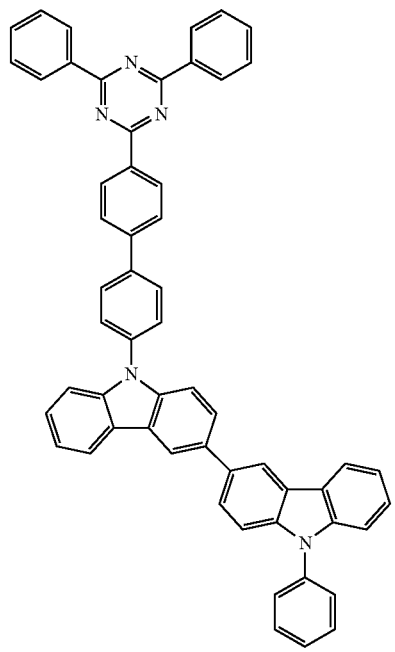

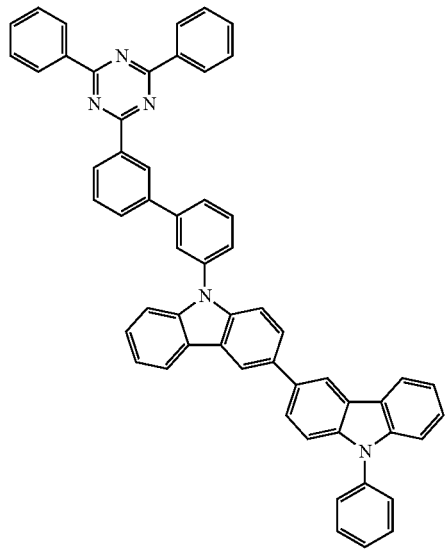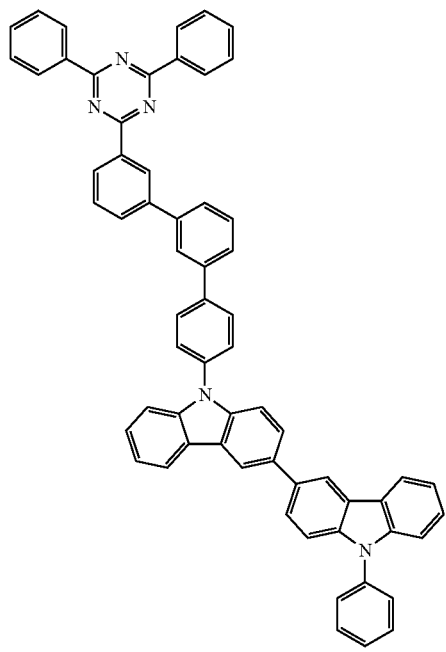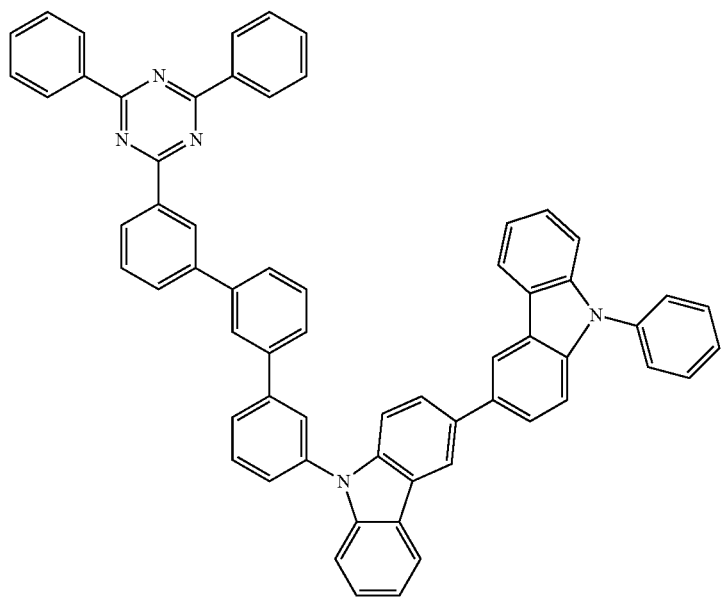

-continued
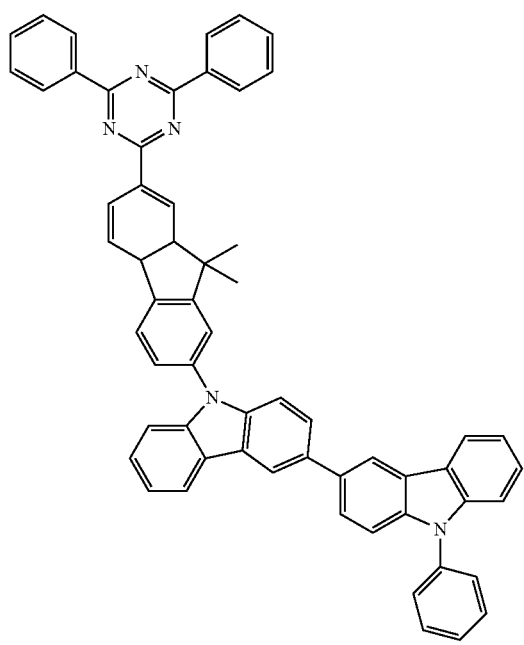
59
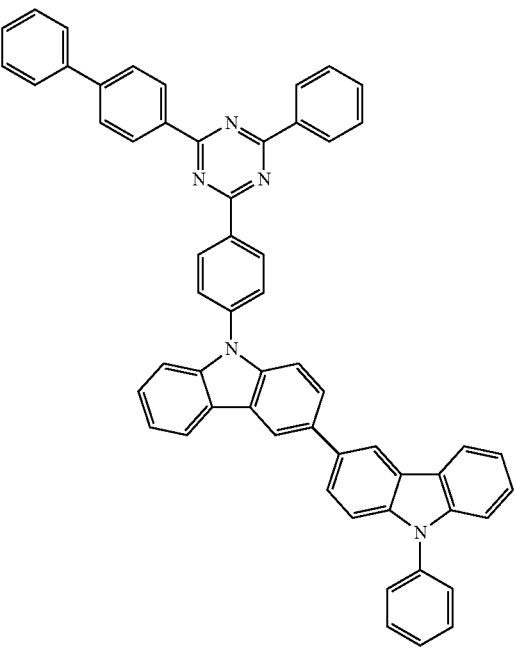
60
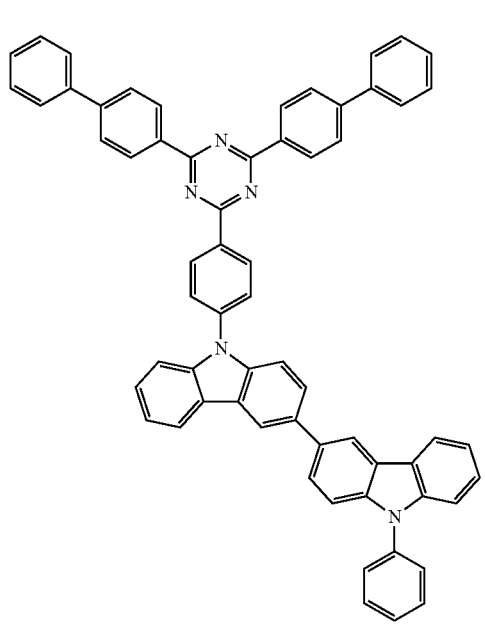
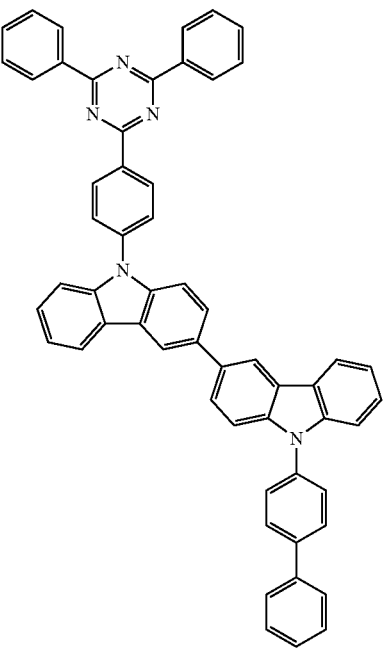

-continued
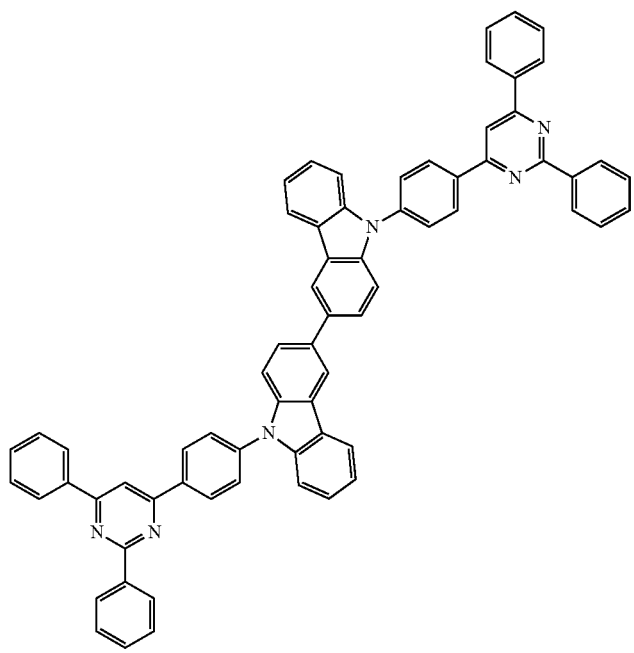
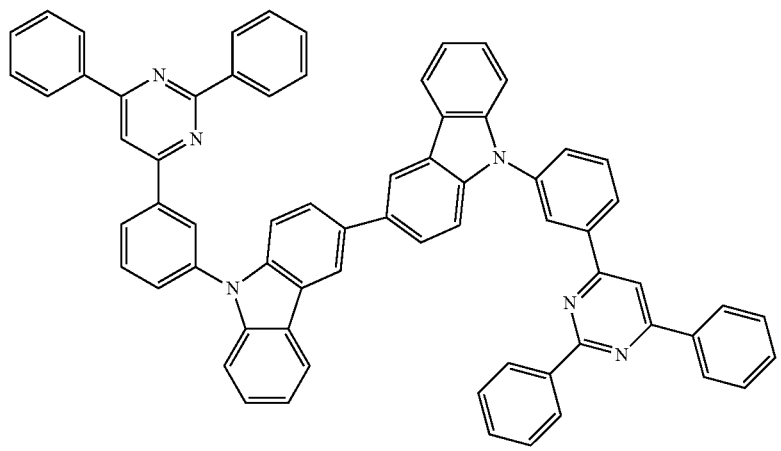
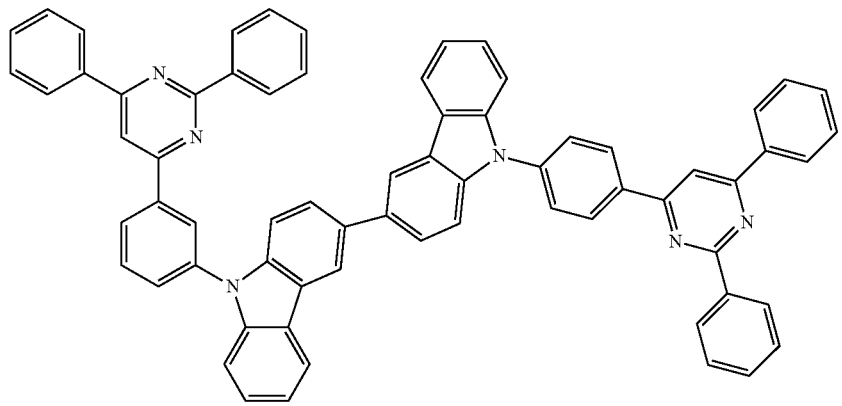

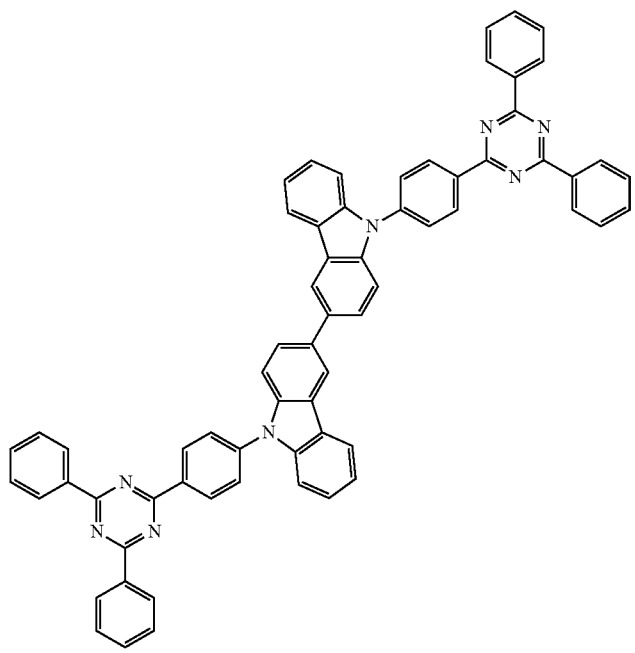
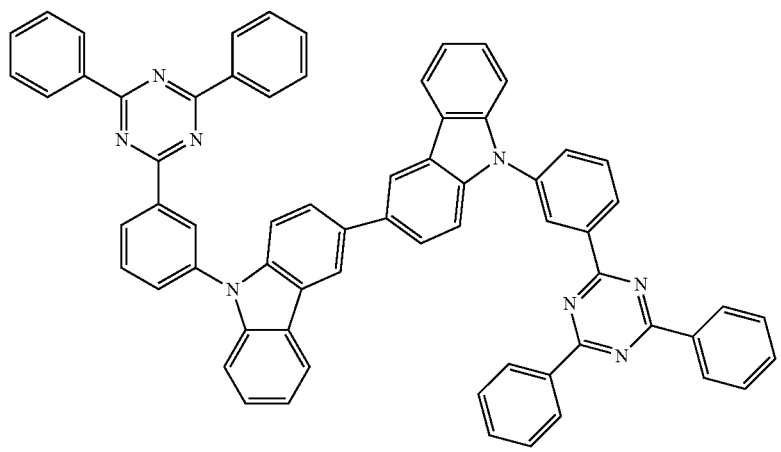
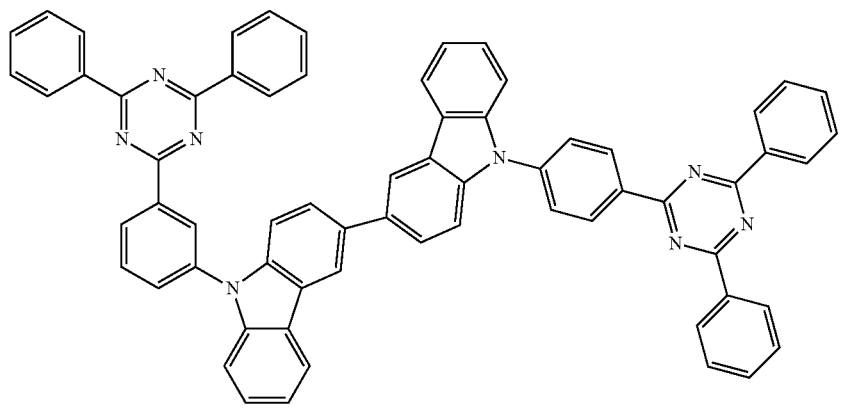

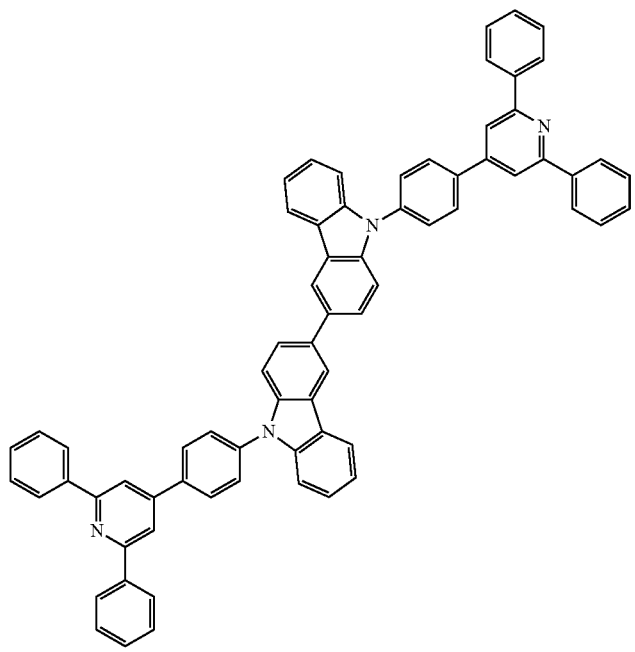
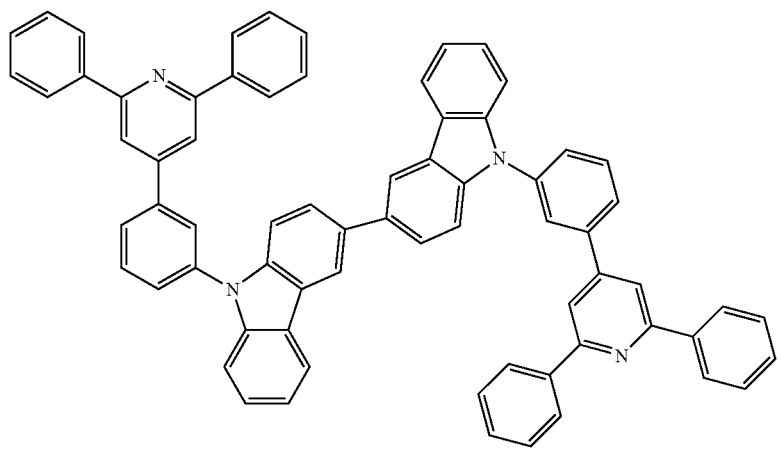
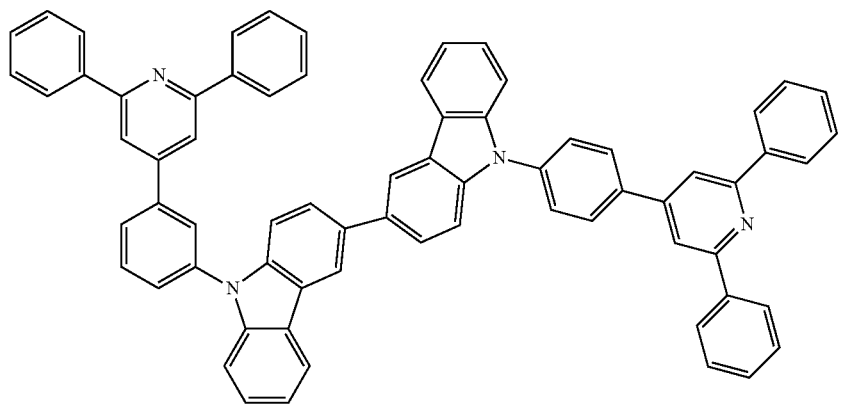

67
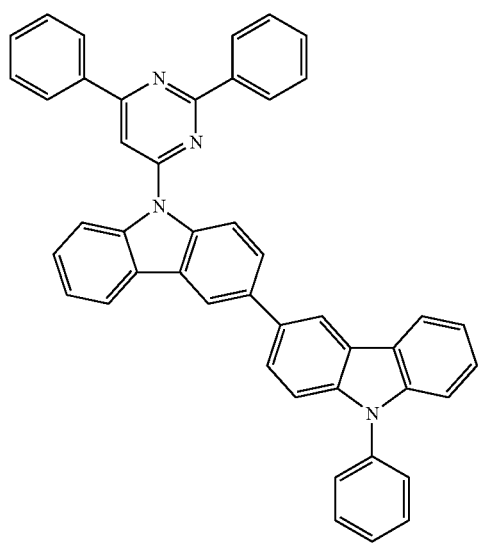
68
-continued
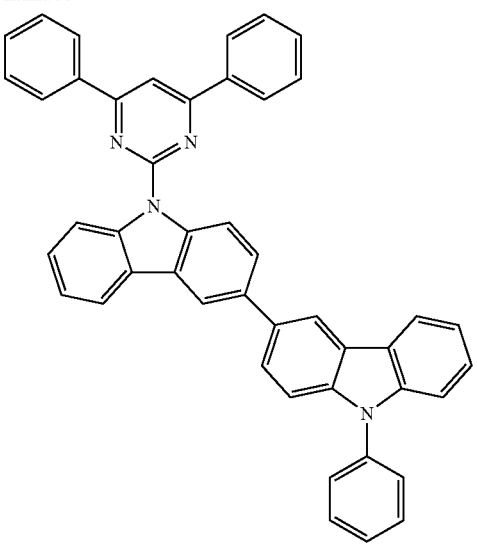
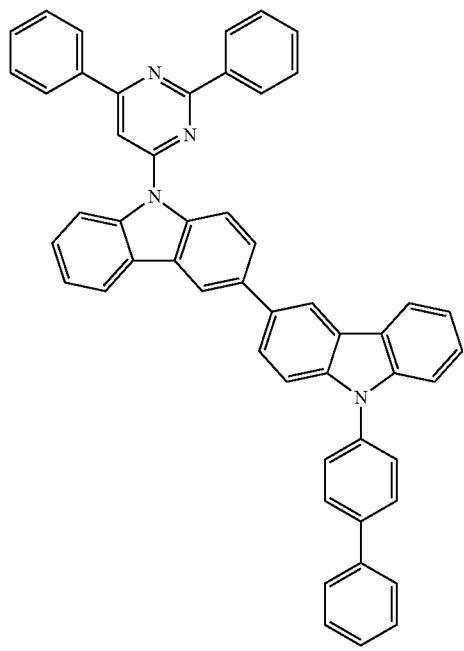
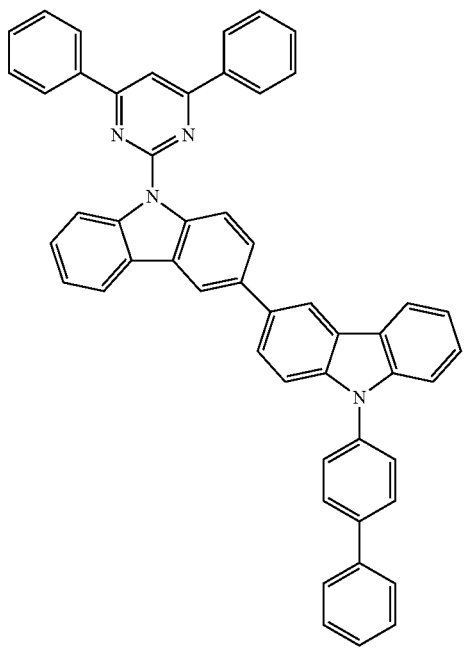

69
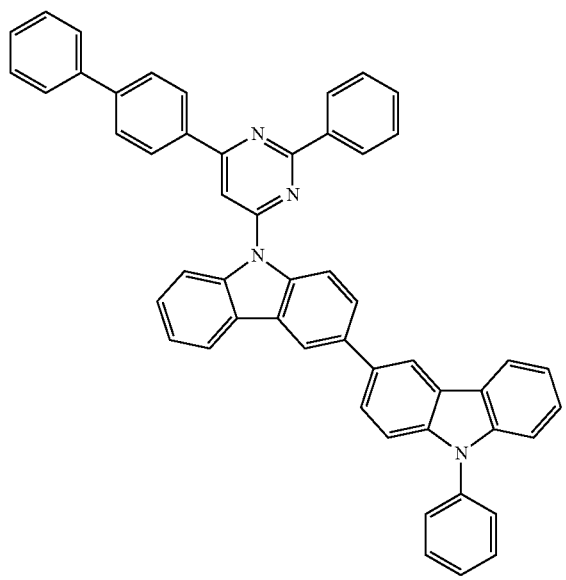
70
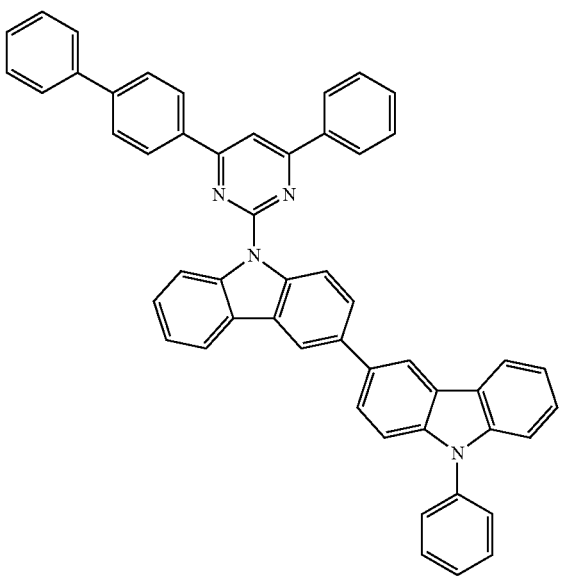
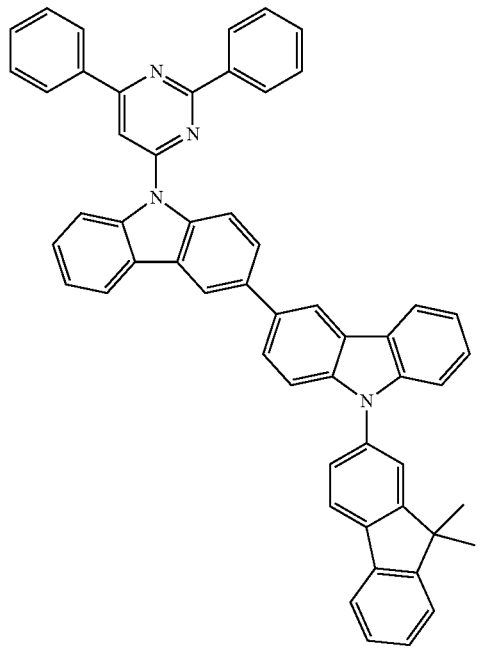
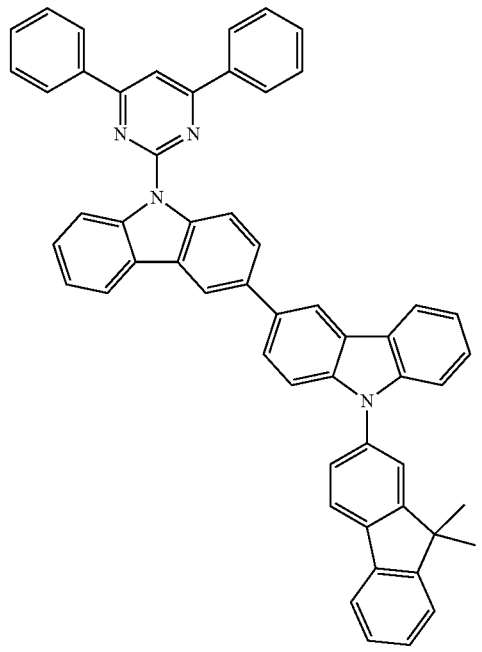

-continued
71
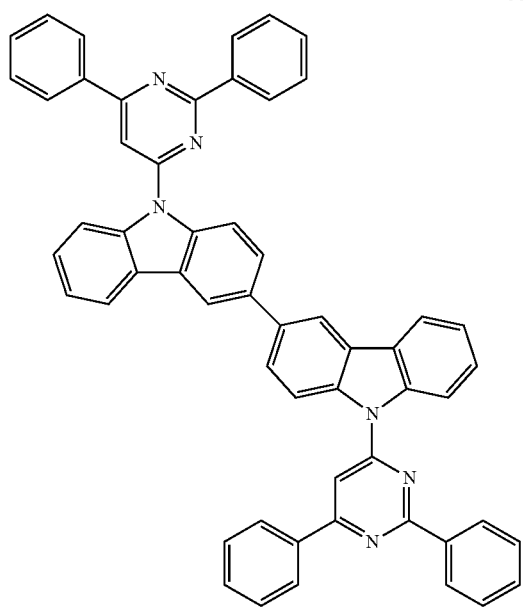
72
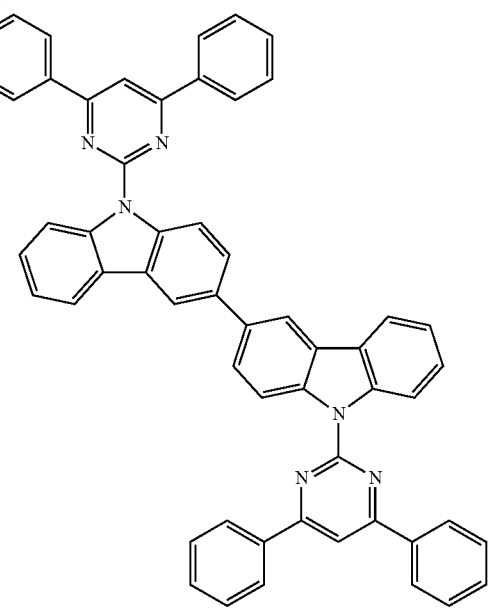
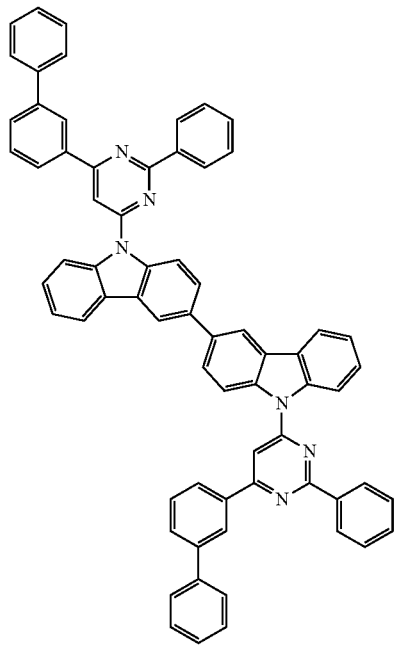
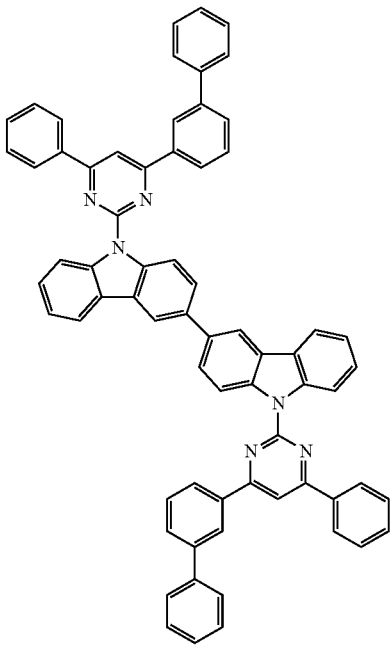

73
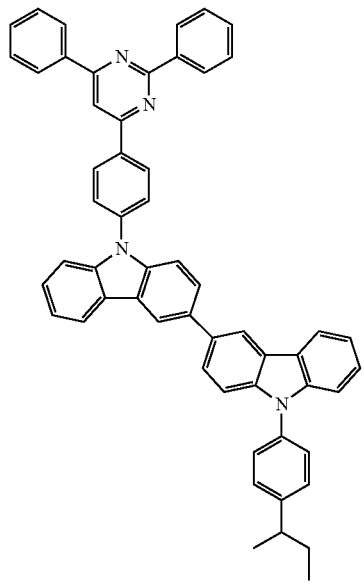
-continued
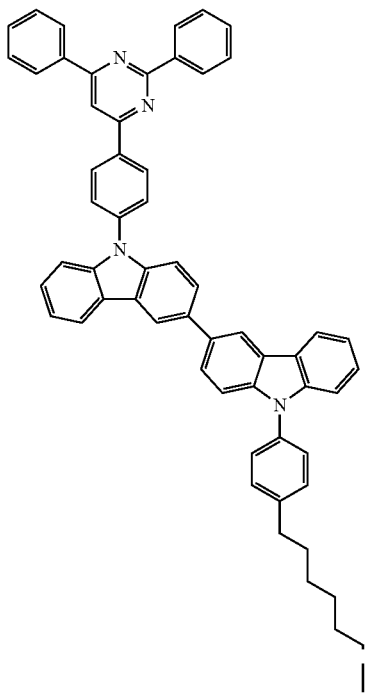
74
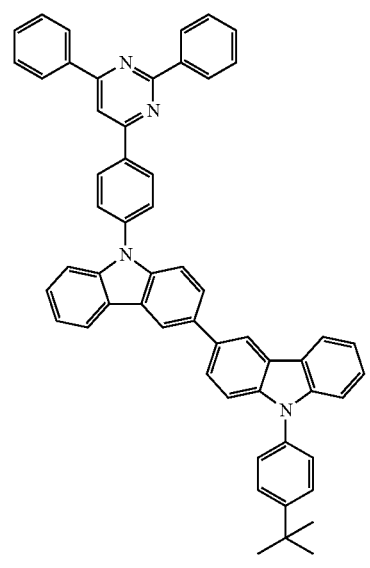
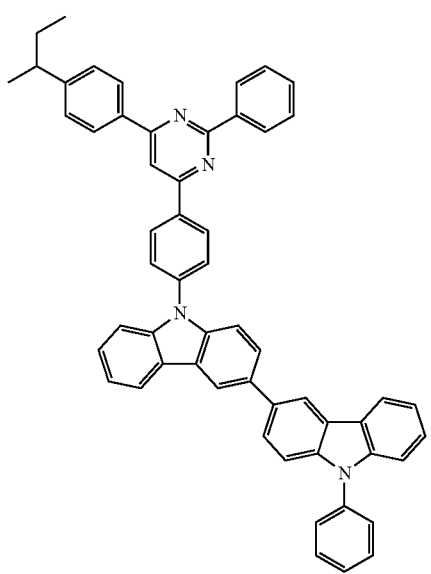
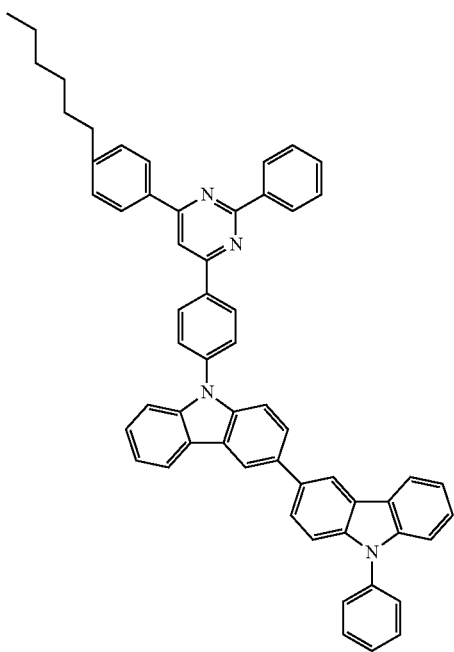

-continued
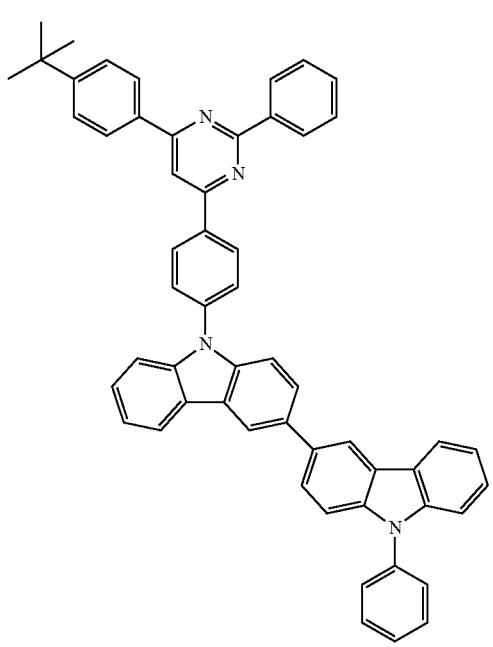
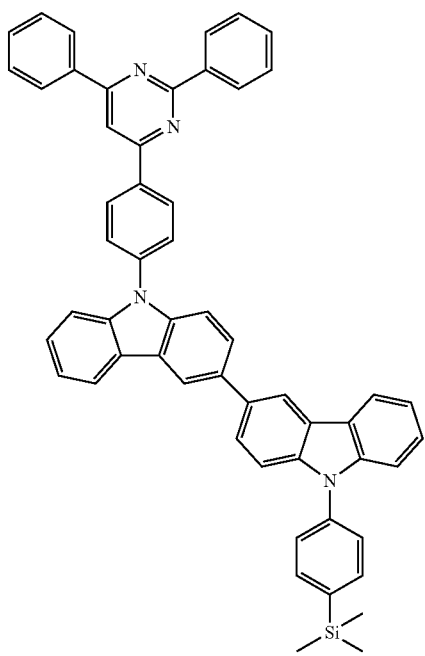
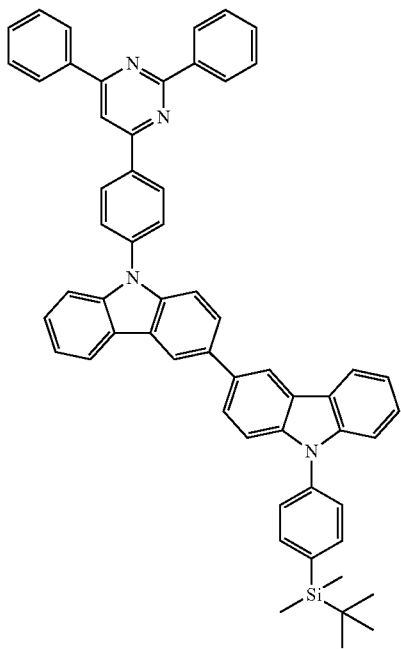
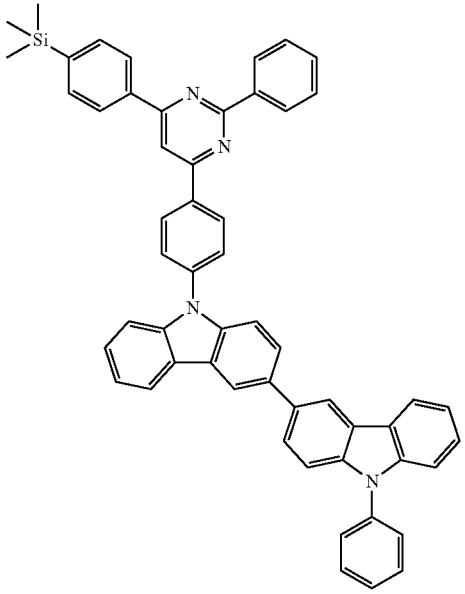

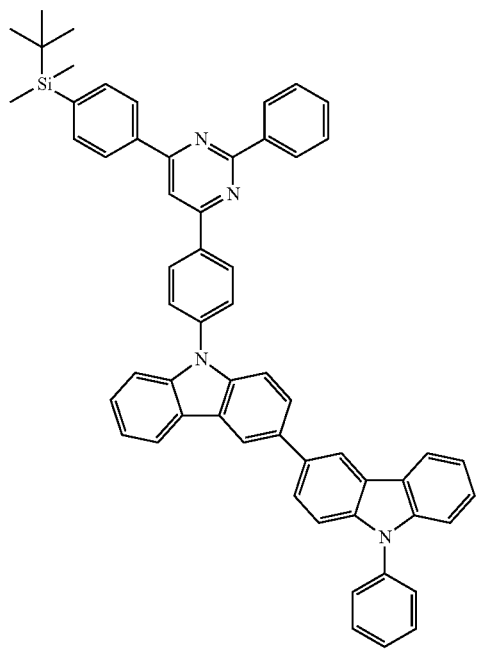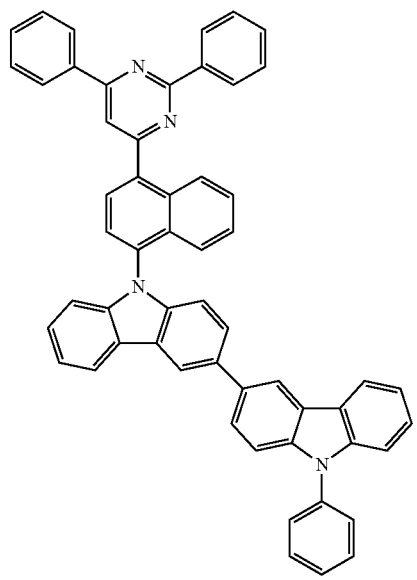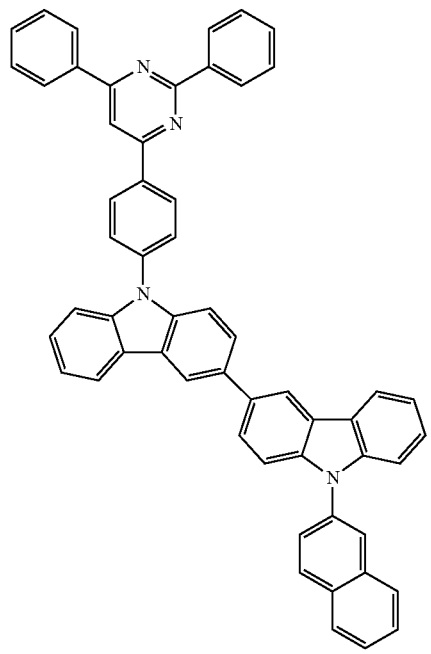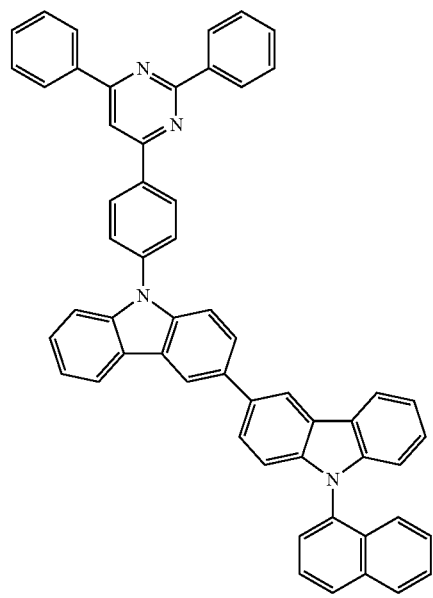

-continued
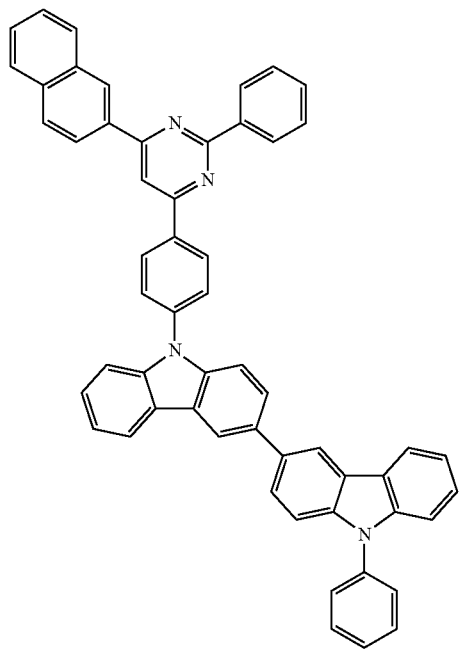
79
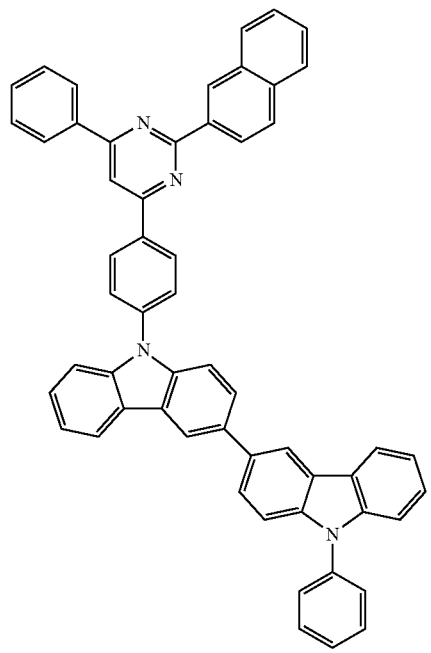
80
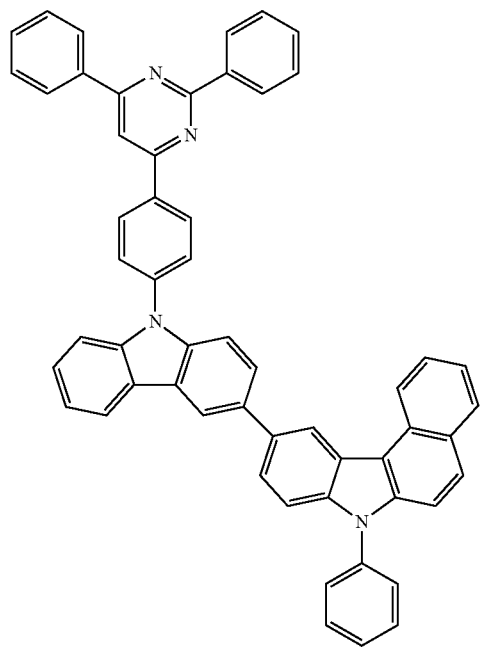
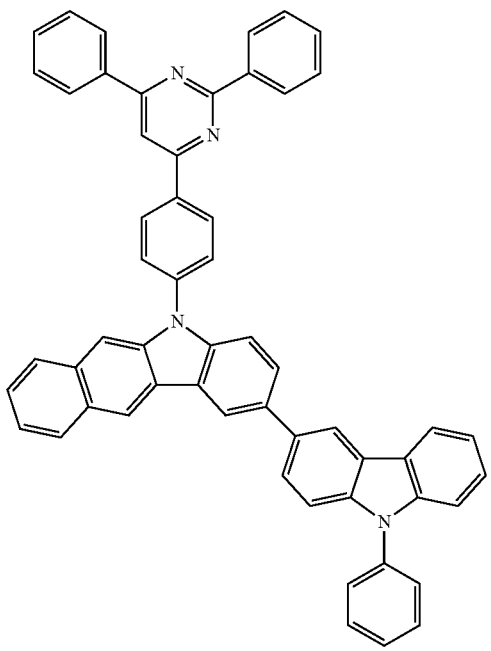

-continued
81
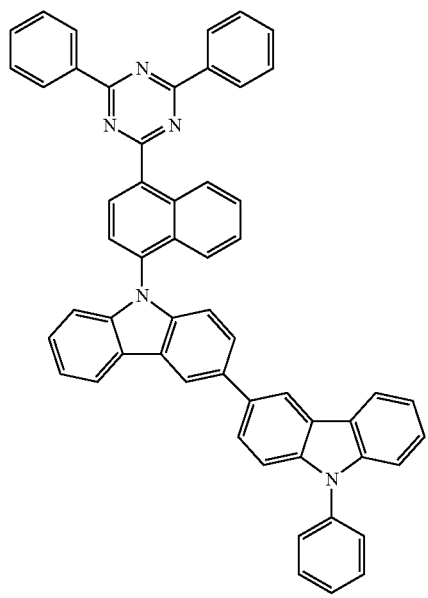
82
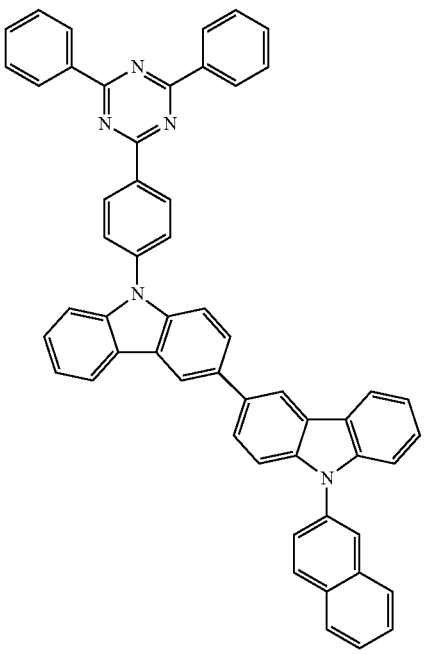
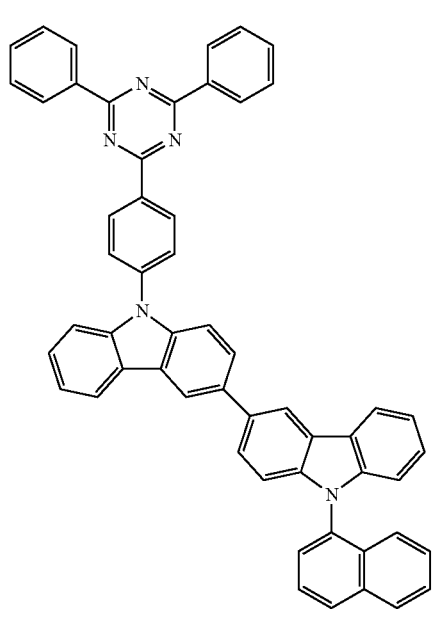
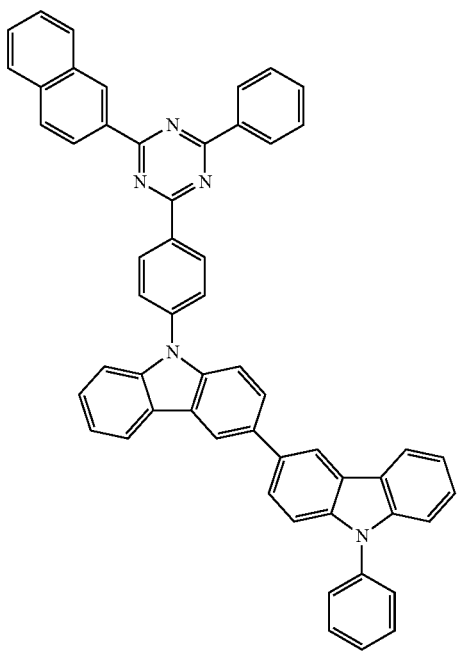

83
84
-continued
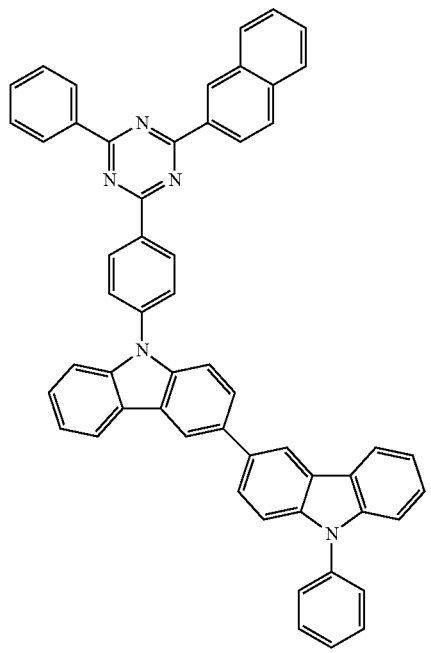
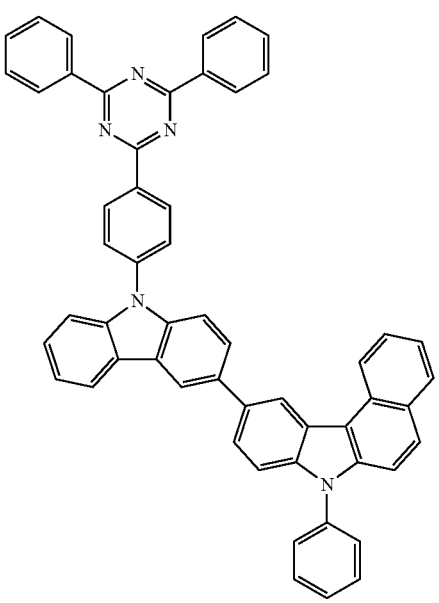
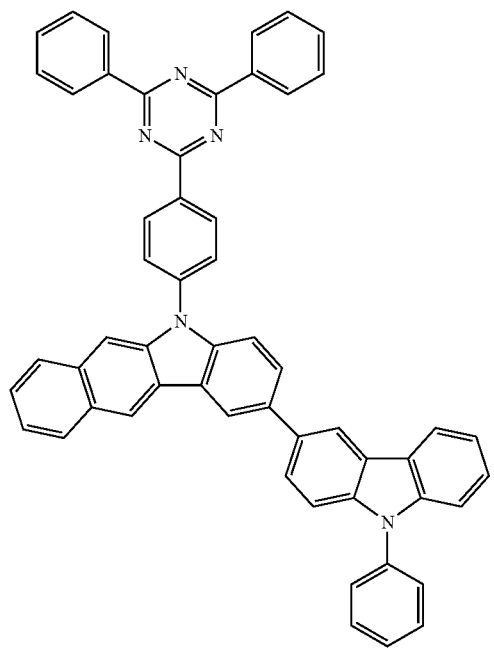
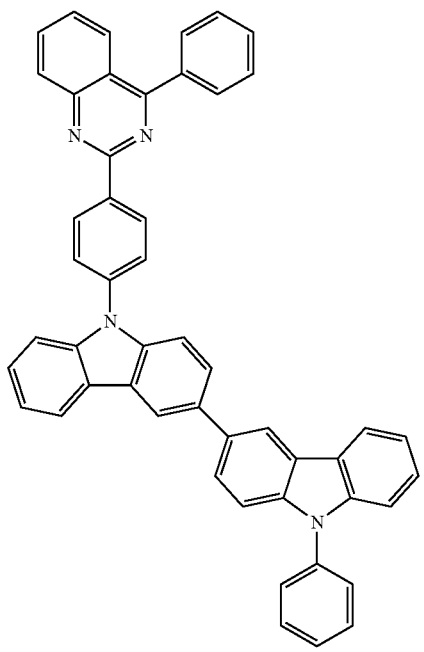

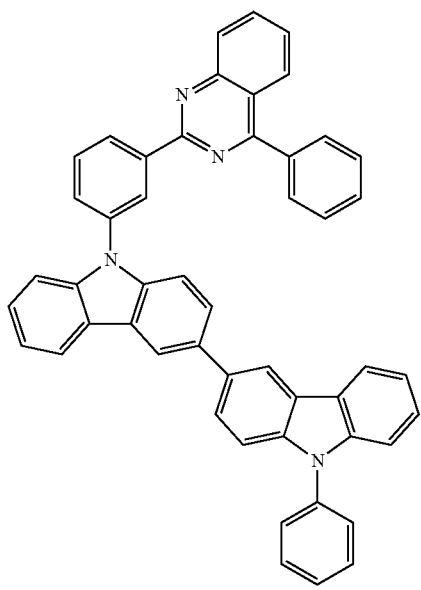
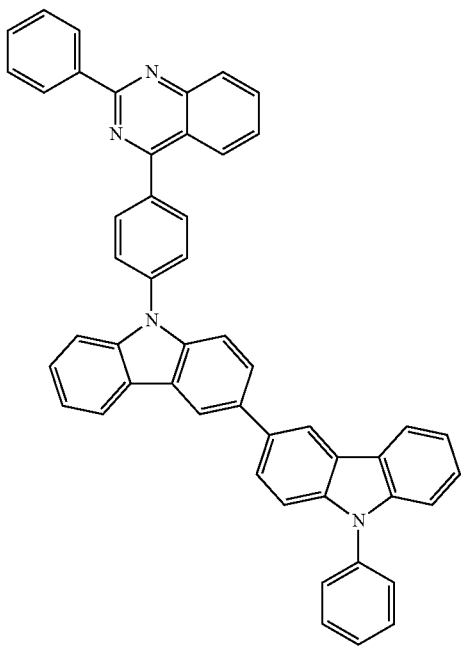
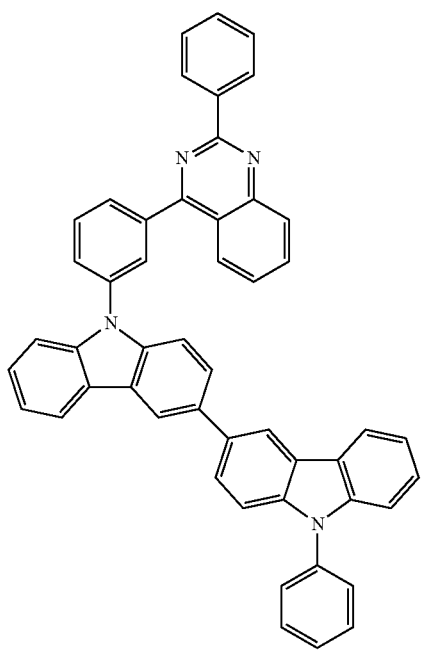
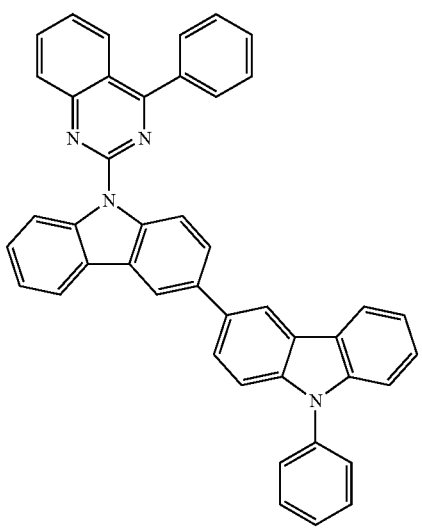

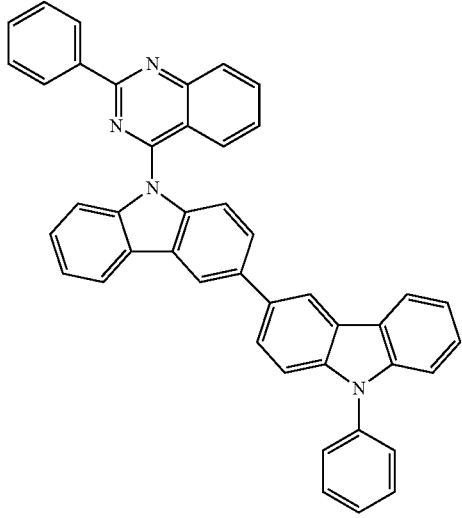
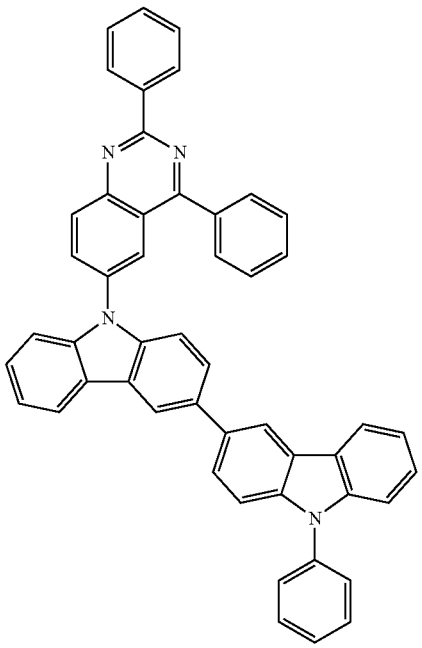
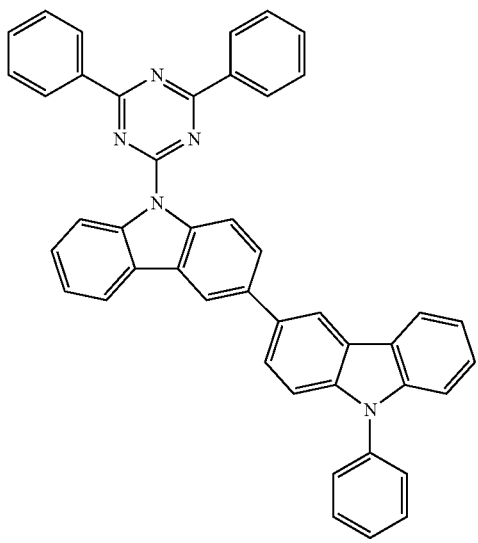
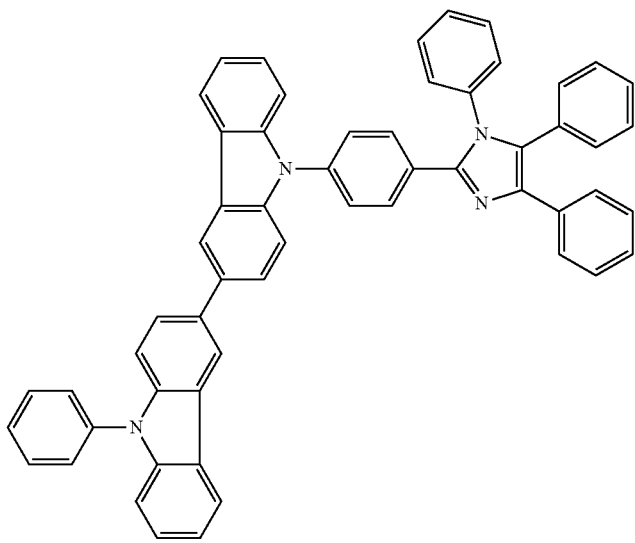

-continued
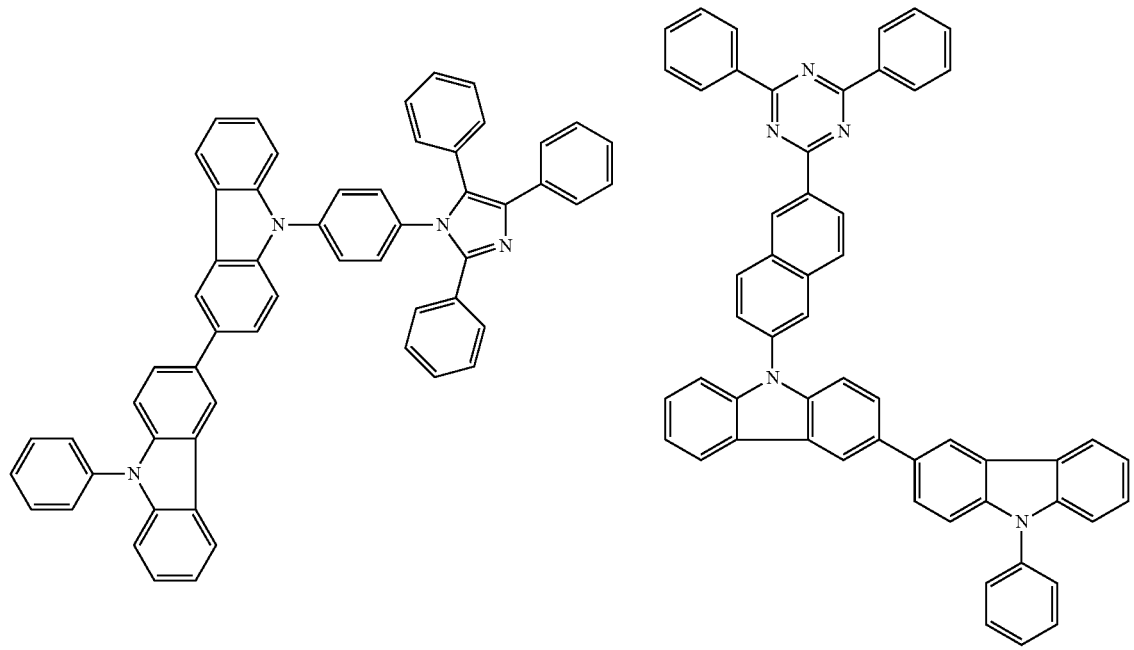
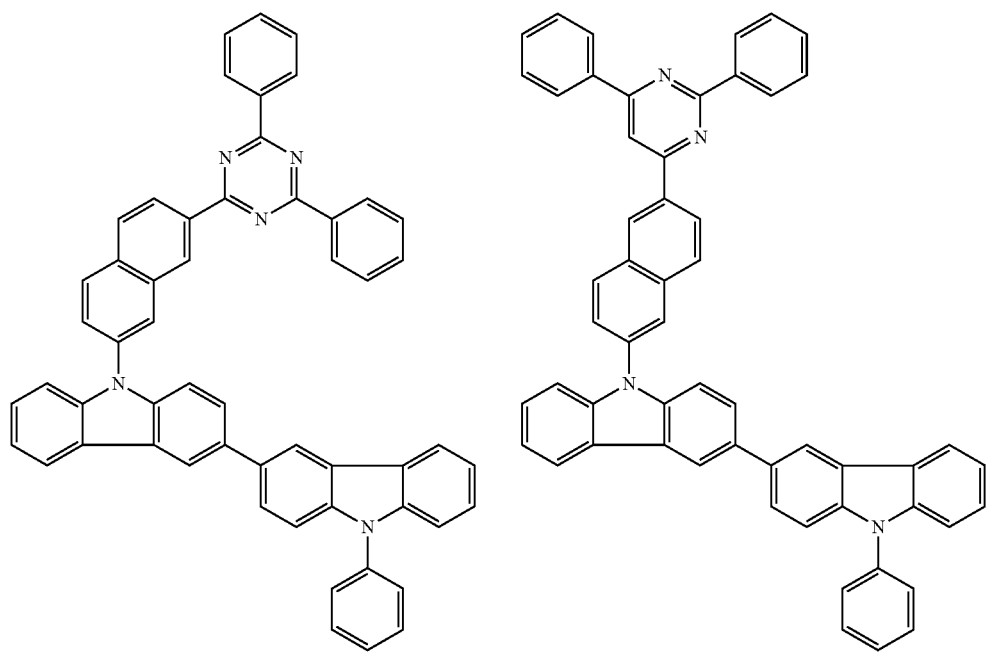

91
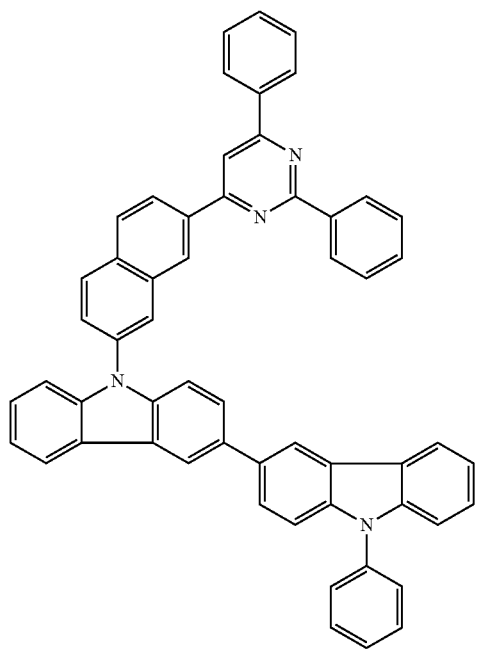
92
-continued
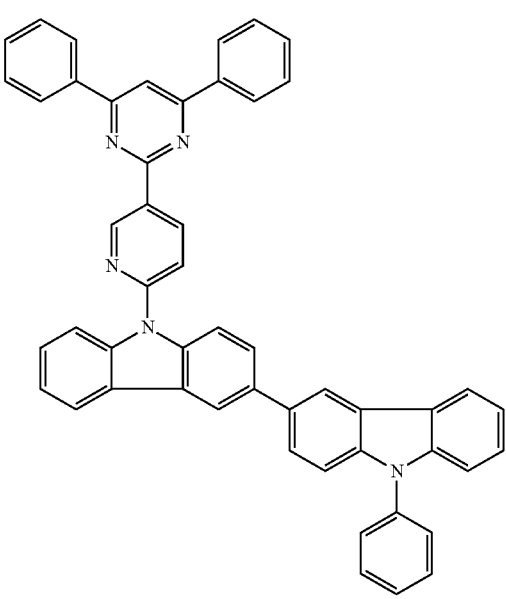
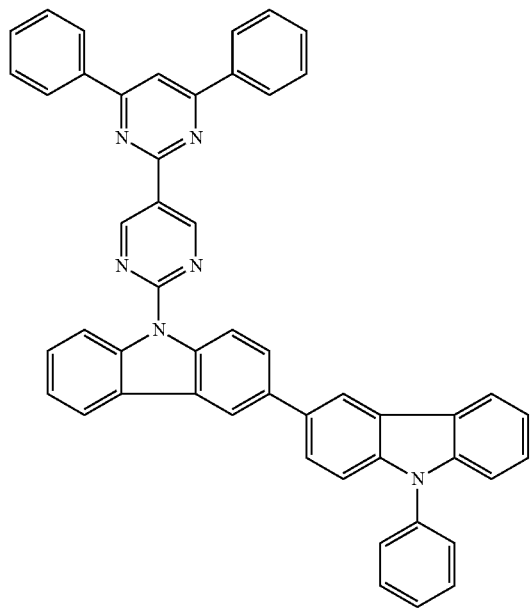
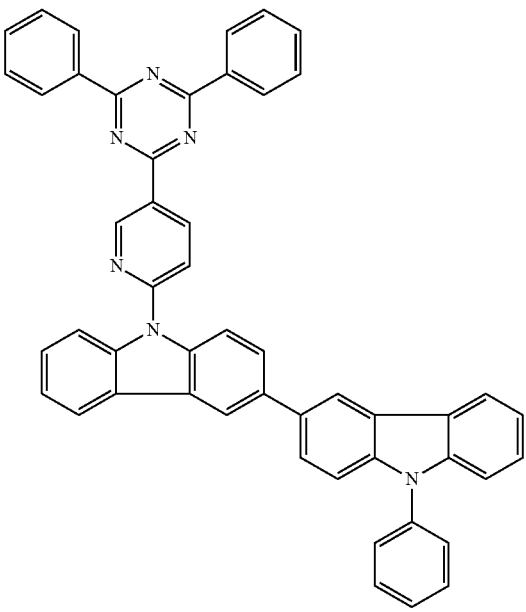

93
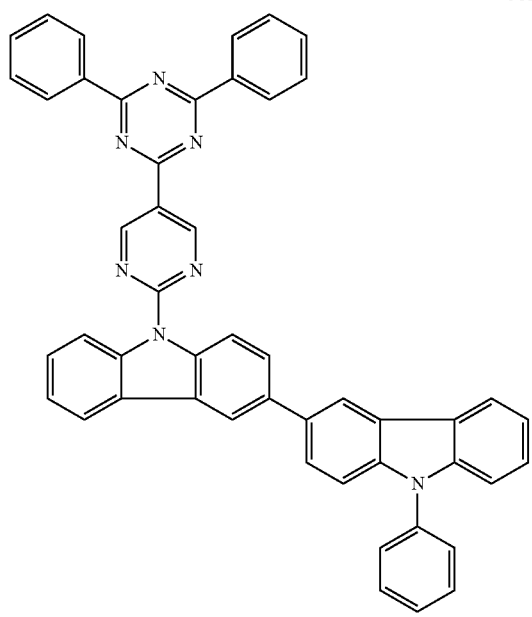
94
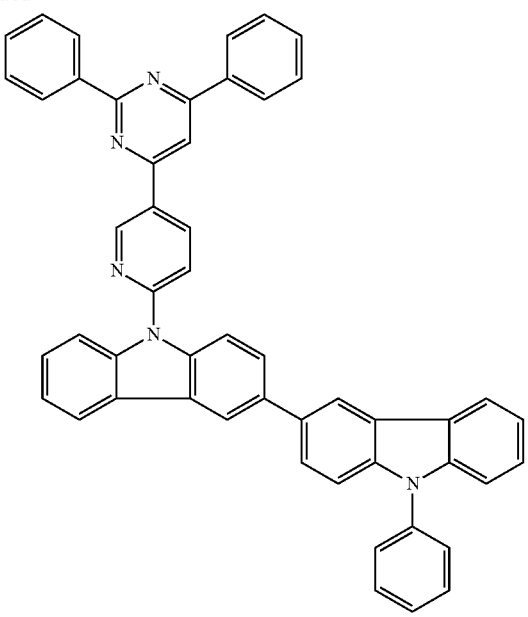
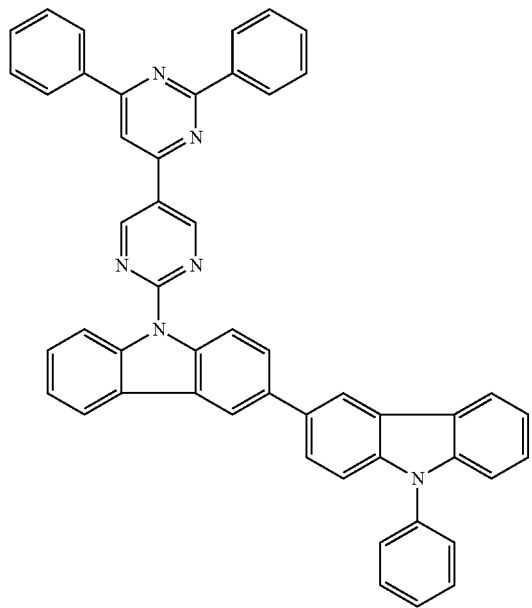
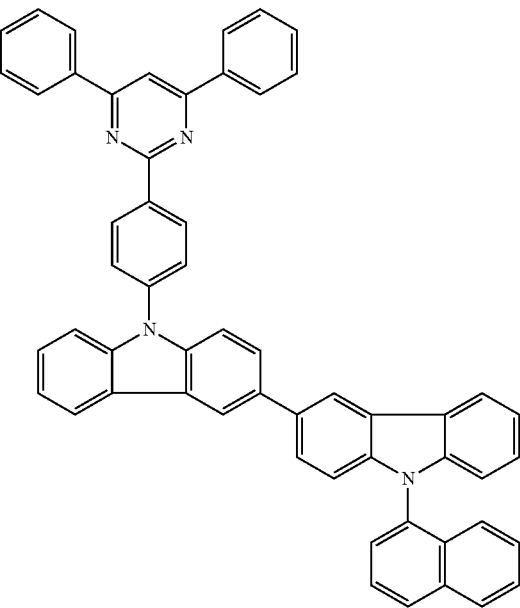

95
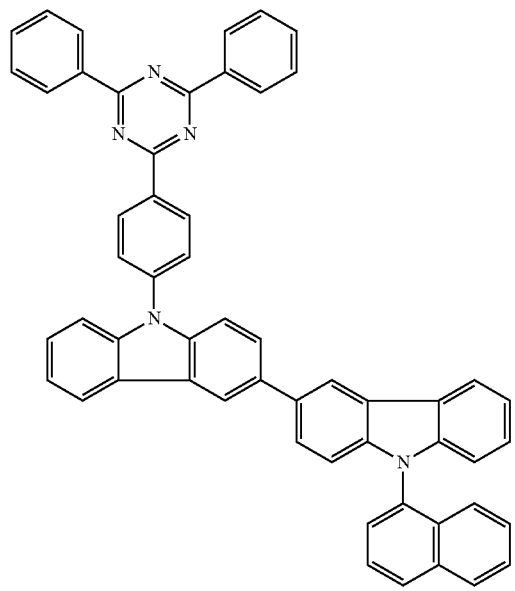
96
-continued
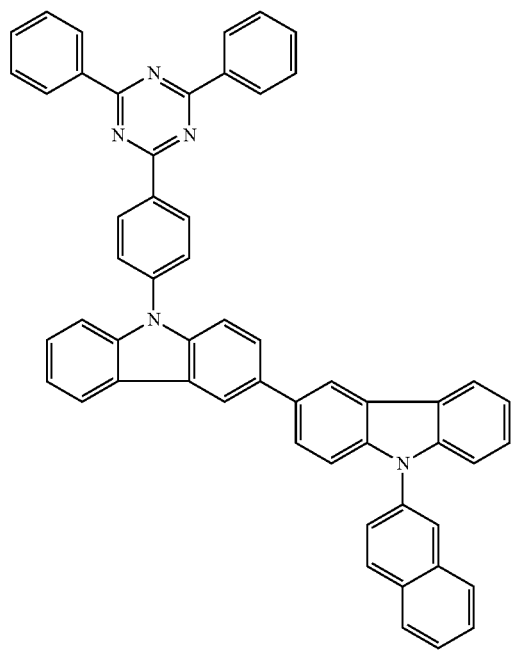
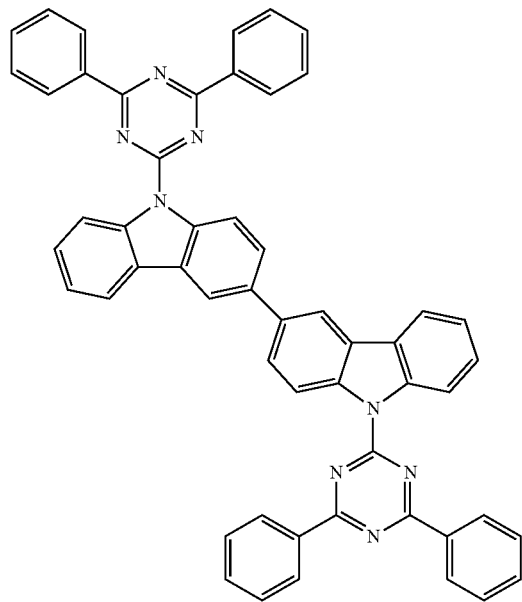
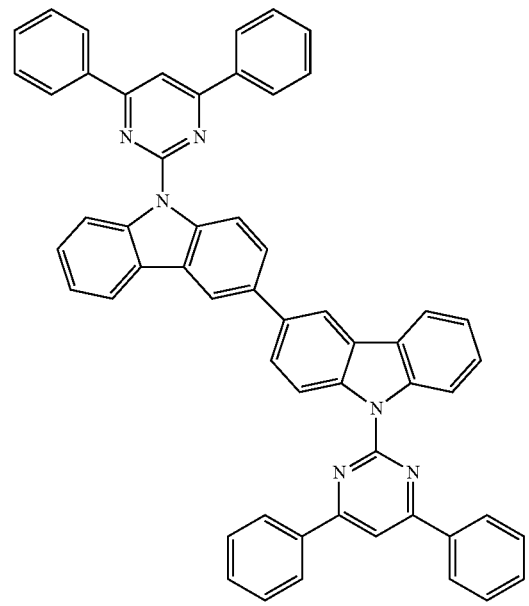

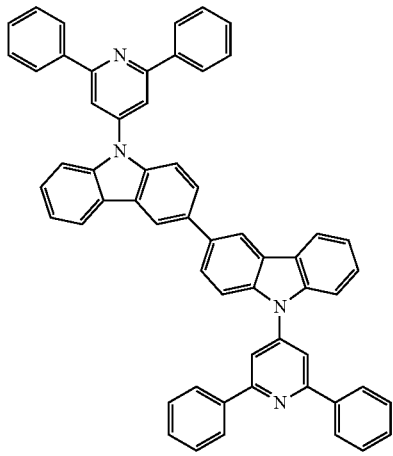

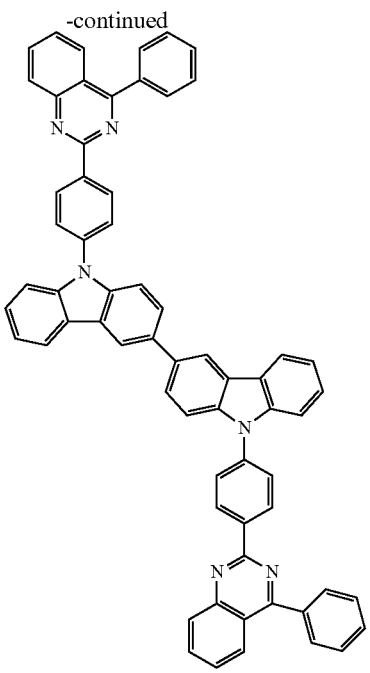

-continued

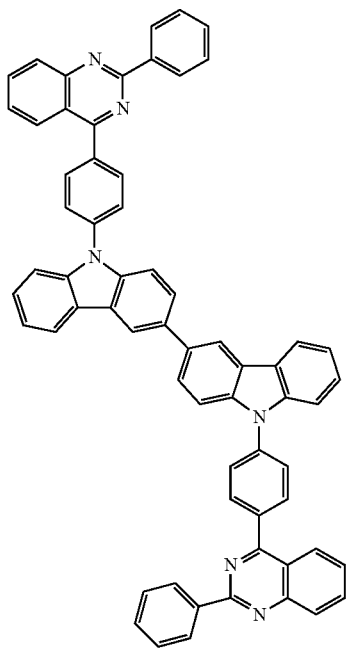 [SMILES: c1ccc(-c2nc(-c3ccc(-n4c5ccccc5c5cc(-c6ccc7c(c6)c6ccccc6n7-c6ccc(-c7nc(-c8ccccc8)nc8ccccc78)cc6)ccc54)cc3)c3ccccc3n2)cc1]

An organic-EL-device material according to this exemplary embodiment contains the above biscarbazole derivative.

The organic-EL-device material according to this exemplary embodiment includes the biscarbazole derivative represented by any one of the above formulae (1) to (3).

The organic EL device according to this exemplary embodiment includes a cathode, an anode, and an organic layer between the cathode and the anode, in which the organic layer include the biscarbazole derivative any one of the above formulae (1) to (3).

In the organic EL device according to this exemplary embodiment, the emitting layer may preferably contain the organic-EL-device material according to this exemplary embodiment.

The organic EL device according to this exemplary embodiment may preferably contain the electron injecting/transporting layer, in which the electron injecting/transporting layer may preferably contain the organic-EL-device material according to this exemplary embodiment.

The organic EL device according to this exemplary embodiment may preferably contain at least one of the electron injecting/transporting layer and the hole blocking layer that contains the organic-EL-device material according to this exemplary embodiment.

The organic EL device according to this exemplary embodiment may preferably include the hole transporting layer (hole injecting layer) that contains the organic-EL-device material according to this exemplary embodiment.

Phosphorescent Material

According to this exemplary embodiment, the phosphorescent material preferably contains a metal complex, and the metal complex preferably has a metal atom selected from Ir, Pt, Os, Au, Cu, Re and Ru, and a ligand. Particularly, the ligand preferably has an ortho-metal bond.

The phosphorescent material is preferably a compound containing a metal selected from iridium (Ir), osmium (Os) and platinum (Pt) because such a compound, which exhibits high phosphorescence quantum yield, can further enhance external quantum efficiency of the emitting device. The phosphorescent material is more preferably a metal complex such as an iridium complex, osmium complex or platinum complex, among which an iridium complex and platinum complex are more preferable and ortho metalation of an iridium complex is the most preferable.

Examples of such a preferable metal complex are shown below.

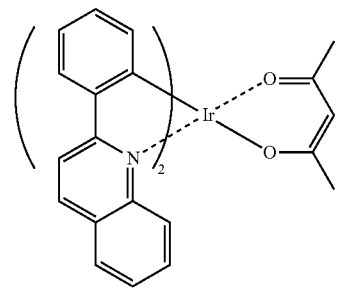

PQIr

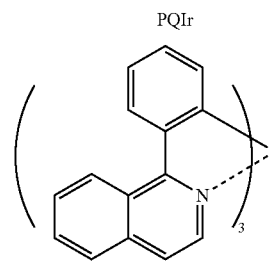

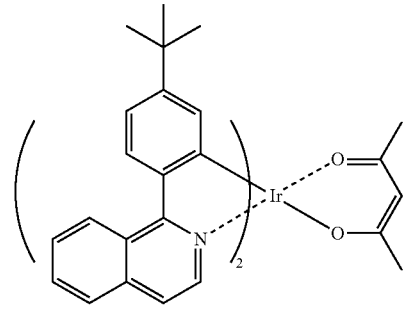

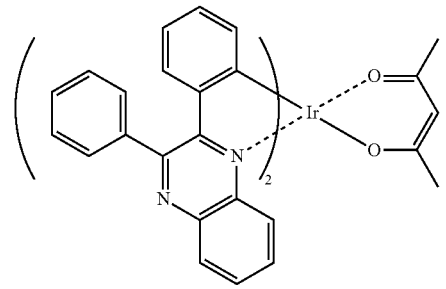

-continued

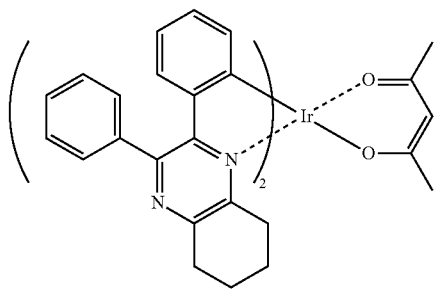

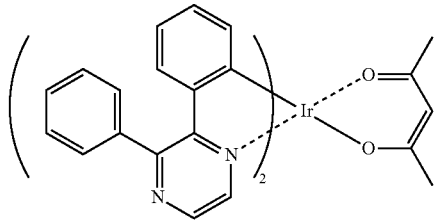

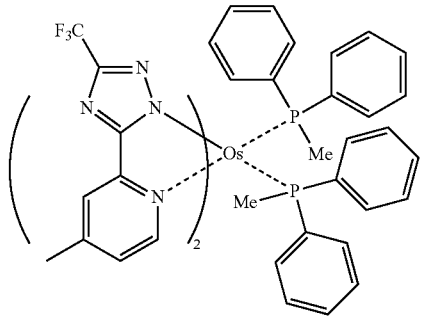

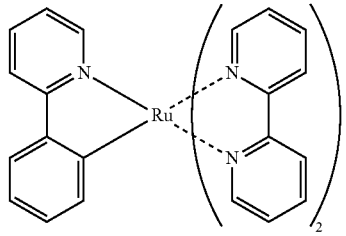

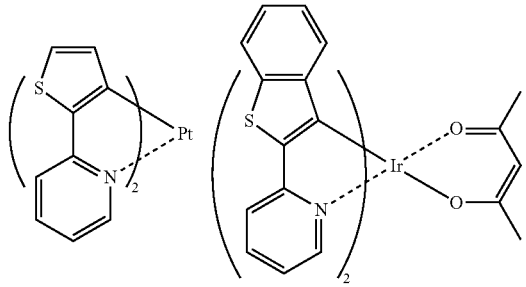

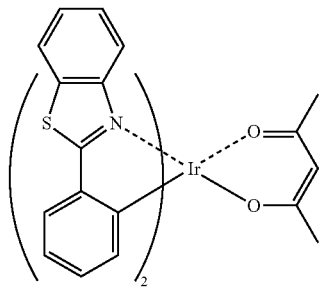

101
-continued
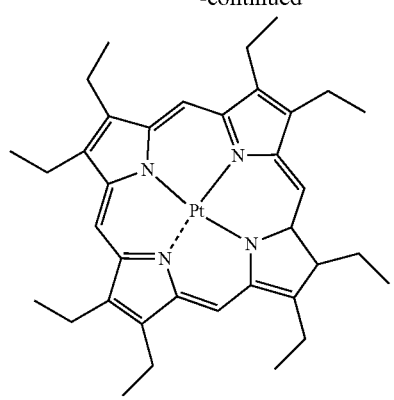
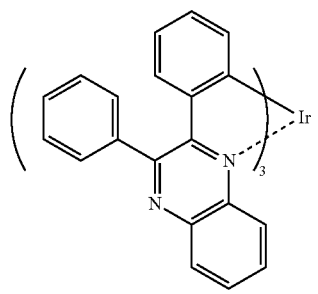
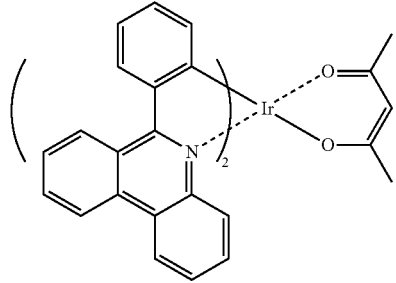
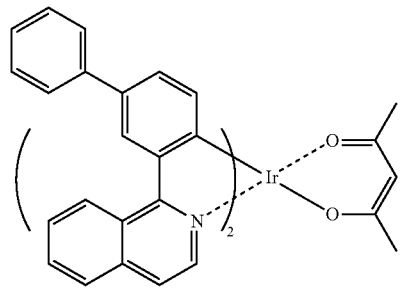
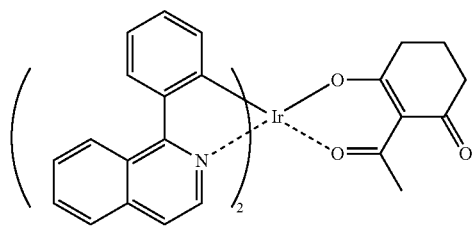
102
-continued
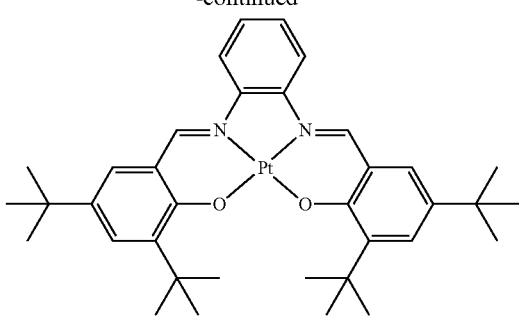
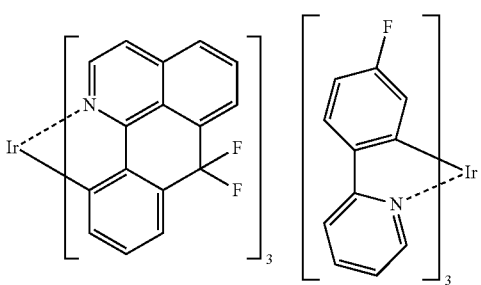
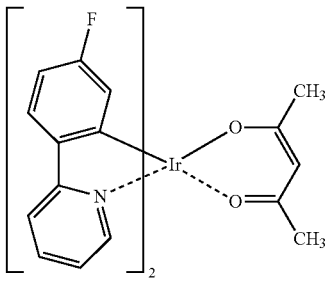

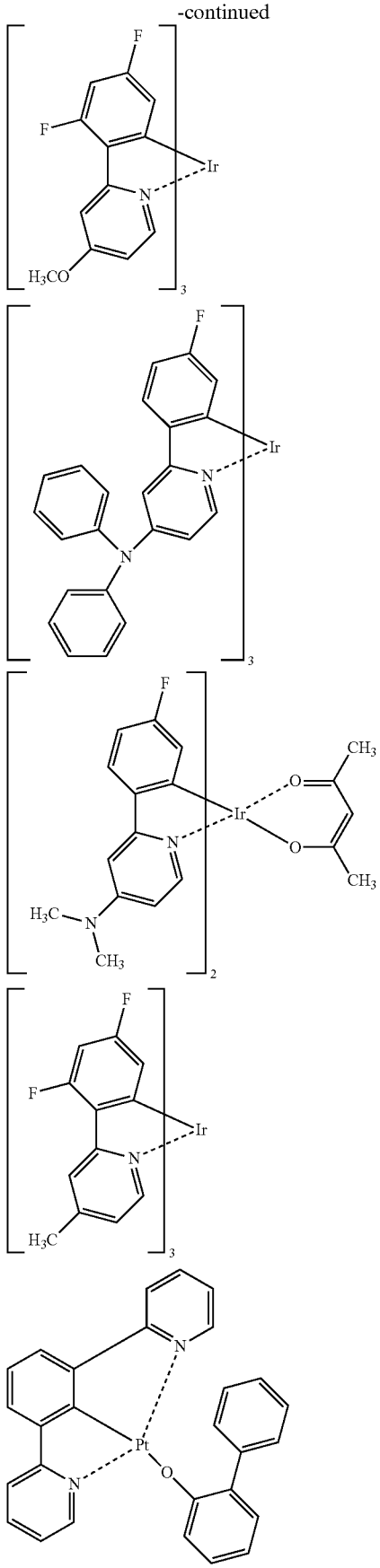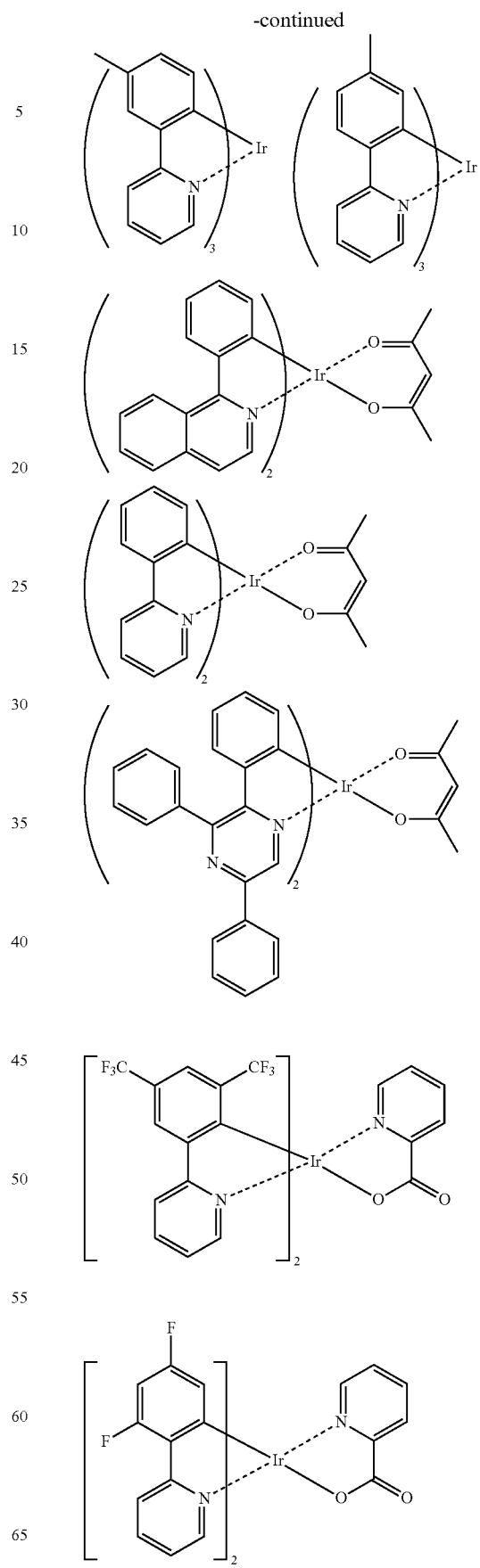

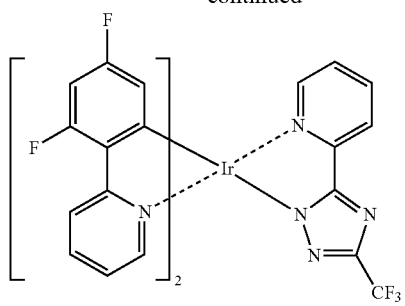
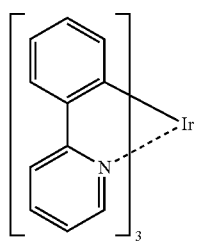
Ir(ppy)₃
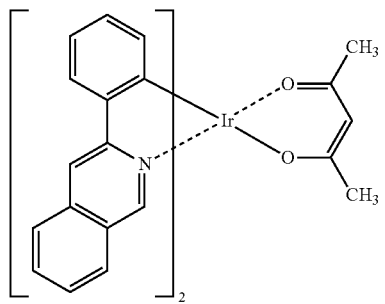
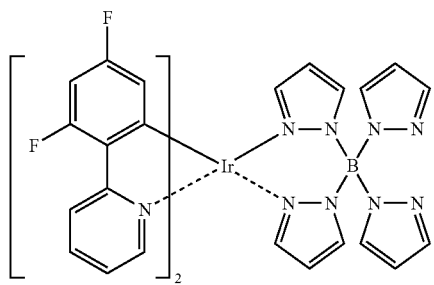
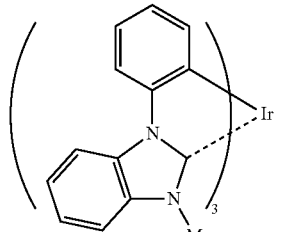
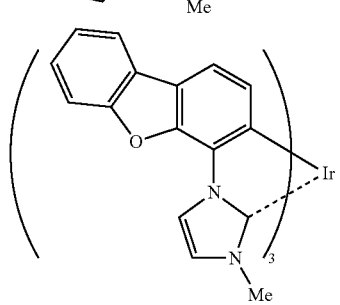
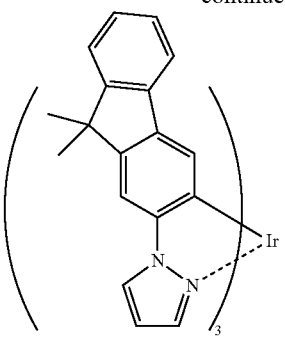
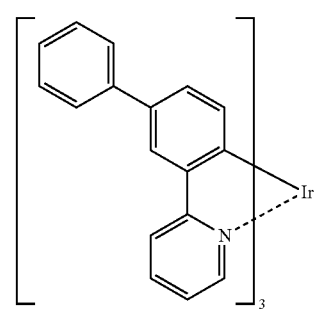
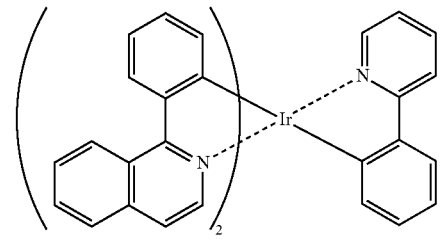
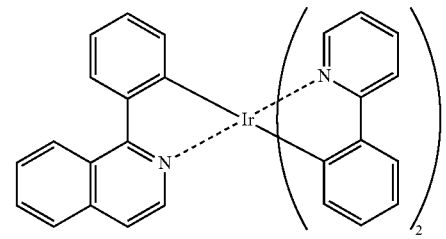
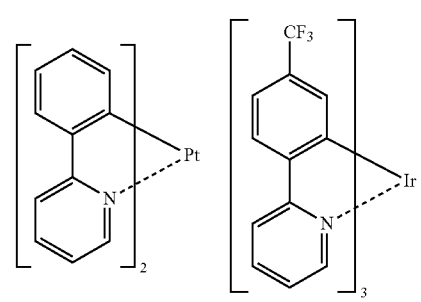
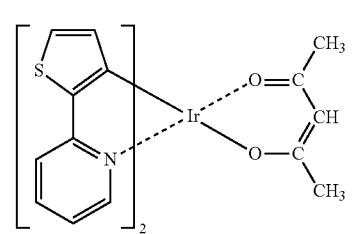

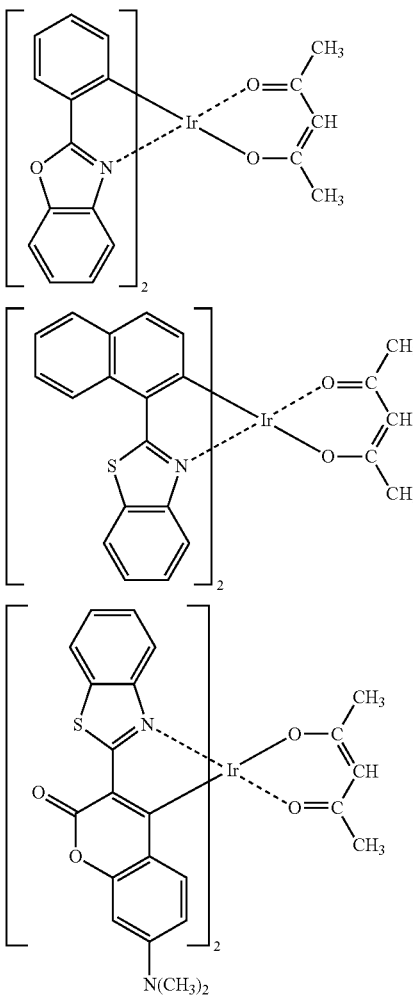

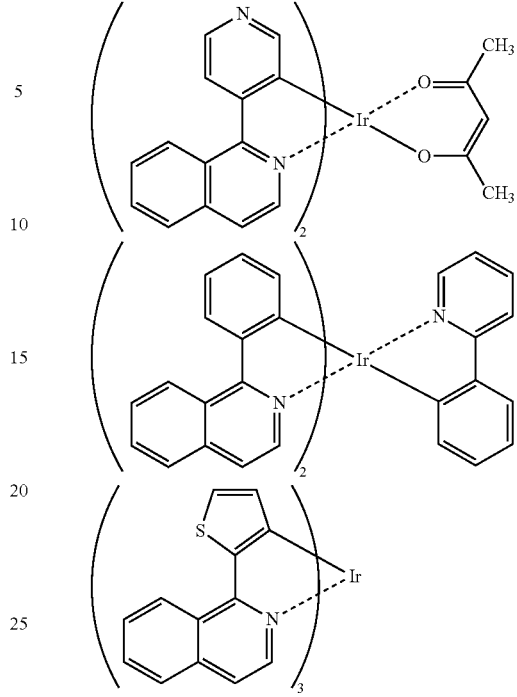

According to this exemplary embodiment, at least one of the phosphorescent material contained in the emitting layer preferably emits light with the maximum wavelength of 450 nm to 720 nm.

By doping the phosphorescent material (phosphorescent dopant) having such an emission wavelength to the specific host material used in this exemplary embodiment so as to form the emitting layer, the organic EL device can exhibit high efficiency.

Reduction-Causing Dopant

In the organic EL device according to this exemplary embodiment, a reduction-causing dopant may be preferably contained in an interfacial region between the cathode and the organic thin-film layer.

With this arrangement, the organic EL device can emit light with enhanced luminance intensity and have a longer lifetime.

The reduction-causing dopant may be at least one compound selected from an alkali metal, alkali metal complex, alkali metal compound, alkali earth metal, alkali earth metal complex, alkali earth metal compound, rare-earth metal, rare-earth metal complex, rare-earth metal compound and the like.

Examples of the alkali metal are Na (work function: 2.36 eV), K (work function: 2.28 eV), Rb (work function: 2.16 eV), Cs (work function: 1.95 eV) and the like, among which a substance having a work function of 2.9 eV or less is particularly preferable. Among the above, the reduction-causing dopant is preferably K, Rb or Cs, more preferably Rb or Cs, the most preferably Cs.

Examples of the alkali earth metal are Ca (work function: 2.9 eV), Sr (work function: 2.0 to 2.5 eV), Ba (work function: 2.52 eV) and the like, among which a substance having a work function of 2.9 eV or less is particularly preferable.

Examples of the rare-earth metal are Sc, Y, Ce, Tb, Yb and the like, among which a substance having a work function of 2.9 eV or less is particularly preferable.

Since the above preferable metals have particularly high reducibility, addition of a relatively small amount of the metals to an electron injecting zone can enhance luminance intensity and lifetime of the organic EL device.

Examples of the alkali metal compound include an alkali oxide such as $Li_2O$, $Cs_2O$ and $K_2O$, and an alkali halide such as LiF, NaF, CsF and KF. LiF, $Li_2O$, and NaF are preferable.

Examples of the alkali earth metal compound include BaO, SrO, CaO and their mixture such as $Ba_xSr_{1-x}O$ (0<x<1) and $Ba_xCa_{1-x}O$ (0<x<1). BaO, SrO, and CaO are preferable.

Examples of the rare earth metal compound include $YbF_3$, $ScF_3$, $ScO_3$, $Y_2O_3$, $Ce_2O_3$, $GdF_3$ and $TbF_3$. $YbF_3$, $ScF_3$, and $TbF_3$ are preferable.

The alkali metal complex, alkali earth metal complex and rare earth metal complex are not specifically limited as long as they contain at least one metal ion of an alkali metal ion, an alkali earth metal ion and a rare earth metal ion. A ligand for each of the complexes is preferably quinolinol, benzoquinolinol, acridinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzoimidazole, hydroxybenzo triazole, hydroxy fluborane, bipyridyl, phenanthroline, phthalocyanine, porphyrin, cyclopentadiene, β-diketones, azomethines, or a derivative thereof, but the ligand is not limited thereto.

The reduction-causing dopant is added to preferably form a layer or an island pattern in the interfacial region. The layer of the reduction-causing dopant or the island pattern of the reduction-causing dopant is preferably formed by depositing the reduction-causing dopant by resistance heating deposition while an emitting material for forming the interfacial region or an organic substance as an electron-injecting material are simultaneously deposited, so that the reduction-causing dopant is dispersed in the organic substance. Dispersion concentration at which the reduction-causing dopant is dispersed in the organic substance is a mole ratio (organic substance to reduction-causing dopant) of 100:1 to 1:100, preferably 5:1 to 1:5.

When the reduction-causing dopant forms the layer, the emitting material or the electron injecting material for forming the organic layer of the interfacial region is initially layered, and the reduction-causing dopant is subsequently deposited singularly thereon by resistance heating deposition to form a preferably 0.1 to 15 nm-thick layer.

When the reduction-causing dopant forms the island pattern, the emitting material or the electron injecting material for forming the organic layer of the interfacial region is initially formed in an island shape, and the reduction-causing dopant is subsequently deposited singularly thereon by resistance heating deposition to form a preferably 0.05 to 1 nm-thick island shape.

A ratio of the main component to the reduction-causing dopant in the organic EL device according to this exemplary embodiment is preferably a mole ratio (main component to reduction-causing dopant) of 5:1 to 1:5, more preferably 2:1 to 1:2.

Electron Injecting Layer and Electron Transporting Layer

The electron injecting layer or the electron transporting layer, which aids injection of the electrons into the emitting layer, has a large electron mobility. The electron injecting layer is provided for adjusting energy level, by which, for instance, sudden changes of the energy level can be reduced.

The organic EL device according to this exemplary embodiment preferably includes the electron injecting layer between the emitting layer and the cathode, and the electron injecting layer preferably contains a nitrogen-containing cyclic derivative as the main component. The electron injecting layer may serve as the electron transporting layer.

It should be noted that "as the main component" means that the nitrogen-containing cyclic derivative is contained in the electron injecting layer at a content of 50 mass % or more.

A preferable example of an electron transporting material for forming the electron injecting layer is an aromatic heterocyclic compound having in the molecule at least one heteroatom. Particularly, a nitrogen-containing cyclic derivative is preferable. The nitrogen-containing cyclic derivative is preferably an aromatic ring having a nitrogen-containing six-membered or five-membered ring skeleton, or a fused aromatic cyclic compound having a nitrogen-containing six-membered or five-membered ring skeleton.

A preferable example of the nitrogen-containing cyclic derivative is a nitrogen-containing cyclic metal chelate complex represented by the following formula (A).

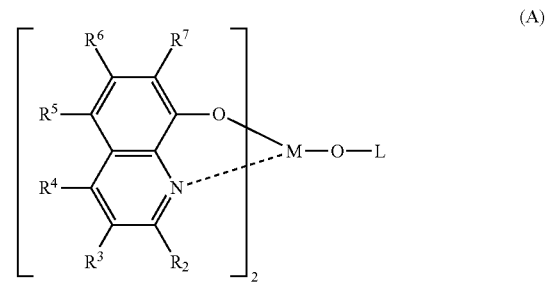

(A)

$R^2$ to $R^7$ in the formula (A) each independently represent a hydrogen atom, a halogen atom, an oxy group, an amino group, a hydrocarbon group having 1 to 40 carbon atoms, an alkoxy group, an aryloxy group, an alkoxycarbonyl group, or an aromatic heterocyclic group. These groups may be substituted or unsubstituted.

Examples of the halogen atom include fluorine, chlorine, bromine, and iodine. In addition, examples of the substituted or unsubstituted amino group include an alkylamino group, an arylamino group, and an aralkylamino group.

The alkoxycarbonyl group is represented by —COOY'. Examples of $Y^1$ are the same as the examples of the alkyl group. The alkylamino group and the aralkylamino group are represented by —$NQ^1Q^2$. Examples for each of $Q^1$ and $Q^2$ are the same as the examples described in relation to the alkyl group and the aralkyl group, and preferable examples for each of $Q^1$ and $Q^2$ are also the same as those described in relation to the alkyl group and the aralkyl group. Either one of $Q^1$ and $Q^2$ may be a hydrogen atom.

The arylamino group is represented by —$NAr^1Ar^2$. Examples for each of $Ar^1$ and $Ar^2$ are the same as the examples described in relation to the non-fused aromatic hydrocarbon group and the fused aromatic hydrocarbon group. Either one of $Ar^1$ and $Ar^2$ may be a hydrogen atom.

M represents aluminum (Al), gallium (Ga) or indium (In), among which In is preferable.

L in the formula (A) represents a group represented by the following formula (A') or the following formula (A").

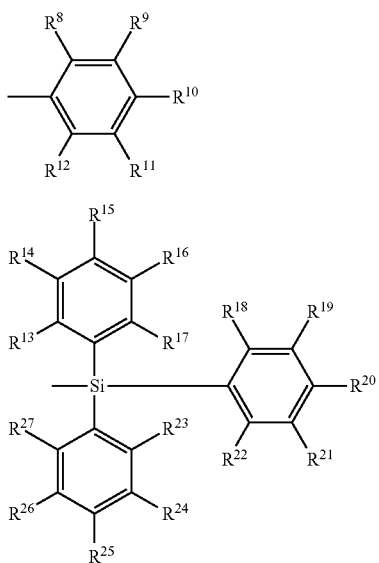

In the formula (A'), $R^8$ to $R^{12}$ each independently represent a hydrogen atom or a substituted or unsubstituted hydrocarbon group having 1 to 40 carbon atoms. Adjacent groups may form a cyclic structure. In the formula (A''), $R^{13}$ to $R^{27}$ each independently represent a hydrogen atom or a substituted or unsubstituted hydrocarbon group having 1 to 40 carbon atoms. Adjacent groups may form a cyclic structure.

Examples of the hydrocarbon group having 1 to 40 carbon atoms represented by each of $R^8$ to $R^{12}$ and $R^{13}$ to $R^{27}$ in the formulae (A') and (A'') are the same as those of $R^2$ to $R^7$ in the formula (A).

Examples of a divalent group formed when an adjacent set of $R^8$ to $R^{12}$ and $R^{13}$ to $R^{27}$ forms a cyclic structure are a tetramethylene group, a pentamethylene group, a hexamethylene group, a diphenylmethane-2,2'-diyl group, a diphenylethane-3,3'-diyl group, a diphenylpropane-4,4'-diyl group and the like.

Moreover, in this exemplary embodiment, the electron transporting layer may contain the biscarbazole derivatives represented by the formulae (1) to (3) (or the formulae (4) to (6)).

As an electron transporting compound for the electron injecting layer or the electron transporting layer, 8-hydroxyquinoline or a metal complex of its derivative, an oxadiazole derivative and a nitrogen-containing heterocyclic derivative are preferable. An example of the 8-hydroxyquinoline or the metal complex of its derivative is a metal chelate oxinoid compound containing a chelate of oxine (typically 8-quinolinol or 8-hydroxyquinoline). For instance, tris(8-quinolinol) aluminum can be used. Examples of the oxadiazole derivative are as follows.

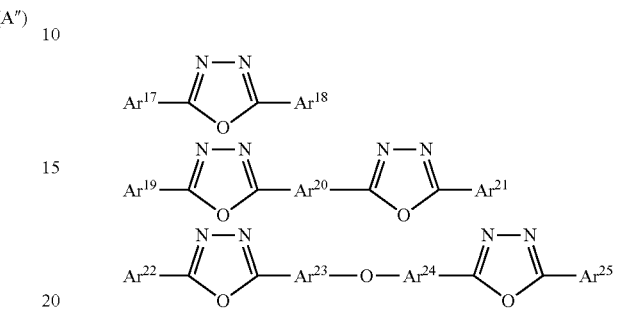

In the formula, $Ar^{17}$, $Ar^{18}$, $Ar^{19}$, $Ar^{21}$, $Ar^{22}$ and $Ar^{25}$ each represent a substituted or unsubstituted aromatic hydrocarbon group or fused aromatic hydrocarbon group having 6 to 40 ring carbon atoms. $Ar^{17}$, $Ar^{19}$ and $Ar^{22}$ may be the same as or different from $Ar^{18}$, $Ar^{21}$ and $Ar^{25}$ respectively. Examples of the aromatic hydrocarbon group or fused aromatic hydrocarbon group having 6 to 40 ring carbon atoms are a phenyl group, biphenyl group, anthranil group, perylenyl group and pyrenyl group. Examples of the substituent therefor are an alkyl group having 1 to 10 carbon atoms, alkoxy group having 1 to 10 carbon atoms and cyano group.

$Ar^{20}$, $Ar^{23}$ and $Ar^{24}$ each represent a substituted or unsubstituted divalent aromatic hydrocarbon group or fused aromatic hydrocarbon group having 6 to 40 ring carbon atoms. $Ar^{23}$ and $Ar^{24}$ may be mutually the same or different.

Examples of the divalent aromatic hydrocarbon group or fused aromatic hydrocarbon group having 6 to 40 ring carbon atoms are a phenylene group, naphthylene group, biphenylene group, anthranylene group, perylenylene group and pyrenylene group. Examples of the substituent therefor are an alkyl group having 1 to 10 carbon atoms, alkoxy group having 1 to 10 carbon atoms and cyano group.

Such an electron transport compound is preferably an electron transport compound that can be favorably formed into a thin film(s). Examples of the electron transporting compounds are as follows.

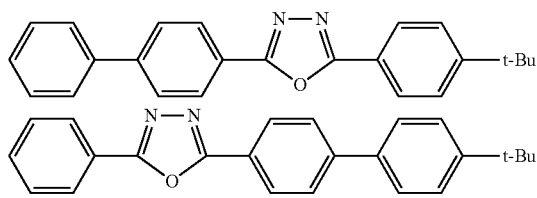

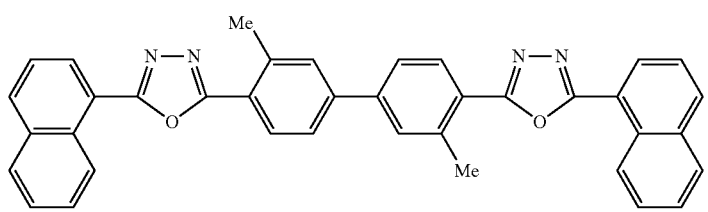

-continued

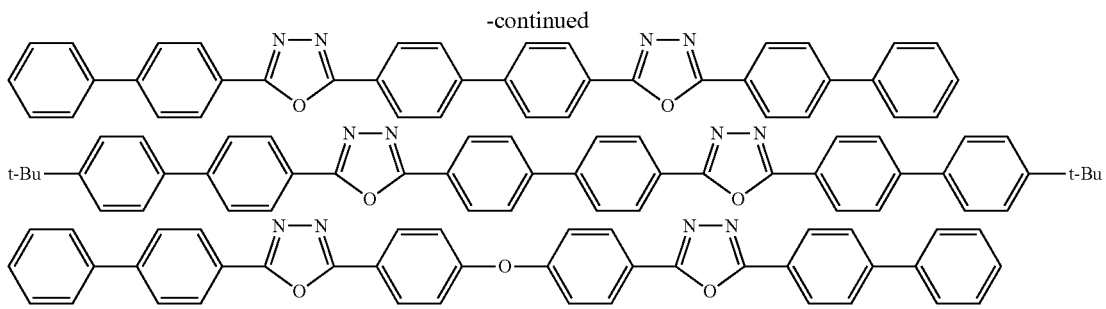

An example of the nitrogen-containing heterocyclic derivative as the electron transporting compound is a nitrogen-containing compound that is not a metal complex, the derivative being formed of an organic compound represented by one of the following general formulae. Examples of the nitrogen-containing heterocyclic derivative are a five-membered ring or six-membered ring derivative having a skeleton represented by the following formula (A) and a derivative having a structure represented by the following formula (B).

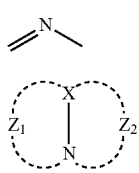

In the formula (B), X represents a carbon atom or a nitrogen atom. $Z_1$ and $Z_2$ each independently represent a group of atoms capable of forming a nitrogen-containing heterocycle.

Preferably, the nitrogen-containing heterocyclic derivative is an organic compound having a nitrogen-containing aromatic polycyclic group having a five-membered ring or six-membered ring. When the nitrogen-containing heterocyclic derivative includes such nitrogen-containing aromatic polycyclic series having plural nitrogen atoms, the nitrogen-containing heterocyclic derivative may be a nitrogen-containing aromatic polycyclic organic compound having a skeleton formed by a combination of the skeletons respectively represented by the formulae (A) and (B), or by a combination of the skeletons respectively represented by the formulae (A) and (C).

A nitrogen-containing group of the nitrogen-containing aromatic polycyclic organic compound is selected from nitrogen-containing heterocyclic groups respectively represented by the following general formulae.

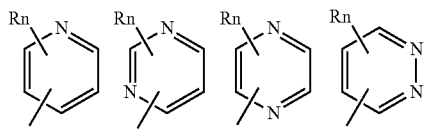

-continued

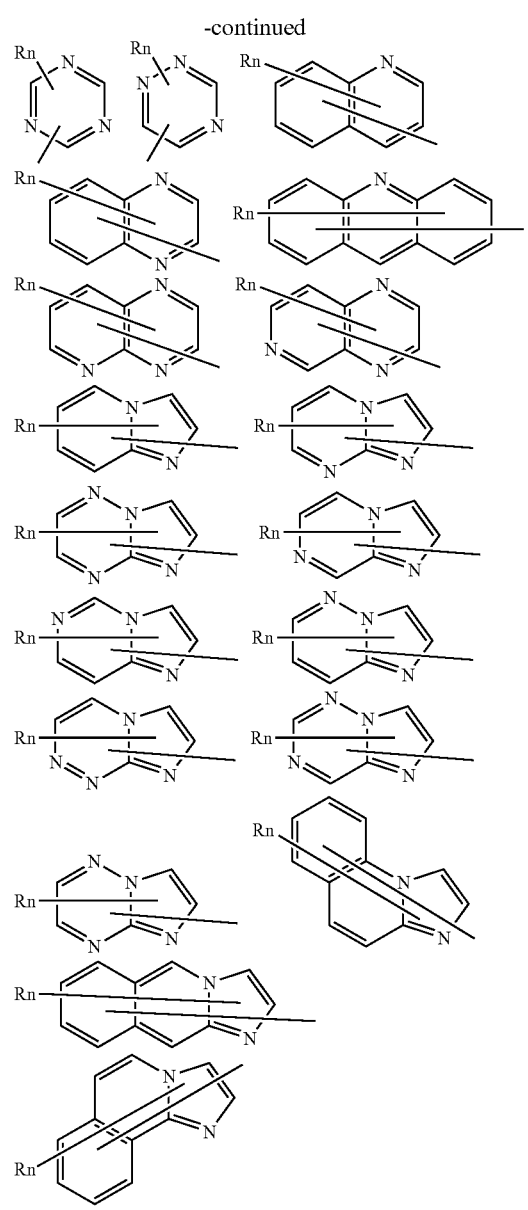

In the formulae: R represents an aromatic hydrocarbon group or fused aromatic hydrocarbon group having 6 to 40 ring carbon atoms; aromatic heterocyclic group or fused aromatic heterocyclic group having 2 to 40 ring carbon atoms; alkyl group having 1 to 20 carbon atoms or alkoxy group having 1 to 20 carbon atoms; and n represents an integer in a range of 0 to 5. When n is an integer of 2 or more, plural R may be mutually the same or different.

A preferable specific compound is a nitrogen-containing heterocyclic derivative represented by the following formula.

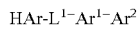

In the formula: HAr represents a substituted or unsubstituted nitrogen-containing heterocyclic group having 1 to 40 ring carbon atoms; L' represents a single bond, substituted or unsubstituted aromatic hydrocarbon group or fused aromatic hydrocarbon group having 6 to 40 ring carbon atoms, or substituted or unsubstituted aromatic heterocyclic group or fused aromatic heterocyclic group having 2 to 40 ring carbon atoms; $Ar^1$ represents a substituted or unsubstituted divalent aromatic hydrocarbon group having 6 to 40 ring carbon atoms; and $Ar^2$ represents a substituted or unsubstituted aromatic hydrocarbon group or fused aromatic hydrocarbon group having 6 to 40 ring carbon atoms, or substituted or unsubstituted aromatic heterocyclic group or fused aromatic heterocyclic group having 2 to 40 ring carbon atoms.

HAr is exemplarily selected from the following group.

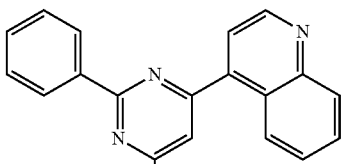

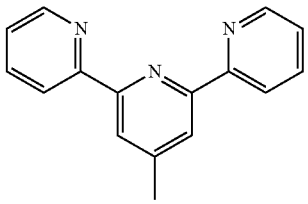

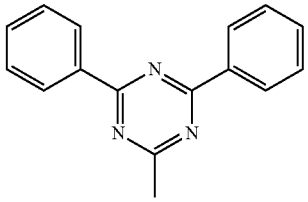

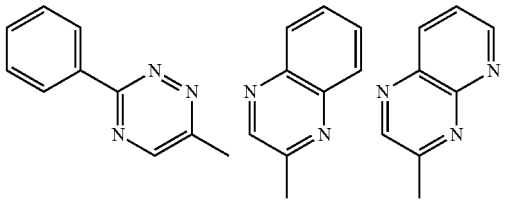

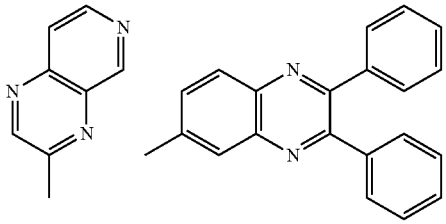

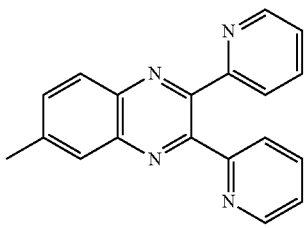

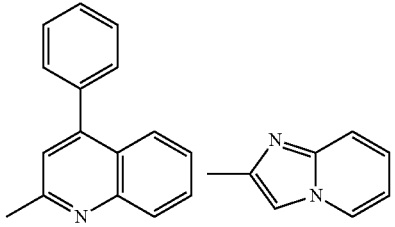

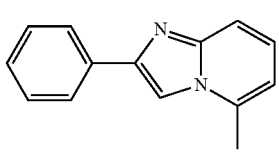

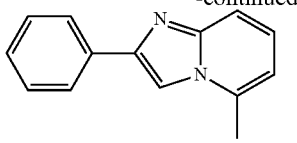

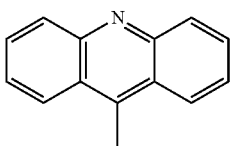

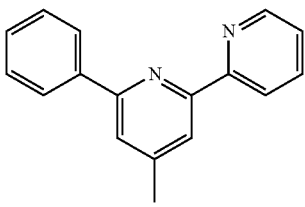

L¹ is exemplarily selected from the following group.

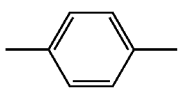 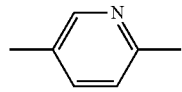

Ar¹ is exemplarily selected from the following arylanthranil groups.

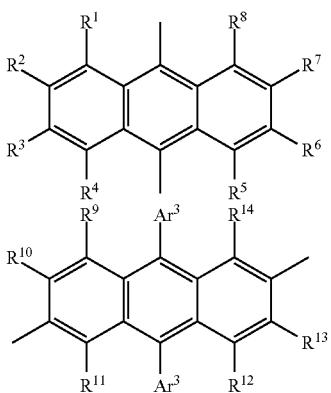

In the formulae: $R^1$ to $R^{14}$ each independently represent a hydrogen atom, halogen atom, alkyl group having 1 to 20 carbon atoms, alkoxy group having 1 to 20 carbon atoms, aryloxy group having 6 to 40 ring carbon atoms, substituted or unsubstituted aromatic hydrocarbon group or fused aromatic hydrocarbon group having 6 to 40 ring carbon atoms, or aromatic heterocyclic group or fused aromatic heterocyclic group having 2 to 40 ring carbon atoms; and $Ar^3$ represents aromatic hydrocarbon group or fused aromatic hydrocarbon group having 6 to 40 ring carbon atoms, or aromatic heterocyclic group or fused aromatic heterocyclic group having 2 to 40 ring carbon atoms.

All of $R^1$ to $R^8$ of a nitrogen-containing heterocyclic derivative may be hydrogen atoms.

Ar² is exemplarily selected from the following group.

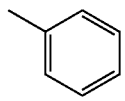 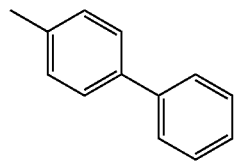

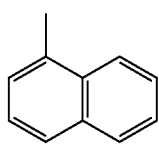 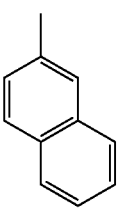

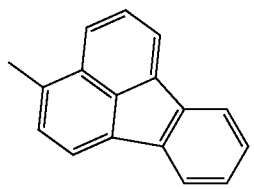 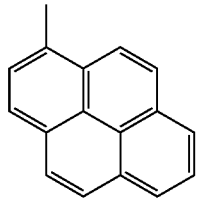

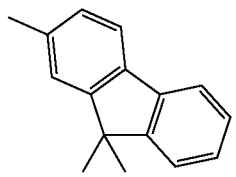

Other than the above, the following compound (see JP-A-9-3448) can be favorably used for the nitrogen-containing aromatic polycyclic organic compound as the electron transporting compound.

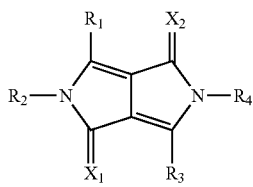

In the formula: $R_1$ to $R_4$ each independently represent a hydrogen atom, substituted or unsubstituted aliphatic group, substituted or unsubstituted alicyclic group, substituted or unsubstituted carbocyclic aromatic cyclic group or substituted or unsubstituted heterocyclic group; and $X_1$ and $X_2$ each independently represent an oxygen atom, sulfur atom or dicyanomethylene group.

The following compound (see JP-A-2000-173774) can also be favorably used for the electron transporting compound.

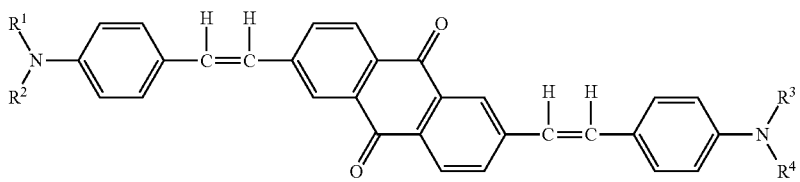

In the formula, $R^1$, $R^2$, $R^3$ and $R^4$, which may be mutually the same or different, each represent an aromatic hydrocarbon group or fused aromatic hydrocarbon group represented by the following formula.

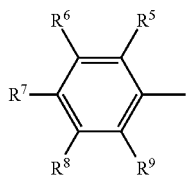

In the formula, $R^5$, $R^6$, $R^7$, $R^8$ and $R^9$, which may be mutually the same or different, each represent a hydrogen atom, a saturated or unsaturated alkoxyl group, alkyl group, amino group or alkylamino group. At least one of $R^5$, $R^6$, $R^7$, $R^8$ and $R^9$ represents a saturated or unsaturated alkoxyl group, alkyl group, amino group or alkylamino group.

A polymer compound containing the nitrogen-containing heterocyclic group or a nitrogen-containing heterocyclic derivative may be used for the electron transporting compound.

The electron transporting layer preferably contains at least one of nitrogen-containing heterocycle derivatives respectively represented by the following formulae (201) to (203).

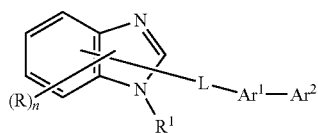 (201)

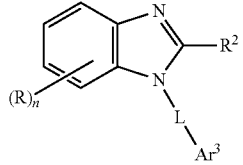 (202)

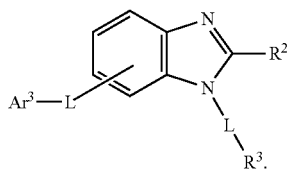 (203)

In the formulae (201) to (203): R represents a hydrogen atom, substituted or unsubstituted aromatic hydrocarbon group or fused aromatic hydrocarbon group having 6 to 60 ring carbon atoms, substituted or unsubstituted pyridyl group, substituted or unsubstituted quinolyl group, substituted or unsubstituted alkyl group having 1 to 20 carbon atoms, or substituted or unsubstituted alkoxy group having 1 to 20 carbon atoms; n is an integer in a range of 0 to 4;

$R^1$ represents a substituted or unsubstituted aromatic hydrocarbon group or fused aromatic hydrocarbon group having 6 to 60 ring carbon atoms, substituted or unsubstituted pyridyl group, substituted or unsubstituted quinolyl group, substituted or unsubstituted alkyl group having 1 to 20 carbon atoms, <<nret>> or alkoxy group having 1 to 20 carbon atoms;

$R^2$ and $R^3$ each independently represent a hydrogen atom, substituted or unsubstituted aromatic hydrocarbon group or fused aromatic hydrocarbon group having 6 to 60 ring carbon atoms, substituted or unsubstituted pyridyl group, substituted or unsubstituted quinolyl group, substituted or unsubstituted alkyl group having 1 to 20 carbon atoms, or a substituted or unsubstituted alkoxy group having 1 to 20 carbon atoms; L represents a substituted or unsubstituted aromatic hydrocarbon group or fused aromatic hydrocarbon group having 6 to 60 ring carbon atoms, substituted or unsubstituted pyridinylene group, substituted or unsubstituted quinolylene group, or substituted or unsubstituted fluorenylene group;

$Ar^1$ represents a substituted or unsubstituted aromatic hydrocarbon group or fused aromatic hydrocarbon group having 6 to 60 ring carbon atoms, substituted or unsubstituted pyridinylene group, substituted or unsubstituted quinolyl group. $Ar^2$ represents a substituted or unsubstituted aromatic hydrocarbon group or fused aromatic hydrocarbon group having 6 to 60 ring carbon atoms, substituted or unsubstituted pyridyl group, substituted or unsubstituted quinolyl group, substituted or unsubstituted alkyl group having 1 to 20 carbon atoms, or substituted or unsubstituted alkoxy group having 1 to 20 carbon atoms; and $Ar^3$ represents a substituted or unsubstituted aromatic hydrocarbon group or fused aromatic hydrocarbon group having 6 to 60 ring carbon atoms, substituted or unsubstituted pyridyl group, substituted or unsubstituted quinolyl group, substituted or unsubstituted alkyl group having 1 to 20 carbon atoms, substituted or unsubstituted alkoxy group having 1 to 20 carbon atoms or group represented by —$Ar^1$—$Ar^2$ ($Ar^1$ and $Ar^2$ may be the same as the above).

In the formulae (201) to (203), R represents a hydrogen atom, a substituted or unsubstituted aromatic hydrocarbon group or fused aromatic hydrocarbon group having 6 to 60 ring carbon atoms, substituted or unsubstituted pyridyl group, substituted or unsubstituted quinolyl group, substituted or unsubstituted alkyl group having 1 to 20 carbon atoms, or substituted or unsubstituted alkoxy group having 1 to 20 carbon atoms.

Although a thickness of the electron injecting layer or the electron transporting layer is not specifically limited, the thickness is preferably 1 nm to 100 nm.

The electron injecting layer preferably contains an inorganic compound such as an insulator or a semiconductor in addition to the nitrogen-containing cyclic derivative. Such an insulator or a semiconductor, when contained in the electron injecting layer, can effectively prevent a current leak, thereby enhancing electron capability of the electron injecting layer.

As the insulator, it is preferable to use at least one metal compound selected from the group consisting of an alkali metal chalcogenide, an alkali earth metal chalcogenide, a halogenide of alkali metal and a halogenide of alkali earth metal. By forming the electron injecting layer from the alkali metal chalcogenide or the like, the electron injecting capability can preferably be further enhanced. Specifically, preferable examples of the alkali metal chalcogenide are $Li_2O$, $K_2O$, $Na_2S$, $Na_2Se$ and $Na_2O$, while preferable example of the alkali earth metal chalcogenide are CaO, BaO, SrO, BeO, BaS and CaSe. Preferable examples of the halogenide of the alkali metal are LiF, NaF, KF, LiCl, KCl and NaCl. Preferable examples of the halogenide of the alkali earth metal are fluorides such as $CaF_2$, $BaF_2$, $SrF_2$, $MgF_2$ and $BeF_2$, and halogenides other than the fluoride.

Examples of the semiconductor are one of or a combination of two or more of an oxide, a nitride or an oxidized nitride containing at least one element selected from Ba, Ca, Sr, Yb, Al, Ga, In, Li, Na, Cd, Mg, Si, Ta, Sb and Zn. An inorganic compound for forming the electron injecting layer is preferably a microcrystalline or amorphous semiconductor film. When the electron injecting layer is formed of such insulator film, more uniform thin film can be formed, thereby reducing pixel defects such as a dark spot. Examples of such an inorganic compound are the above-described alkali metal chalcogenide, alkali earth metal chalcogenide, halogenide of the alkali metal and halogenide of the alkali earth metal.

When the electron injecting layer contains such an insulator or such a semiconductor, a thickness thereof is preferably in a range of approximately 0.1 nm to 15 nm. The electron injecting layer in this exemplary embodiment may preferably contain the above-described reduction-causing dopant.

Hole Injecting Layer and Hole Transporting Layer

The hole injecting layer or the hole transporting layer (including the hole injecting/transporting layer) may contain an aromatic amine compound such as an aromatic amine derivative represented by the following (I).

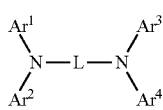
(I)

In the above (I), $Ar^1$ to $Ar^4$ each represent a substituted or unsubstituted aromatic hydrocarbon group or fused aromatic hydrocarbon group having 6 to 50 ring carbon atoms, substituted or unsubstituted aromatic heterocyclic group or fused aromatic heterocyclic group having 2 to 40 ring carbon atoms, or a group formed by combining the aromatic hydrocarbon group or the fused aromatic hydrocarbon group with the aromatic heterocyclic group or fused aromatic heterocyclic group.

Examples of the compound represented by the formula (I) are shown below. However, the compound represented by the formula (I) is not limited thereto.

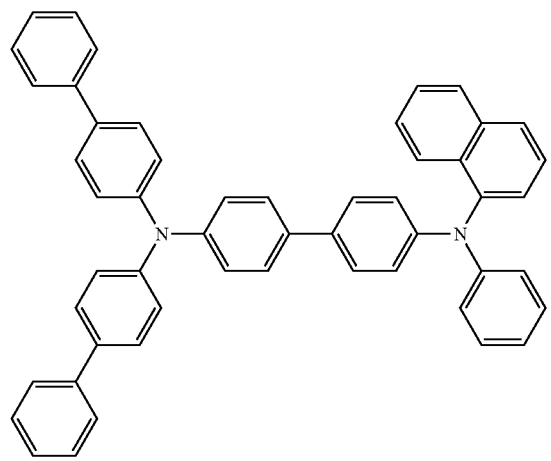

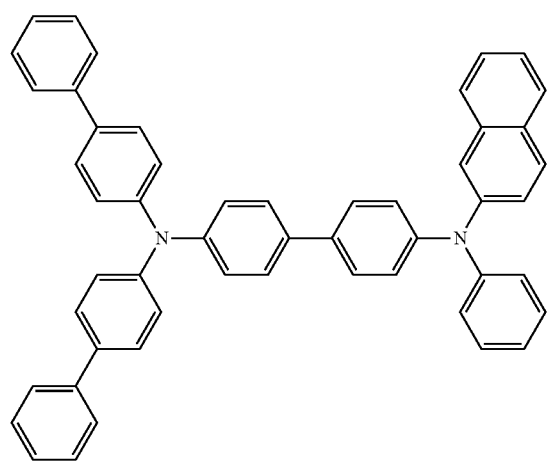

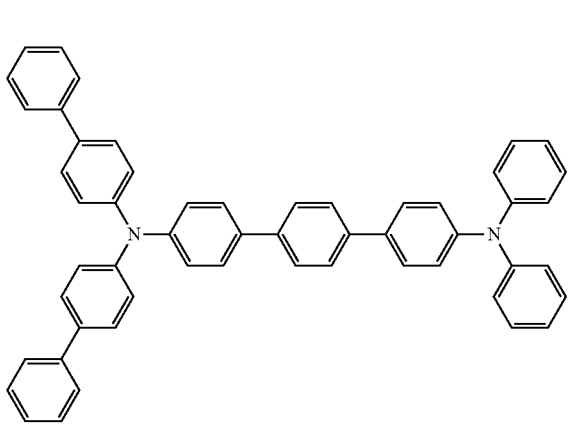

123
-continued
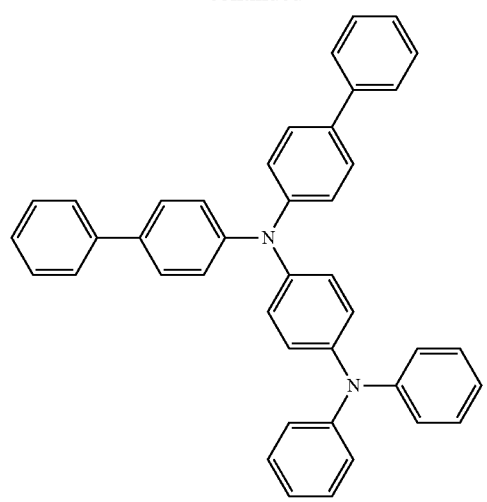
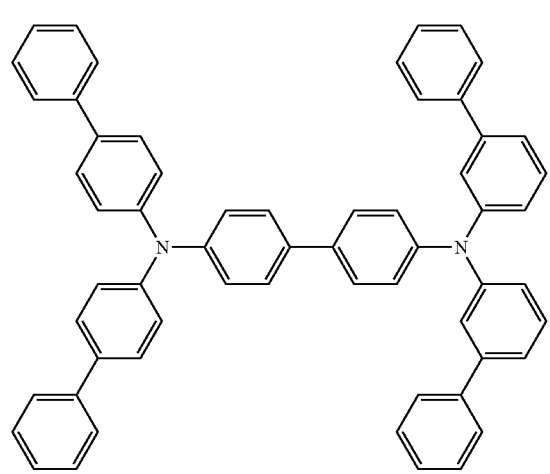
124
-continued
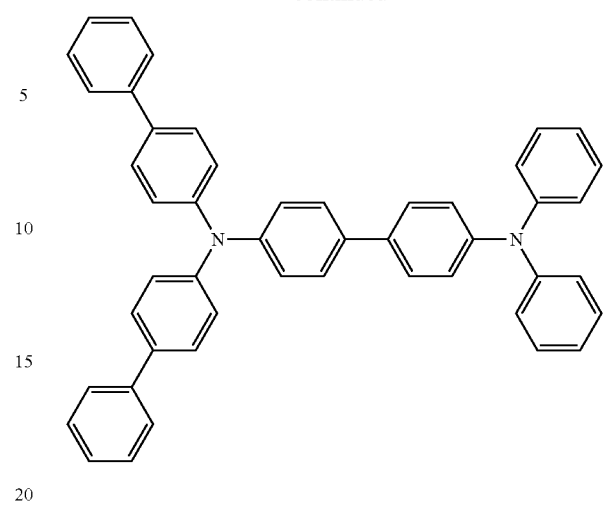
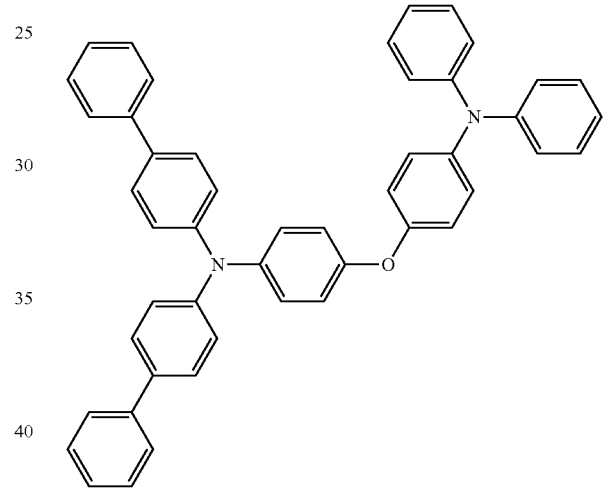
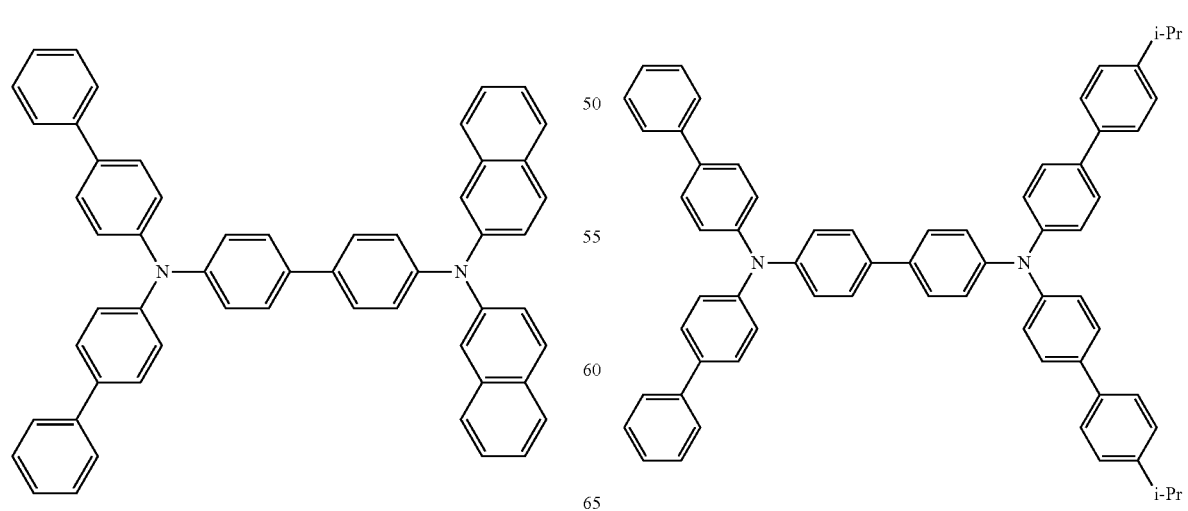

125
-continued
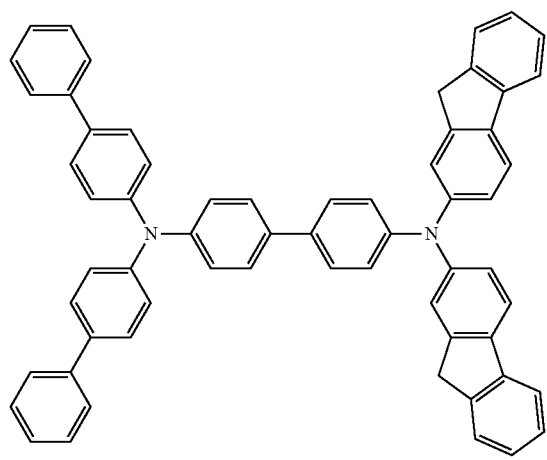
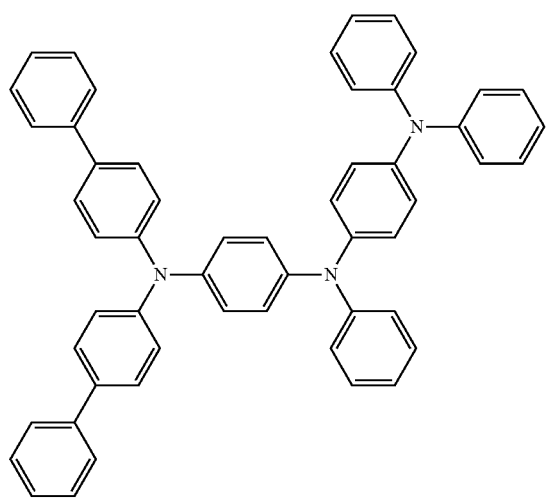
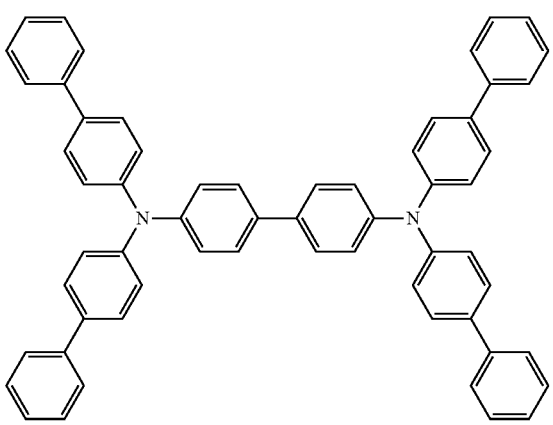
126
-continued
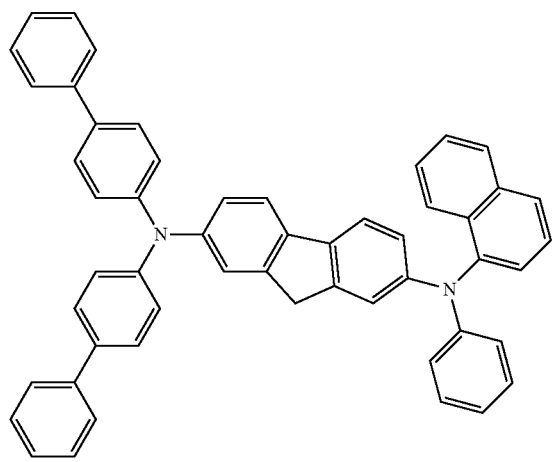
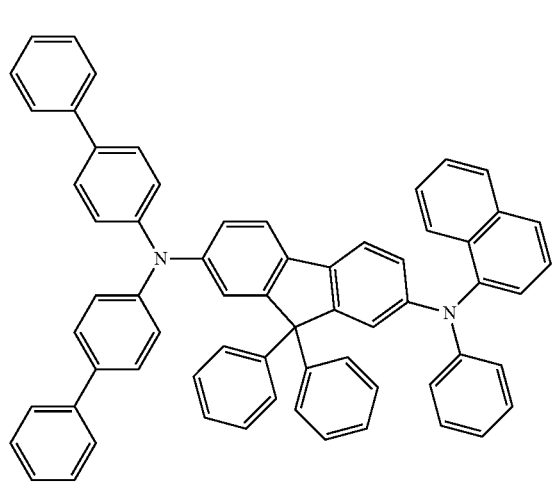
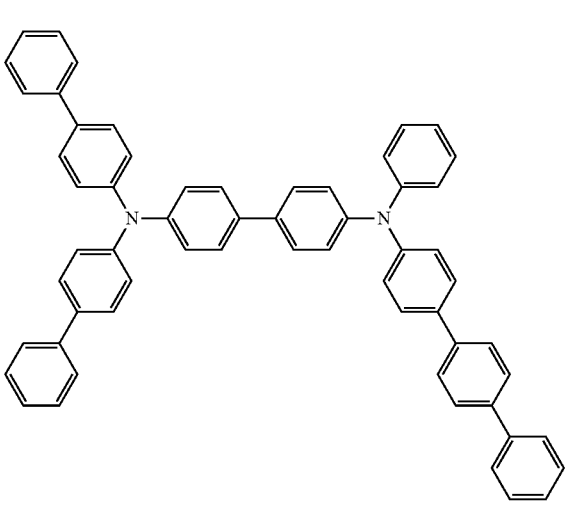

127
-continued
128
-continued
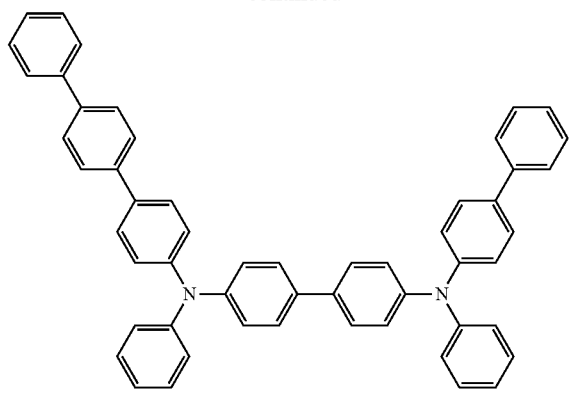
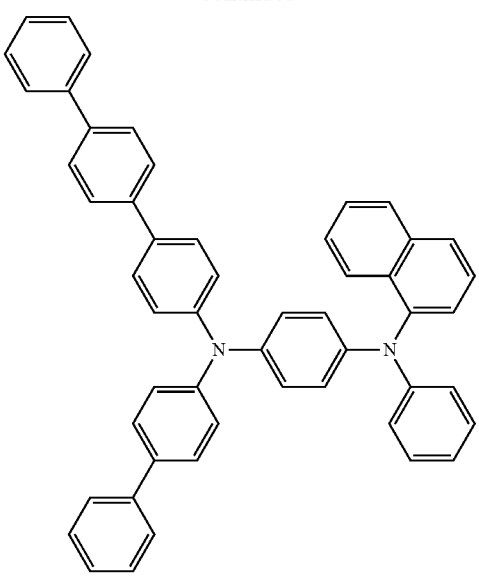
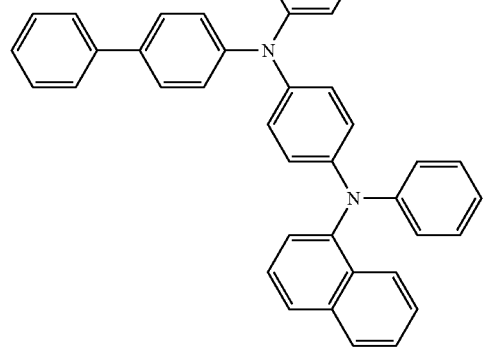
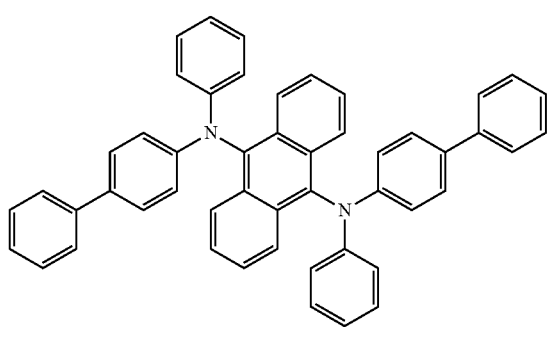
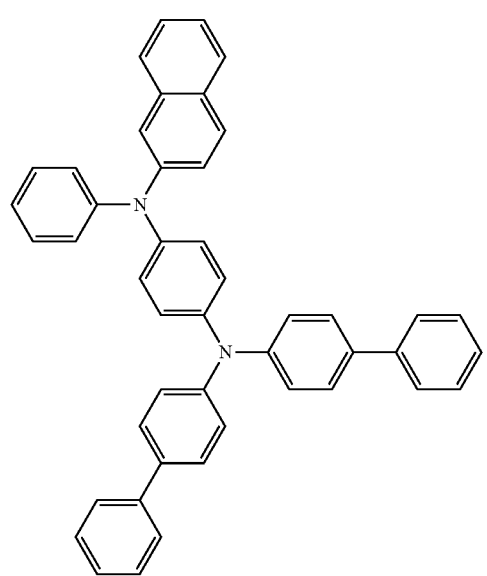
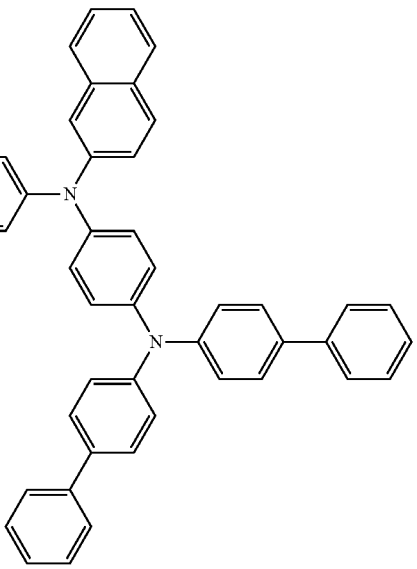

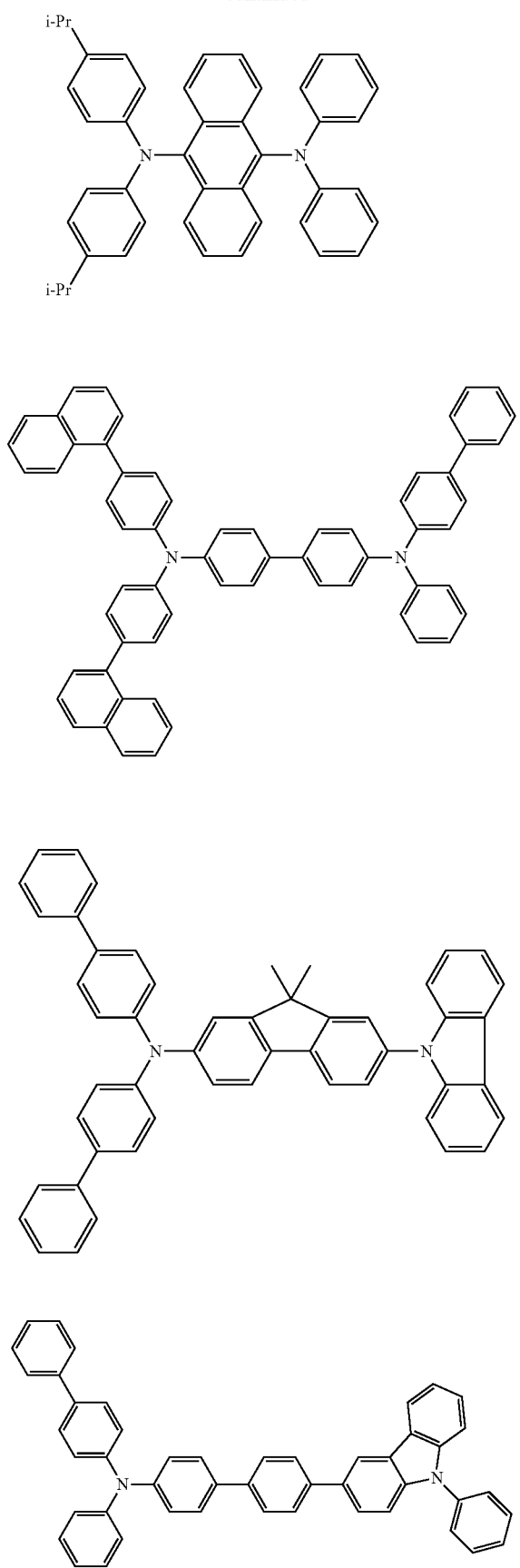

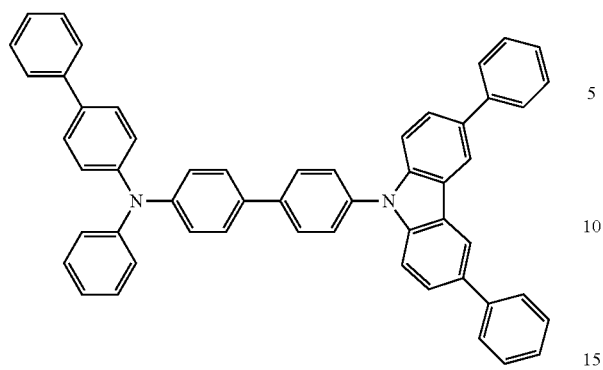

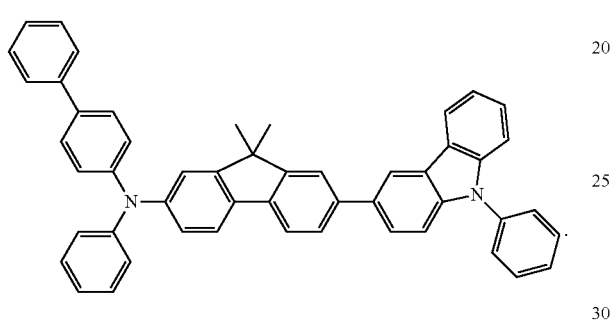

Aromatic amine represented by the following (II) can also be preferably used for forming the hole injecting layer or the hole transporting layer.

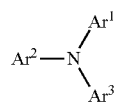 (II)

In the above (II), $Ar^1$ to $Ar^3$ each represent the same as $Ar^1$ to $Ar^4$ of the above (I). Examples of the compound represented by the general formula (II) are shown below. However, the compound represented by the formula (II) is not limited thereto.

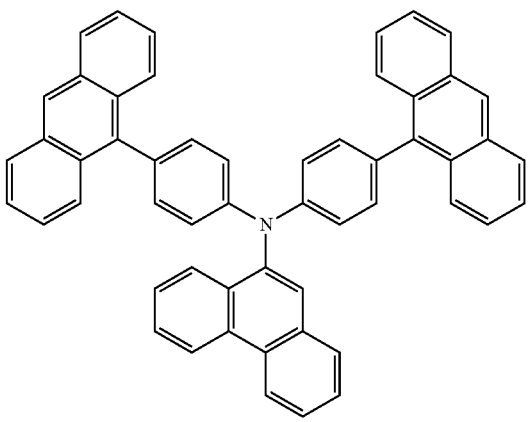

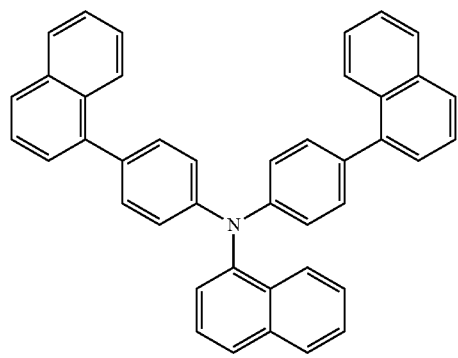

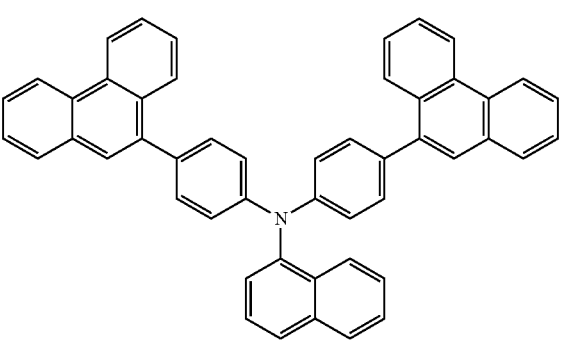

133
-continued
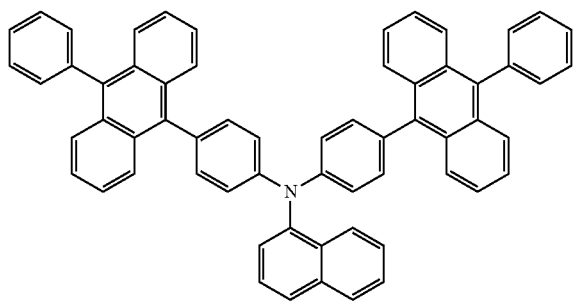
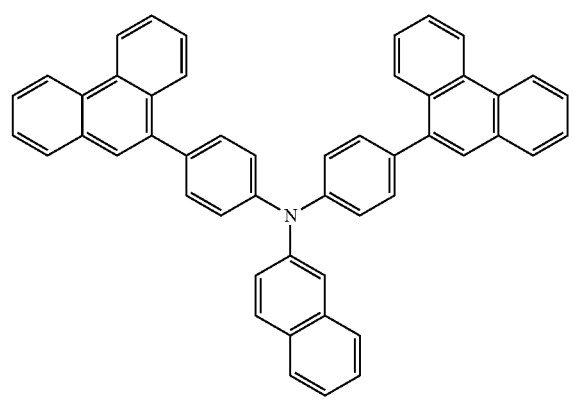
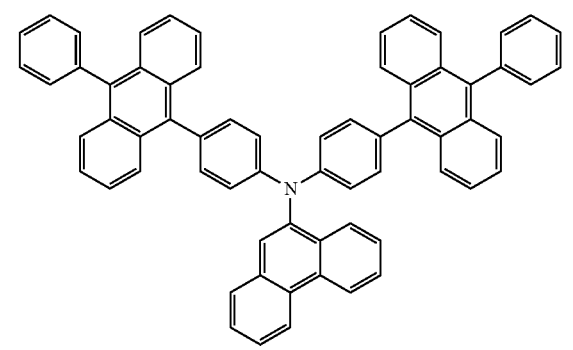
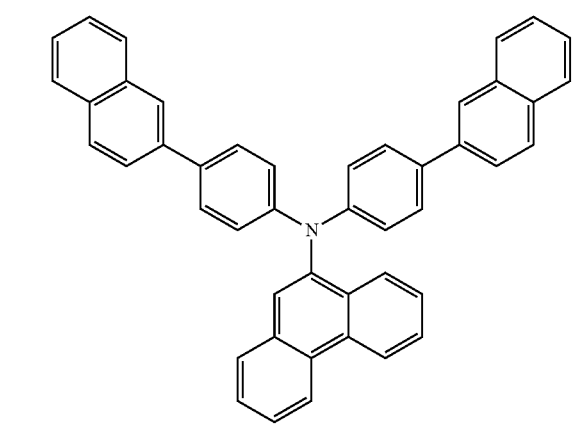
134
-continued
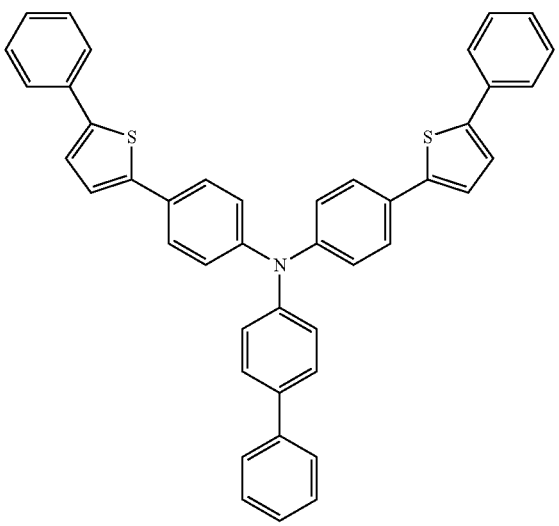
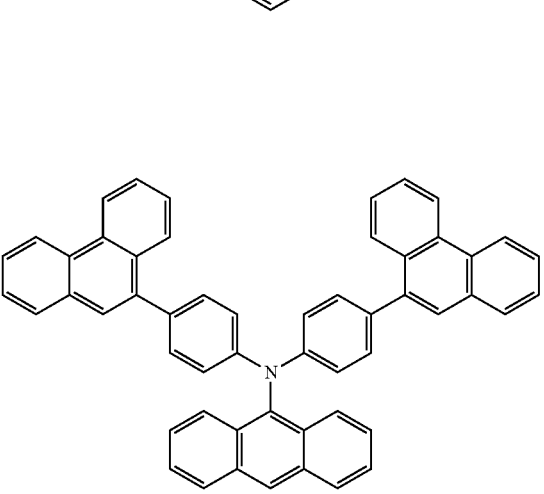
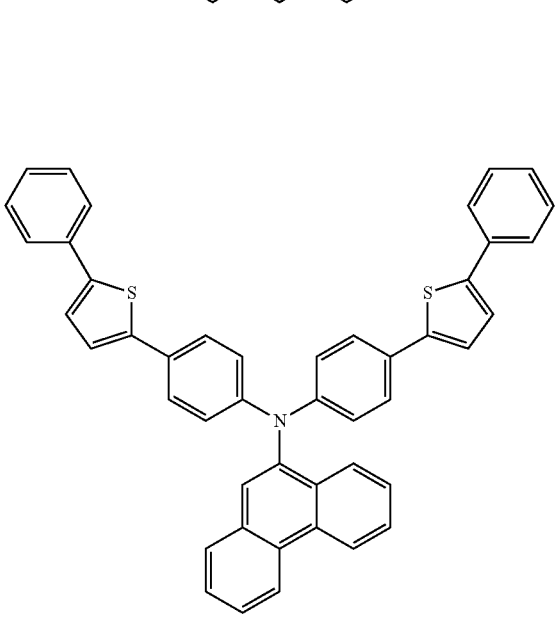

-continued

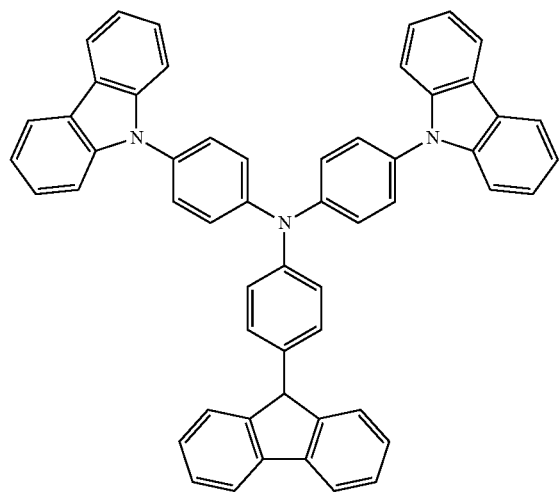

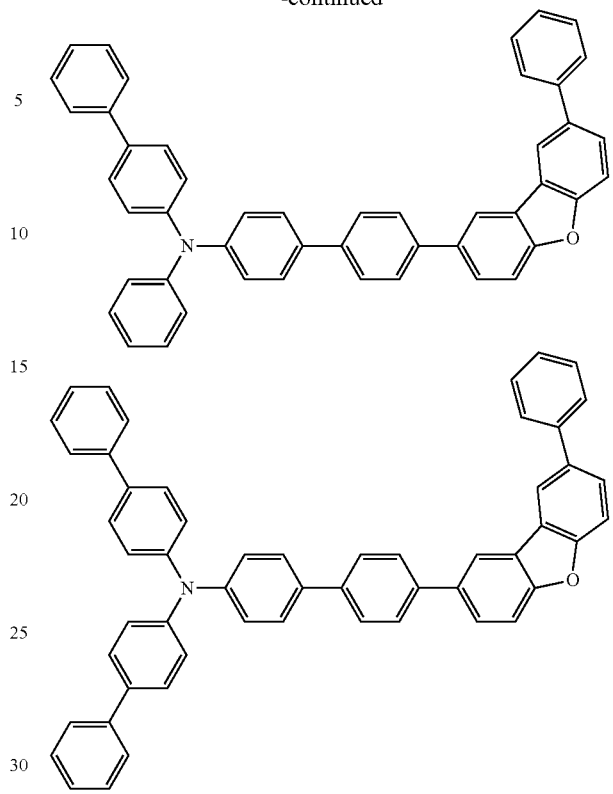

A method of forming each of the layers in the organic EL device according to this exemplary embodiment is not particularly limited. Conventionally-known methods such as vacuum deposition and spin coating may be employed for forming the layers. The organic thin-film layer containing the compound represented by the formula (1), which is used in the organic EL device according to this exemplary embodiment, may be formed by a conventional coating method such as vacuum deposition, molecular beam epitaxy (MBE method) and coating methods using a solution such as a dipping, spin coating, casting, bar coating, and roll coating.

Although the thickness of each organic layer of the organic EL device according to this exemplary embodiment is not particularly limited, the thickness is generally preferably in a range of several nanometers to 1 µm because an excessively-thinned film likely entails defects such as a pin hole while an excessively-thickened film requires high voltage to be applied and deteriorates efficiency.

Second Exemplary Embodiment

Next, an organic EL device according to a second exemplary embodiment will be described below.

The organic EL device according to the second exemplary embodiment is different in that the emitting layer includes the first host material, the second host material and the phosphorescent material. In this case, the first host material is the biscarbazole derivative according to the exemplary embodiment represented by the formulae (1) to (3).

The organic-EL-device material represented by the formulae (1) to (3) has a biscarbazole skeleton having an excellent hole transporting capability and a heterocyclic skeleton having an excellent electron transporting capability, which leads to a bi-polar performance sufficient for functioning as a single host. However, a luminous efficiency and a lifetime of the multilayered organic EL device depend on a carrier balance of an entire organic EL device. Main factors for controlling the carrier balance are carrier transporting capability of each of the organic layers and carrier injecting capability in the interfacial region of separate organic layers. In order to balance the carrier injecting capability to neighboring layers in the emitting layer (recombination region), it is preferable to adjust the carrier balance not by a single host material but by a plurality of host materials. Specifically, it is preferable that, in addition to the first host material, the second host material is suitably selected as a cohost and used in the emitting layer.

When a material having a poor electron injecting capability (e.g., metal chelate complex) is used as the cathode, a carrier balance in the emitting layer becomes shifted toward the cathode. For improving such a disadvantage, it is preferable to select a material having a high electron transporting capability as the second host material. Specifically, the host material of this exemplary embodiment is preferably represented by a formula (5) or (6).

$$(Cz^-)_a A^3 \qquad (5)$$

$$Cz(^-A^3)_b \qquad (6)$$

In the formula (5) or (6): Cz represents a substituted or unsubstituted arylcarbazolyl group or carbazolylaryl group;

$A^3$ represents a group represented by a formula (7A) below; and a and b each represent an integer of 1 to 3.

$$(M^1)_c\text{-}(L^5)_d\text{-}(M^2)_e \qquad (7A)$$

In the formula (7A): $M^1$ and $M^2$ each independently represent a substituted or unsubstituted nitrogen-containing aromatic heterocyclic ring or nitrogen-containing fused aromatic heterocyclic ring having 2 to 40 ring carbon atoms; $M^1$ and $M^2$ may be the same or different;

$L^5$ represents a single bond, substituted or unsubstituted aromatic hydrocarbon group having 6 to 30 carbon atoms, substituted or unsubstituted fused aromatic hydrocarbon group having 6 to 30 carbon atoms, substituted or unsubstituted cycloalkylene group having 5 to 30 carbon atoms, substituted or unsubstituted aromatic heterocyclic group having 2 to 30 carbon atoms, or substituted or unsubstituted fused aromatic heterocyclic group having 2 to 30 carbon atoms;

c represents an integer of 0 to 2; d represents an integer of 1 to 2; e represents an integer of 0 to 2; and c+e represents 1 or more.

Compounds Represented by Formulae (5) and (6)

Cz is a substituted or unsubstituted arylcarbazolyl group or substituted or unsubstituted carbazolylaryl group.

An arylcarbazolyl group means a carbazolyl group having at least one aryl group or heteroaryl group as a substituent, in which a position where the aryl group or heteroaryl group is substituted does not matter.

Specific examples are as follows. In the following chemical formulae, Ar represents an aryl group or heteroaryl group. * represents a position where another group is bonded.

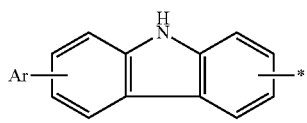

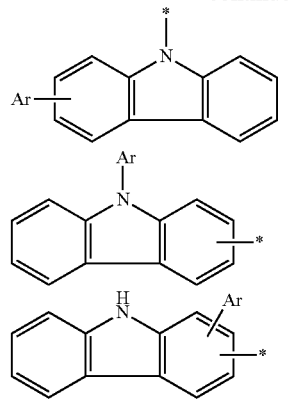

A carbazolylaryl group means an aryl group having at least one carbazolyl group as a substituent, in which a position where the aryl group is substituted does not matter.

Specific examples are as follows. In the following chemical formulae, Ar represents an aryl group. * represents a position where another group is bonded.

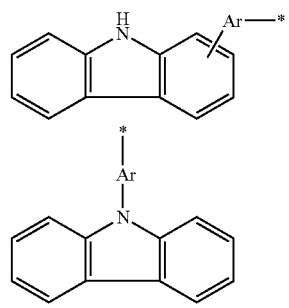

A substituted arylcarbazolyl group means the arylcarbazolyl group having at least one substituent irrespective of a substitution position. A substituted carbazolylaryl group means the carbazolylaryl group having at least one substituent irrespective of a substitution position.

In the formulae (5) and (6), a and b each represent an integer of 1 to 3.

An aryl group in the arylcarbazolyl group or carbazolylaryl group preferably has 6 to 30 carbon atoms. Examples of the aryl group are a phenyl group, naphthyl group, anthryl group, phenanthryl group, naphthacenyl group, pyrenyl group, fluorenyl group, biphenyl group and terphenyl group, among of which a phenyl group, naphthyl group, biphenyl group and terphenyl group are preferable.

Examples of the heteroaryl group in the arylcarbazolyl group are groups formed based on rings of pyridine, pyrimidine, pyrazine, triazine, aziridine, azaindolizine, indolizine, imidazoles; indole, isoindole, indazole, purine, pteridine, d-carboline, naphthyridine, quinoxaline, terpyridine, bipyridine, acridine, phenanthroline, phenazine and imidazopyridine, among which rings of pyridine, terpyridine, pyrimidine, imidazopyridine and triazine are preferable.

A in the formulae (5) and (6) is a group represented by the formula (7A).

In the formula (7A), $M^1$ and $M^2$ each independently represent a substituted or unsubstituted nitrogen-containing heterocyclic group having 2 to 40 ring carbon atoms. $M^1$ and $M^2$ may be the same or different.

Examples of the nitrogen-containing heterocyclic ring in the arylcarbazolyl group are groups formed based on rings of pyridine, pyrimidine, pyrazine, triazine, aziridine, azaindolizine, indolizine, imidazoles, indole, isoindole, indazole, purine, pteridine, â-carboline, naphthyridine, quinoxaline, terpyridine, bipyridine, acridine, phenanthroline, phenazine and imidazopyridine, among which rings of pyridine, terpyridine, pyrimidine, imidazopyridine and triazine are preferable.

$L^5$ represents a single bond, substituted or unsubstituted aromatic hydrocarbon group or fused aromatic hydrocarbon group having 6 to 30 carbon atoms, substituted or unsubstituted cycloalkylene group having 5 to 30 carbon atoms, or substituted or unsubstituted aromatic heterocyclic group or fused aromatic heterocyclic group having 2 to 30 carbon atoms.

c represents an integer of 0 to 2; d represents an integer of 1 to 2; e represents an integer of 0 to 2; and c+e represents 1 or more.

Examples of the aromatic hydrocarbon group or fused aromatic hydrocarbon group having 6 to 30 carbon atoms are a phenyl group, biphenyl group, terphenyl group, naphthyl group, anthranil group, phenanthryl group, pyrenyl group, crycenyl group, fluoranthenyl group and perfluoroaryl group, fluorenyl group, and 9,9-dimethylfluorenyl group, among which a phenyl group, biphenyl group, terphenyl group and perfluoroaryl group are preferable.

Examples of the cycloalkylene group having 5 to 30 carbon atoms are cyclopentyl group, cyclohexylene group, and cyclohepthylene group, among which a cyclohexylene group is preferable.

Examples of the aromatic heterocyclic group or fused aromatic heterocyclic group having 2 to 30 carbon atoms are 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthirolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group, among which a pyridinyl group and quinolyl group are preferable.

Examples of the substituents for Cz, $M^1$ and $M^2$ in the formulae (5), (6) and (7A) are a halogen atom such as chlorine, bromine and fluorine, carbazole group, hydroxyl group, substituted or unsubstituted amino group, nitro group, cyano group, silyl group, trifluoromethyl group, carbonyl group, carboxyl group, substituted or unsubstituted alkyl group, substituted or unsubstituted alkenyl group, substituted or unsubstituted arylalkyl group, substituted or unsubstituted aromatic hydrocarbon group or fused aromatic hydrocarbon group, substituted or unsubstituted aromatic heterocyclic group or fused aromatic heterocyclic group, substituted or unsubstituted aralkyl group, substituted or unsubstituted aryloxy group, and substituted or unsubstituted alkyloxy group. Among these, a fluorine atom, methyl group, perfluorophenylene group, phenyl group, naphthyl group, pyridyl group, pyrazil group, pyrimidyl group, adamantyl group, benzyl group, cyano group and silyl group are preferable.

Bonding patterns of the compound represented by the formula (5) or (6) are shown in Table 1 below in accordance with values of a and b.

TABLE 1

| a = b = 1 | a = 2 | a = 3 | b = 2 | b = 3 |
|---|---|---|---|---|
| Cz — $A^3$ | Cz — $A^3$ — Cz | Cz—$A^3$—Cz<br>\|<br>Cz | $A^3$—Cz—$A^3$ | $A^3$—Cz—$A^3$<br>\|<br>$A^3$ |

Bonding patterns of the compound represented by the formula (7A) are shown in Tables 2 and 3 below in accordance with values of c, d and e.

TABLE 2

| No | c | d | e | Bonding Patterns |
|---|---|---|---|---|
| (1) | 0 | 1 | 1 | $L^5-M^2$ |
| (2) | 0 | 1 | 2 | $L^5-M^2-M^2$, $M^2-L^5-M^2$ |
| (3) | 0 | 2 | 1 | $L^5-L^5-M^2$, $L^5-M^2-L^5$ |
| (4) | 0 | 2 | 2 | $L^5-L^5-M^2-M^2$, $M^2-L^5-L^5-M^2$, $$L-M^2-M^2-L^5 \atop \underset{L^5}{\mid} \quad \underset{L^5}{\mid}$$, $$M^2-L^5-M^2 \atop \underset{L^5}{\mid}$$, $$L^5-M^2-L^5 \atop \underset{M^2}{\mid}$$ |
| (5) | 1 | 1 | 0 | the same as [1] ($M^2$ is replaced with $M^1$) |
| (6) | 1 | 1 | 1 | $M^1-L^5-M^2$ |
| (7) | 1 | 1 | 2 | $M^1-L^5-M^2-M^2$, $$M^1-L^5-M^2 \atop \underset{M^2}{\mid}$$ |
| (8) | 1 | 2 | 0 | the same as [3] ($M^2$ is replaced with $M^1$) |
| (9) | 1 | 2 | 1 | $M^1-L^5-L^5-M^2$, $L^5-M^1-L^5-M^2$, $L^5-M^1-L^5-M^2$ |
| (10) | 1 | 2 | 2 | $M^1-L^5-L^5-M^2-M^2$, $M^2-L^5-M^1-L^5-M^2$, $M^2-M^2-L^5-M^1-L^5$, $$M^1-L^5-L^5 \atop \underset{M^2}{\mid} \underset{M^2}{\mid}$$, $$M^1-L^5-L^5-M^2 \atop \underset{M^2}{\mid}$$, $$L^5-L^5-M^2-M^2 \atop \underset{M^1}{\mid}$$, $$L^5-M^1-L^5-M^2 \atop \underset{M^2}{\mid}$$, $$M^1-L^5-L^5 \atop \underset{M^2}{\mid}{}_2$$ |
| (11) | 2 | 1 | 0 | the same as [2] ($M^2$ is replaced with $M^1$) |
| (12) | 2 | 1 | 1 | the same as [7] ($M^2$ is replaced with $M^1$) |
| (13) | 2 | 1 | 2 | $M^1-M^1-L^5-M^2-M^2$, $$M^1-L^5-M^1 \atop \underset{M^2}{\mid}$$, $$M^1-L^5-M^2-M^2 \atop \underset{M^1}{\mid}$$ |

TABLE 3

| No | c | d | e | Bonding Patterns |
|---|---|---|---|---|
| (14) | 2 | 2 | 0 | the same as [4] ($M^2$ is replaced with $M^1$) |
| (15) | 2 | 2 | 1 | the same as [10] ($M^2$ is replaced with $M^1$) |
| (16) | 2 | 2 | 2 | $M^1-M^1-L^5-L^5-M^2-M^2$, $$M^1-M^1-L^5-M^2-M^2 \atop \underset{L^5}{\mid}$$, $$M^1-L^5-L^5-M^2-M^2 \atop \underset{M^1}{\mid}$$, $$M^1-L^5-L^5 \atop \underset{M^2}{\diagup}\underset{M^2}{\diagdown}$$, $$M^1-M^1-L^5-L^5-M^2 \atop \underset{M^2}{\mid}$$, $$M^1 \atop \underset{L^5-L^5-M^2-M^2}{\mid}$$, $$M^1-L^5-L^5-M^1 \atop \underset{M^2}{\mid}\ \underset{M^2}{\mid}$$ |

Cz bonded to A may be bonded to any one of $M^1$, $L^5$ and $M^2$ of the formula (7A) representing A.

For instance, when a=b=1 and Cz-$A^3$-Cz are given in the formula (5) or (6) and [6] (c=d=e=1) of Table 2 is given in the formula (A), three bonding patterns of Cz-$M^1$-$L^5$-$M^2$, $M^1$-$L^5$(Cz)-$M^2$, and $M^1$-$L^5$-$M^2$-Cz are listed.

Moreover, for instance, when a=2 and Cz-$A^3$-Cz are given in the formula (5) and [7] (c=d=1, e=2) Table 2 is given in the formula (7A), the following bonding patterns are listed.

$$Cz-M^1-L^5-M^2-M^2 \atop \underset{Cz}{\mid} \qquad Cz-M^1-L^5-M^2-M^2 \atop \underset{Cz}{\mid}$$

-continued $$Cz-M^1-L^5-M^2-M^2 \quad Cz-M^1-L^5-M^2-M^2-Cz$$
$$\phantom{Cz-M^1-L^5-M^2-M^2\quad Cz-M^1-L^5-M^2-M^2-}\underset{Cz}{|}$$

$$\underset{Cz}{\overset{Cz}{M^1-L^5-M^2-M^2}} \quad \underset{Cz\ Cz}{M^1-L^5-M^2-M^2}$$

$$\underset{Cz}{M^1-L^5-M^2-M^2-Cz} \quad \underset{Cz}{M^1-L^5-M^2-M^2}$$

$$\underset{Cz}{M^1-L^5-M^2-M^2-Cz} \quad \underset{Cz}{M^1-L^5-M^2-M^2-Cz}$$

$$\underset{Cz\ M^2}{Cz-M^1-L^5-M^2} \quad \underset{M^2}{\overset{Cz}{Cz-M^1-L^5-M^2}}$$

$$\underset{\underset{Cz}{M^2}}{Cz-M^1-L^5-M^2} \quad \underset{M^2}{\overset{Cz\diagdown\diagup Cz}{M^1-L^5-M^2}}$$

$$\underset{M^2}{M^1-L^5-M^2-Cz} \quad \underset{Cz-M^2-Cz}{M^1-L^5-M^2} \quad \underset{M^2-Cz}{M^1-L^5-M^2-Cz}$$

In the bonding patterns of the formulae (5), (6) and (7A) and exemplary combinations of the groups as described above, compounds represented by [1] to [4] below are preferable.

[1] a=1 is given in the formula (5) and c=1 and d=0 are given in the formula (7A).

In the formula (5), Cz is a substituted or unsubstituted arylcarbazolyl group or substituted or unsubstituted carbazolylaryl group.

In the formula (7A): $M^1$ is a substituted or unsubstituted nitrogen-containing six-membered or seven-membered hetero ring having 4 to 5 ring carbon atoms, substituted or unsubstituted nitrogen-containing five-membered hetero ring having 2 to 4 ring carbon atoms, substituted or unsubstituted nitrogen-containing hetero ring having 8 to 11 ring carbon atoms, substituted or unsubstituted imidazopyridinyl ring; and $L^5$ is a substituted or unsubstituted aryl group or aromatic hydrocarbon group or fused aromatic hydrocarbon group having 6 to 30 carbon atoms and substituted or unsubstituted aromatic heterocyclic group or fused aromatic heterocyclic group having 2 to 30 carbon atoms.

[2] a=2 is given in the formula (5) and c=1 and e=0 are given in the formula (7A).

In the formula (5), Cz is a substituted or unsubstituted arylcarbazolyl group or substituted or unsubstituted carbazolylaryl group.

In the formula (7A): $M^1$ is a substituted or unsubstituted nitrogen-containing six-membered or seven-membered hetero ring having 4 to 5 ring carbon atoms, substituted or unsubstituted nitrogen-containing five-membered hetero ring having 2 to 4 ring carbon atoms, substituted or unsubstituted nitrogen-containing hetero ring having 8 to 11 ring carbon atoms, substituted or unsubstituted imidazopyridinyl ring; and $L^5$ is a substituted or unsubstituted aryl group or aromatic hydrocarbon group or fused aromatic hydrocarbon group having 6 to 30 carbon atoms and substituted or unsubstituted aromatic heterocyclic group or fused aromatic heterocyclic group having 2 to 30 carbon atoms.

[3] a=1 is given in the formula (5) and c=2 and e=0 are given in the formula (7A).

In the formula (5), Cz is a substituted or unsubstituted arylcarbazolyl group or substituted or unsubstituted carbazolylaryl group.

In the formula (7A): $M^1$ is a substituted or unsubstituted nitrogen-containing six-membered or seven-membered hetero ring having 4 to 5 ring carbon atoms, substituted or unsubstituted nitrogen-containing five-membered hetero ring having 2 to 4 ring carbon atoms, substituted or unsubstituted nitrogen-containing hetero ring having 8 to 11 ring carbon atoms, substituted or unsubstituted imidazopyridinyl ring; and $L^5$ is a substituted or unsubstituted aryl group or aromatic hydrocarbon group or fused aromatic hydrocarbon group having 6 to 30 carbon atoms and substituted or unsubstituted aromatic heterocyclic group or fused aromatic heterocyclic group having 2 to 30 carbon atoms.

[4] b=2 is given in the formula (6) and c=d=1 is given in the formula (7A).

In the formula (6), Cz is a substituted or unsubstituted arylcarbazolyl group or substituted or unsubstituted carbazolylaryl group.

In the formula (7A): $M^1$ is a substituted or unsubstituted nitrogen-containing six-membered or seven-membered hetero ring having 4 to 5 ring carbon atoms, substituted or unsubstituted nitrogen-containing five-membered hetero ring having 2 to 4 ring carbon atoms, substituted or unsubstituted nitrogen-containing hetero ring having 8 to 11 ring carbon atoms, substituted or unsubstituted imidazopyridinyl ring; and $L^5$ is a substituted or unsubstituted aryl group or aromatic hydrocarbon group or fused aromatic hydrocarbon group having 6 to 30 carbon atoms and substituted or unsubstituted aromatic heterocyclic group or fused aromatic heterocyclic group having 2 to 30 carbon atoms.

In the formulae (5) and (6), Cz is preferably a substituted or unsubstituted arylcarbazolyl group, more preferably phenylcarbozolyl group. Moreover, an aryl site of the arylcarbazolyl group is preferably substituted by a carbazolyl group.

Specific examples of the compound represented by the formula (5) according to this exemplary embodiment are shown below, but the compound represented by the formula (25) is not limited thereto.

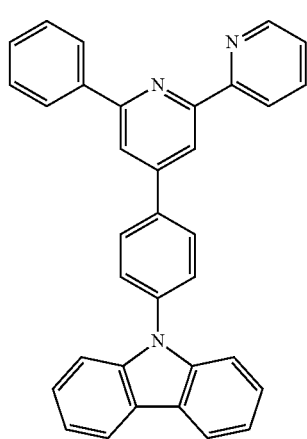

(A1)

-continued
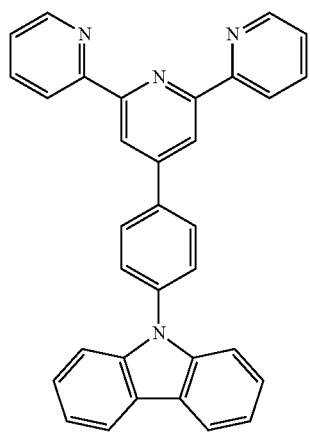
(A2)
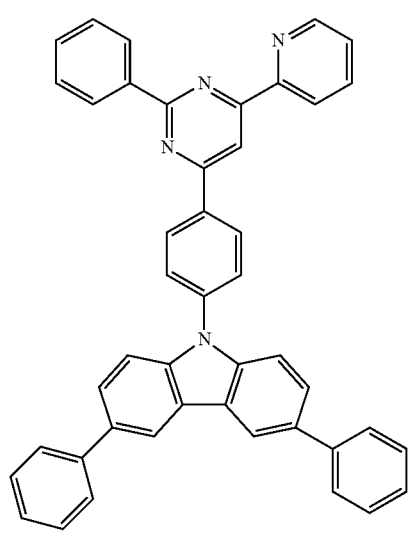
(A3)
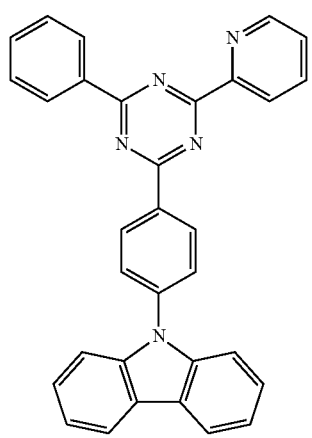
(A4)
-continued
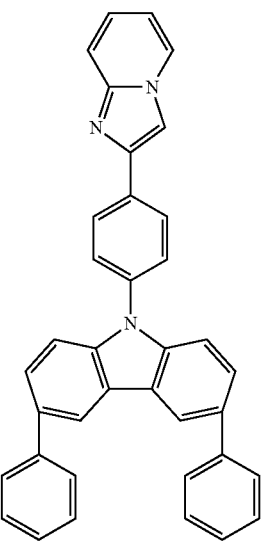
(A5)
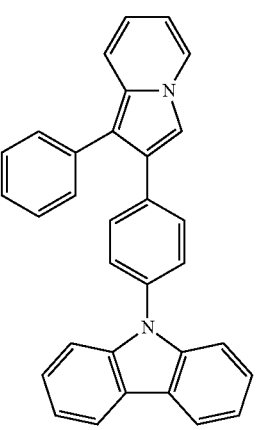
(A6)
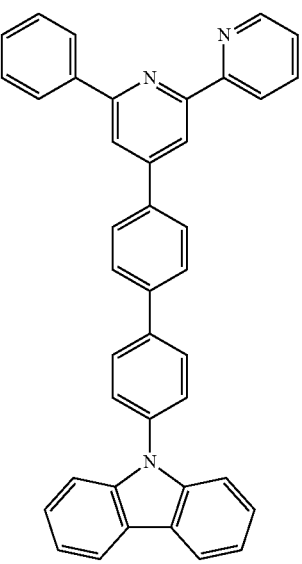
(A7)

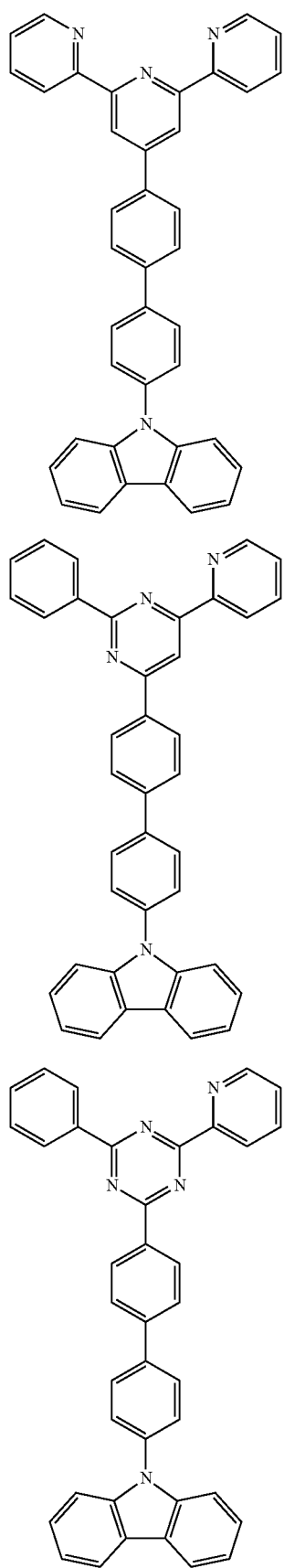
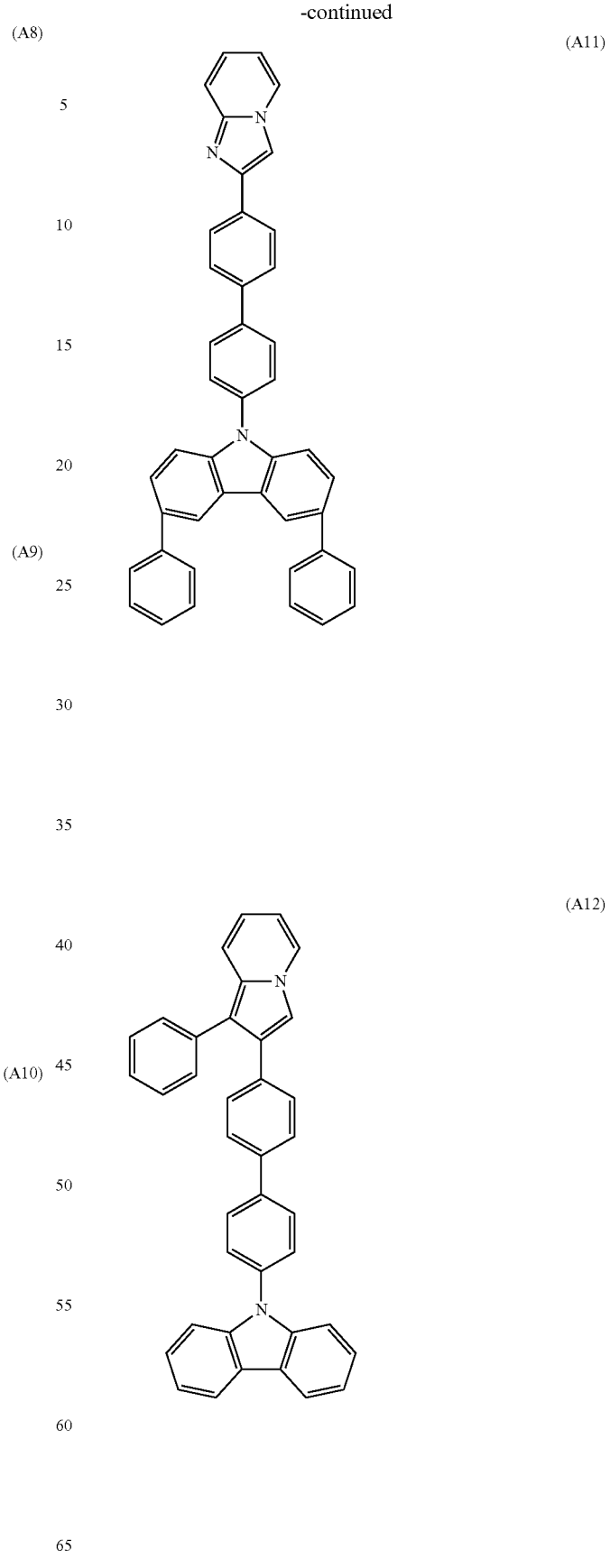

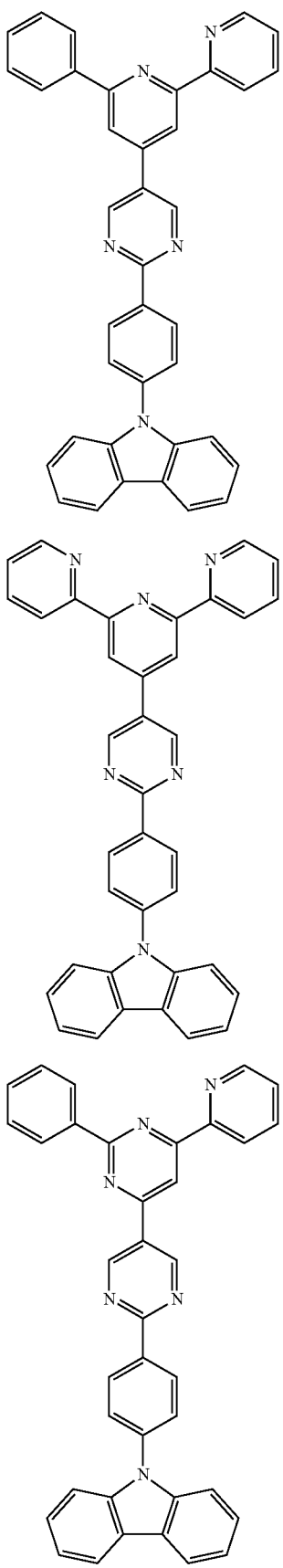
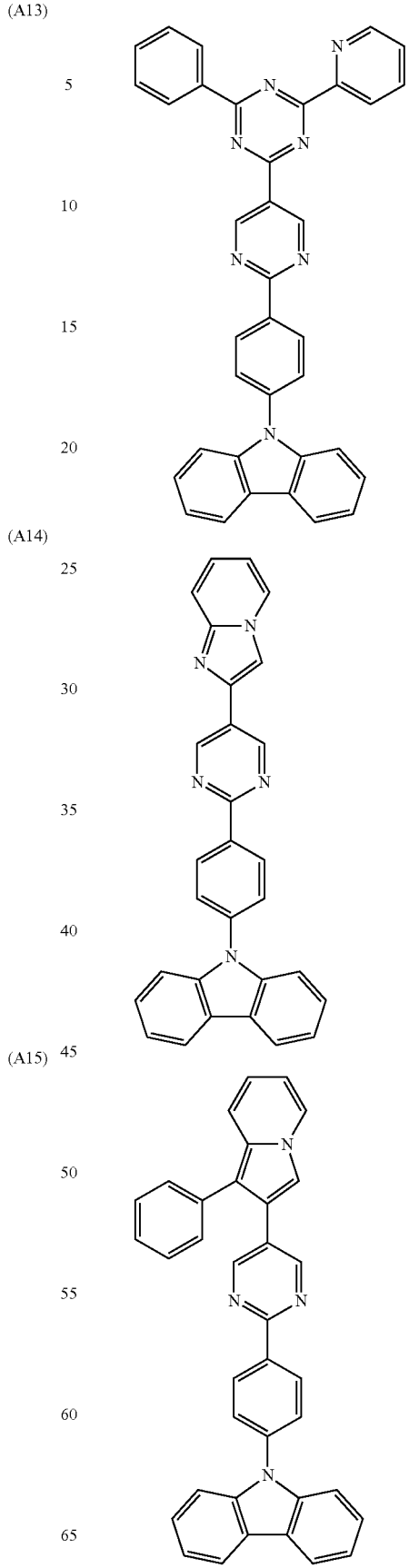

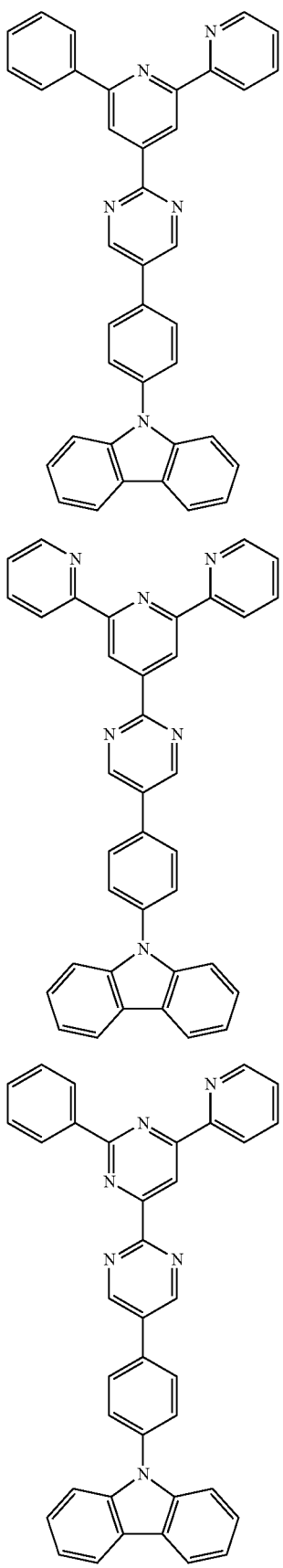
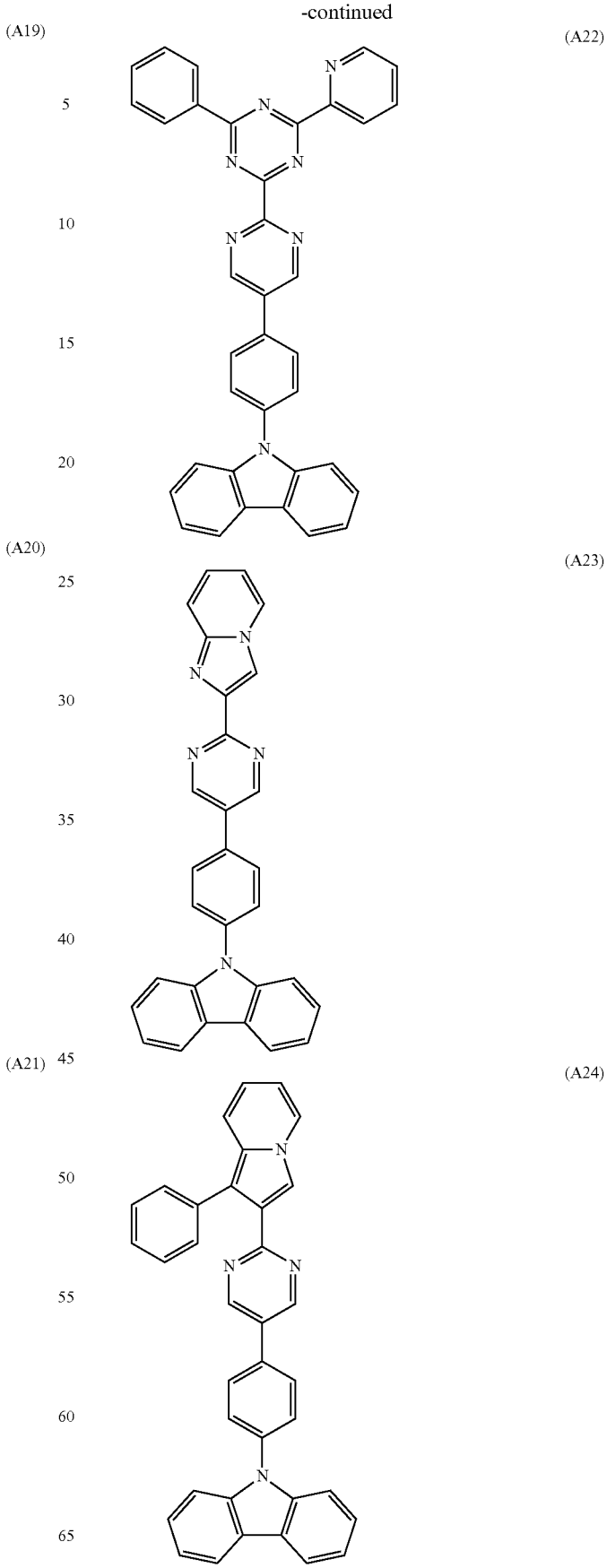

(A25)
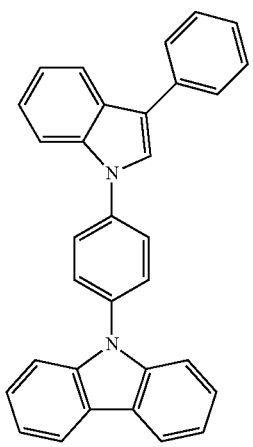
(A28)
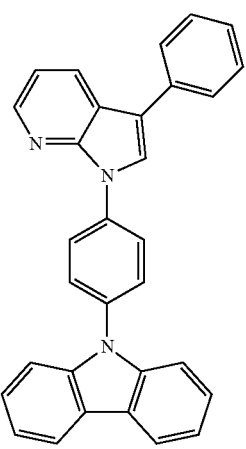
(A26)
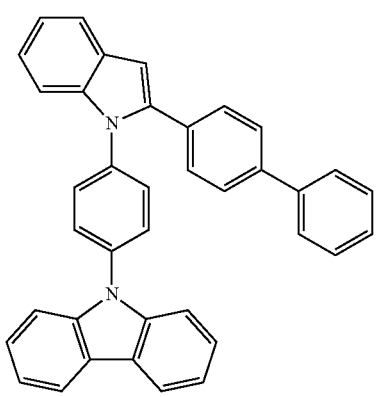
(A29)
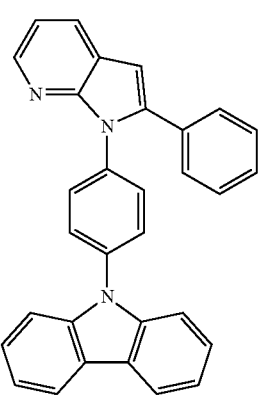
(A27)
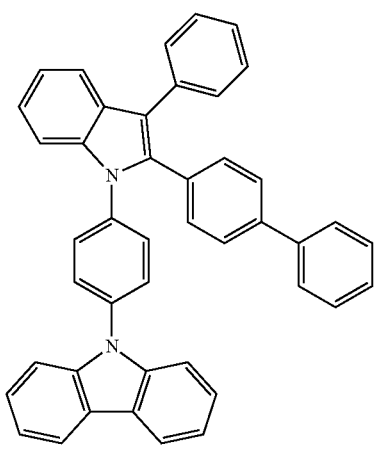
(A30)
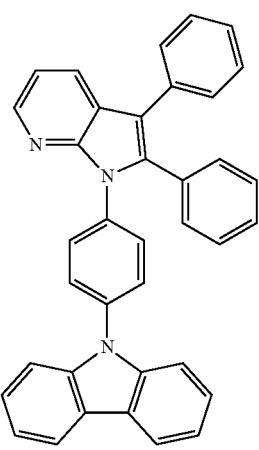

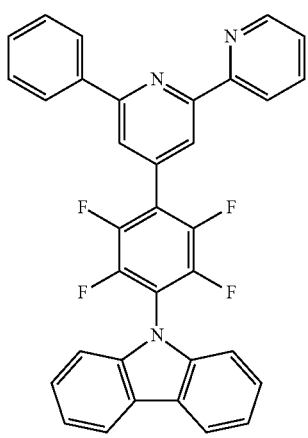 (A31)
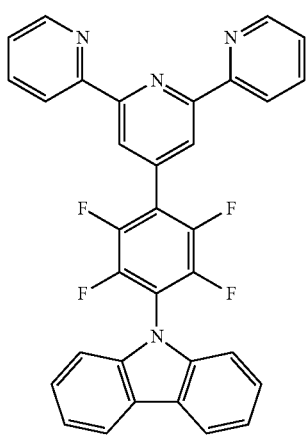 (A32)
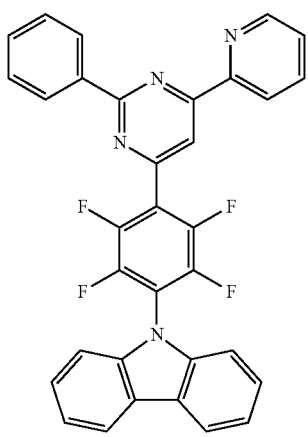 (A33)
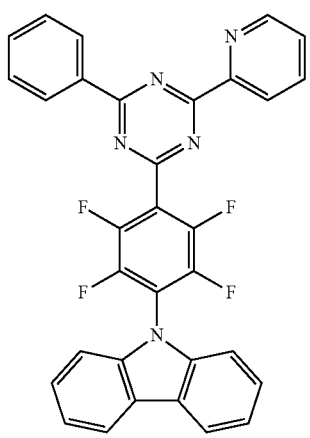 (A34)
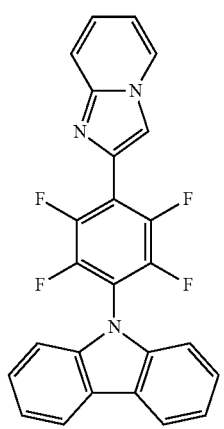 (A35)
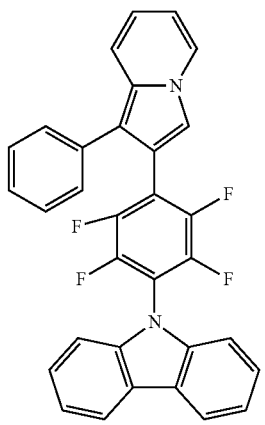 (A36)

-continued
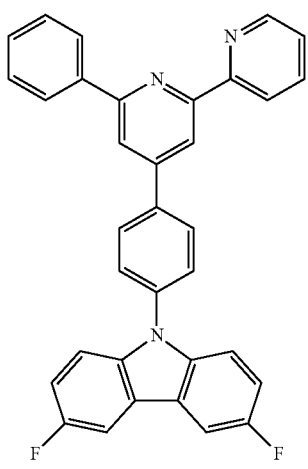 (A37)
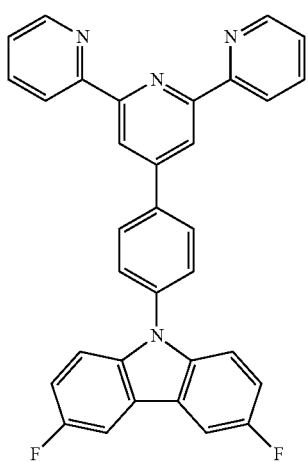 (A38)
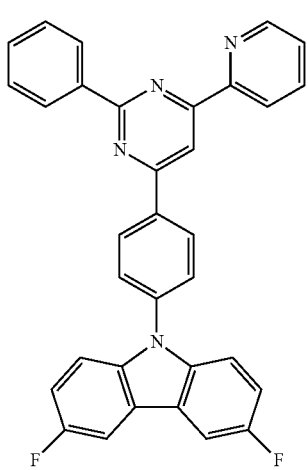 (A39)
-continued
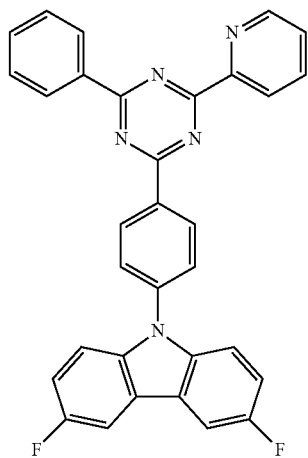 (A40)
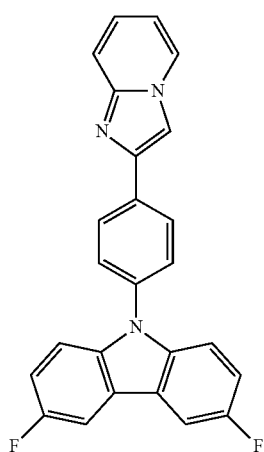 (A41)
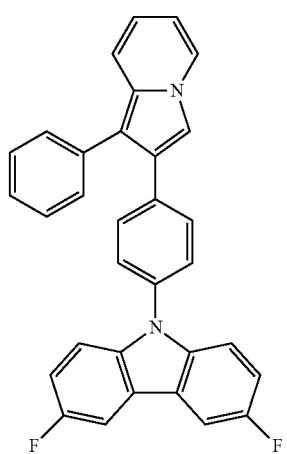 (A42)

(A43) 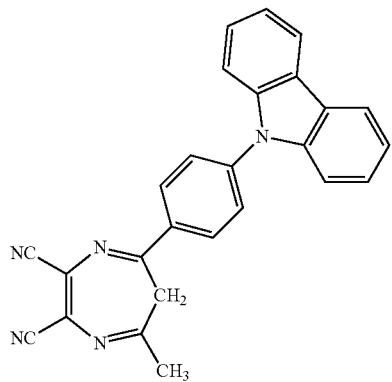
(A44) 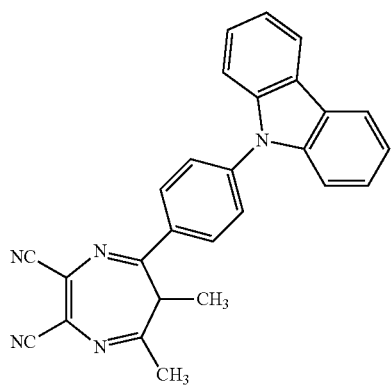
(A45) 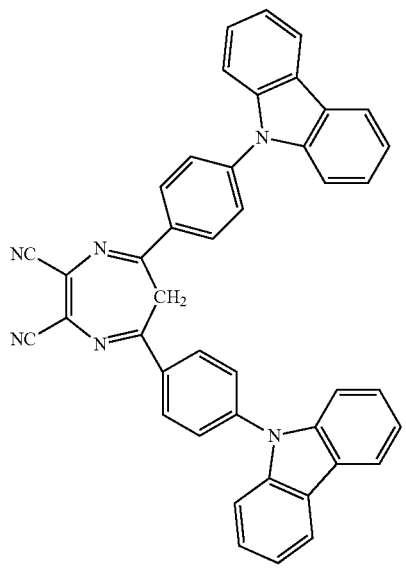
(A46) 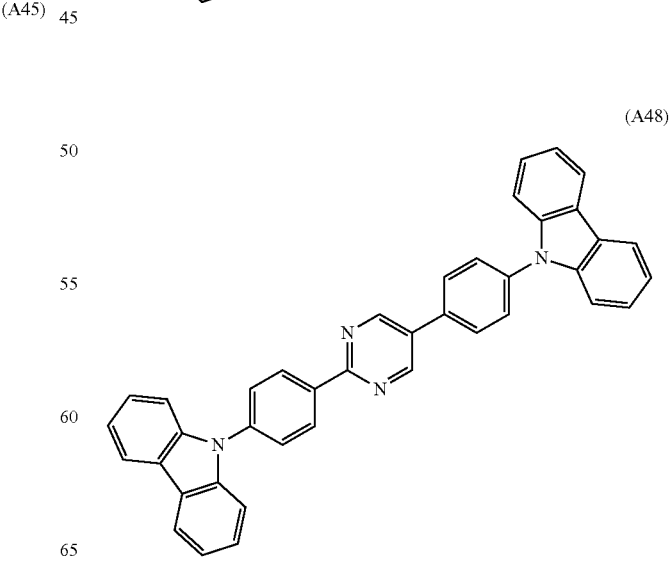
(A47)
(A48)

(A49)
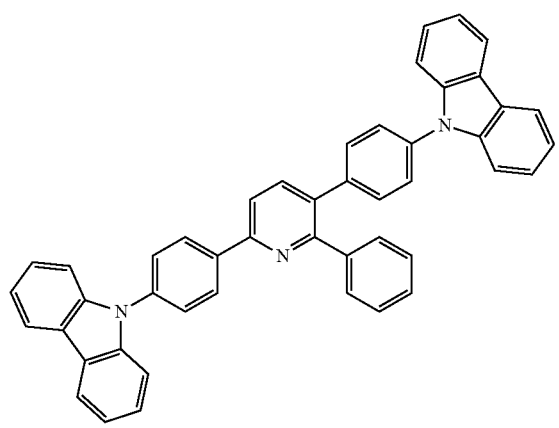
(A50)
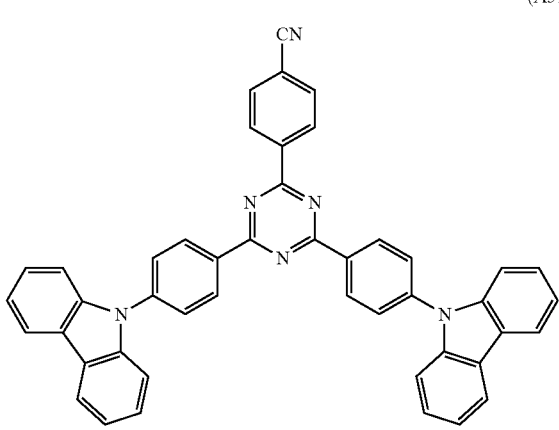
(A51)
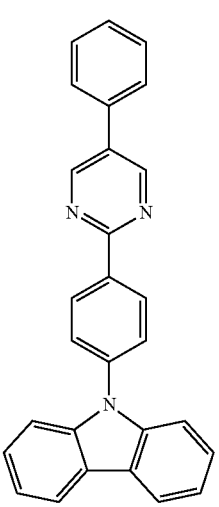
(A52)
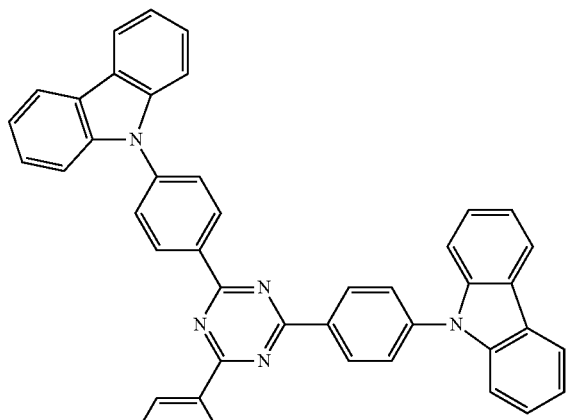
(A53)
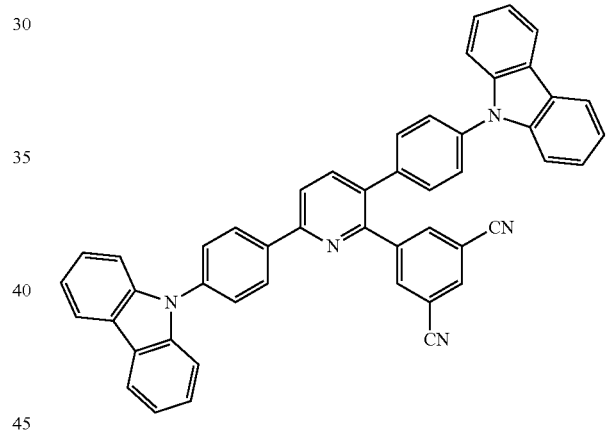
(A54)
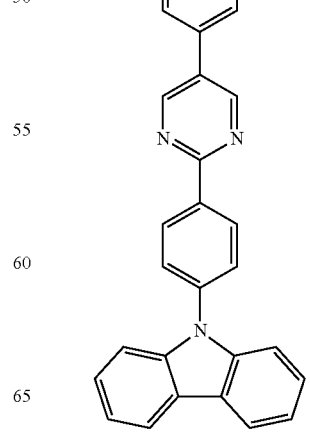

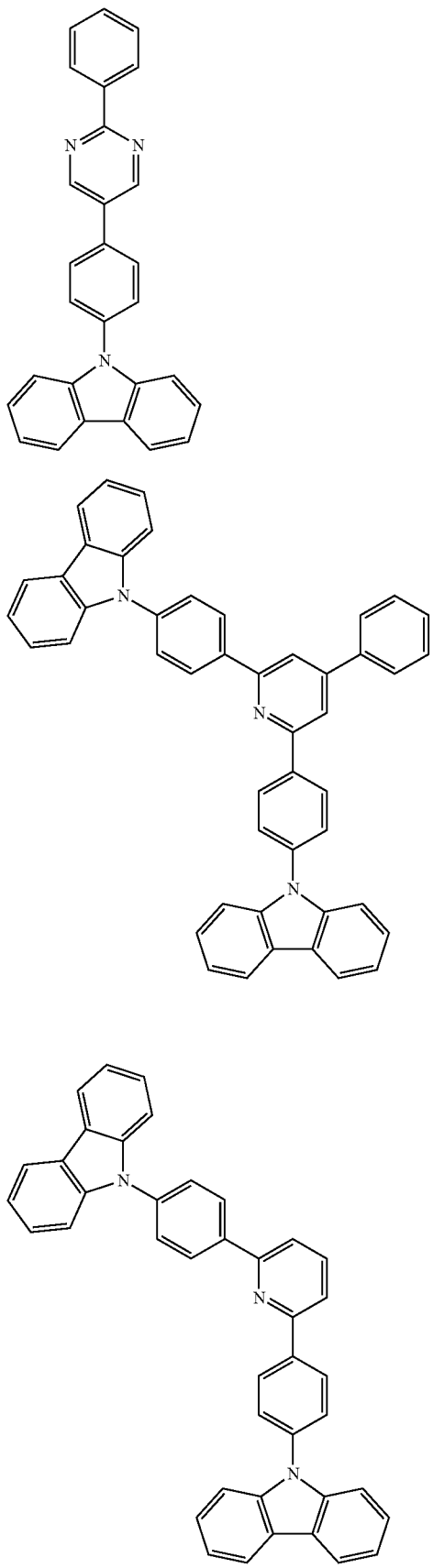
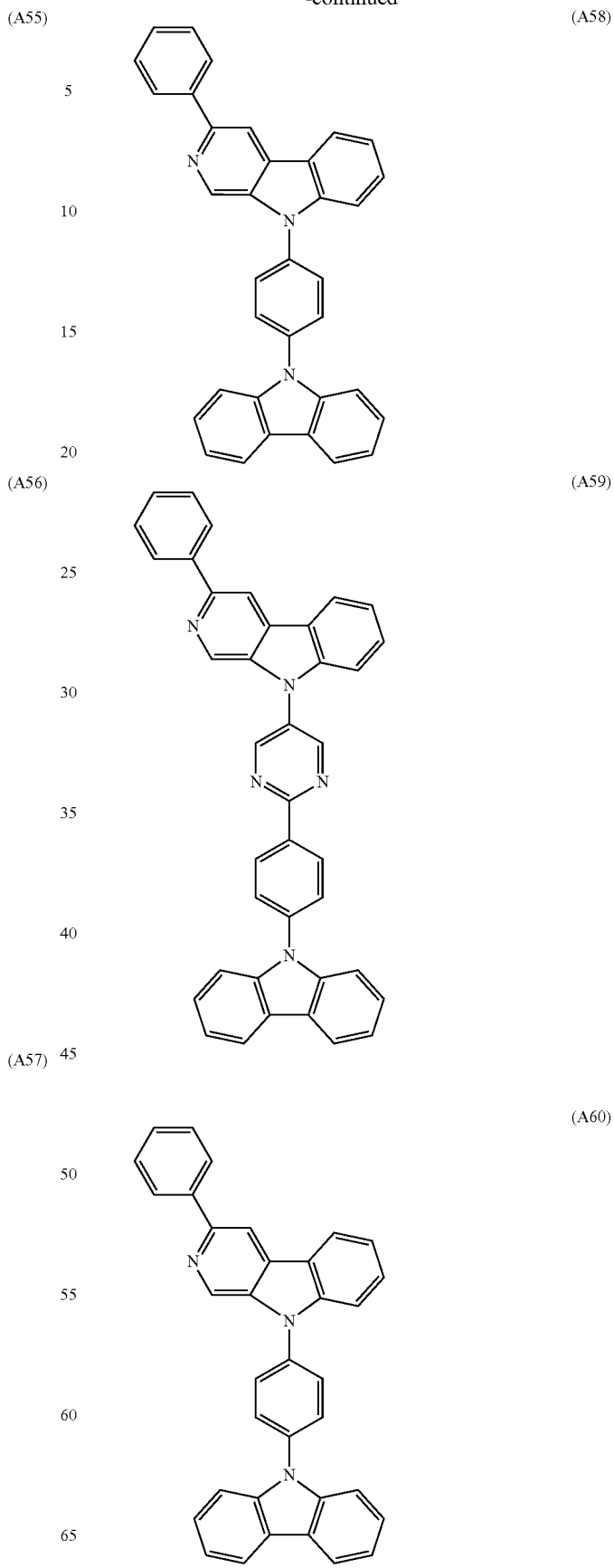

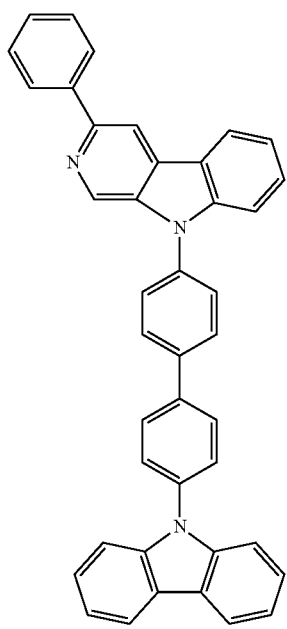
(A61)
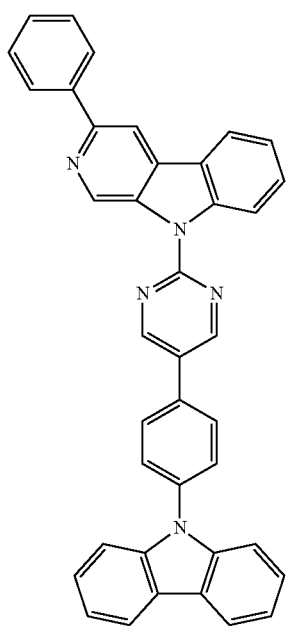
(A62)
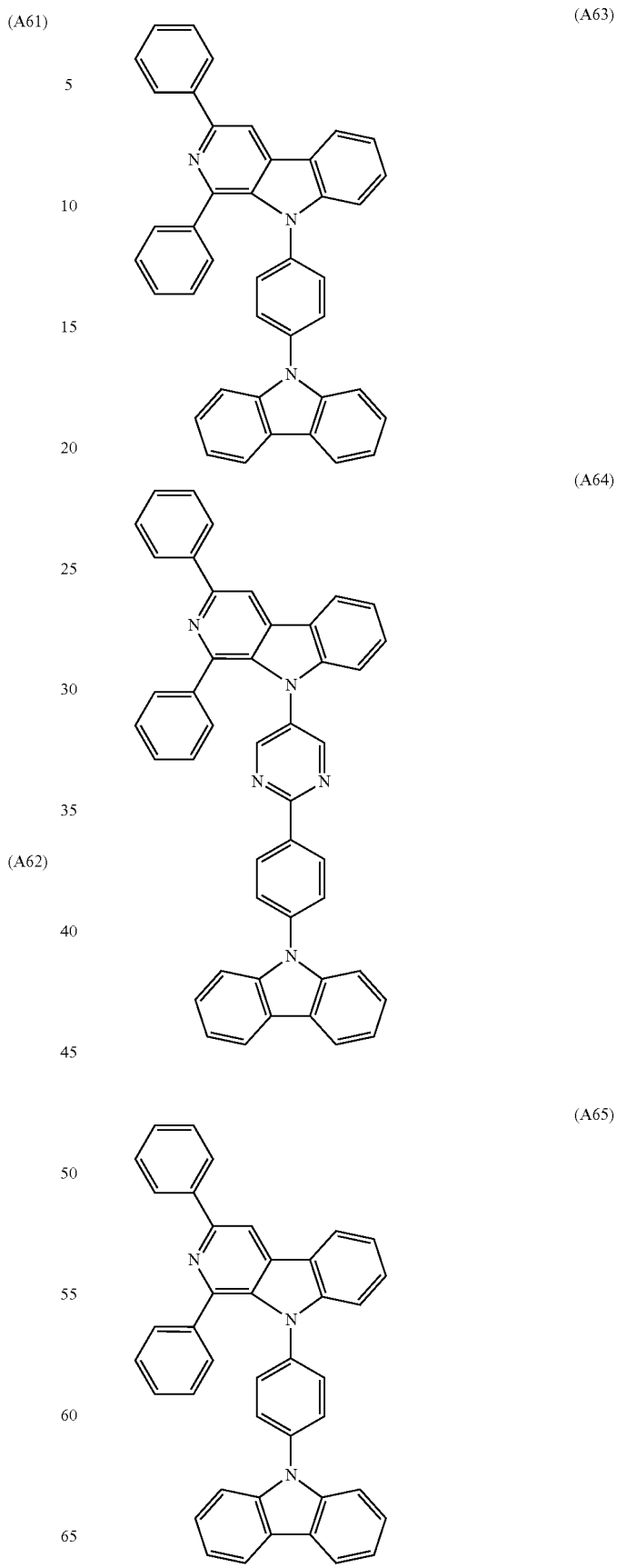

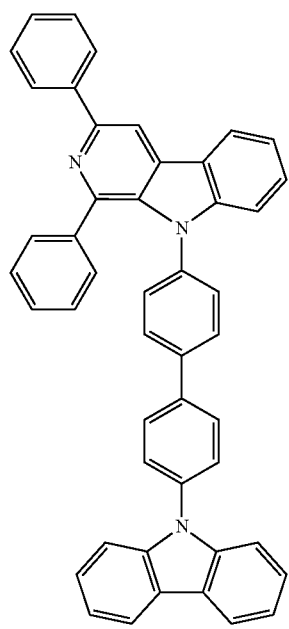 (A66)
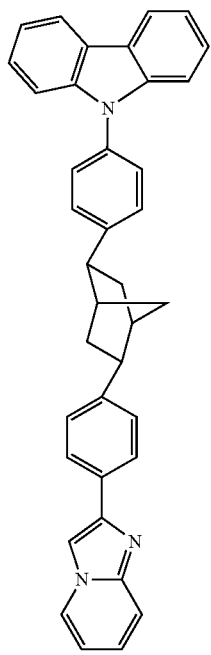 (A69)
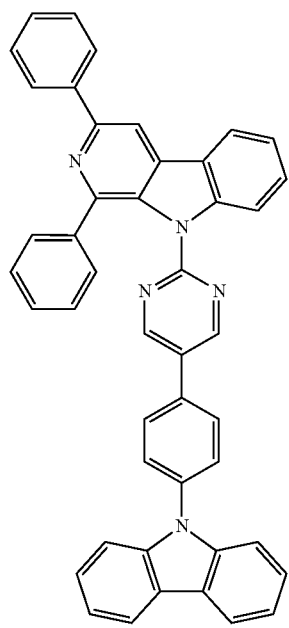 (A67)
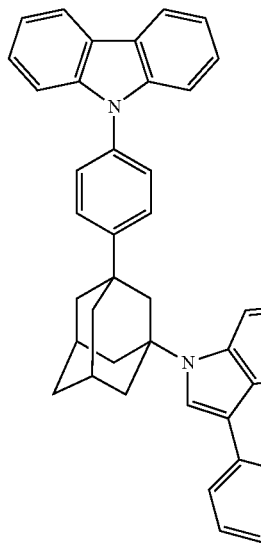 (A70)
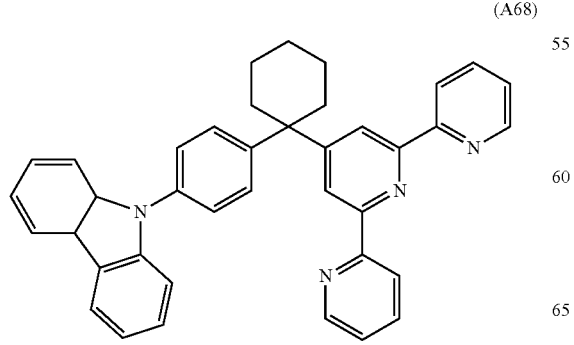 (A68)

-continued
(A71)
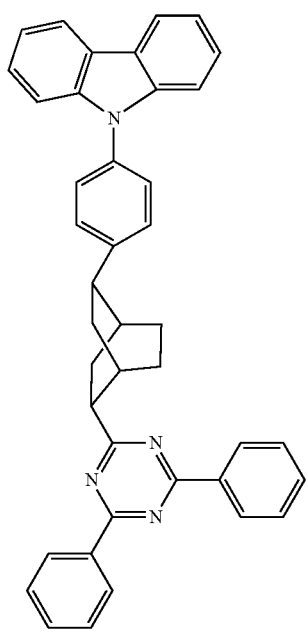
(A72)
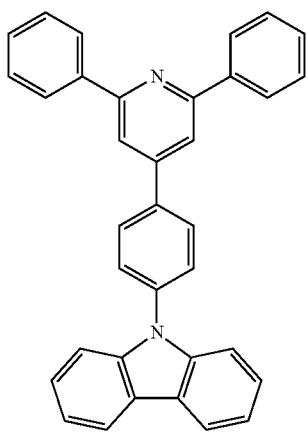
(A73)
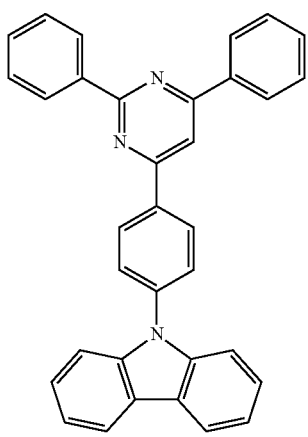
-continued
(A74)
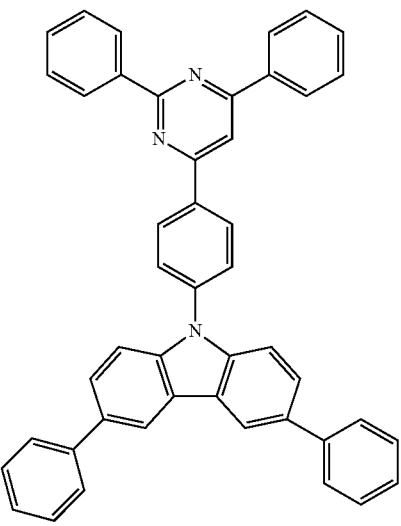
(A75)
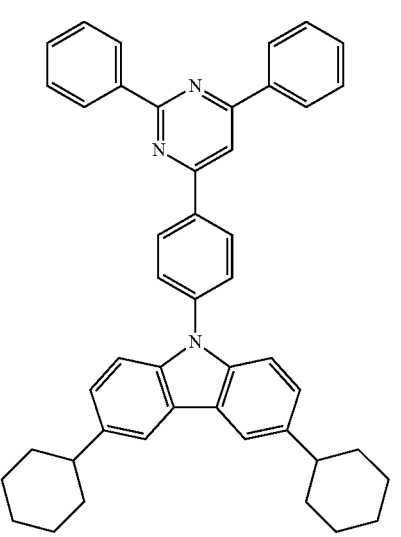
(A76)
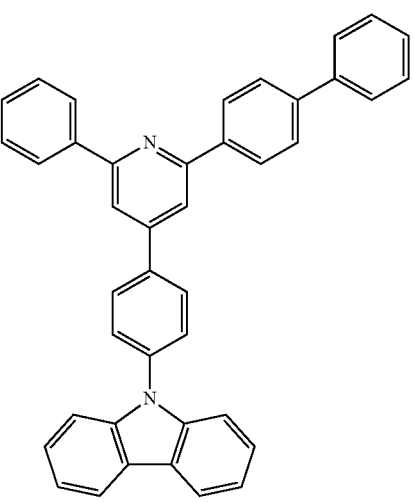

-continued
(A77)
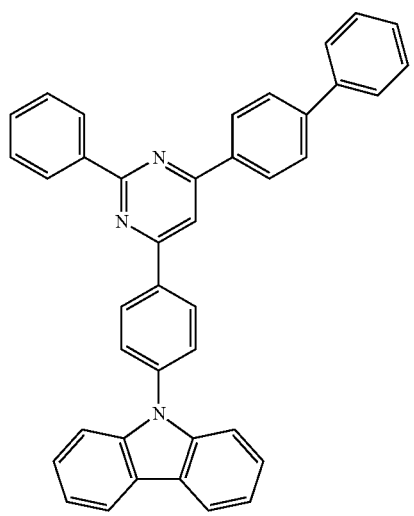
(A78)
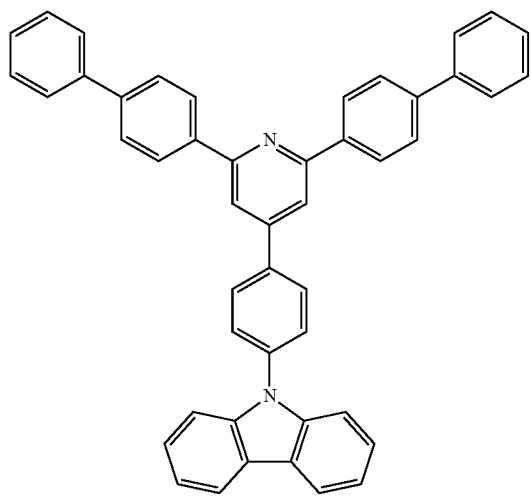
(A79)
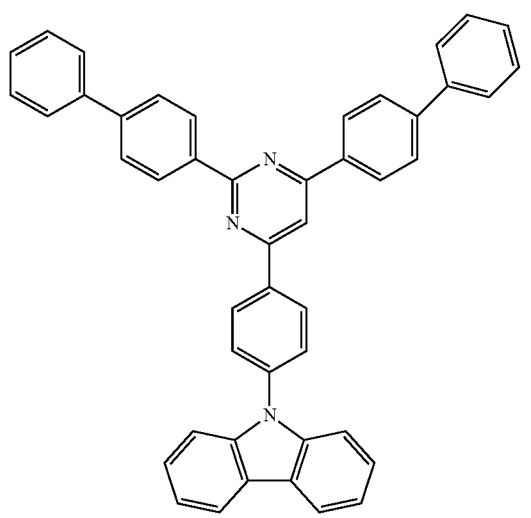
-continued
(A80)
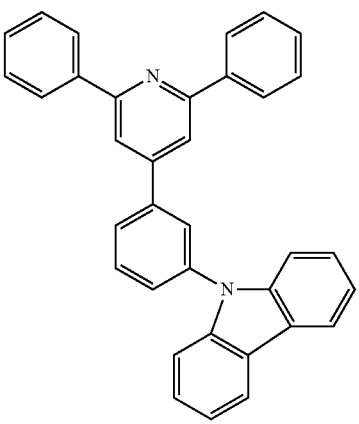
(A81)
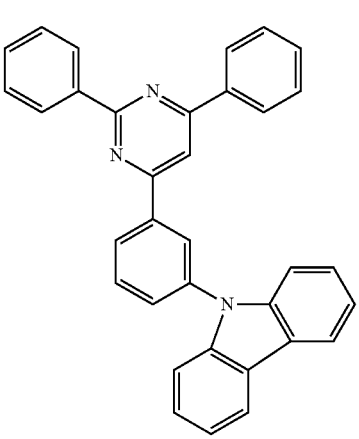
(A82)
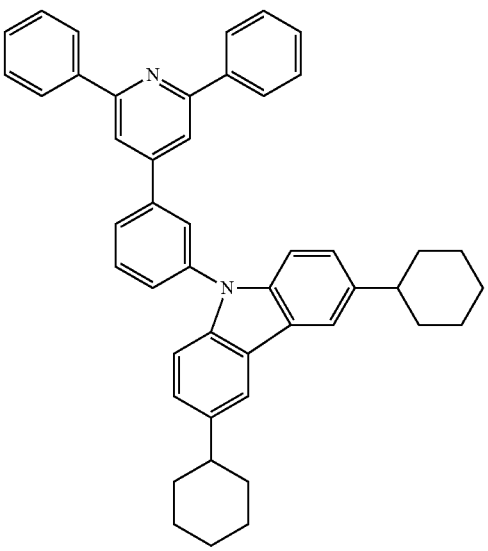

-continued
(A83)
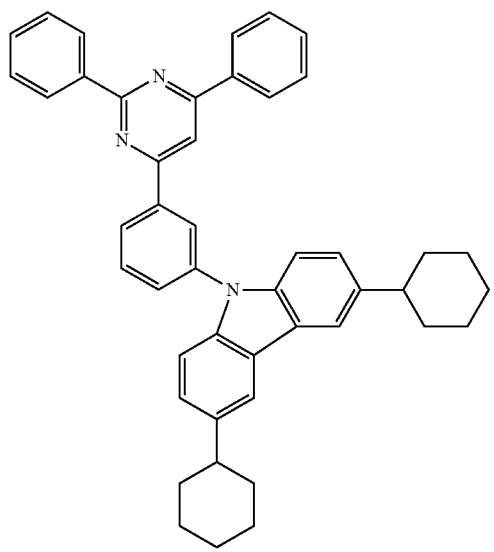
(A84)
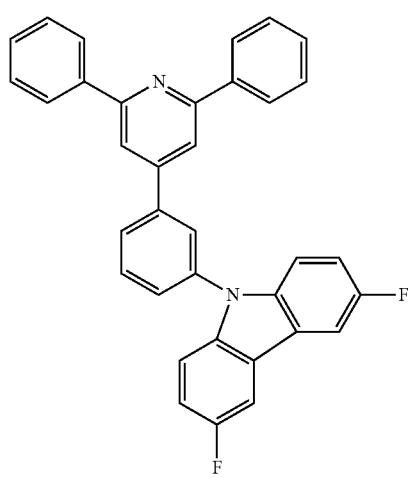
(A85)
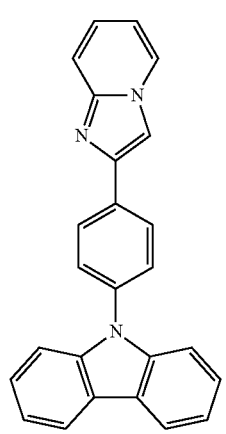
-continued
(A86)
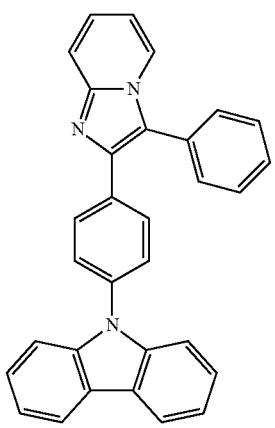
(A87)
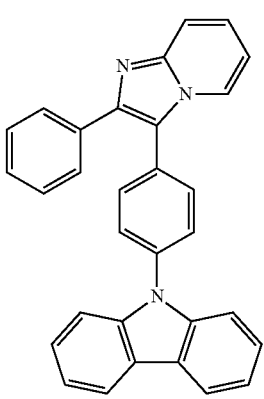
(A88)
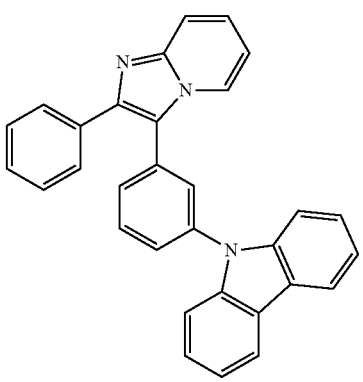
(A89)
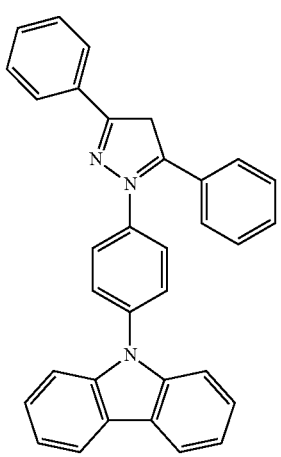

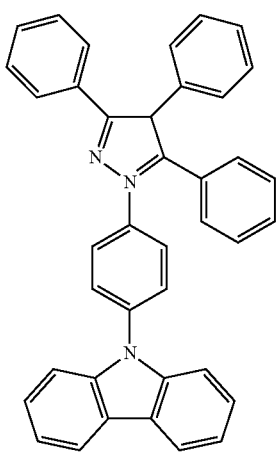
(A90)
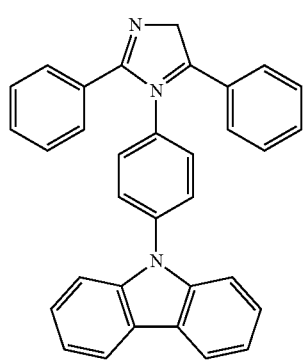
(A91)
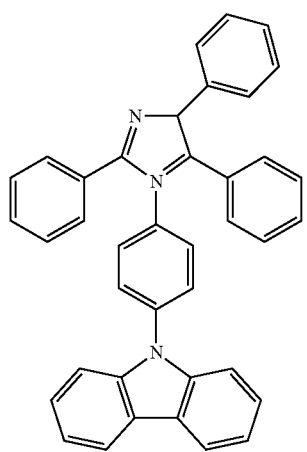
(A92)
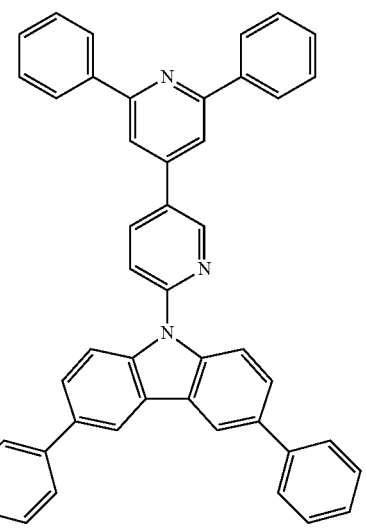
(A93)
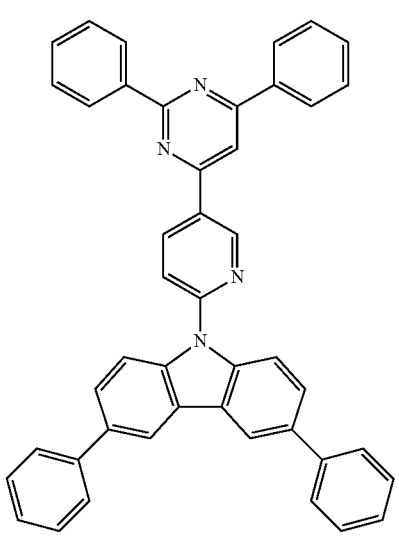
(A94)
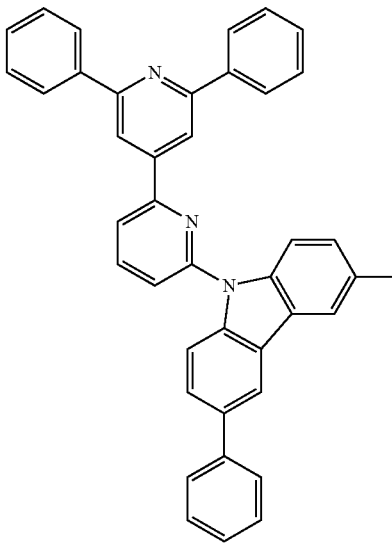
(A95)

-continued
(A96)
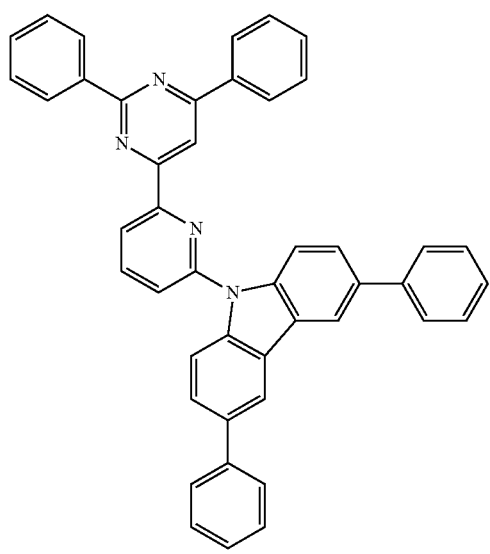
(A97)
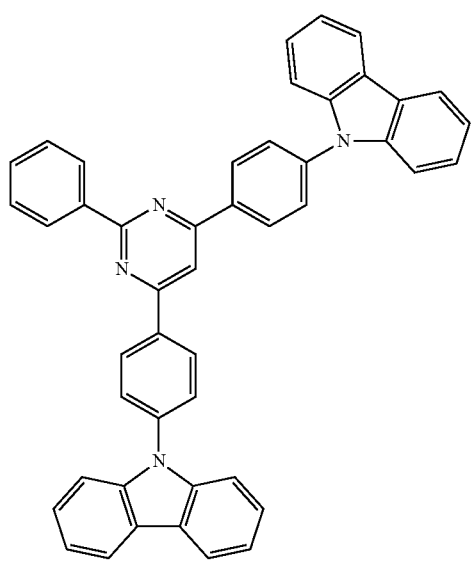
(A99)
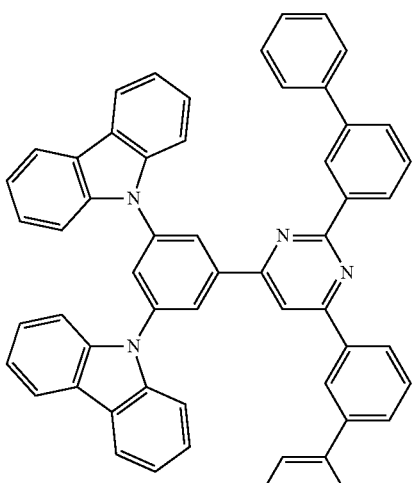
(A100)
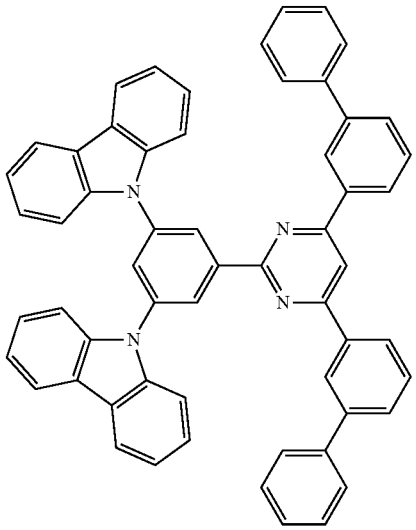
(A101)
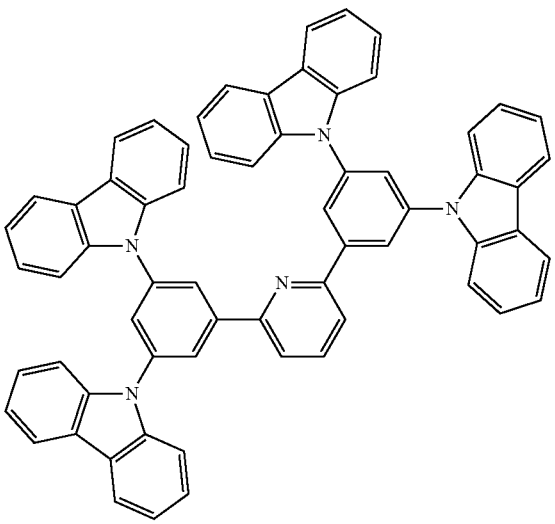

(A102)
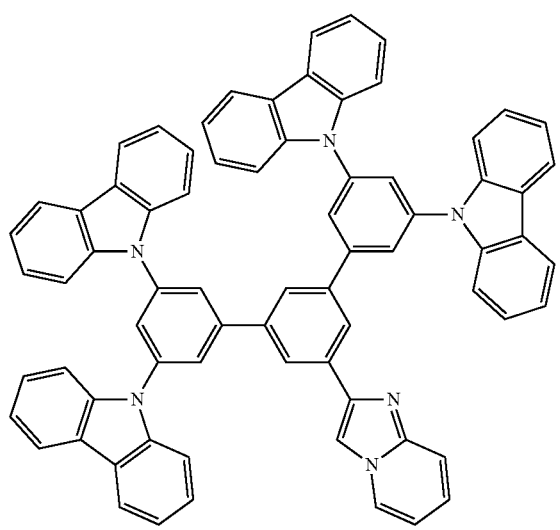
(A103)
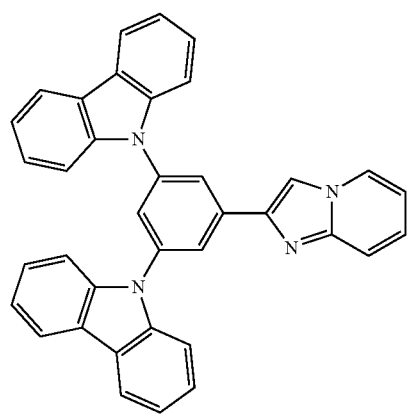
(A104)
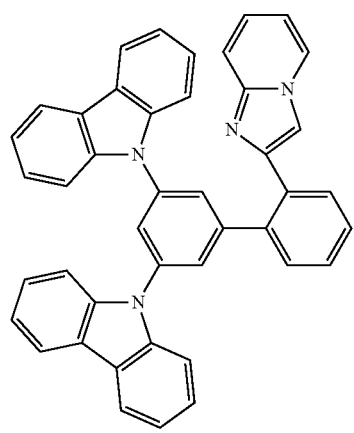
(A105)
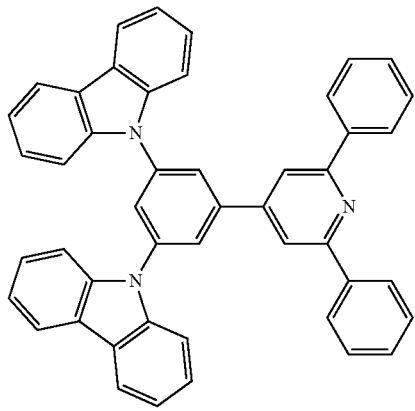
(A106)
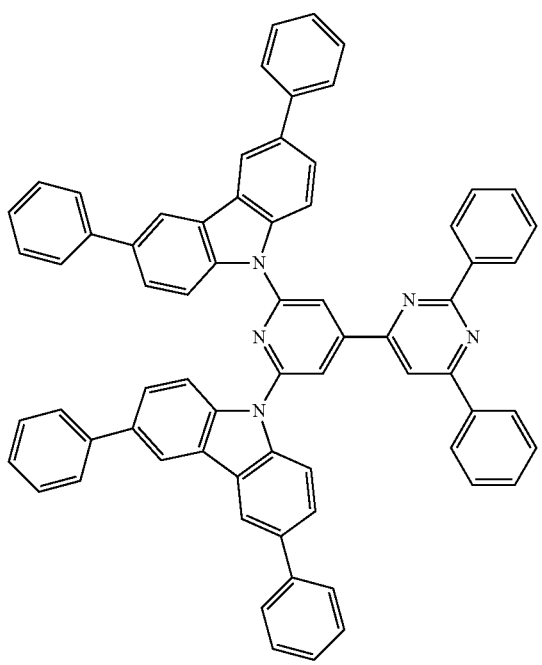
(A107)
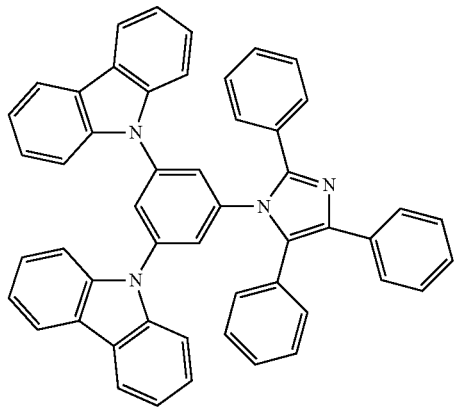

(A108)
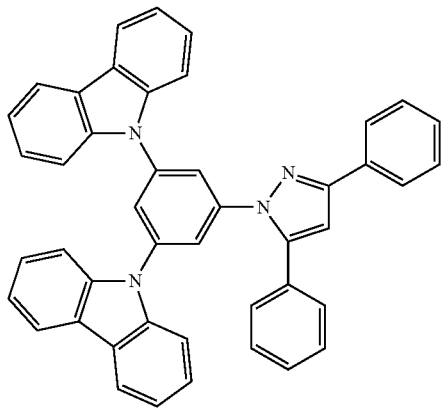
(A109)
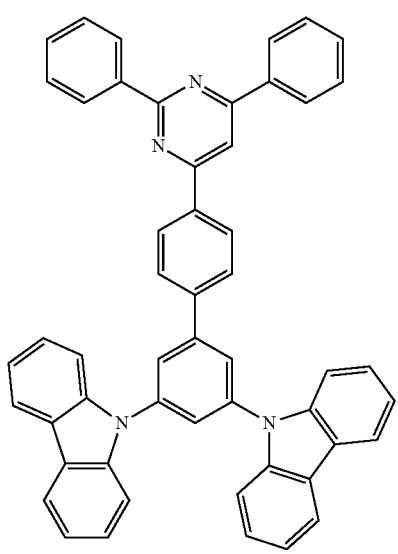
(A110)
(A111)
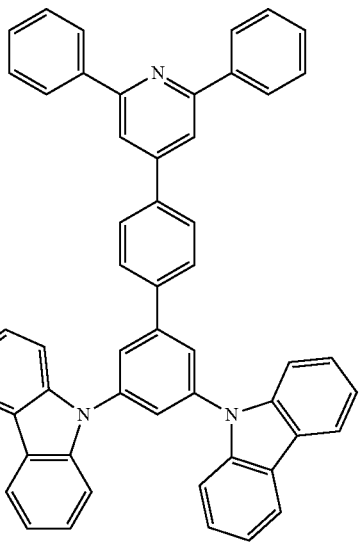
(A112)
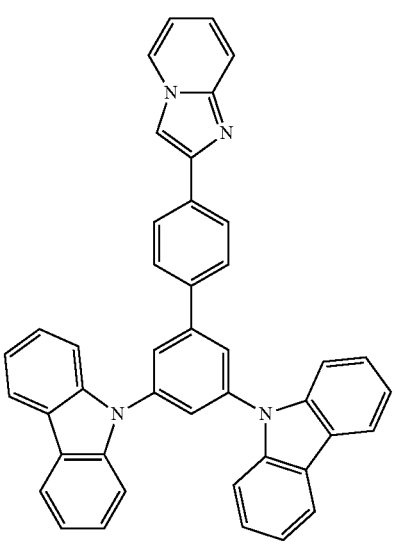
(A113)
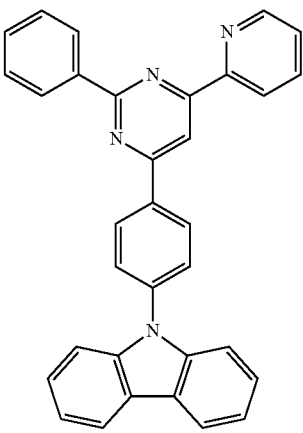

(A114)
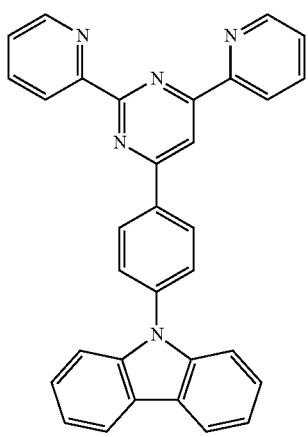
Specific examples of the compound represented by the formula (6) are shown below, but the compound represented by the formula (6) is not limited thereto.
(B1)
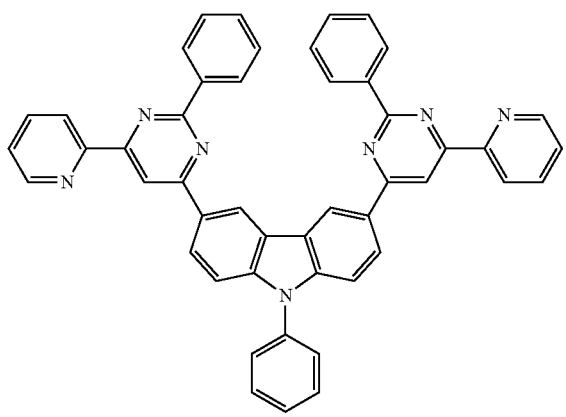
(B2)
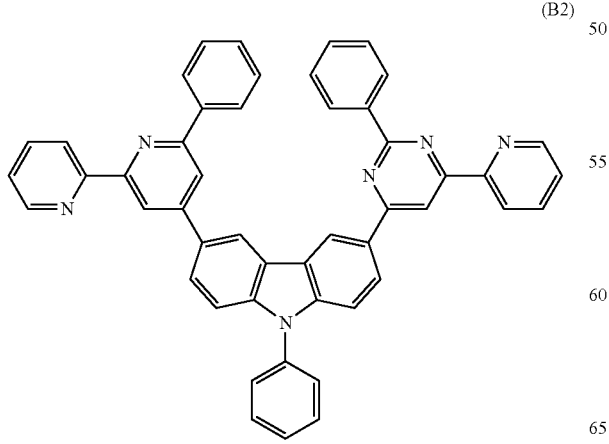
(B3)
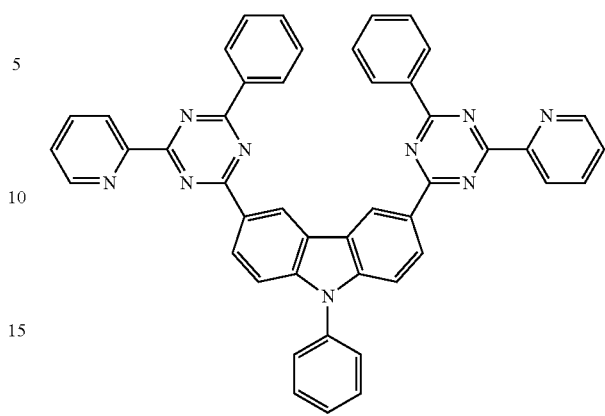
(B4)
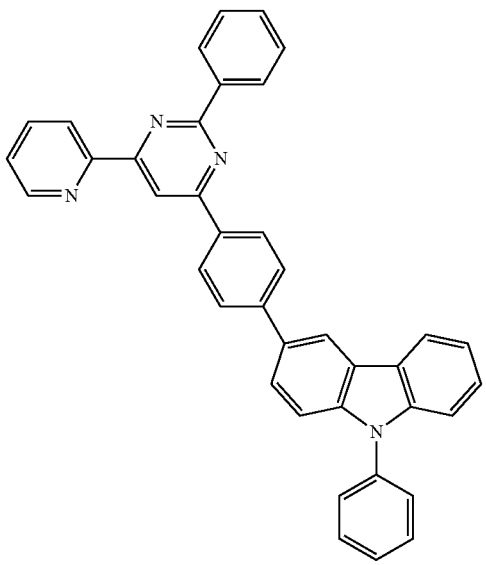
(B5)
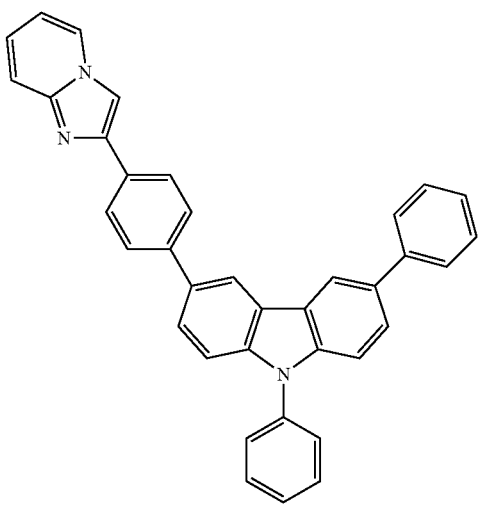

(B6)
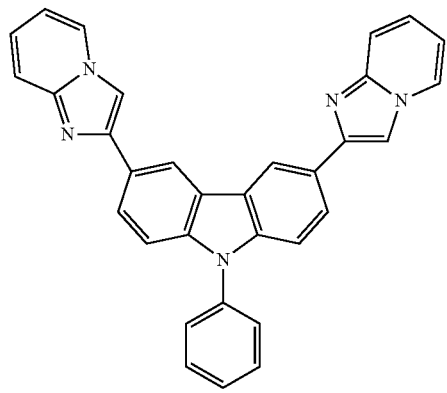
(B9)
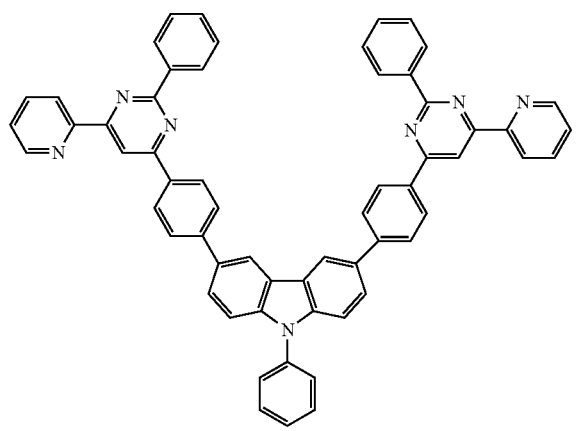
(B7)
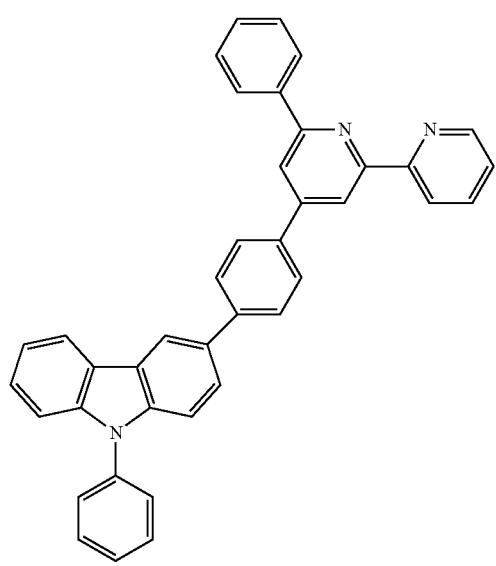
(B10)
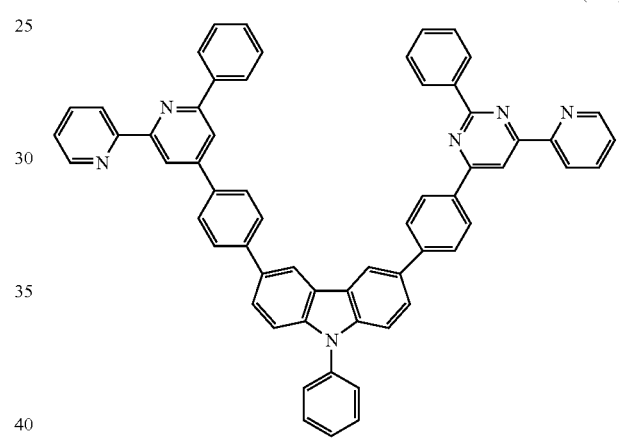
(B8)
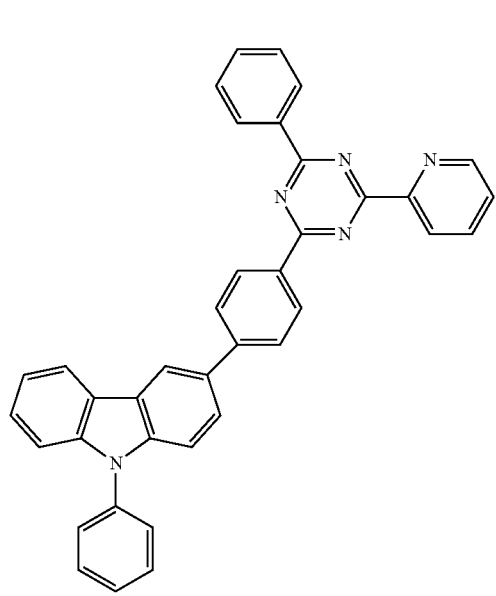
(B11)
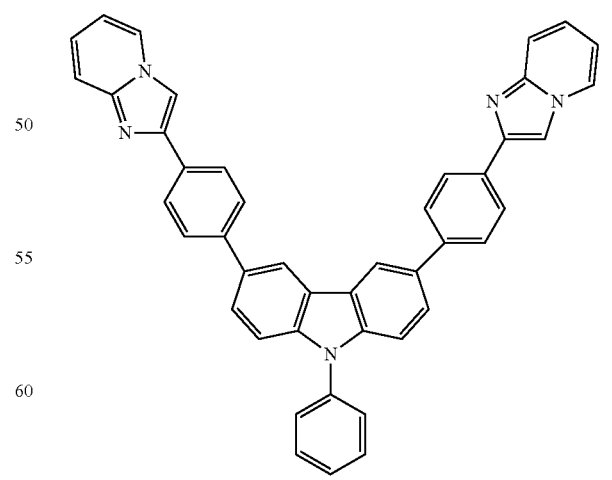

-continued (B12)
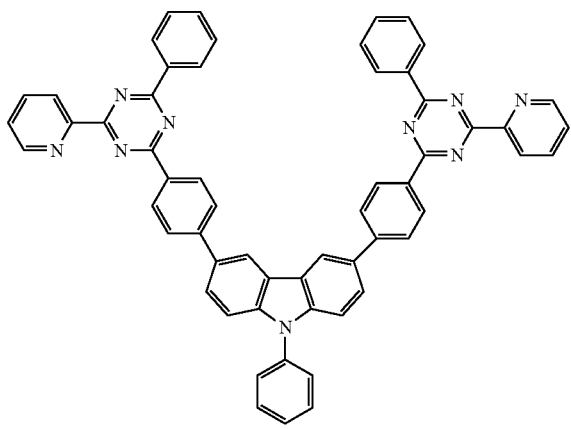

(B13)
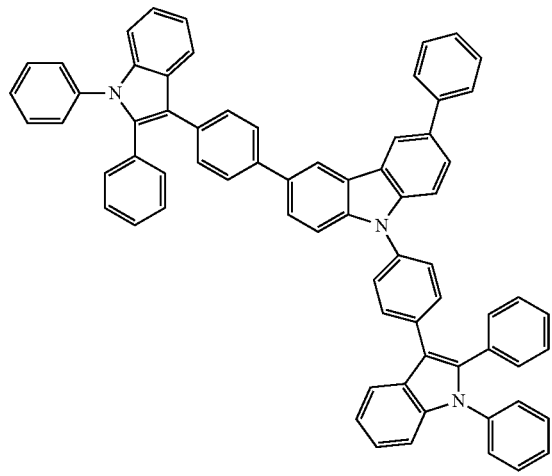

(B14)
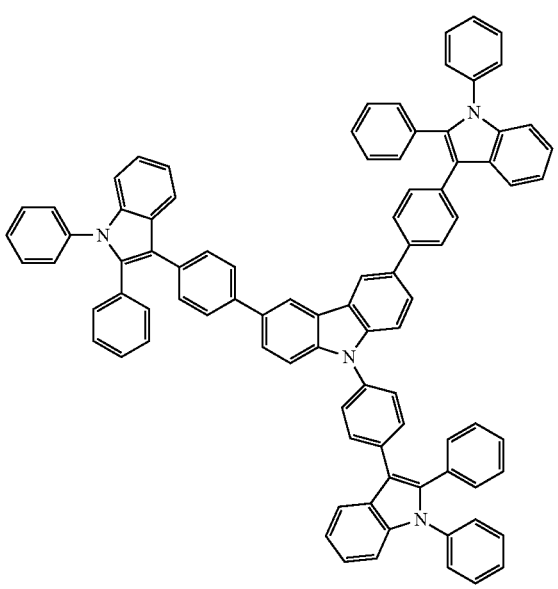

The compound represented by the formula (5) or (6) in this exemplary embodiment has triplet energy gap of 2.5 eV to 3.3 eV, preferably 2.5 eV to 3.2 eV.

The compound represented by the formula (5) or (6) in this exemplary embodiment has singlet energy gap of 2.8 eV to 3.8 eV, preferably 2.9 eV to 3.7 eV.

Third Exemplary Embodiment

An organic EL device according to a third exemplary embodiment is different from the organic EL device according to the second exemplary embodiment in that a material having a poor electron capability is used as the second material.

When a material having an excellent electron injecting capability from the electrode (e.g., LiF) is used as the cathode, a carrier balance in the emitting layer becomes shifted toward the anode. For improving such a disadvantage, it is preferable to select a material having a poor electron injecting capability as the second host material. Specifically, the second host material of this exemplary embodiment is preferably a compound in which $A^3$ is a group represented by the following formula (7B) in the formula (5) or (6).

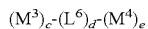 (7B)

In the formula (7B): $M^3$ and $M^4$ each independently represent a substituted or unsubstituted aromatic hydrocarbon group having 6 to 40 ring carbon atoms; $M^3$ and $M^4$ may be the same or different; $L^6$ represents a single bond, substituted or unsubstituted aromatic hydrocarbon group having 6 to 30 carbon atoms, substituted or unsubstituted fused aromatic hydrocarbon group having 6 to 30 carbon atoms, or substituted or unsubstituted cycloalkylene group having 5 to 30 carbon atoms;

c represents an integer of 0 to 2; d represents an integer of 1 to 2; e represents an integer of 0 to 2; and c+e represents 1 or more.

In the formula (7B), as the aromatic hydrocarbon group for $M^3$ and $M^4$ and the aromatic hydrocarbon group, fused aromatic hydrocarbon group and cycloalkylene group for $L^6$, those represented by the formula (26A) can be used. As bonding patterns of the groups represented by the formula (27B), the same bonding patterns as those of the formula (7A) can be used. Specifically, in the bonding patterns of the formula (7A), $M^1$, $L^5$ and $M^2$ may be respectively replaced with $M^3$, $L^6$ and $M^4$.

In the bonding patterns of the formulae (5), (6) and (7B) and exemplary combinations of the groups as described above, compounds represented by [5] to [8] below are preferable.

[5] a=1 is given in the formula (5) and c=1 and d=0 are given in the formula (7B).

In the formula (5), Cz is a substituted or unsubstituted arylcarbazolyl group or substituted or unsubstituted carbazolylaryl group.

In the formula (7B): $M^3$ is a substituted or unsubstituted nitrogen-containing six-membered or seven-membered hetero ring having 4 to 5 ring carbon atoms, substituted or unsubstituted nitrogen-containing five-membered hetero ring having 2 to 4 ring carbon atoms, substituted or unsubstituted nitrogen-containing hetero ring having 8 to 11 ring carbon atoms, substituted or unsubstituted imidazopyridinyl ring; and $L^6$ is a substituted or unsubstituted aryl group or aromatic hydrocarbon group or fused aromatic hydrocarbon group having 6 to 30 carbon atoms and substituted or unsubstituted aromatic heterocyclic group or fused aromatic heterocyclic group having 2 to 30 carbon atoms.

[6] a=2 is given in the formula (5) and c=1 and e=0 are given in the formula (7B).

In the formula (5), Cz is a substituted or unsubstituted arylcarbazolyl group or substituted or unsubstituted carbazolylaryl group.

In the formula (7B): $M^3$ is a substituted or unsubstituted nitrogen-containing six-membered or seven-membered hetero ring having 4 to 5 ring carbon atoms, substituted or unsubstituted nitrogen-containing five-membered hetero ring having 2 to 4 ring carbon atoms, substituted or unsubstituted nitrogen-containing hetero ring having 8 to 11 ring carbon atoms, substituted or unsubstituted imidazopyridinyl ring; and $L^6$ is a substituted or unsubstituted aromatic hydrocarbon group or fused aromatic hydrocarbon group having 6 to 30 carbon atoms and substituted or unsubstituted aromatic heterocyclic group or fused aromatic heterocyclic group having 2 to 30 carbon atoms.

[7] a=1 is given in the formula (5) and c=2 and e=0 are given in the formula (7B).

In the formula (5), Cz is a substituted or unsubstituted arylcarbazolyl group or substituted or unsubstituted carbazolylaryl group.

In the formula (7B): $M^3$ is a substituted or unsubstituted nitrogen-containing six-membered or seven-membered hetero ring having 4 to 5 ring carbon atoms, substituted or unsubstituted nitrogen-containing five-membered hetero ring having 2 to 4 ring carbon atoms, substituted or unsubstituted nitrogen-containing hetero ring having 8 to 11 ring carbon atoms, substituted or unsubstituted imidazopyridinyl ring; and $L^6$ is a substituted or unsubstituted aromatic hydrocarbon group or fused aromatic hydrocarbon group having 6 to 30 carbon atoms and substituted or unsubstituted aromatic heterocyclic group or fused aromatic heterocyclic group having 2 to 30 carbon atoms.

[8] b=2 is given in the formula (6) and c=d=1 is given in the formula (7B).

In the formula (6), Cz is a substituted or unsubstituted arylcarbazolyl group or substituted or unsubstituted carbazolylaryl group.

In the formula (7B): $M^3$ is a substituted or unsubstituted nitrogen-containing six-membered or seven-membered hetero ring having 4 to 5 ring carbon atoms, substituted or unsubstituted nitrogen-containing five-membered hetero ring having 2 to 4 ring carbon atoms, substituted or unsubstituted nitrogen-containing hetero ring having 8 to 11 ring carbon atoms, substituted or unsubstituted imidazopyridinyl ring; and $L^6$ is a substituted or unsubstituted aromatic hydrocarbon group or fused aromatic hydrocarbon group having 6 to 30 carbon atoms and substituted or unsubstituted aromatic heterocyclic group or fused aromatic heterocyclic group having 2 to 30 carbon atoms.

In the formulae (5) and (6), Cz is preferably a substituted or unsubstituted arylcarbazolyl group, more preferably phenylcarbozolyl group. Moreover, an aryl site of the arylcarbazolyl group is preferably substituted by a carbazolyl group.

Examples of the compound in which $A^3$ is a group represented by the following formula (7B) in the formula (5) or (6) are listed below.

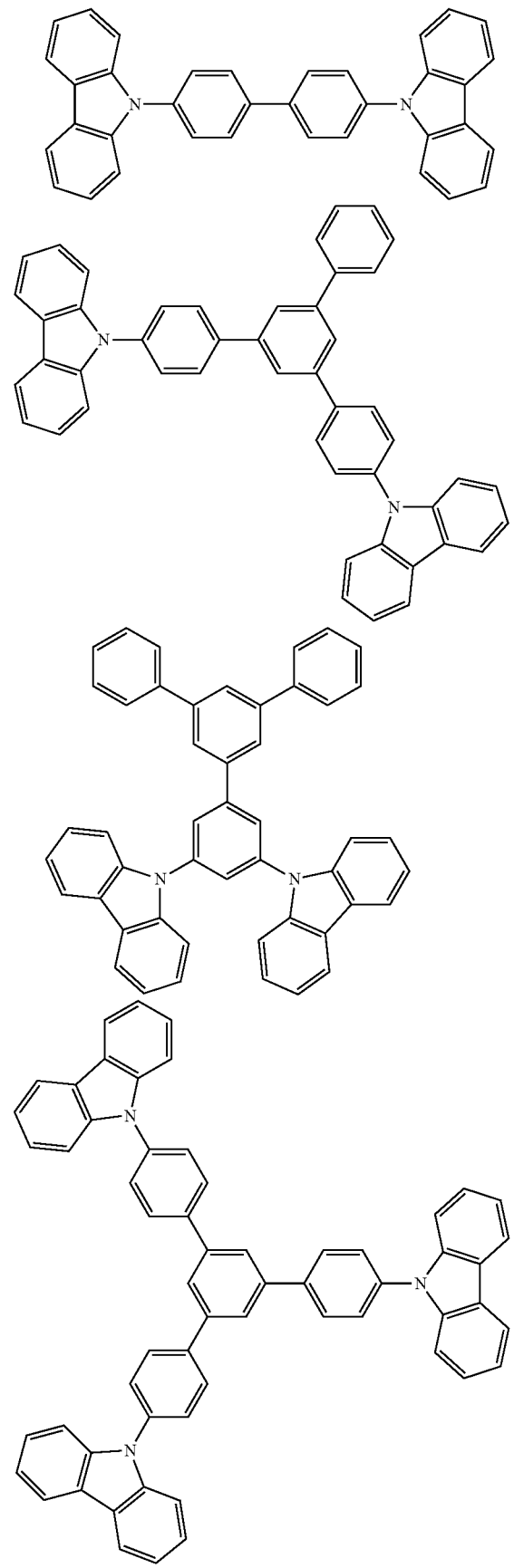

191
-continued
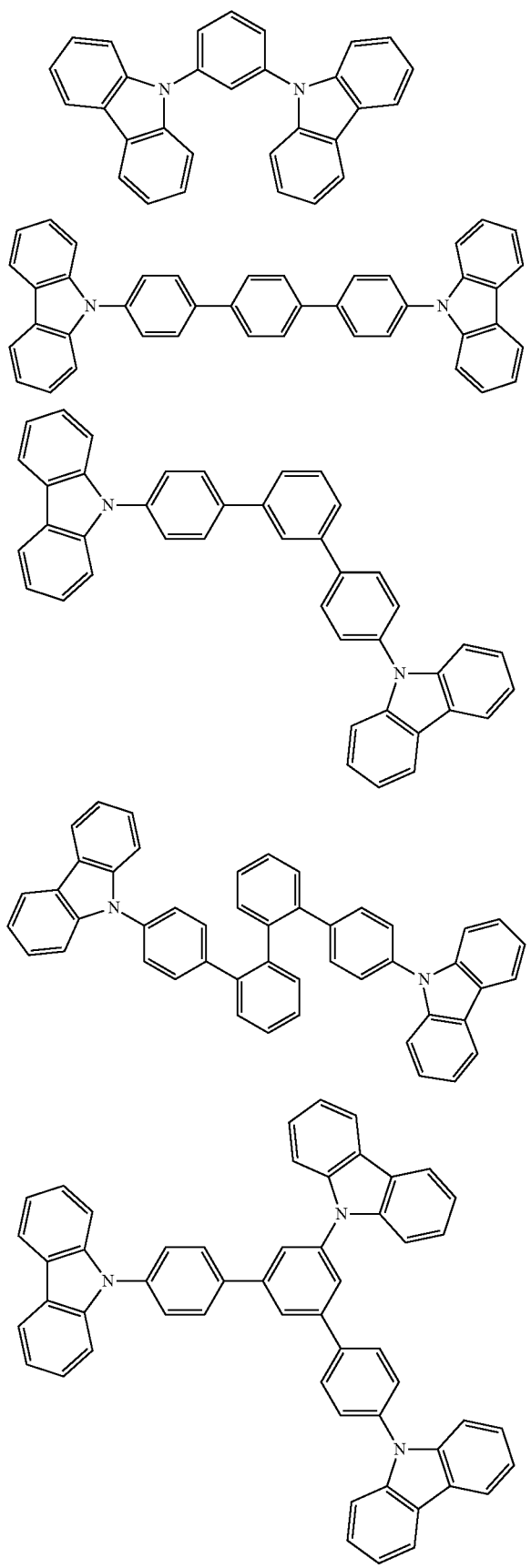
192
-continued
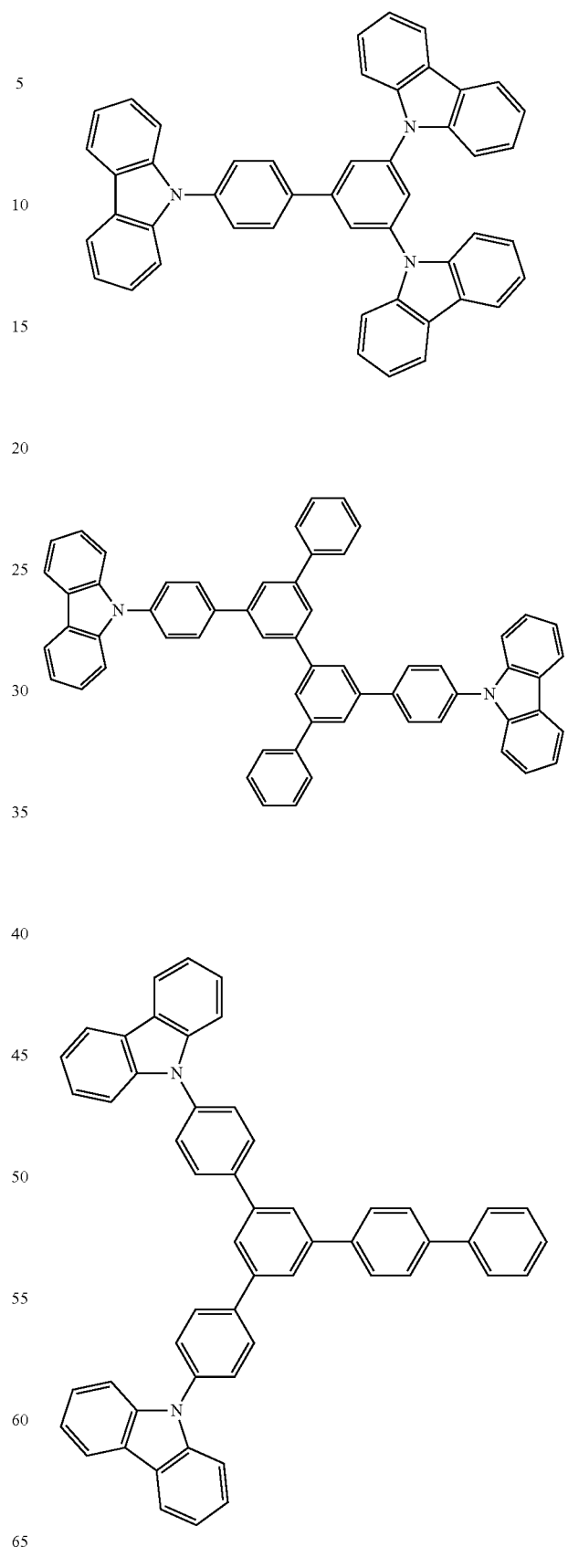

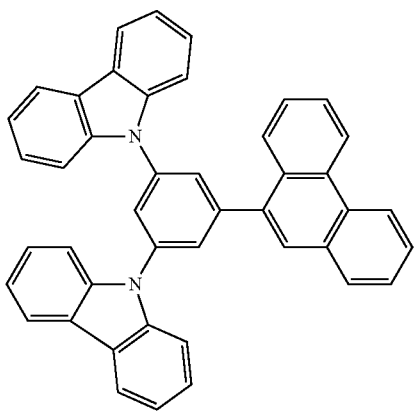

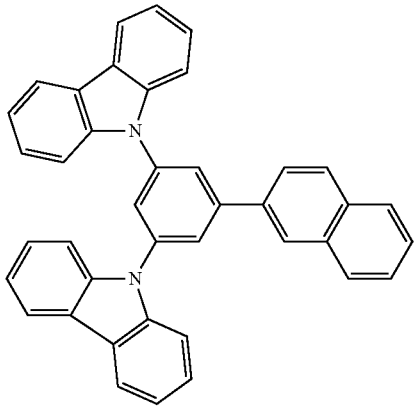

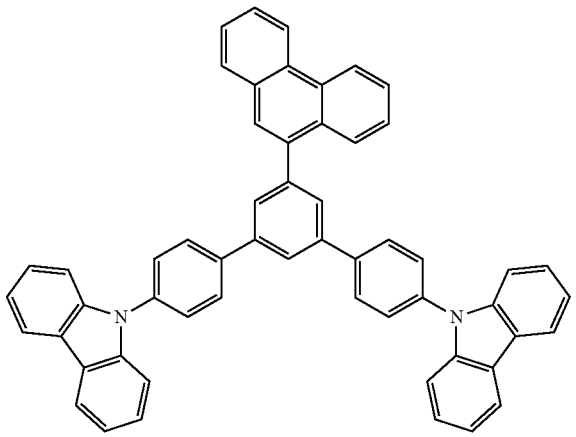

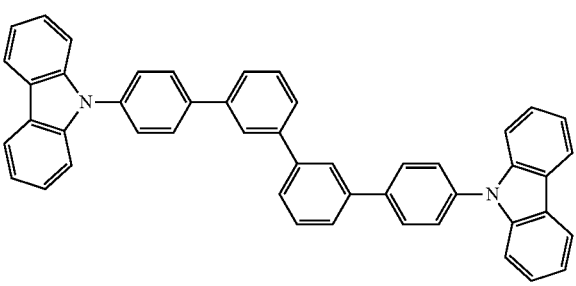

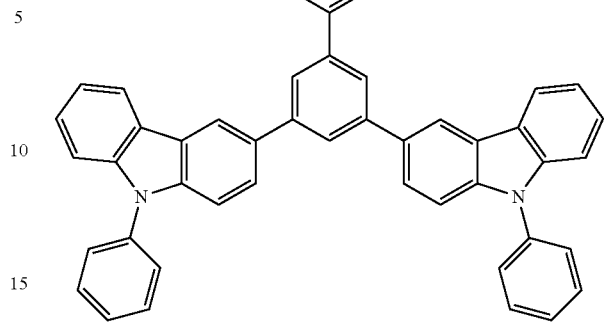

As the second host material of this exemplary embodiment, a compound represented by a formula (8) below may be used.

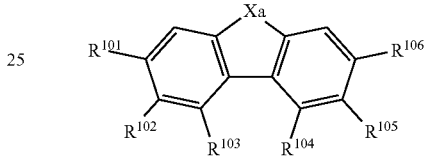

(8)

In the formula (8): $R^{101}$ to $R^{106}$ each independently represent a hydrogen atom, halogen atom, substituted or unsubstituted alkyl group having 1 to 40 carbon atoms, substituted or unsubstituted cycloalkyl group having 3 to 15 carbon atoms, substituted or unsubstituted heterocyclic group having 3 to 20 carbon atoms, substituted or unsubstituted alkoxy group having 1 to 40 carbon atoms, substituted or unsubstituted aryl group having 6 to 40 carbon atoms, substituted or unsubstituted aryloxy group having 6 to 20 carbon atoms, substituted or unsubstituted aralkyl group having 7 to 20 carbon atoms, substituted or unsubstituted arylamino group having 6 to 40 carbon atoms, substituted or unsubstituted alkylamino group having 1 to 40 carbon atoms, substituted or unsubstituted aralkylamino group having 7 to 60 carbon atoms, substituted or unsubstituted arylcarbonyl group having 7 to 40 carbon atoms, substituted or unsubstituted arylthio group having 6 to 20 carbon atoms, substituted or unsubstituted halogenated alkyl group having 1 to 40 carbon atoms or cyano group;

at least one of $R^{101}$ to $R^{106}$ is a substituted or unsubstituted 9-carbazolyl group, substituted or unsubstituted azacarbazolyl group having 2 to 5 nitrogen atoms, or -L-9-carbazolyl group;

L represents a substituted or unsubstituted alkyl group having 1 to 40 carbon atoms, substituted or unsubstituted cycloalkyl group having 3 to 15 carbon atoms, substituted or unsubstituted heterocyclic group having 3 to 20 carbon atoms, substituted or unsubstituted alkoxy group having 1 to 40 carbon atoms, substituted or unsubstituted aryl group having 6 to 40 carbon atoms, substituted or unsubstituted aryloxy group having 6 to 20 carbon atoms, substituted or unsubstituted aralkyl group having 7 to 20 carbon atoms, substituted or unsubstituted arylamino group having 6 to 40 carbon atoms, substituted or unsubstituted alkylamino group having 1 to 40 carbon atoms, substituted or unsubstituted aralkylamino group having 7 to 60 carbon atoms, substituted or unsubstituted arylcarbonyl group having 7 to 40 carbon atoms, substituted or unsubstituted arylthio group having 6 to 20 carbon atoms, or substituted or unsubstituted halogenated alkyl group having 1 to 40 carbon atoms;

Xa represents a sulfur atom, oxygen atom or N—R$^{108}$; and R$^{108}$ represents the same as R$^{101}$ to R$^{106}$.

Specific examples of the substituted or unsubstituted azacarbazolyl group having 2 to 5 nitrogen atoms are shown below (in which any substituent is omitted), but the substituted or unsubstituted azacarbazolyl group is not limited thereto.

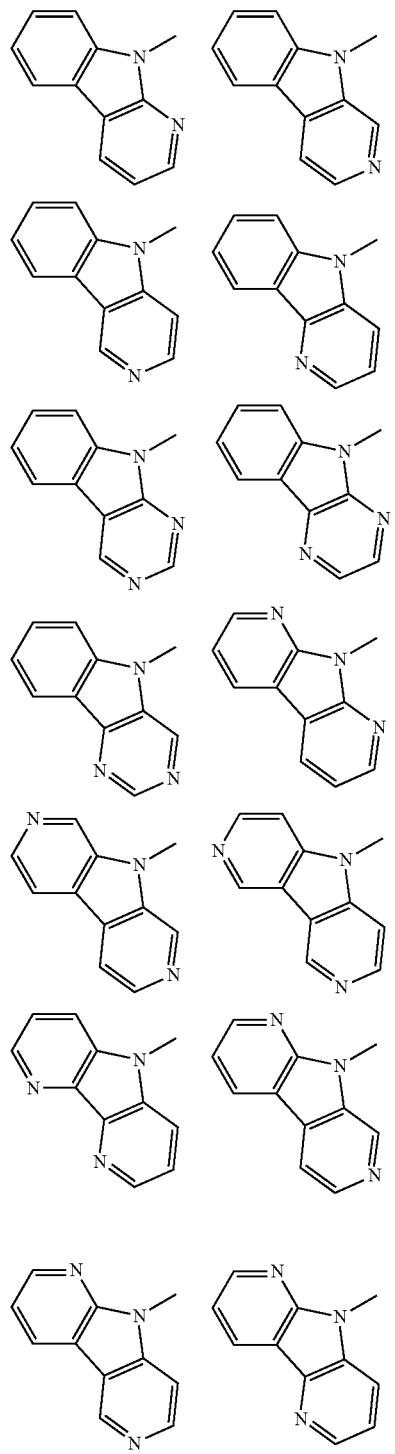
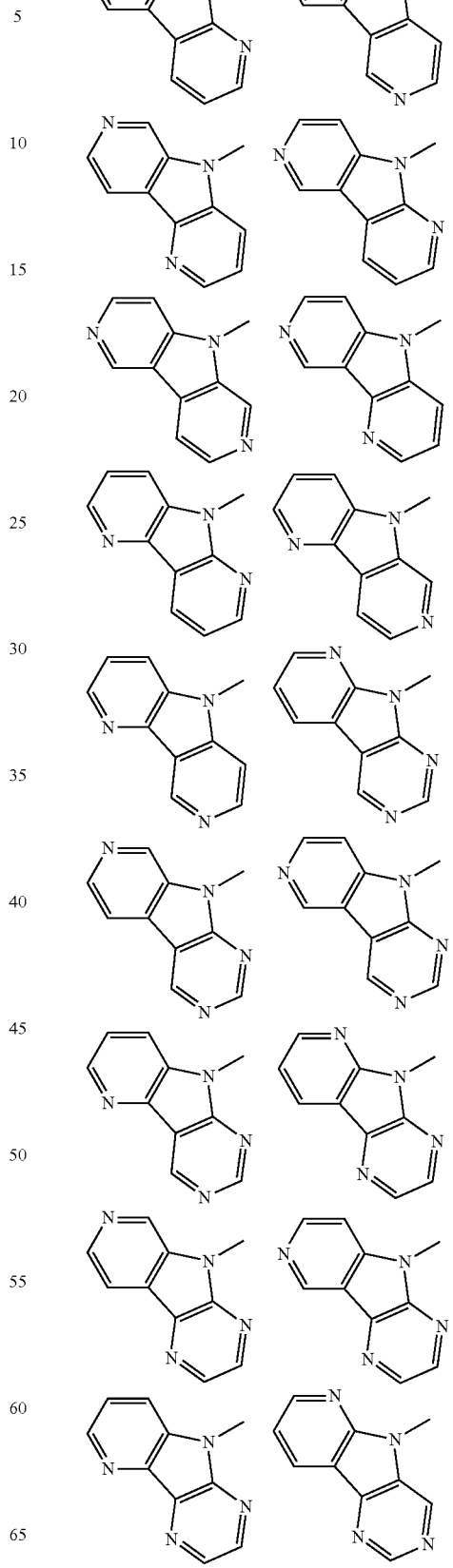

-continued
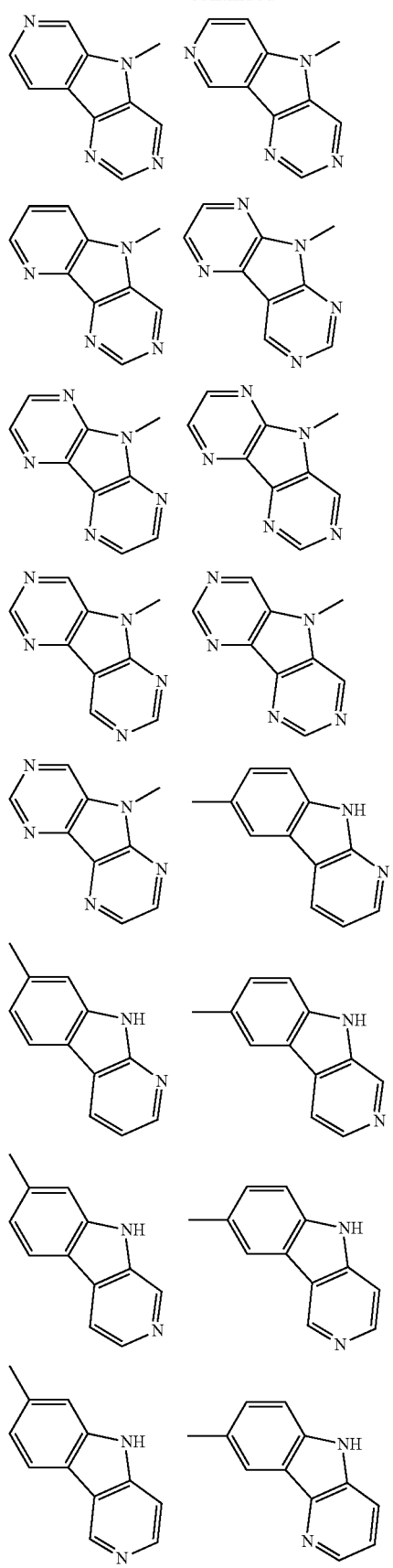
-continued
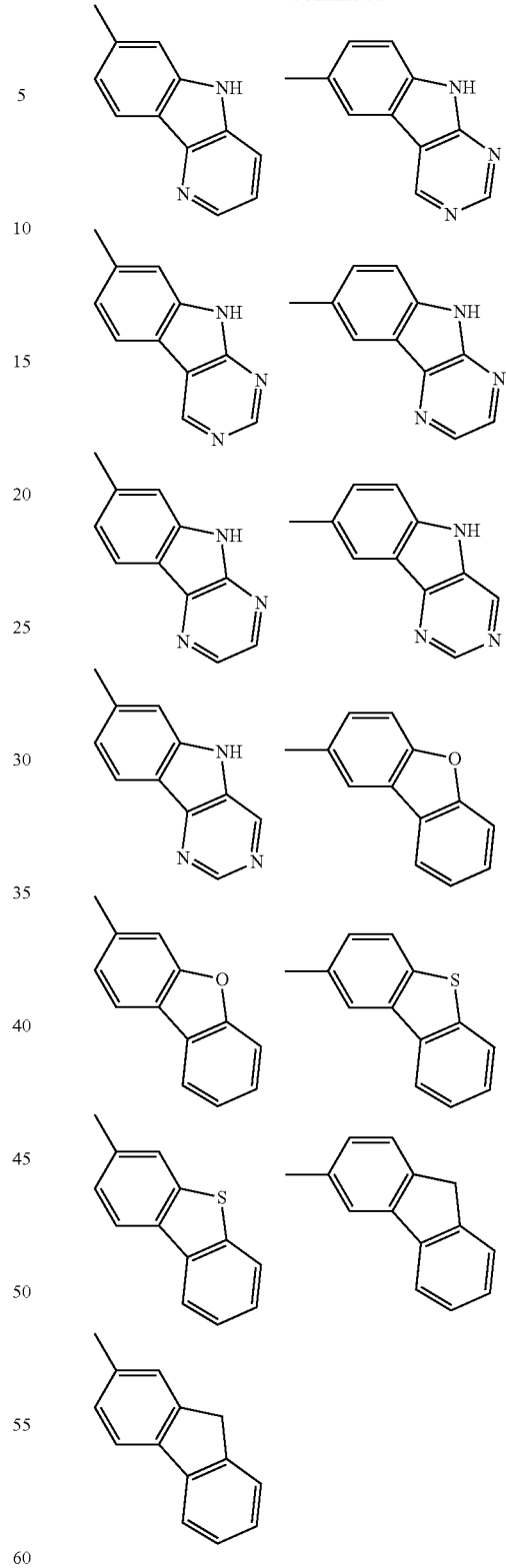
Examples of the halogen atom include fluorine, chlorine, bromine, and iodine.
Examples of the substituted or unsubstituted alkyl group having 1 to 40 carbon atoms include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, a 3-methylpentyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 1,2-dinitroethyl group, a 2,3-dinitro-t-butyl group, and a 1,2,3-trinitropropyl group, among of which a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 1-pentylhexyl group, a 1-butylpentyl group, a 1-heptyloctyl group are preferable. The alkyl group (excluding a substituent) preferably has 1 to 10 carbon atoms.

Examples of the substituted or unsubstituted cycloalkyl group having 3 to 15 carbon atoms include a cyclopentyl group, cyclohexyl group, cyclooctyl group, and 3,5,5,5-tetramethylcyclohexyl group. A cyclohexyl group, cyclooctyl group, and 3,5-tetramethylcyclohexyl group are preferable. The cycloalkyl group (excluding a substituent) preferably has 3 to 12 carbon atoms.

Examples of the substituted or unsubstituted heterocyclic group having 3 to 20 carbon atoms are a 1-pyroryl group, 2-pyroryl group, 3-pyroryl group, pyrazinyl group, 2-pyridinyl group, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridinyl, 3-imidazopyridinyl, 5-imidazopyridinyl, 6-imidazopyridinyl, 7-imidazopyridinyl, 8-imidazopyridinyl, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-silafluorenyl group, 2-silafluorenyl group, 3-silafluorenyl group, 4-silafluorenyl group, 1-germafluorenyl group, 2-germafluorenyl group, 3-germafluorenyl group and 4-germafluorenyl group.

Among the above, the heterocyclic group is preferably a 2-pyridinyl group, 1-indolidinyl, 2-indolidinyl, 3-indolidinyl, 5-indolidinyl, 6-indolidinyl, 7-indolidinyl, 8-indolidinyl, 2-imidazopyridinyl, 3-imidazopyridinyl, 5-imidazopyridinyl, 6-imidazopyridinyl, 7-imidazopyridinyl, 8-imidazopyridinyl, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 9-carbazolyl group, 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-silafluorenyl group, 2-silafluorenyl group, 3-silafluorenyl group, 4-silafluorenyl group, 1-germafluorenyl group, 2-germafluorenyl group, 3-germafluorenyl group, 4-germafluorenyl group, azacarbazolyl-1-yl group, azacarbazolyl-2-yl group, azacarbazolyl-3-yl group, azacarbazolyl-4-yl group, azacarbazolyl-5-yl group, azacarbazolyl-6-yl group, azacarbazolyl-7-yl group, azacarbazolyl-8-yl group, and azacarbazolyl-9-yl group. The heterocyclic group (excluding a substituent) preferably has 3 to 14 carbon atoms.

The substituted or unsubstituted alkoxy group having 1 to 40 carbon atoms is a group represented by —OY. Examples of Y are the same as those described in relation to the alkyl group. Preferred examples are also the same.

Examples of the substituted or unsubstituted aryl group having 6 to 40 carbon atoms (including a fused aromatic hydrocarbon group and a ring assembly aromatic hydrocarbon group) are a phenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl-p-terphenyl-4-yl group, o-cumenyl group, m-cumenyl group, p-cumenyl group, 2,3-xylyl group, 3,4-xylyl group, 2,5-xylyl group, mesityl group and m-quater-phenyl group. Among the above, the substituted or unsubstituted aryl group is preferably a phenyl group, 2-biphenylyl group, 3-biphenylyl group, 4-biphenylyl group, m-terphenyl-4-yl group, m-terphenyl-3-yl group, m-terphenyl-2-yl group, p-tolyl group, 3,4-xylyl group, m-quarterphenyl-2-yl group, 1-naphtyl group, 2-naphtyl group, 1-phenanthrenyl group, 2-phenanthrenyl group, 3-phenanthrenyl group, 4-phenanthrenyl group, 9-phenanthrenyl group, 1-triphenylenyl group, 2-triphenylenyl group, 3-triphenylenyl group, 4-triphenylenyl group, 1-chrysenyl group, 2-chrysenyl group, 3-chrysenyl group, 4-chrysenyl group, 5-chrysenyl group, and 6-chrysenyl group. The aryl group (excluding a substituent) preferably has 6 to 24 carbon atoms. The aryl group preferably further includes a 9-carbazolyl group as a substituent.

The substituted or unsubstituted aryloxy group having 6 to 20 carbon atoms is a group represented by —OAr. Examples of Ar are the same as those described in relation to the aryl group. Preferred examples are also the same.

Examples of the substituted or unsubstituted aralkyl group having 7 to 20 carbon atoms are a benzyl group, 1-phenylethyl group, 2-phenylethyl group, 1-phenylisopropyl group, 2-phenylisopropyl group, phenyl-t-butyl group, á-naphthylmethyl group, 1-á-naphthylethyl group, 2-á-naphthylethyl group, 1-á-naphthylisopropyl group, 2-á-naphthylisopropyl group, á-naphthylmethyl group, 1-á-naphthylethyl group, 2-á-naphthylethyl group, 1-á-naphthylisopropyl group, 2-á-naphthylisopropyl group, 1-pyrorylmethyl group, 2-(1-pyroryl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, 1-chloro-2-phenylisopropyl group and the like. Among these, preferred are a benzyl group, a p-cyanobenzyl group, m-cyanobenzyl group, o-cyanobenzyl group, 1-phenylethyl group, 2-phenylethyl group, 1-phenylisopropyl group, and 2-phenylisopropyl group. An alkyl portion of the aralkyl group preferably has 1 to 8 carbon atoms. An aryl portion thereof (including heteroaryl) preferably has 6 to 18 carbon atoms.

The substituted or unsubstituted arylamino group having 6 to 40 carbon atoms, the substituted or unsubstituted alkylamino group having 1 to 40 carbon atoms, and the substituted or unsubstituted aralkylamino group having 7 to 60 carbon atoms each are represented by —NQ$^1$Q$^2$. Examples of Q$^1$ and Q$^2$ each are independently the same as those described in relation to the alkyl group, aryl group and aralkyl group. Preferred examples are also the same.

The substituted or unsubstituted arylcarbonyl group having 7 to 40 carbon atoms is represented by —COAr$^2$. Examples of Ar$^2$ are the same as those described in relation to the aryl group. Preferred examples are also the same.

The substituted or unsubstituted arylthio group having 6 to 20 carbon atoms is exemplified by a group obtained by replacing an oxygen atom of the aryloxy group represented by —OAr with a sulfur atom. Preferred examples are also the same.

The substituted or unsubstituted halogenated alkyl group having 1 to 40 carbon atoms is exemplified by a halogenated alkyl group in which at least one hydrogen atom of the alkyl group is substituted by a halogen atom. Preferred examples are also the same.

The compound represented by the general formula (8) preferably has triplet energy gap of 2.2 eV to 3.2 eV. Specific examples of the formula (8) are shown below.

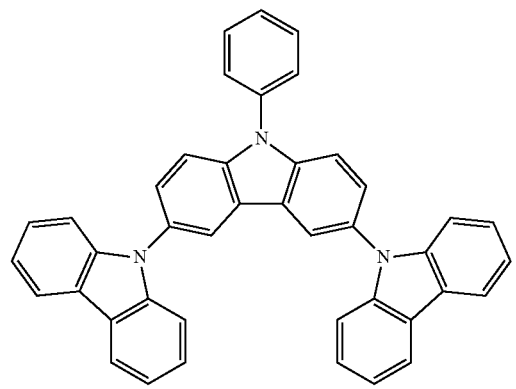

-continued
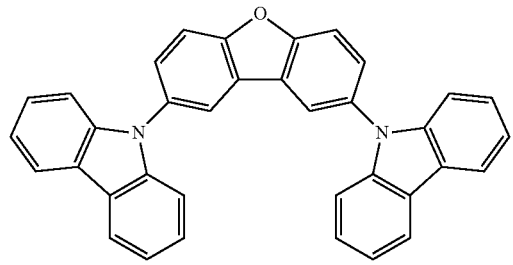
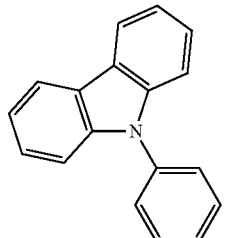  No. 3
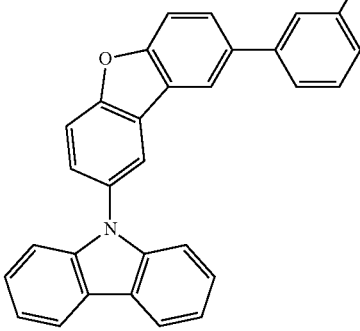
No. 1
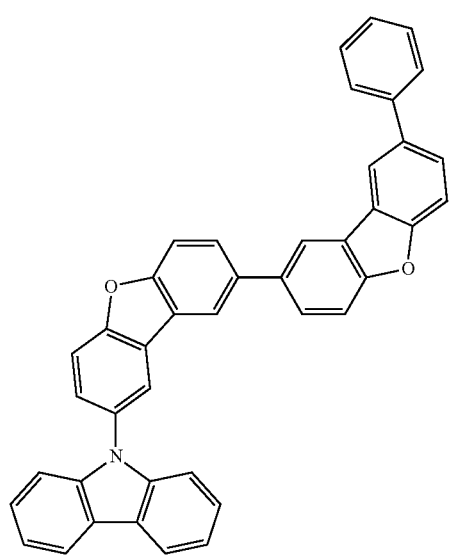
No. 4
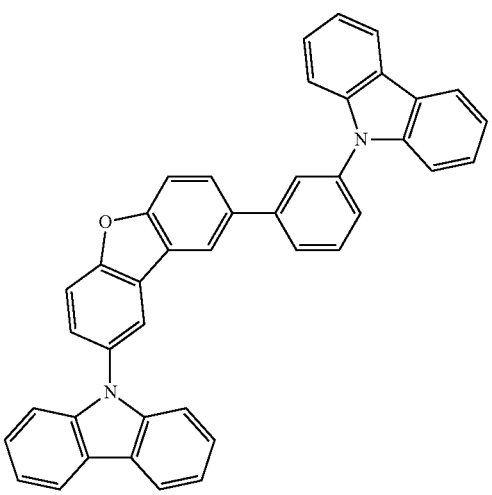
No. 2
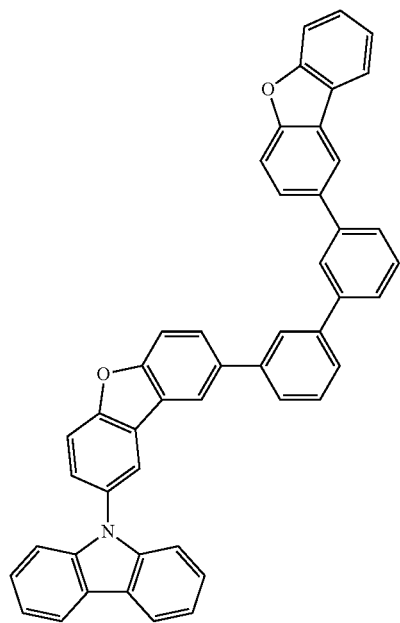
No. 5
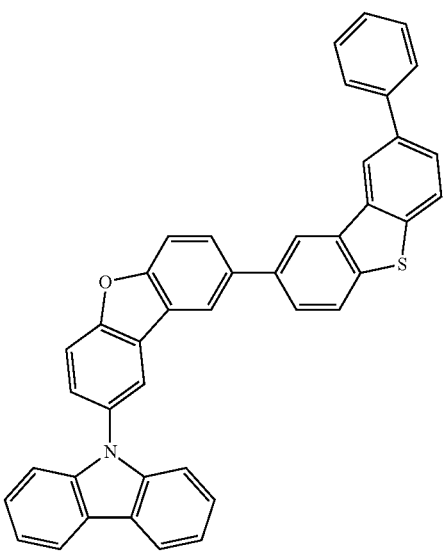

No. 6
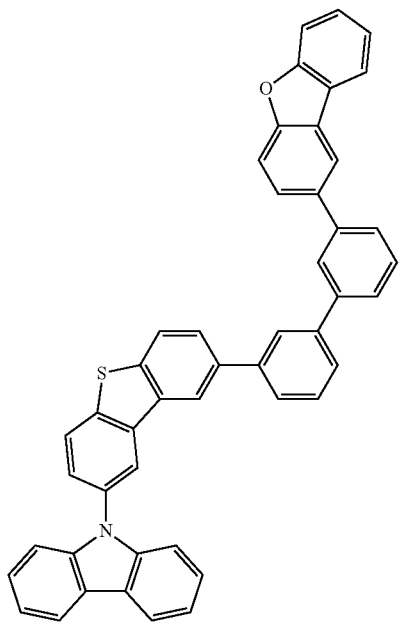
No. 7
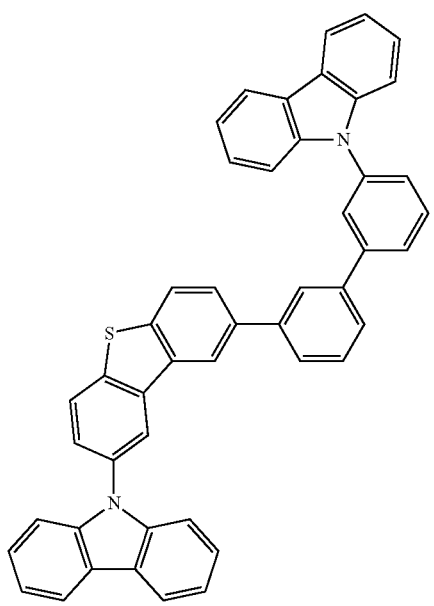
No. 8
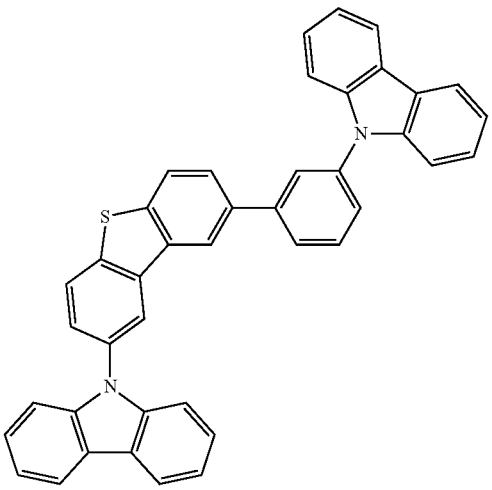
No. 9
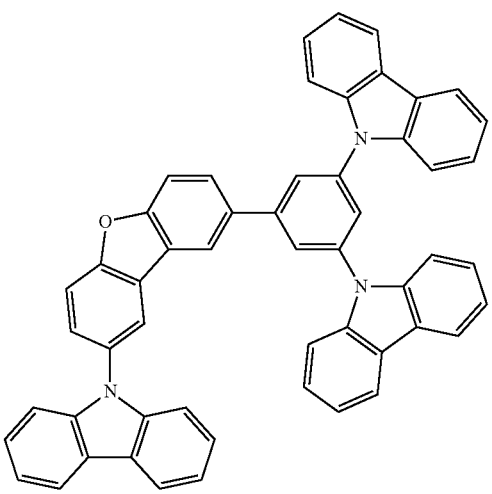
No. 10
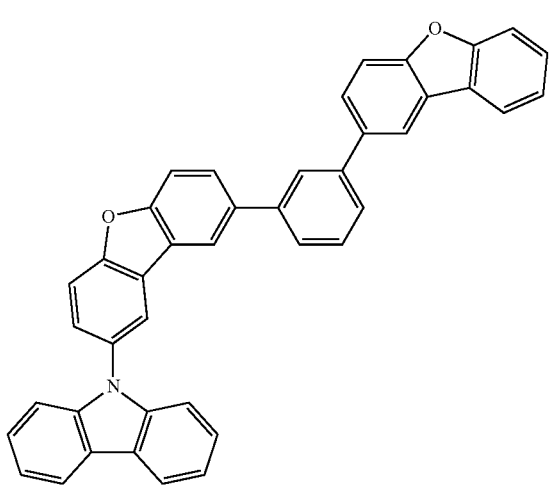

-continued
No.11
No.12
No.13
No.14
No.15
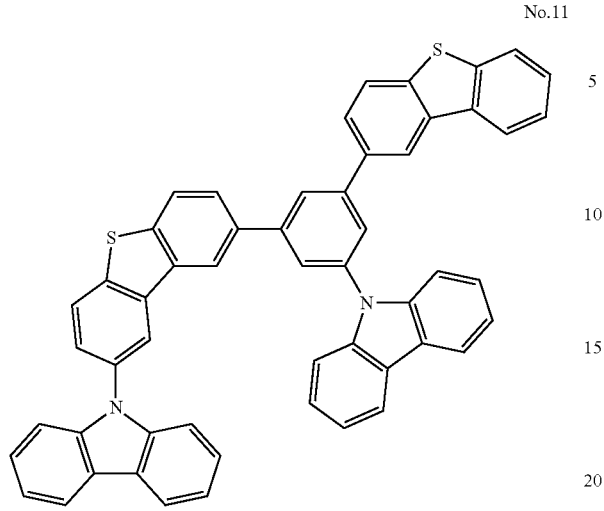
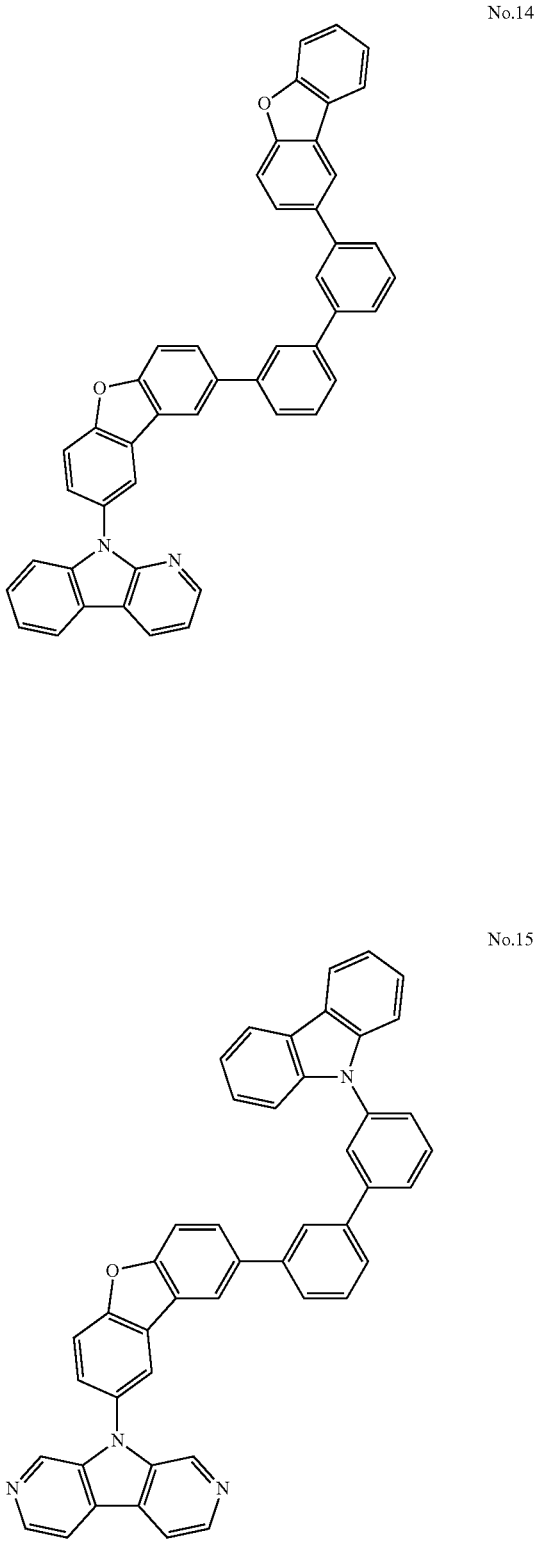

No. 16
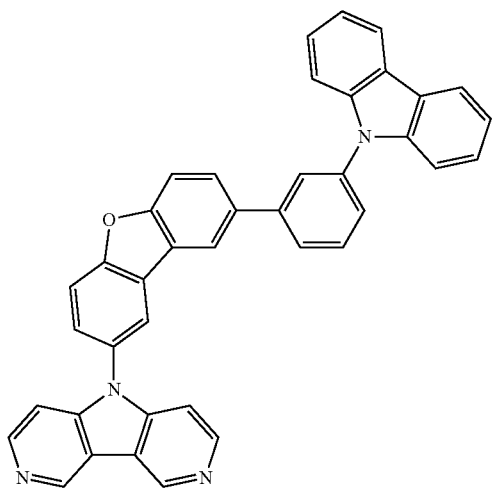
No. 17
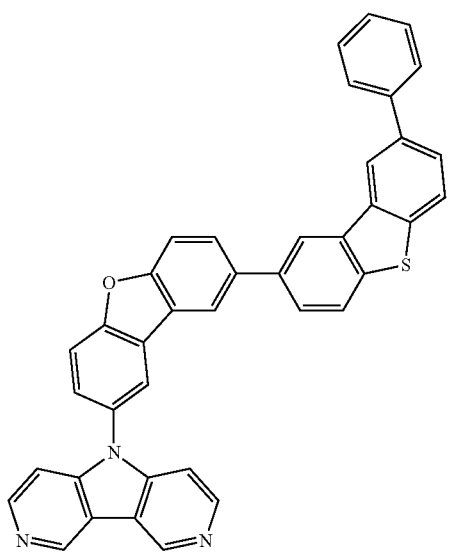
No. 18
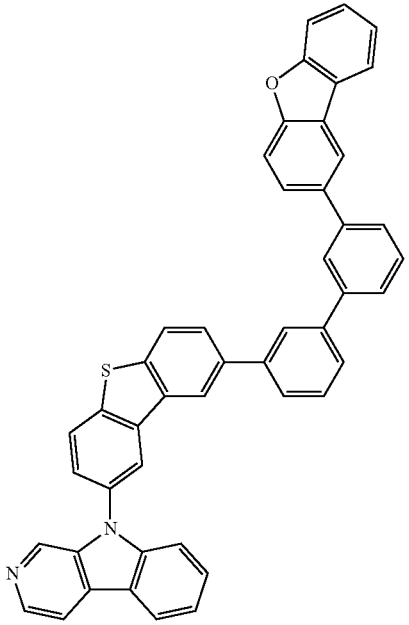
No. 19
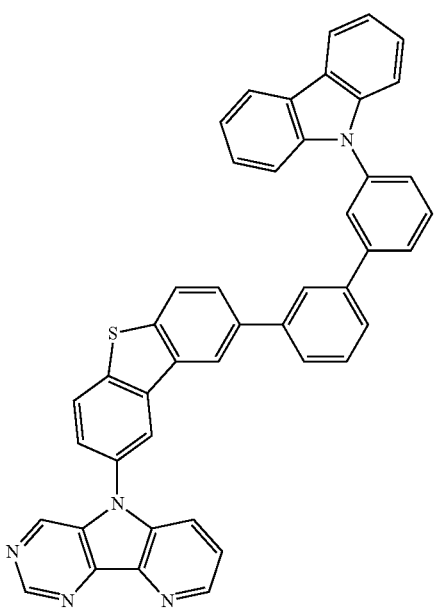

No. 20
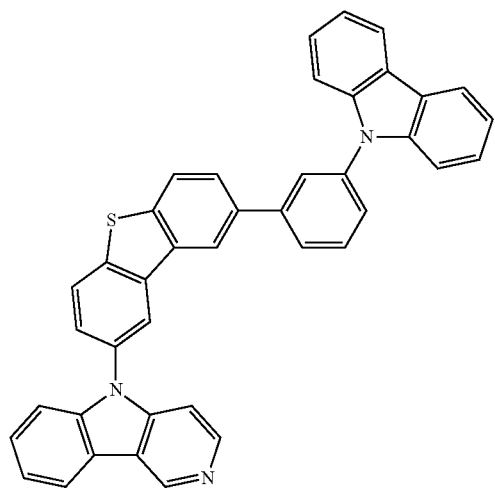
No. 23
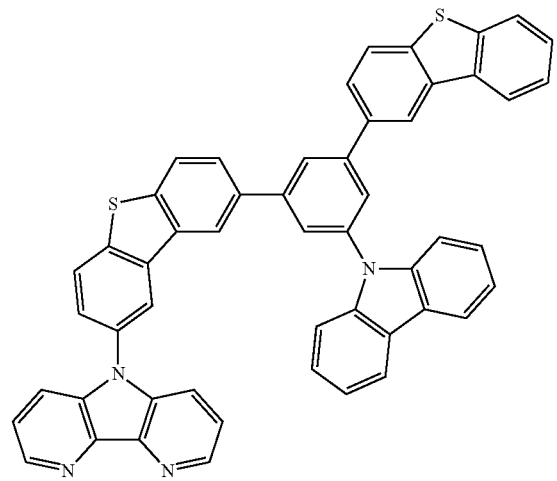
No. 21
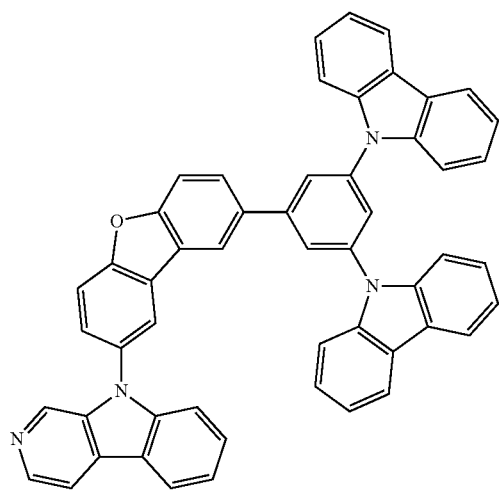
No. 24
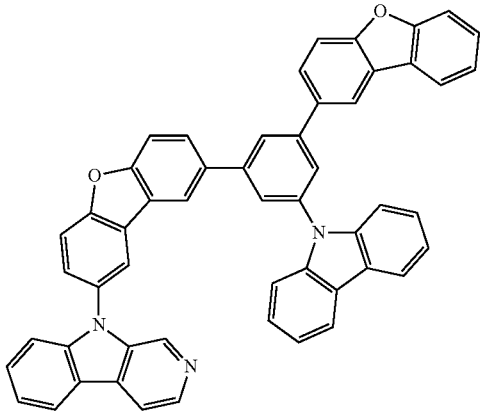
No. 22
No. 25
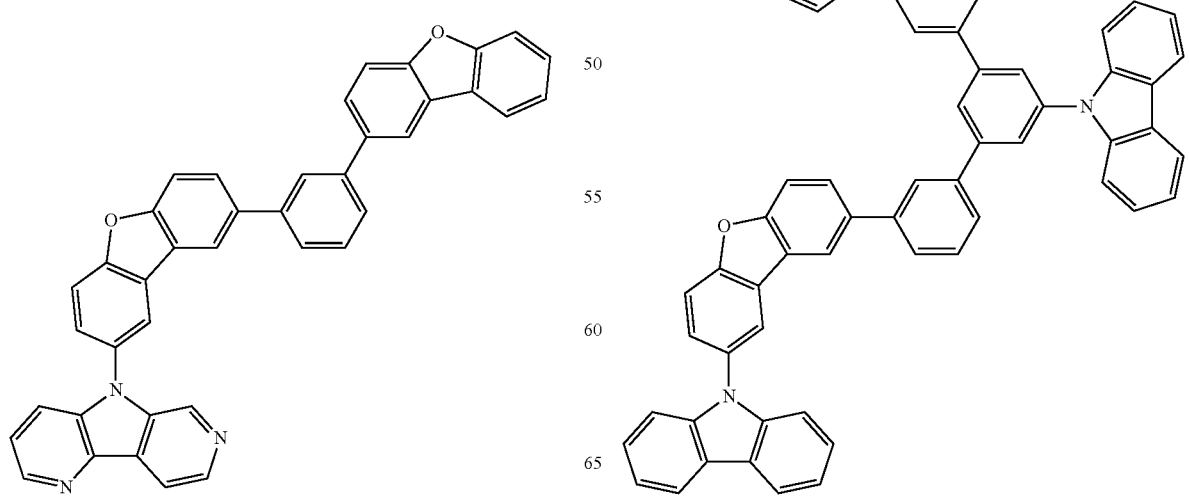

No.26
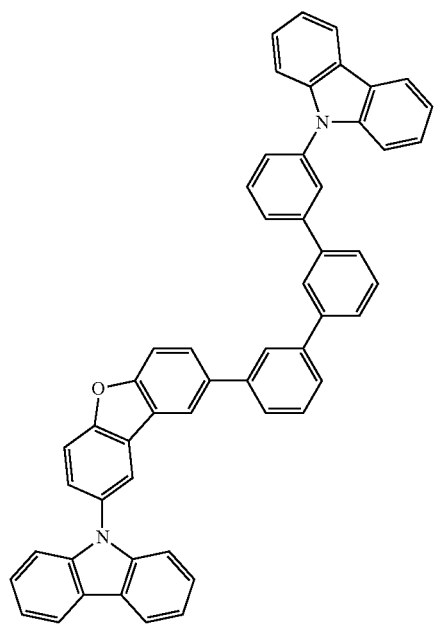
No.28
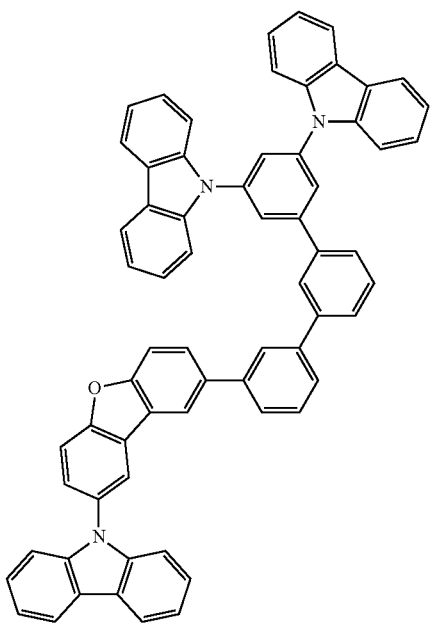
No.27
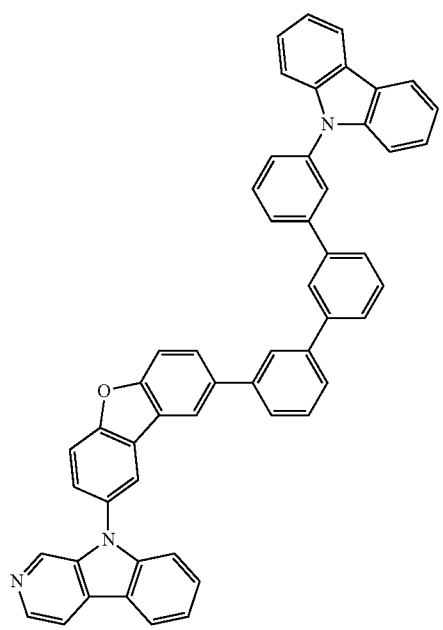
No.29
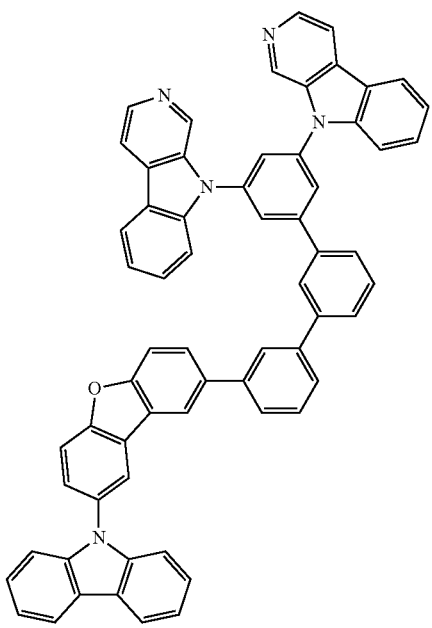

No.30
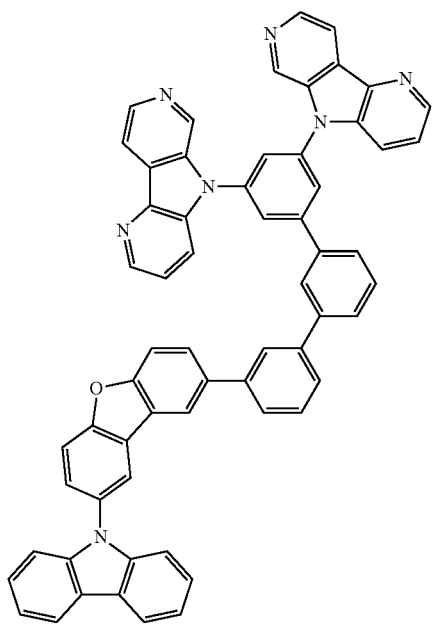
No.33
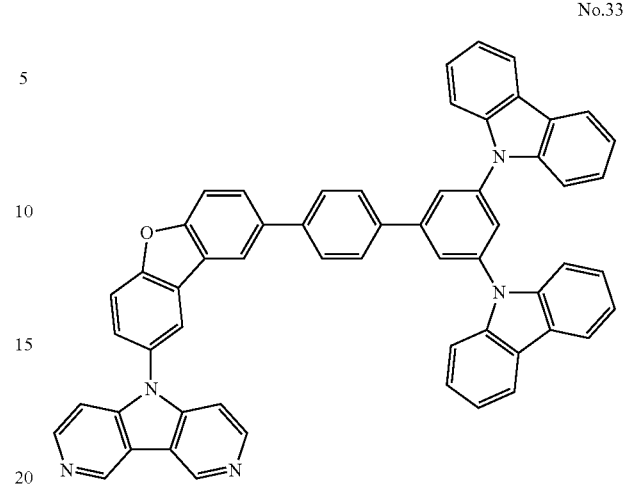
No.31
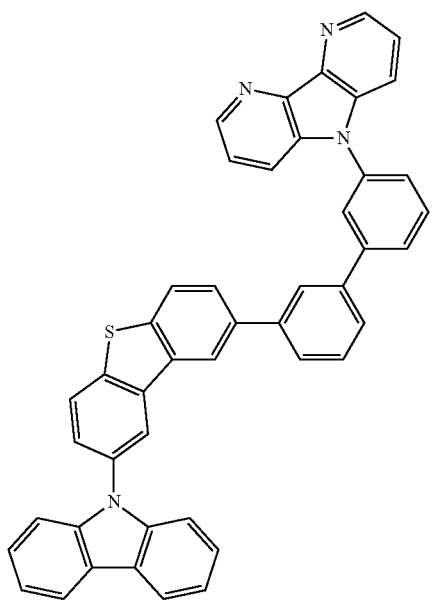
No.34
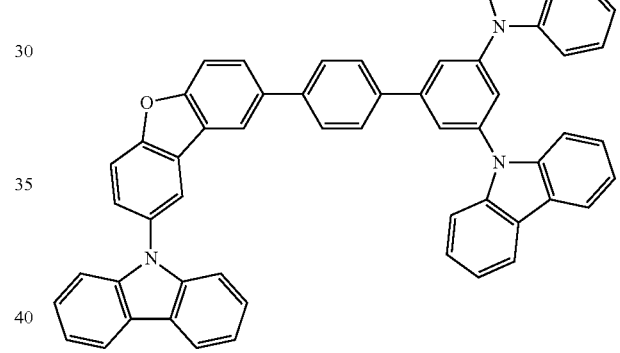
No.32
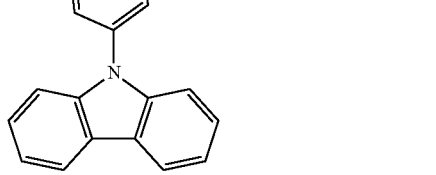
No.35
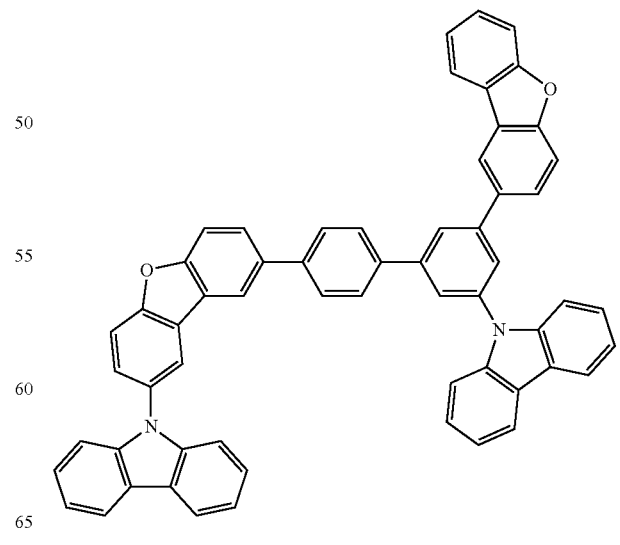
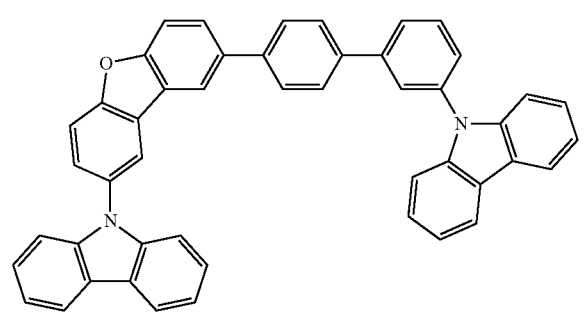

No. 36
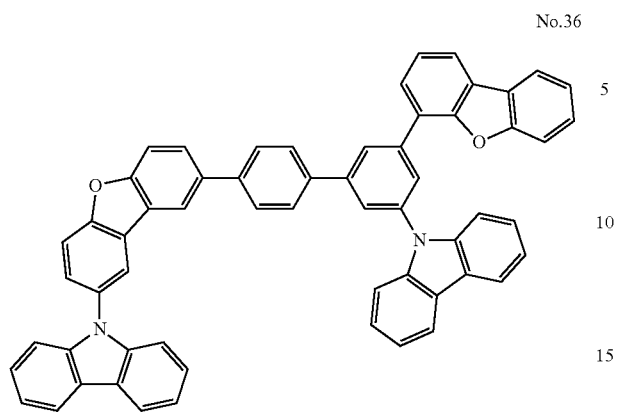
No. 39
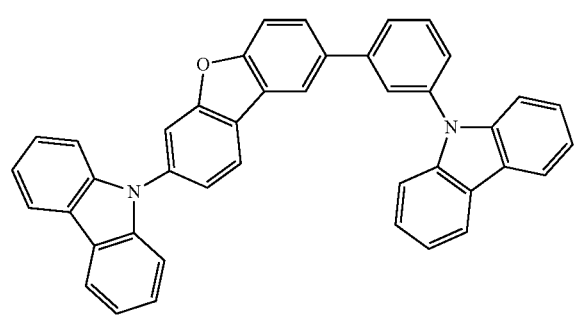
No. 40
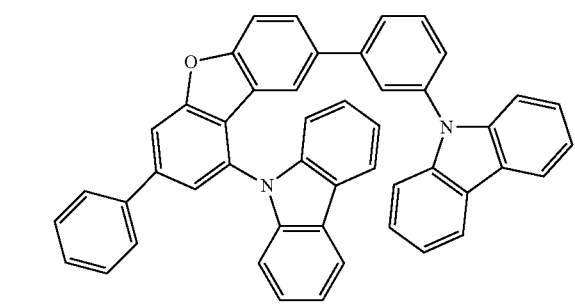
No. 42
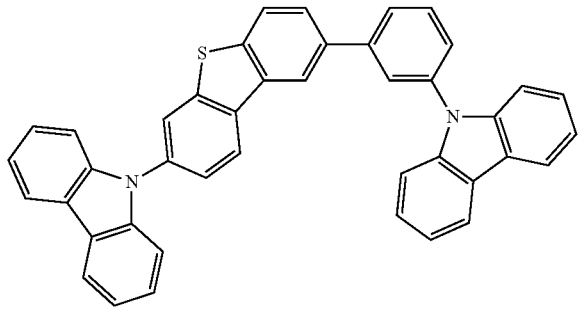
No. 43
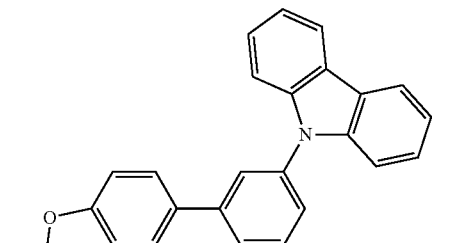
No. 45
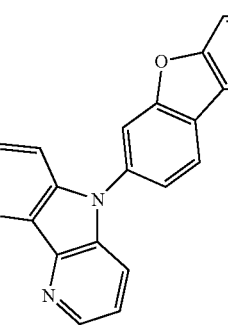
No. 46
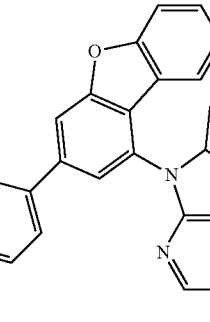
No. 48
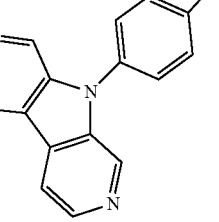

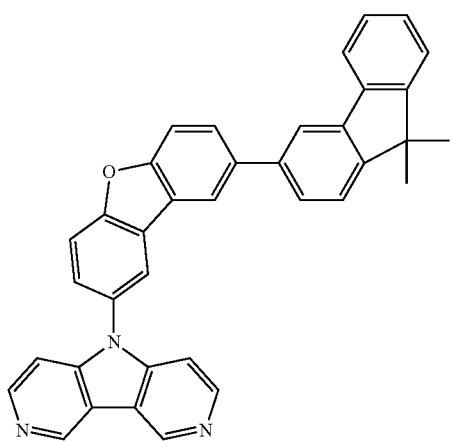
No.49
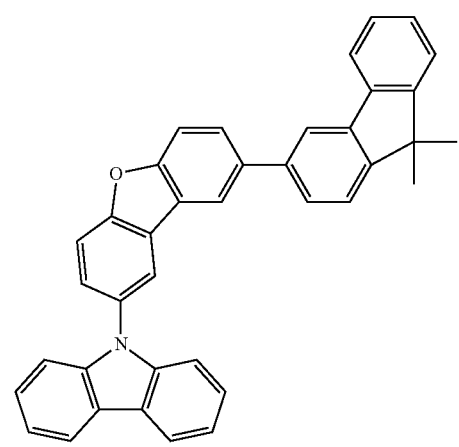
No.50
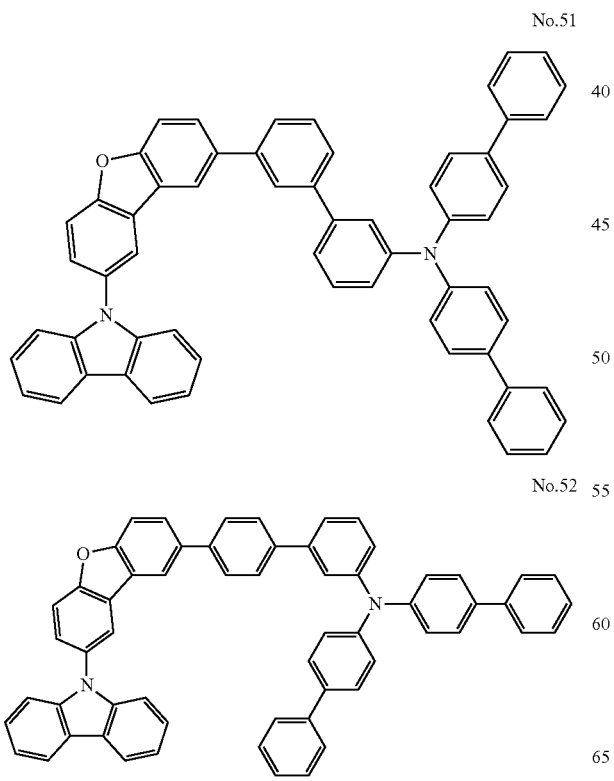
No.51
No.52
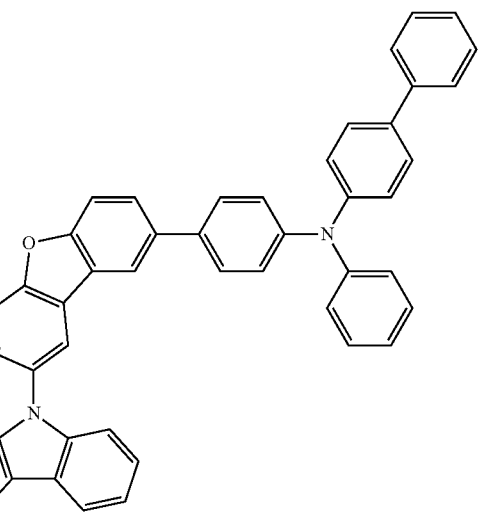
No.53
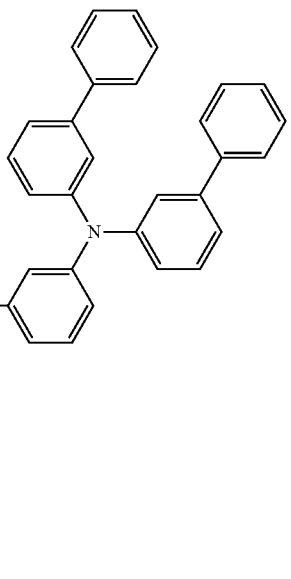
No.54

No.55
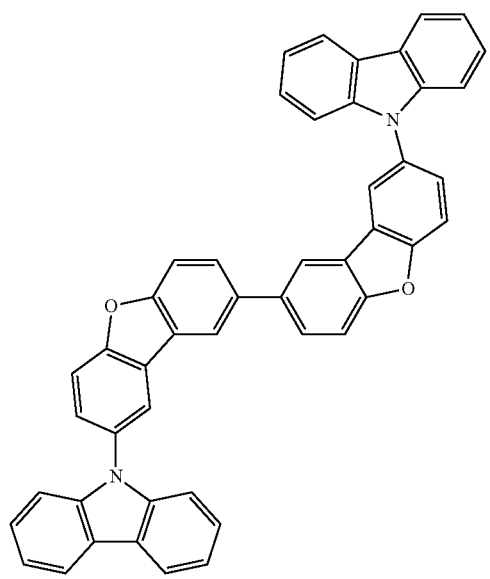
No.56
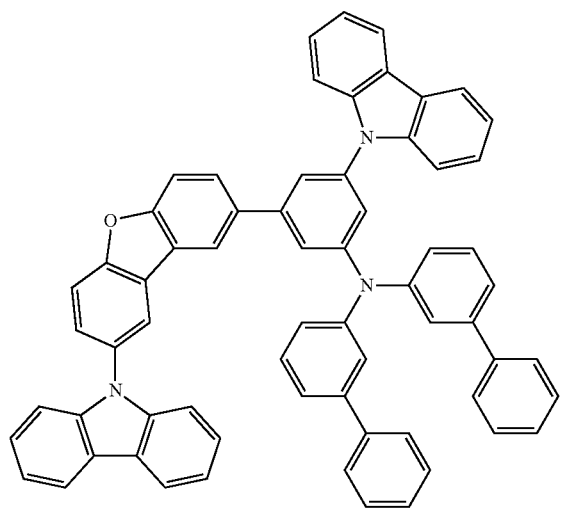
No.58
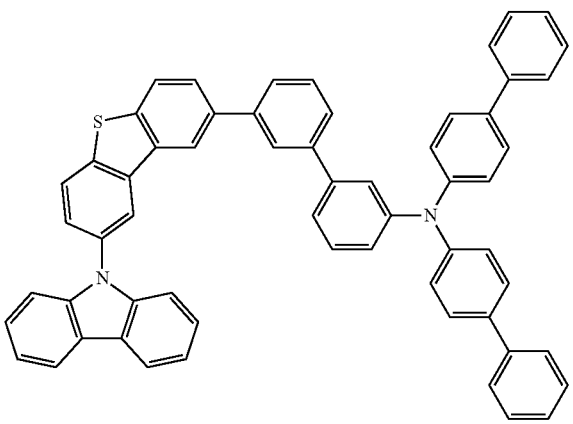
No.59
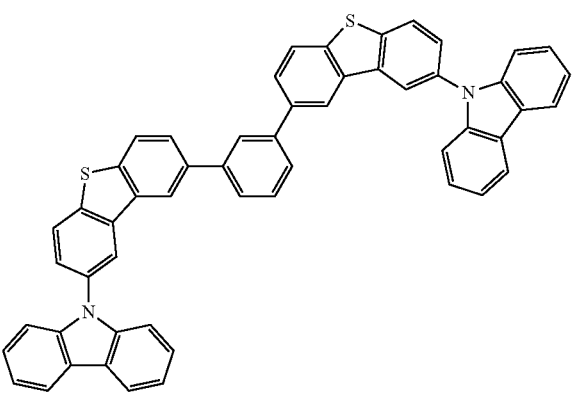
No.57
No.62
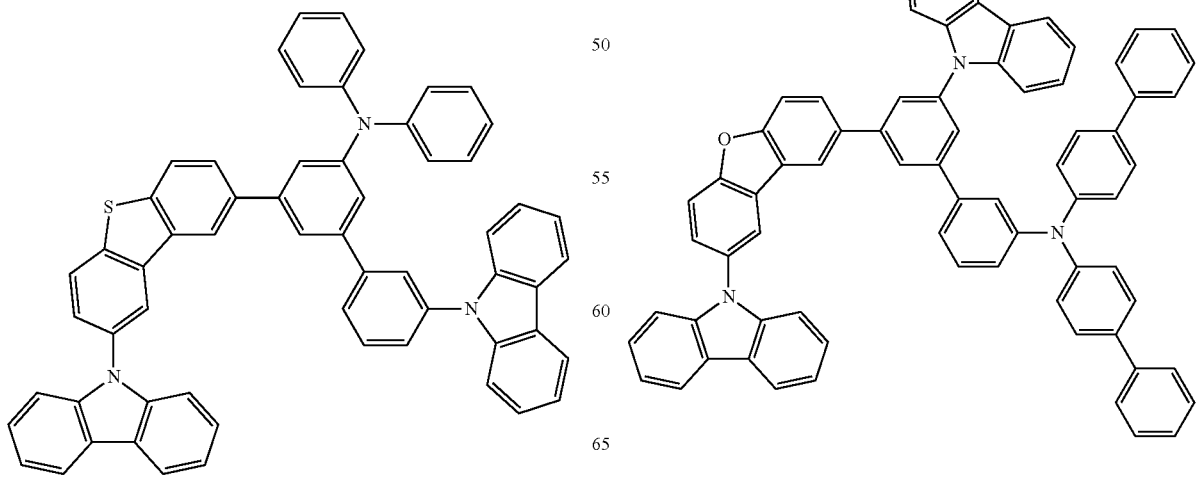

No.63

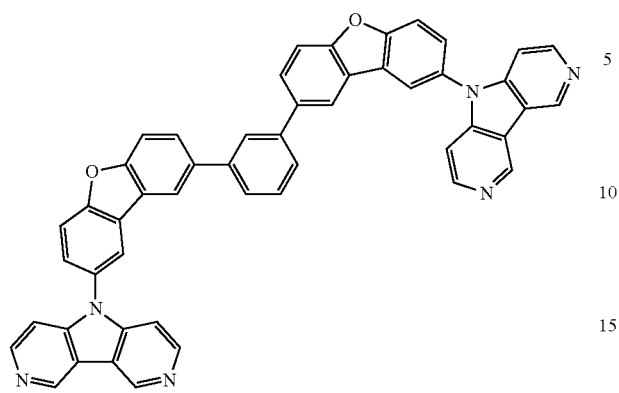

No.64

No.65

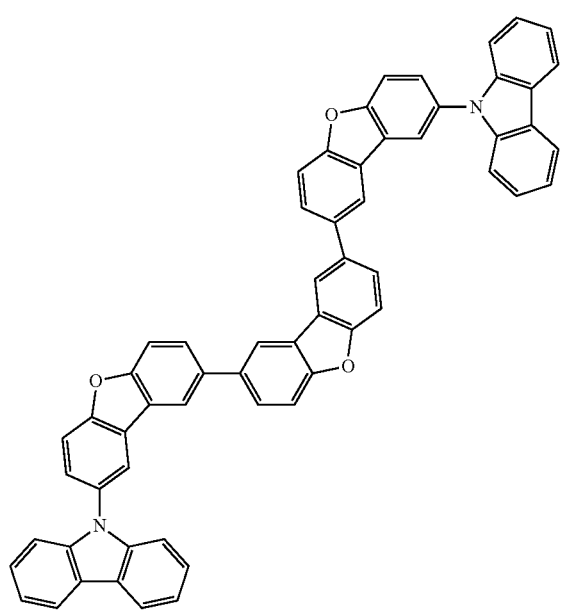

No.66

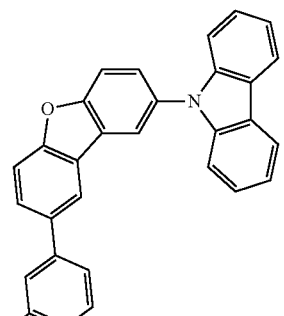

No.67

Fourth Exemplary Embodiment

An organic EL device according to a fourth exemplary embodiment is different from the organic EL devices according to the second and third exemplary embodiments in being a red phosphorescent device.

The compound according to this exemplary embodiment is not disclosed as a phosphorescent host material of which color is specified. However, since having a high resistance against oxidation and reduction, the compound is also applicable to a red phosphorescent device. As a red phosphorescent device, a hydrocarbon material, which exhibits a small triplet energy and broad 6 electron clouds compared with a green phosphorescent material, can be used. Although the hydrocarbon material is difficult to be used as a green phosphorescent material because of its small triplet energy, the hydrocarbon material is highly appropriate as a red phosphorescent host material because of its high oxidation and reduction. Accordingly, by using the hydrocarbon material as the second host material, a red phosphorescent device can become highly efficient.

The second host material is preferably a compound selected from the group consisting of polycyclic aromatic compounds represented by formulae (9A), (9B) and (9C) below.

  (9A)

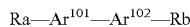  (9B)

  (9C)

In the formulae (9A) to (9C), $Ar^{101}$, $Ar^{102}$, $Ar^{103}$, Ra and Rb represent a substituted or unsubstituted aryl group having 6 to 60 ring carbon atoms.

$Ar^{101}$, $Ar^{102}$, $Ar^{103}$, Ra and Rb preferably represent a polycyclic aromatic skeleton selected from a substituted or unsubstituted benzene ring, substituted or unsubstituted naphthalene ring, substituted or unsubstituted chrysene ring, substituted or unsubstituted fluoranthene ring, substituted or unsubstituted phenanthrene ring, substituted or unsubstituted benzophenanthrene ring, substituted or unsubstituted dibenzophenanthrene ring, substituted or unsubstituted triphenylene ring, substituted or unsubstituted benzo[A]triphenylene ring, substituted or unsubstituted benzochrysene ring, substituted or unsubstituted benzo[b]fluoranthene ring, substituted or unsubstituted fluorene ring and substituted or unsubstituted picene ring.

It is further preferable that substituents for Ra and Rb are not aryl groups; and $Ar^{101}$, $Ar^{102}$, $Ar^{103}$, Ra and Rb are not substituted or unsubstituted benzene ring at the same time.

Moreover, in the formulae (9A) to (9C), either one or both of Ra and Rb are preferably selected from the group consisting of a substituted or unsubstituted phenanthrene ring, substituted or unsubstituted benzo[c]phenanthrene ring and substituted or unsubstituted fluoranthene ring.

The polycyclic aromatic skeleton of the polycyclic aromatic compound may be substituted.

Examples of the substituent for the polycyclic aromatic skeleton are a halogen atom, hydroxyl group, substituted or unsubstituted amino group, nitro group, cyano group, substituted or unsubstituted alkyl group, substituted or unsubstituted alkenyl group, substituted or unsubstituted cycloalkyl group, substituted or unsubstituted alkoxy group, substituted, or unsubstituted aromatic hydrocarbon group, substituted or unsubstituted aromatic heterocyclic group, substituted or unsubstituted aralkyl group, substituted or unsubstituted aryloxy group, substituted or unsubstituted alkoxycarbonyl group, and carboxyl group. Preferred examples of the aromatic hydrocarbon group are naphthalene, phenanthrene, fluorene, chrysene, fluoranthene and triphenylene.

When the polycyclic aromatic skeleton has a plurality of substituents, the substituents may form a ring.

The polycyclic aromatic skeleton is preferably any one selected from the group consisting of compounds represented by formulae (9-1) to (9-4) below.

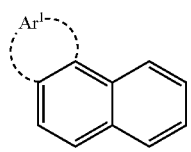  (9-1)

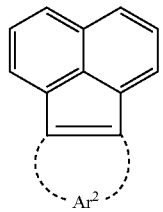  (9-2)

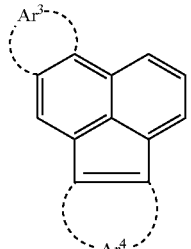  (9-3)

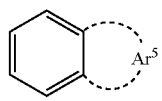  (9-4)

In the formulae (9-1) to (9-4), $Ar^1$ to $Ar^5$ each represent a substituted or unsubstituted fused ring structure having 4 to 16 ring carbon atoms.

Examples of the compound represented by the formula (9-1) are elementary substances or derivatives of substituted or unsubstituted phenanthrene and chrysene.

Examples of the compound represented by the formula (9-2) are elementary substances or derivatives of substituted or unsubstituted acenaphthylene, acenaphthene and fluoranthene.

Examples of the compound represented by the formula (9-3) are elementary substances or derivatives of substituted or unsubstituted benzofluoranthene.

Examples of the compound represented by the formula (9-4) are elementary substances or derivatives of substituted or unsubstituted benzofluoranthene.

The naphthalene derivative is exemplified by a formula (9-5) below.

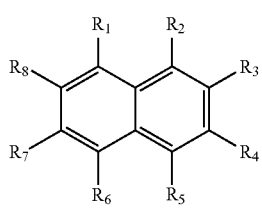  (9-5)

In the formula (9-5), $R_1$ to $R_8$ each independently represent a hydrogen atom, or a substituent consisting of one of or a combination of two or more of substituted or unsubstituted aryl group having 5 to 30 ring carbon atoms, branched or linear alkyl group having 1 to 30 carbon atoms and substituted or unsubstituted cycloalkyl group having 3 to 20 carbon atoms.

The naphthalene derivative is exemplified by a formula (9-6) below.

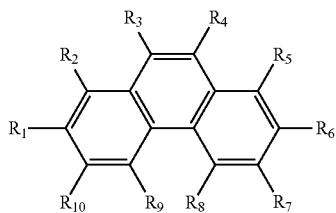

(9-6)

In the formula (9-6), $R_1$ to $R_{10}$ each independently represent a hydrogen atom, or a substituent consisting of one of or a combination of two or more of substituted or unsubstituted aryl group having 5 to 30 ring carbon atoms, branched or linear alkyl group having 1 to 30 carbon atoms and substituted or unsubstituted cycloalkyl group having 3 to 20 carbon atoms.

The chrysene derivative is exemplified by a formula (9-7) below.

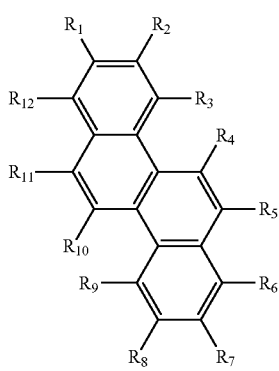

(9-7)

In the formula (9-7), $R_1$ to $R_{12}$ each independently represent a hydrogen atom, or a substituent consisting of one of or a combination of two or more of substituted or unsubstituted aryl group having 5 to 30 ring carbon atoms, branched or linear alkyl group having 1 to 30 carbon atoms and substituted or unsubstituted cycloalkyl group having 3 to 20 carbon atoms.

The polyaromatic skeleton is preferably benzo[c]phenanthrene or its derivative. The benzo[c]phenanthrene derivative is exemplified by a formula (9-8) below.

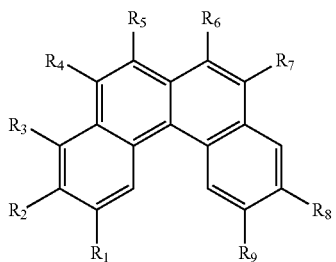

(9-8)

In the formula (9-8), $R_1$ to $R_9$ each independently represent a hydrogen atom, or a substituent consisting of one of or a combination of two or more of substituted or unsubstituted aryl group having 5 to 30 ring carbon atoms, branched or linear alkyl group having 1 to 30 carbon atoms and substituted or unsubstituted cycloalkyl group having 3 to 20 carbon atoms.

The polycyclic aromatic skeleton is preferably benzo[c]chrysene or its derivative. The benzo[c]phenanthrene derivative is exemplified by a formula (9-9) below.

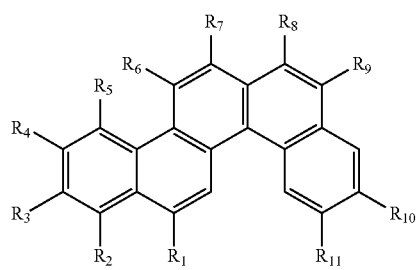

(9-9)

In the formula (9-9), $R_1$ to $R_{11}$ each independently represent a hydrogen atom, or a substituent consisting of one of or a combination of two or more of substituted or unsubstituted aryl group having 5 to 30 ring carbon atoms, branched or linear alkyl group having 1 to 30 carbon atoms and substituted or unsubstituted cycloalkyl group having 3 to 20 carbon atoms.

The polycyclic aromatic skeleton is preferably dibenzo[c,g]phenanthrene represented by a formula (9-10) below or its derivative.

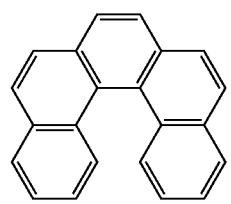

(9-10)

The polycyclic aromatic skeleton is preferably fluoranthene or its derivative. The fluoranthene derivative is exemplified by a formula (9-11) below.

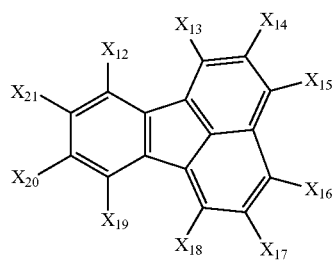

(9-11)

In the formula (9-11), $X_{12}$ to $X_{21}$ each represent a hydrogen atom; halogen atom; linear, branched or cyclic alkyl group; linear, branched or cyclic alkoxy group; substituted or unsubstituted aryl group; or substituted or unsubstituted heteroaryl group.

The polycyclic aromatic skeleton is preferably triphenylene or its derivative. The triphenylene derivative is exemplified by a formula (9-12) below.

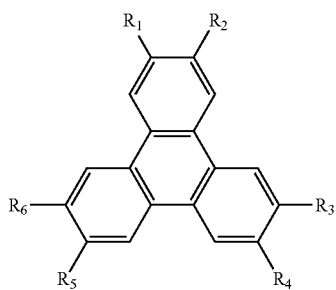

(9-12)

In the formula (9-12), $R_1$ to $R_6$ each independently represent a hydrogen atom, or a substituent consisting of one of or a combination of two or more of substituted or unsubstituted aryl group having 5 to 30 ring carbon atoms, branched or linear alkyl group having 1 to 30 carbon atoms and substituted or unsubstituted cycloalkyl group having 3 to 20 carbon atoms.

The polycyclic aromatic compound may be represented by a formula (9-13) below.

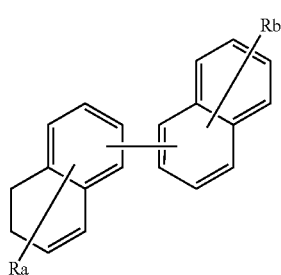

(9-13)

In the formula (9-13), Ra and Rb represent the same as Ra and Rb in the formulae (9A) to (9C). When Ra, Rb and the naphthalene ring have a single or plural substituent(s), the single or plural substituent(s) are an alkyl group having 1 to 20 carbon atoms, haloalkyl group having 1 to 20 carbon atoms, cycloalkyl group having 5 to 18 carbon atoms, silyl group having 3 to 20 carbon atoms, cyano group or halogen atom, while substituents for the naphthalene rings other than Ra and Rb are further allowed to be an aryl group having 6 to 22 carbon atoms.

In the formula (9-13), Ra and Rb each preferably represent a group selected from fluorene ring, phenanthrene ring, triphenylene ring, benzophenanthrene ring, dibenzophenanthrene ring, benzotriphenylene ring, fluoranthene ring, benzochrysene ring, benzo[b]fluoranthene ring and picene ring.

Fifth Exemplary Embodiment

The second host material is preferably a monoamine derivative represented by any one of formulae (10) to (12) below.

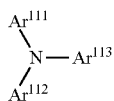

(10)

In the formula (10), $Ar^{111}$, $Ar^{112}$ and $Ar^{113}$ each are a substituted or unsubstituted aryl group or heteroaryl group.

The aryl group has 6 to 50 ring carbon atoms (preferably 6 to 30 ring carbon atoms, more preferably 6 to 20 ring carbon atoms). Examples of the aryl group are a phenyl group, naphthyl group, phenanthrenyl group, benzophenanthrenyl group, dibenzophenanthrenyl group, benzochrysenyl group, dibenzochrysenyl group, fluoranthenyl group, benzofluoranthenyl group, triphenylenyl group, benzotriphenylenyl group, dibenzotriphenylenyl group, picenyl group, benzopicenyl group, dibenzopicenyl group, phenalenyl group, acenaphthenyl group, and diazaphenanthrenyl group. Among the above, a phenyl group or naphthyl group is preferable.

The heteroaryl group has 5 to 50 ring atoms (preferably 6 to 30 ring atoms, more preferably 6 to 20 ring atoms). Examples of the heteroaryl group are a pyrimidyl group and diazaphenanthrenyl group.

At least one of $Ar^{111}$, $Ar^{112}$ and $Ar^{113}$ is preferably a fused aromatic hydrocarbon group selected from a phenanthrenyl group, benzophenanthrenyl group, dibenzophenanthrenyl group, benzochrysenyl group, dibenzochrysenyl group, fluoranthenyl group, benzofluoranthenyl group, triphenylenyl group, benzotriphenylenyl group, dibenzotriphenylenyl group, picenyl group, benzopicenyl group, dibenzopicenyl group, phenalenyl group, and diazaphenanthrenyl group. Among the above, a benzochrysenyl group, triphenylenyl group, or phenanthrenyl group is more preferable. Preferably, the fused aromatic hydrocarbon group is unsubstituted.

In the monoamine derivative represented by the formula (10), $Ar^{111}$ and $Ar^{112}$ each are preferably a phenyl group or naphthyl group, and $Ar^{113}$ is preferably a benzochrysenyl group, triphenylenyl group, or phenanthrenyl group.

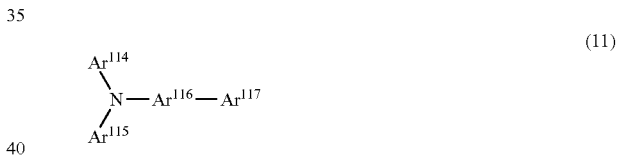

(11)

In the formula (11), $Ar^{114}$, $Ar^{115}$ and $Ar^{117}$ each are a substituted or unsubstituted aryl group or heteroaryl group.

Examples of the aryl group or heteroaryl group are the same as those defined as the aryl group or heteroaryl group for $Ar^{111}$, among which a phenyl group or naphthyl group is preferable.

$Ar^{116}$ is a substituted or unsubstituted arylene group or heteroarylene group.

The arylene group has 6 to 50 ring carbon atoms (preferably 6 to 30 ring carbon atoms, more preferably 6 to 20 ring carbon atoms). Examples of the arylene group are a phenylene group, naphthylene group, phenanthrenylene group, naphthacenylene group, pyrenylene group, biphenylene group, terphenylenylene group, benzophenanthrenylene group, dibenzophenanthrenylene group, benzochrysenylene group, dibenzochrysenylene group, fluoranthenylene group, benzofluoranthenylene group, triphenylenylene group, benzotriphenylenylene group, dibenzotriphenylenylene group, picenylene group, benzopicenylene group, and dibenzopicenylene group. Among the above, a phenylene group or naphthylene group is preferable.

The heteroaryl group has 5 to 50 ring atoms (preferably 5 to 30 ring atoms, more preferably 6 to 20 ring atoms). Examples of the heteroaryl group are a pyridylene group, pyrimidylene group, dibenzofuranylene group, and dibenzothiophenylene group.

$Ar^{117}$ is preferably a fused aromatic hydrocarbon group selected from a phenanthrenyl group, benzophenanthrenyl group, dibenzophenanthrenyl group, benzochrysenyl group, dibenzochrysenyl group, fluoranthenyl group, benzofluoranthenyl group, triphenylenyl group, benzotriphenylenyl group, dibenzotriphenylenyl group, picenyl group, benzopicenyl group, and dibenzopicenyl group. Among the above, a benzochrysenyl group, triphenylenyl group, or phenanthrenyl group is more preferable. Preferably, the fused aromatic hydrocarbon group is unsubstituted.

In the monoamine derivative of the formula (11), more preferably, $Ar^{114}$ and $Ar^{115}$ each are a phenyl group or naphthyl group, $Ar^{116}$ is a phenyl group or naphthyl group, and $Ar^{117}$ is a benzochrysenyl group, triphenylenyl group, or phenanthrenyl group.

(12)

In the formula (12), $Ar^{118}$, $Ar^{119}$ and $Ar^{121}$ are a substituted or unsubstituted aryl group or heteroaryl group.

Examples of the aryl group or heteroaryl group are the same as those defined as the aryl group or heteroaryl group for $Ar^{111}$ and are preferably a phenyl group.

$Ar^{120}$ is a substituted or unsubstituted arylene group or heteroarylene group and the same as those defined as the arylene group or heteroarylene group for $Ar^{116}$.

$Ar^{120}$ is preferably a phenylene group or naphthylene group.

n is an integer of 2 to 5, preferably 2 to 4, more preferably 2 to 3. When n is 2 or more, $Ar^{126}$ may be mutually the same or different.

$Ar^{121}$ is preferably a fused aromatic hydrocarbon group selected from a phenyl group, naphthyl group, phenanthrenyl group, benzophenanthrenyl group, dibenzophenanthrenyl group, benzochrysenyl group, dibenzochrysenyl group, fluoranthenyl group, benzofluoranthenyl group, triphenylenyl group, benzotriphenylenyl group, dibenzotriphenylenyl group, picenyl group, benzopicenyl group, dibenzopicenyl group, phenalenyl group, and diazaphenanthrenyl group. Among the above, a benzochrysenyl group, triphenylenyl group, or phenanthrenyl group is more preferable.

In the exemplary embodiment, for the second host material in the formula (12), $Ar^{118}$ and $Ar^{119}$ each are preferably a phenyl group or naphthyl group; $Ar^{126}$ is preferably a phenylene group or naphthylene group; and $Ar^{121}$ is preferably a benzochrysenyl group, triphenylenyl group, or phenanthrenyl group.

When $Ar^{101}$ to $Ar^{121}$ have substituent(s), the substituent(s) is preferably an alkyl group having 1 to 20 carbon atoms, haloalkyl group having 1 to 20 carbon atoms, cycloalkyl group having 3 to 18 carbon atoms, aryl group having 6 to 30 ring carbon atoms, silyl group having 3 to 20 carbon atoms, cyano group, and halogen atom.

Examples of the alkyl group are a methyl group, ethyl group, propyl group, isopropyl group, n-butyl group, 1-methylpropyl group and 1-propylbutyl group.

Examples of the aryl group are the same as those for $Ar^{111}$.

The haloalkyl group is exemplified by a 2,2,2-trifluoroethyl group.

Examples of the cycloalkyl group are a cyclopropyl group, cyclobutyl group, cyclopentyl group, cyclohexyl group and cyclooctyl group.

Examples of the silyl group are a trimethylsilyl group and triethylsilyl group.

Examples of the halogen atom are fluorine, chlorine, bromine, and iodine.

When the monoamine derivatives represented by the formulae (10) to (12) do not have a substituent, it is meant that a hydrogen atom is substituted. The hydrogen atom of the monoamine derivatives represented by the formulae (10) to (12) includes light hydrogen and deuterium. "Carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a ring including a saturated ring, unsaturated ring, or aromatic ring.

Specific examples of the monoamine derivatives represented by the formula (10) are shown below.

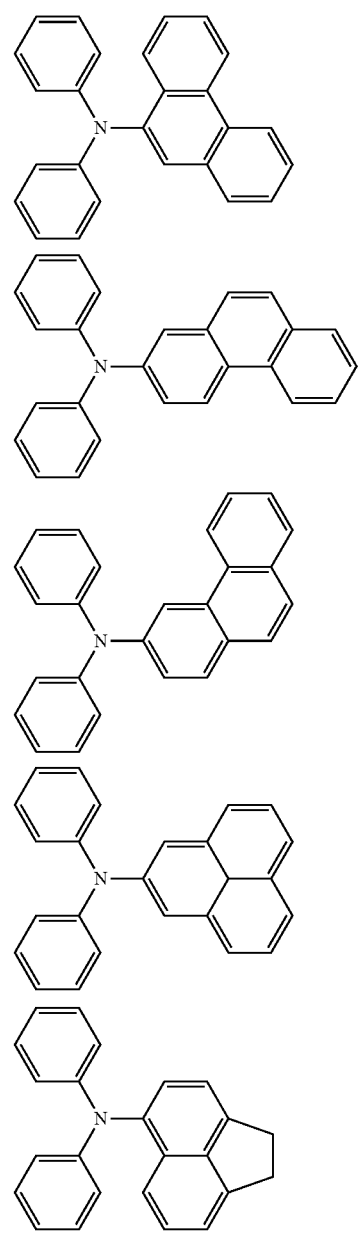

233
-continued
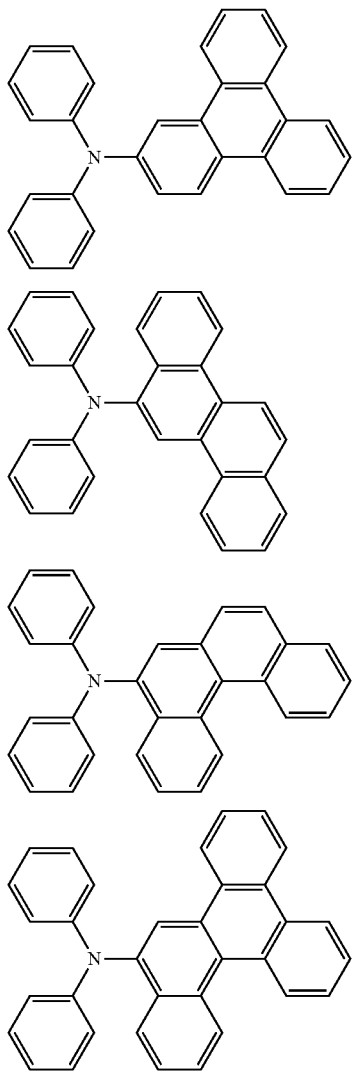
234
-continued
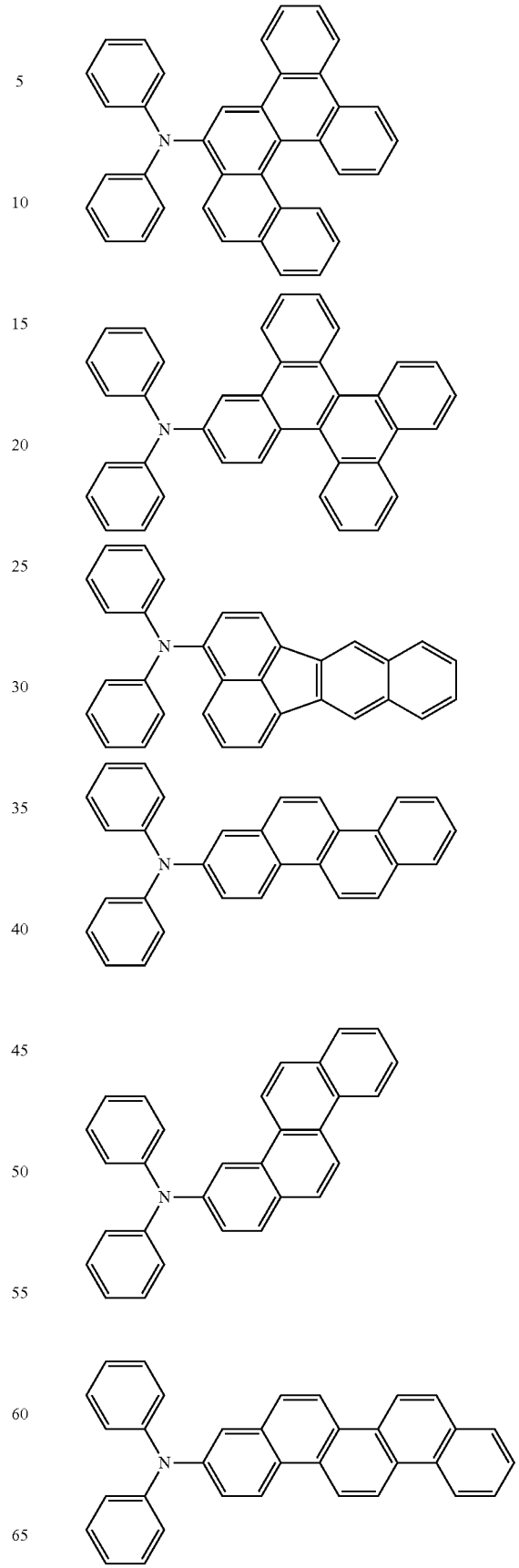

-continued
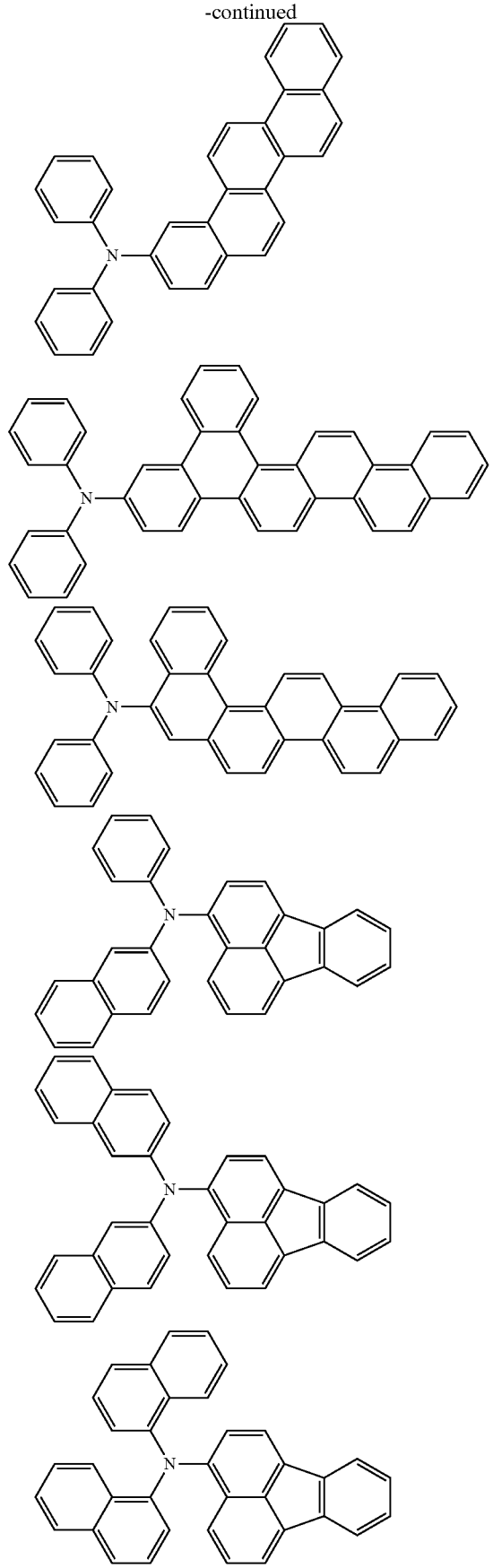
-continued
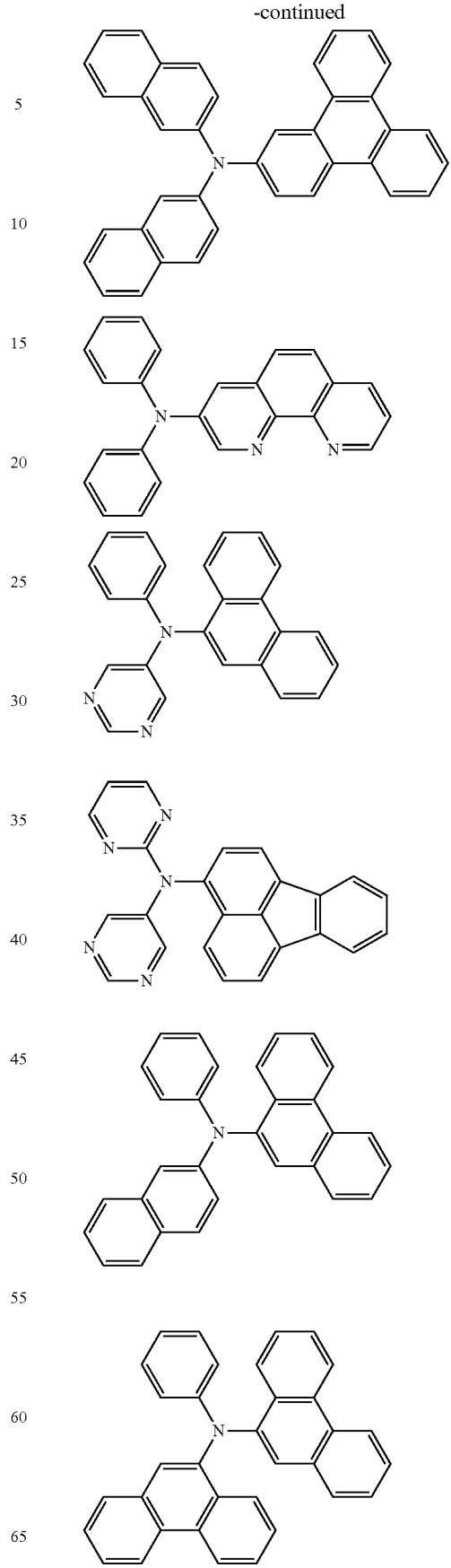

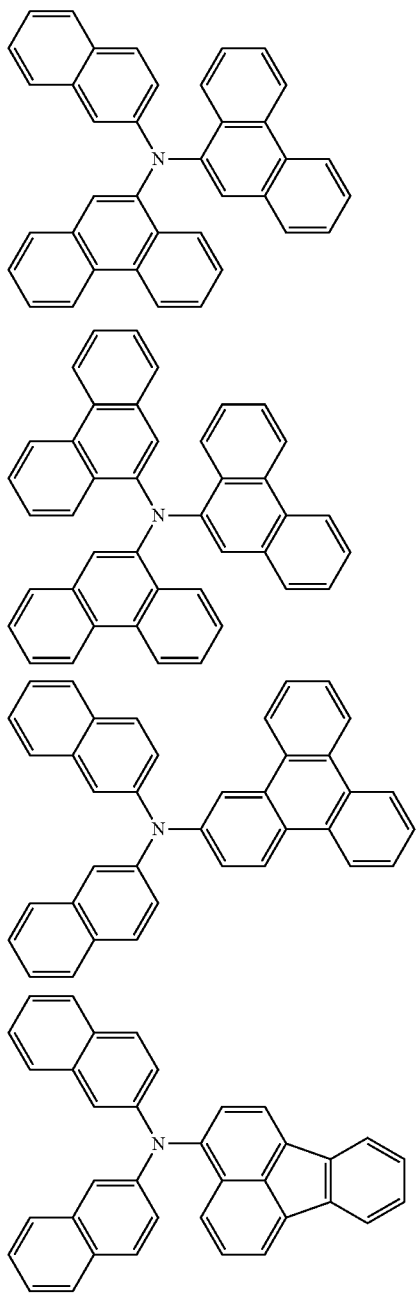
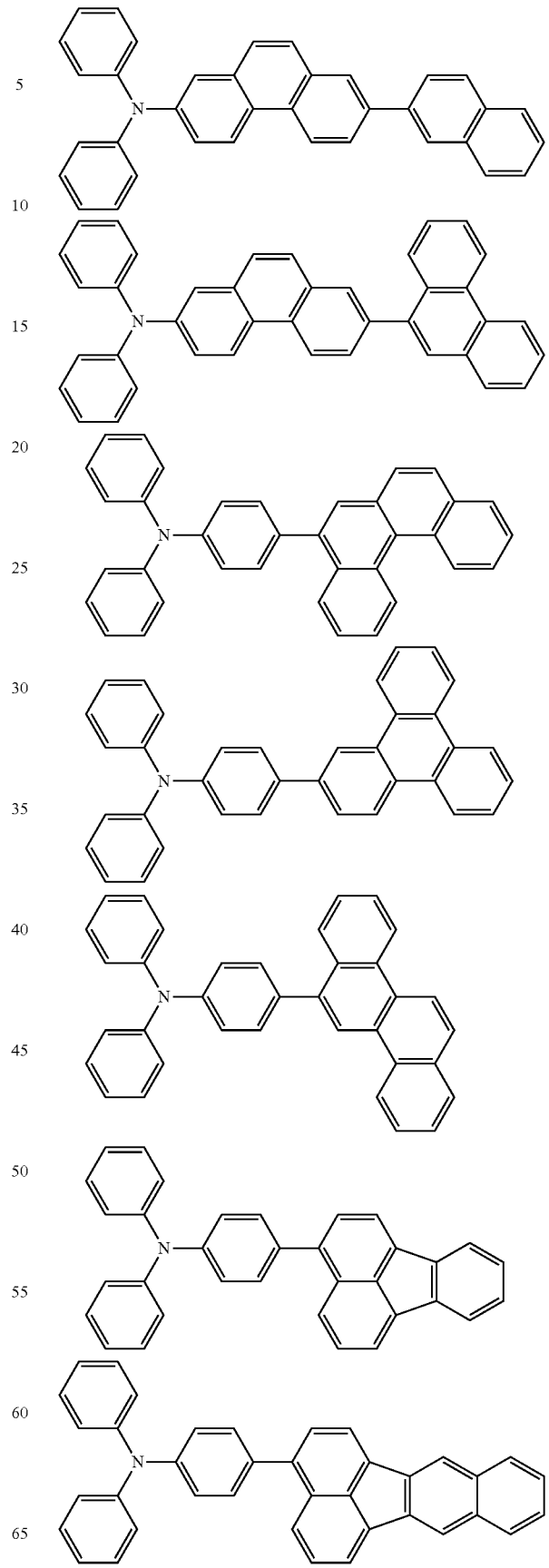
Specific examples of the monoamine derivatives represented by the formula (11) are shown below.
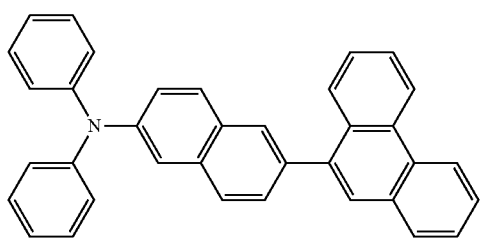

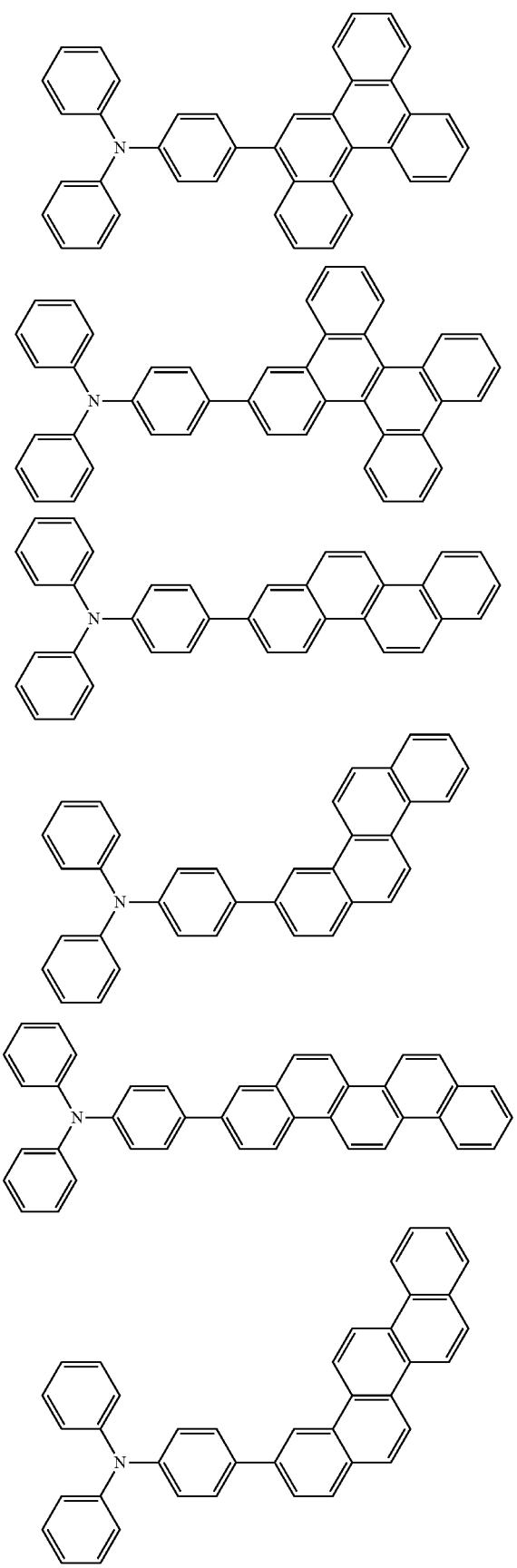
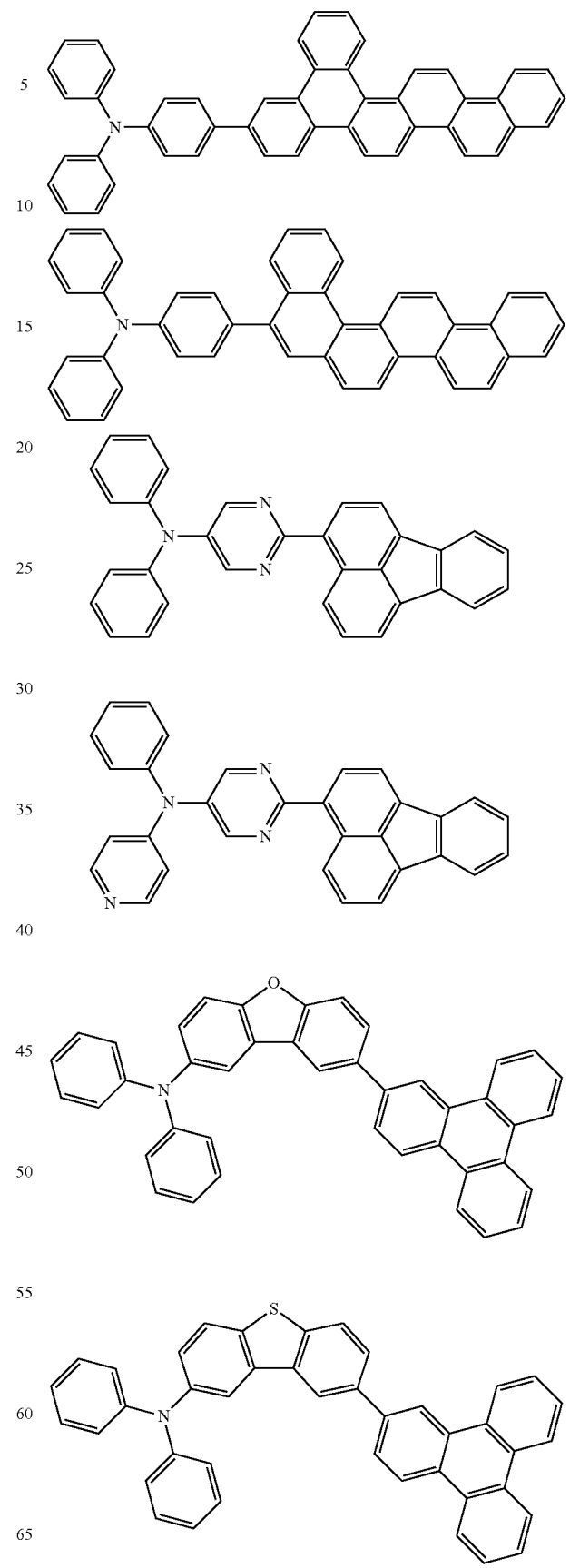

241
-continued
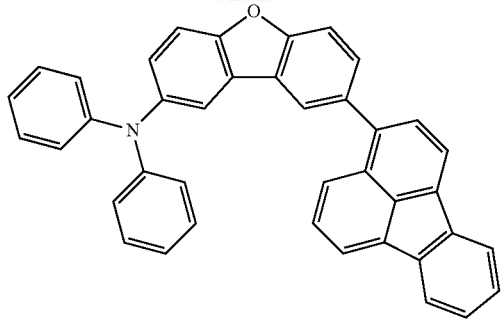
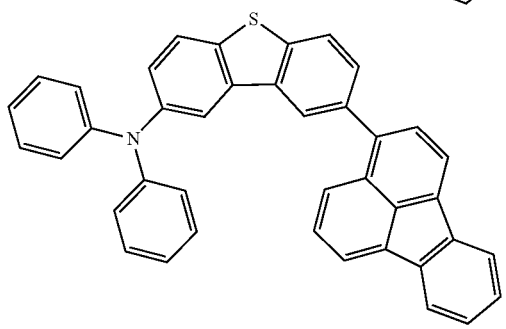
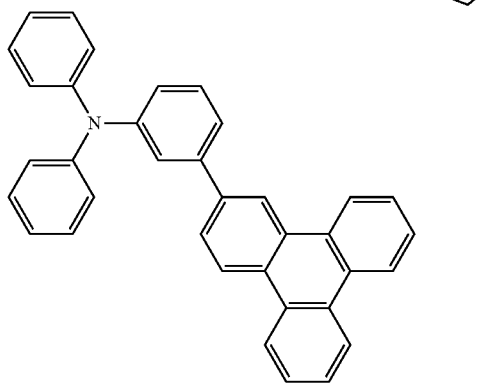
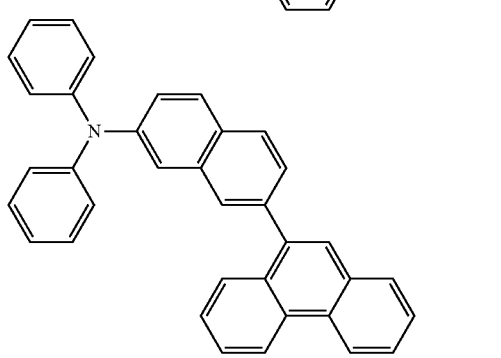
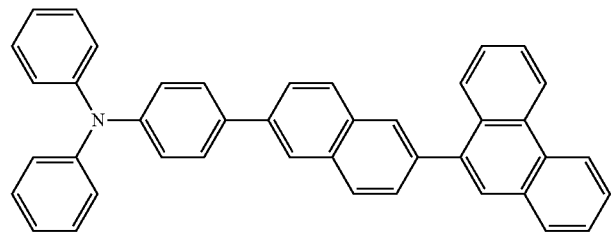
242
-continued
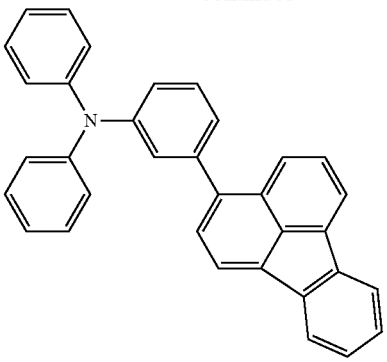
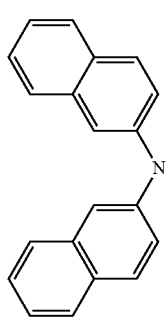
Specific examples of the monoamine derivatives represented by the formula (12) are shown below.

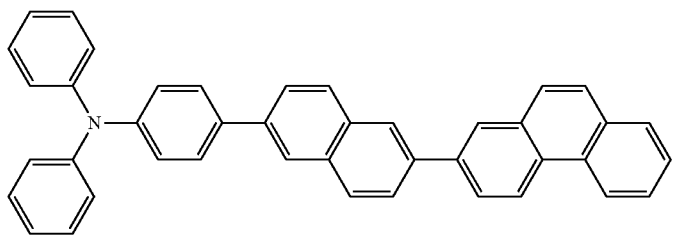
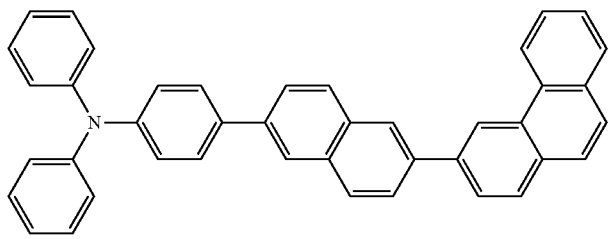
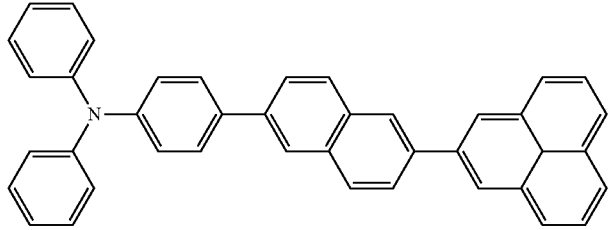
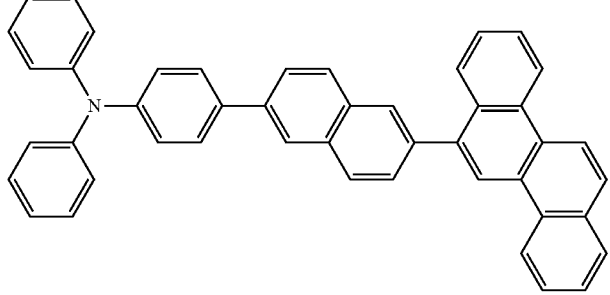
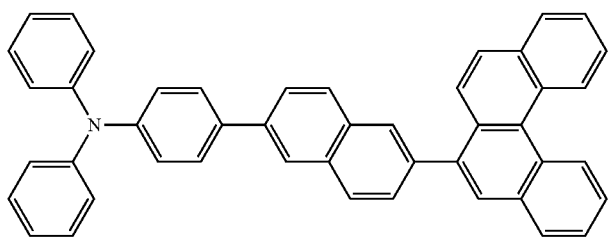
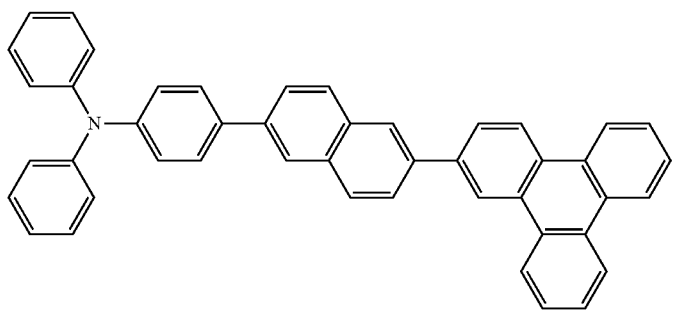

-continued
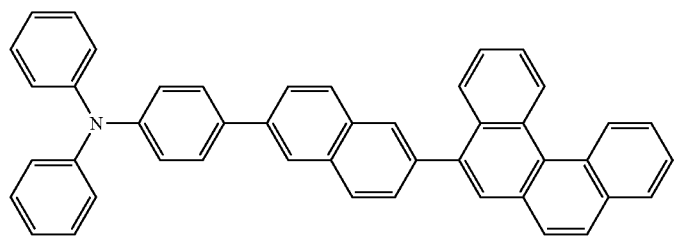
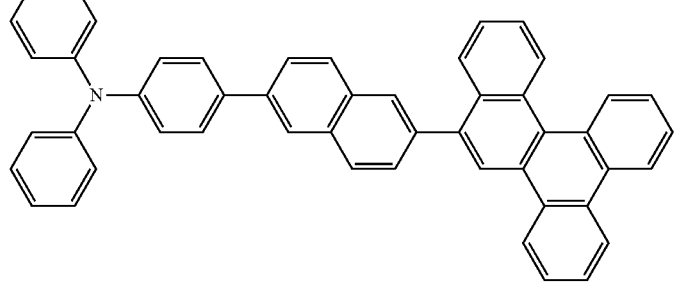
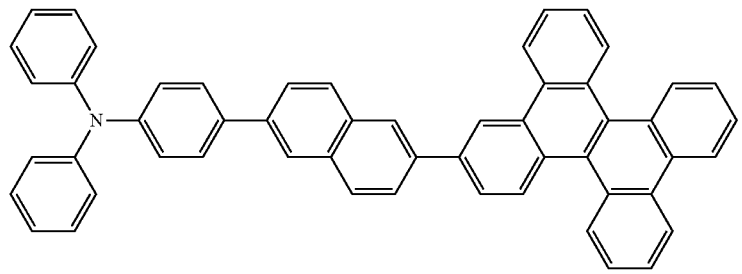
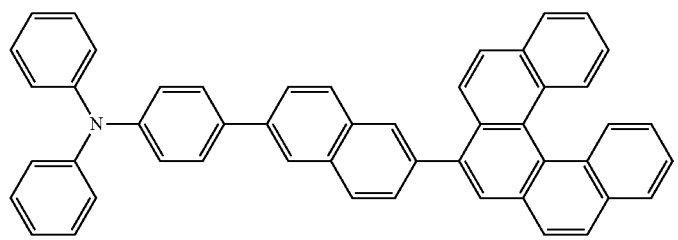
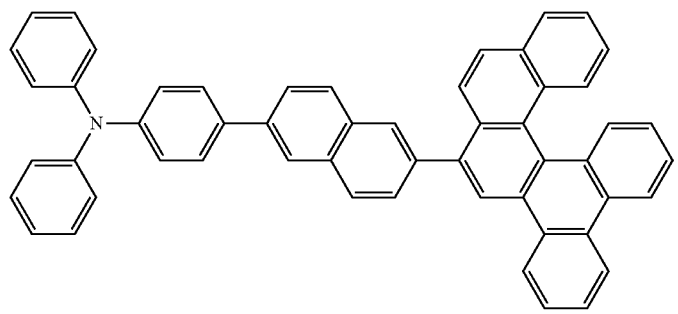
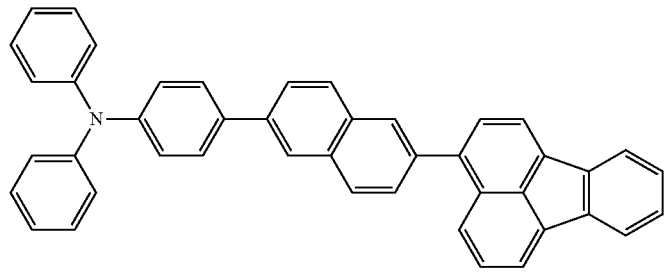

-continued
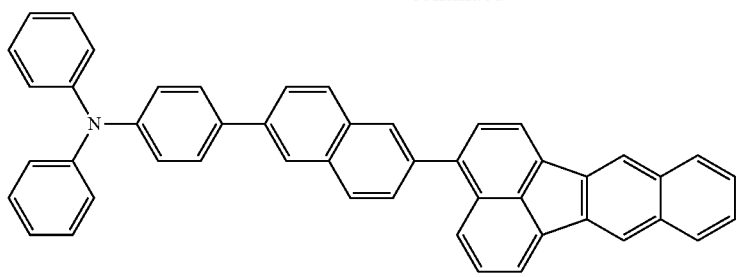
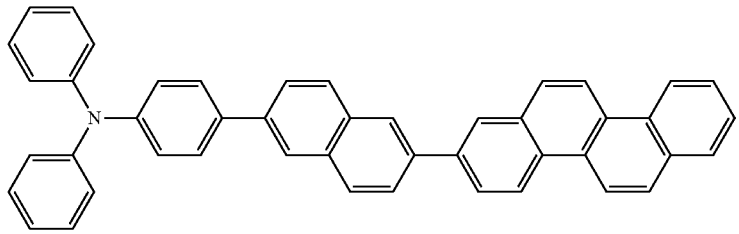
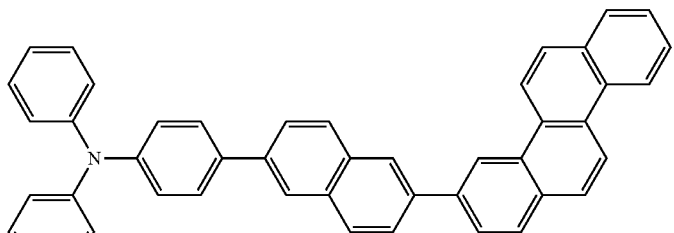
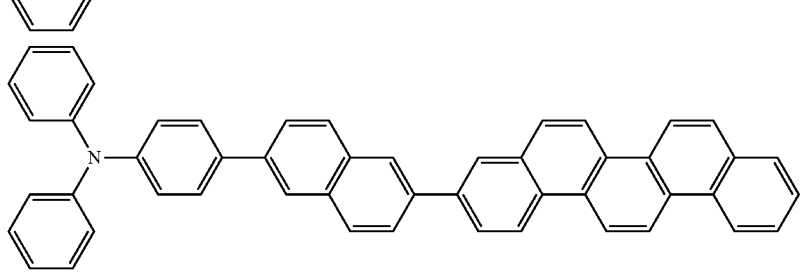
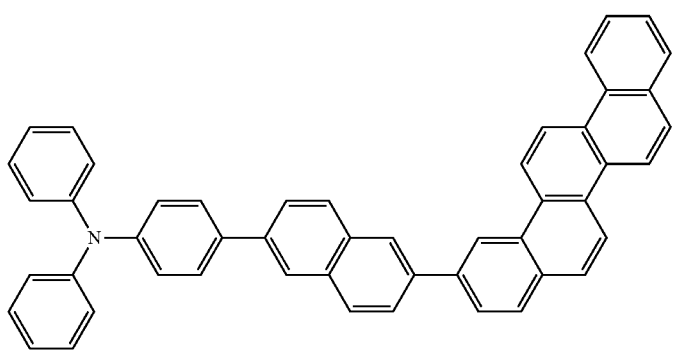
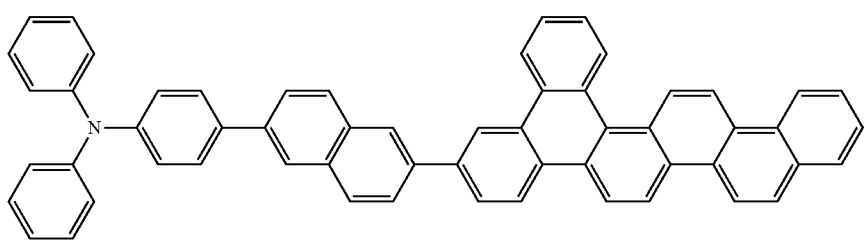

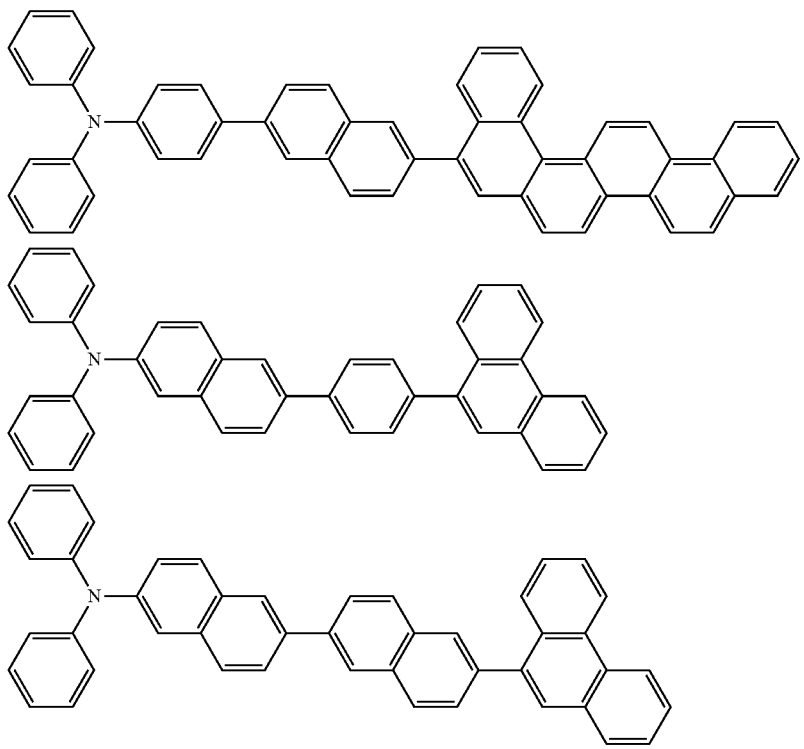
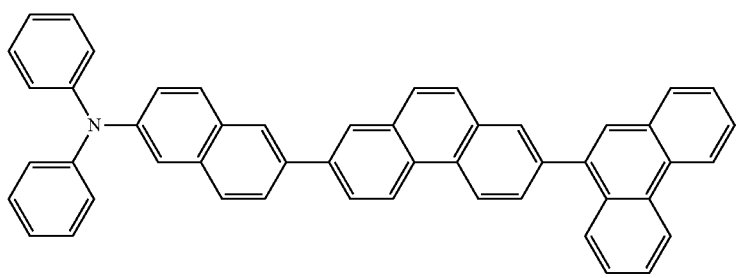
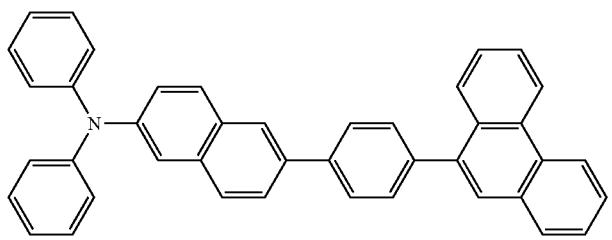
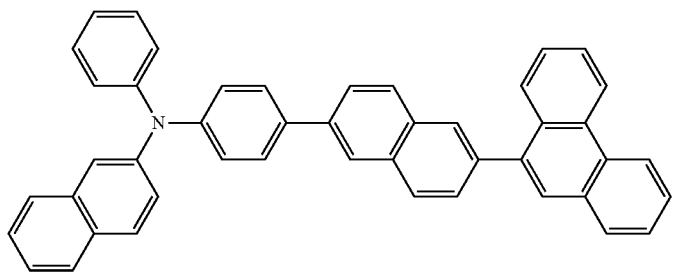

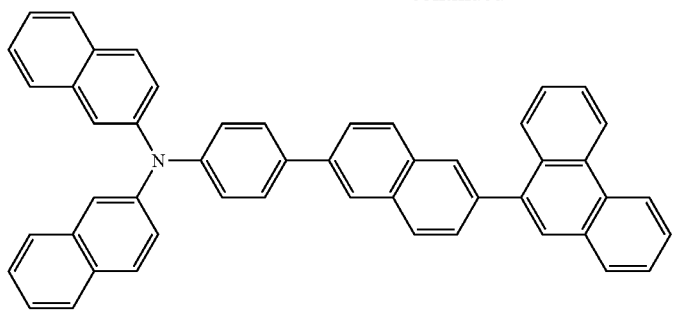
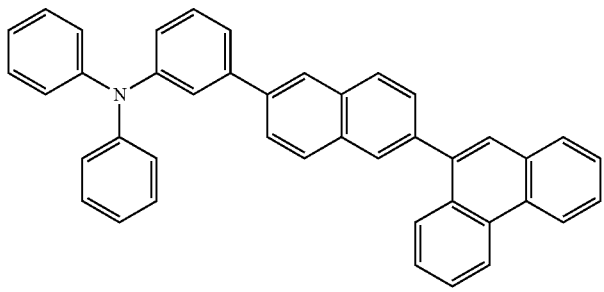
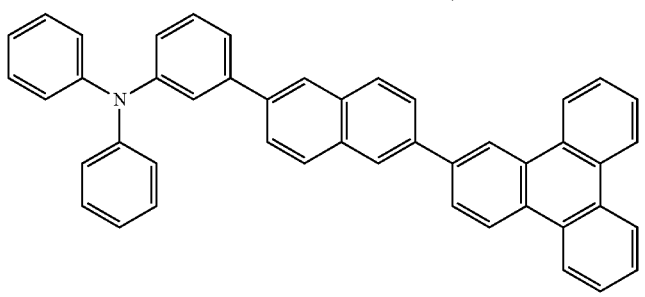
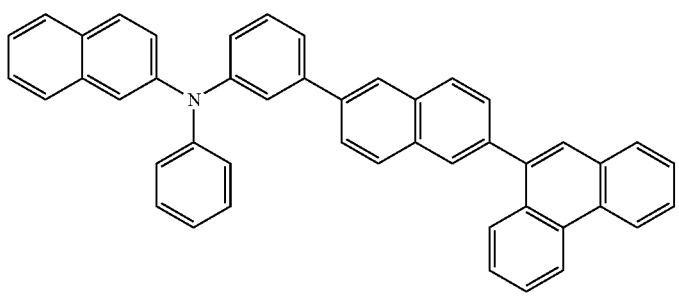
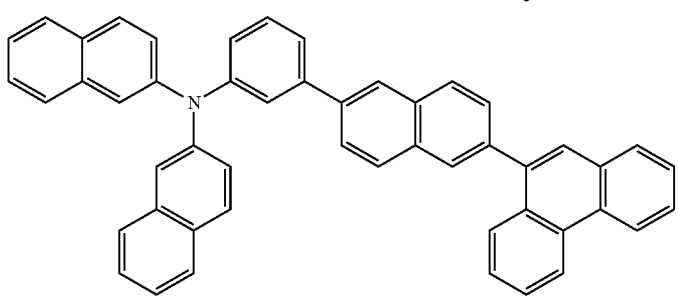
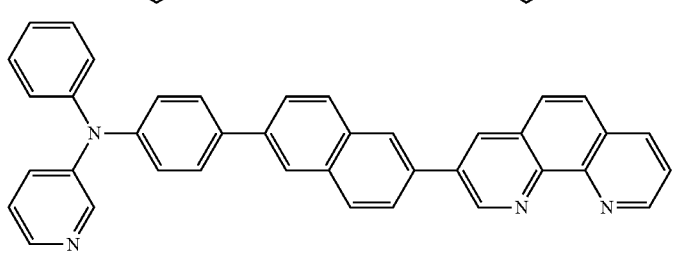

-continued
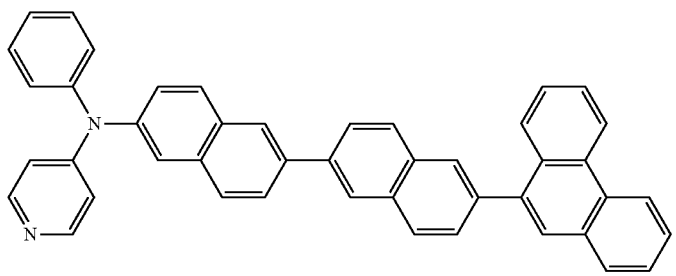
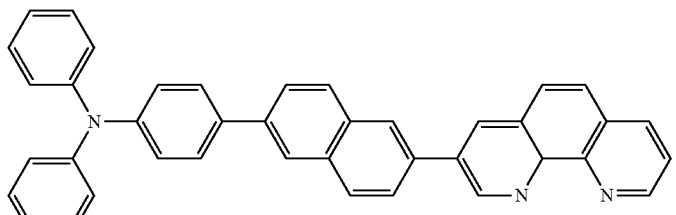
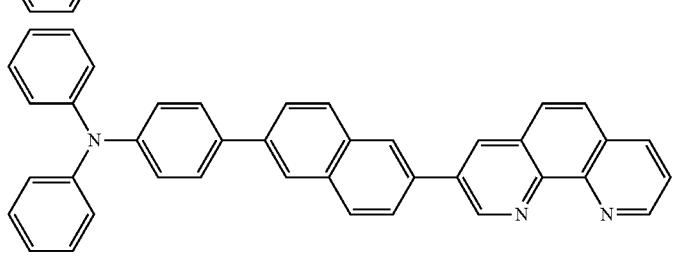
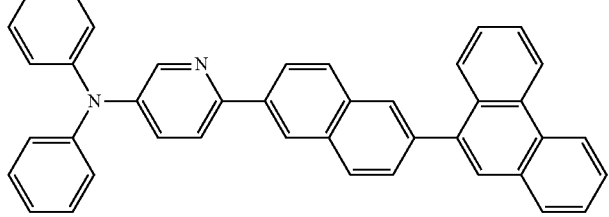
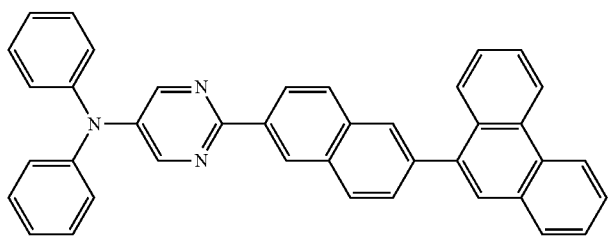
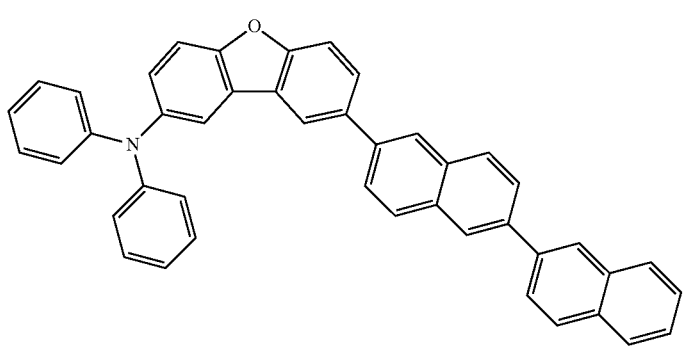

-continued
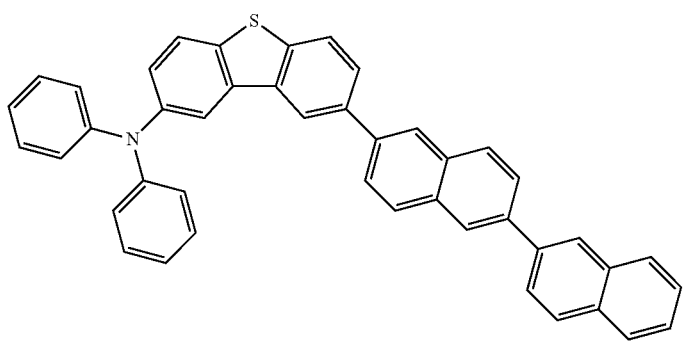
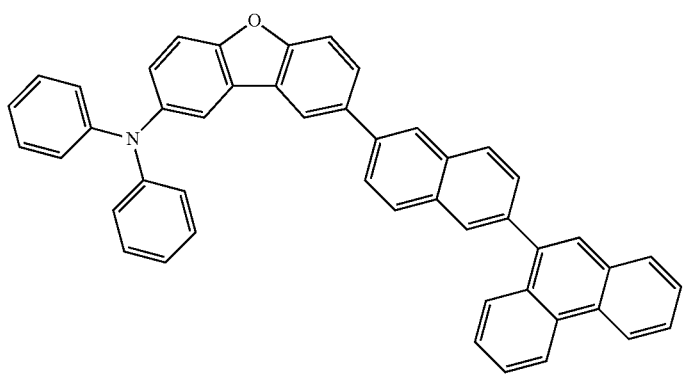
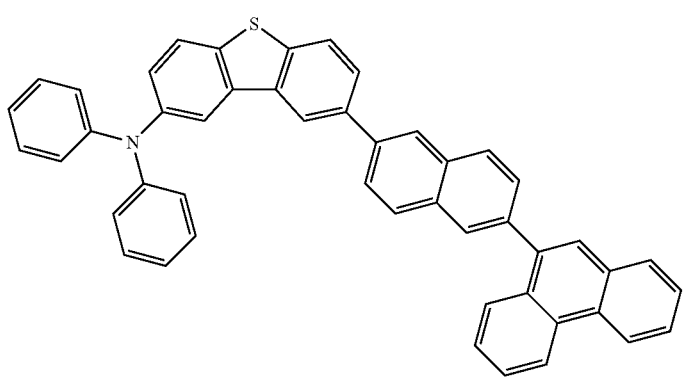
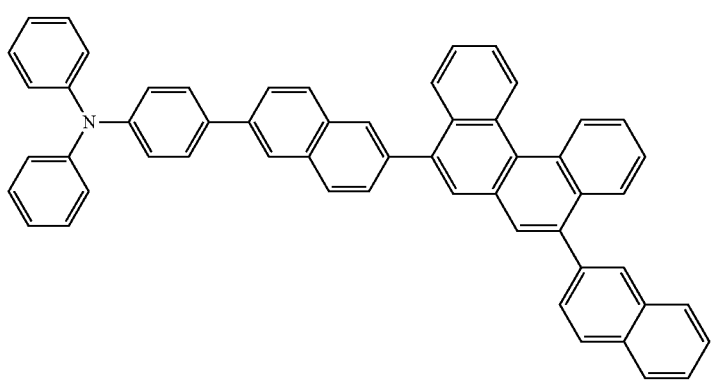
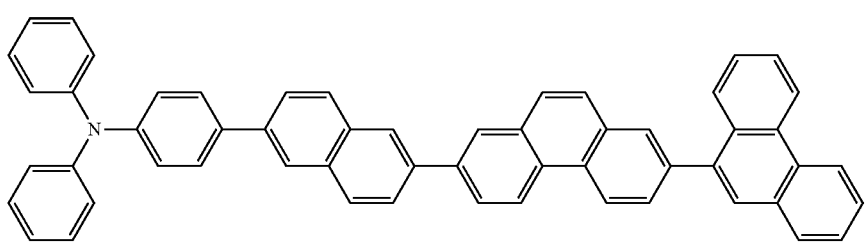

-continued
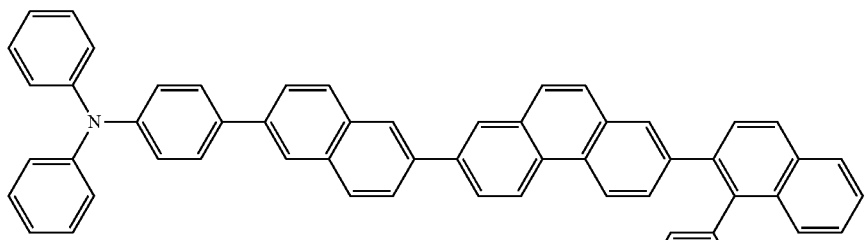
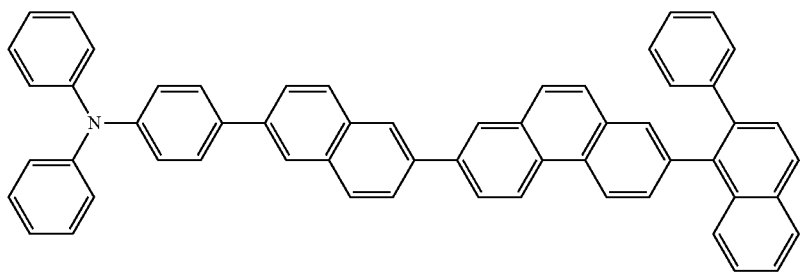
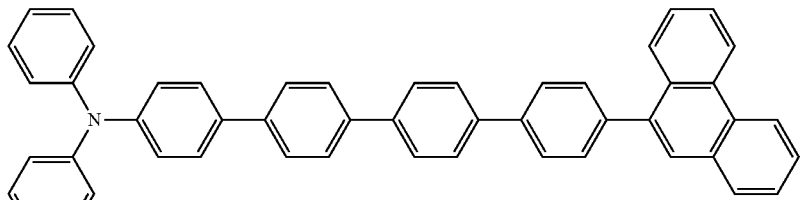
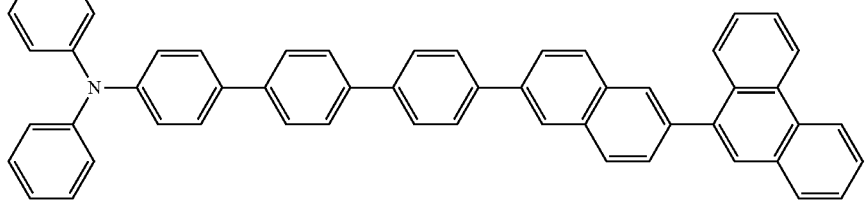
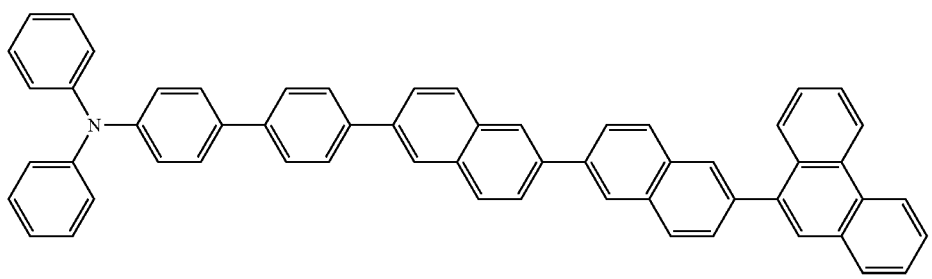
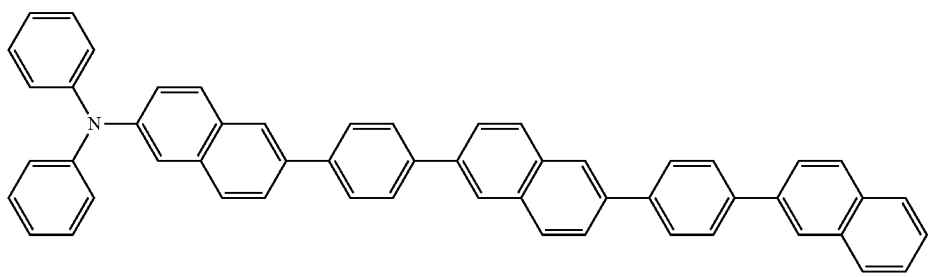

-continued

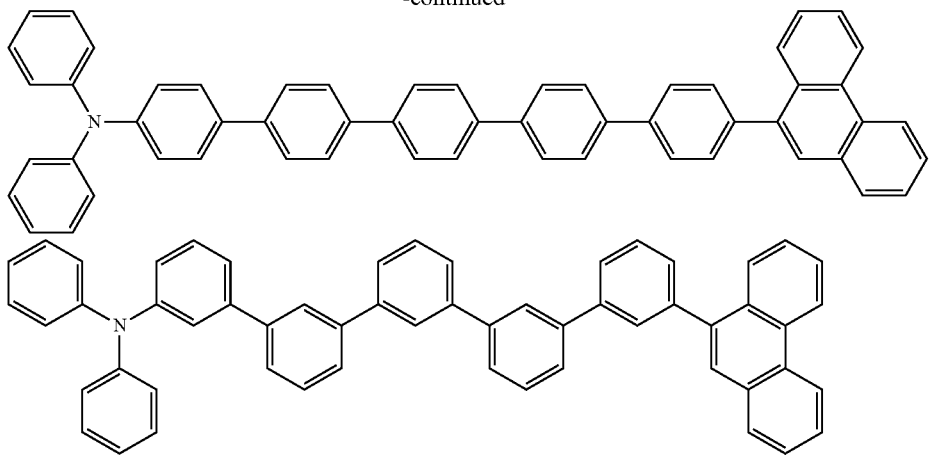

Sixth Exemplary Embodiment

In an organic EL device according to a sixth exemplary embodiment, an aromatic amine compound is used as the second host material.

An example of the aromatic amine compound is preferably a compound represented by the formula (13) or (14).

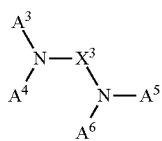
(13)

In the formula (13): $X^3$ represents a substituted or unsubstituted arylene group having 10 to 40 ring carbon atoms; and $A^3$ to $A^6$ represent a substituted or unsubstituted aryl group having 6 to 60 ring carbon atoms, or heteroaryl group having 6 to 60 ring atoms.

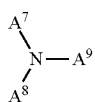
(14)

In the formula (14), $A^7$ to $A^9$ represent a substituted or unsubstituted aryl group having 6 to 60 ring carbon atoms, or heteroaryl group having 6 to 60 ring atoms.

The second host material represented by the formula (13) or (14) is preferably represented by formulae (15) to (19).

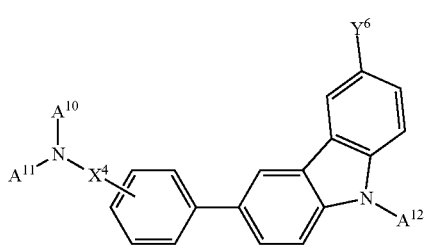
(15)

-continued

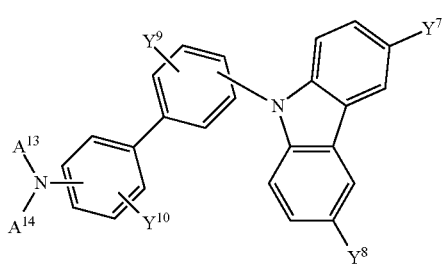
(16)

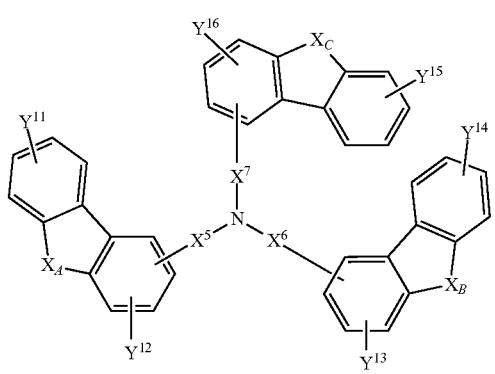
(17)

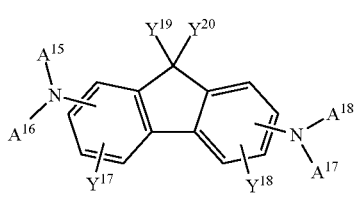
(18)

-continued (19)

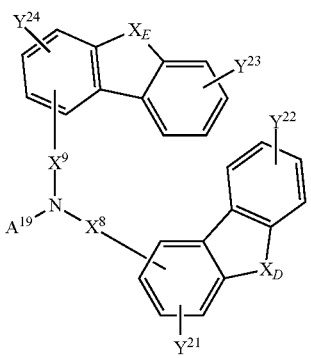

In the formulae (15) to (19): $A^{10}$ to $A^{19}$ each represent a substituted or unsubstituted aryl group having 6 to 40 carbon atoms, substituted or unsubstituted aromatic heterocyclic group having 2 to 40 carbon atoms, substituted or unsubstituted aryl group having 8 to 40 carbon atoms bonded with an aromatic amino group, or substituted or unsubstituted aryl group having 8 to 40 carbon atoms bonded with an aromatic heterocyclic group;

$A^{10}, A^{13}, A^{15}$ and $A^{17}$ are adapted to be respectively bonded to $A^{11}, A^{14}, A^{16}$ and $A^{18}$ to form a ring;

$X^4$ to $X^9$ represent a single bond or a linking group having 1 to 30 carbon atoms;

$Y^6$ to $Y^{24}$ represent a hydrogen atom, halogen atom, substituted or unsubstituted alkyl group having 1 to 40 carbon atoms, substituted or unsubstituted heterocyclic group having 3 to 20 carbon atoms, substituted or unsubstituted aryl group having 6 to 40 carbon atoms, substituted or unsubstituted aralkyl group having 7 to 20 carbon atoms, substituted or unsubstituted alkenyl group having 2 to 40 carbon atoms, substituted or unsubstituted alkylamino group having 1 to 40 carbon atoms, substituted or unsubstituted aralkylamino group having 7 to 60 carbon atoms, substituted or unsubstituted alkylsilyl group having 3 to 20 carbon atoms, substituted or unsubstituted arylsilyl group having 8 to 40 carbon atoms, substituted or unsubstituted aralkylsilyl group having 8 to 40 carbon atoms, or substituted or unsubstituted halogenated alkyl group having 1 to 40 carbon atoms; and $X_A$, $X_B$, $X_C$, $X_D$, $X_E$ each represent a sulfur atom, an oxygen atom or a monoaryl-substituted nitrogen atom.

Examples of compounds represented by the formulae (13), (14), and (15) to (19) are as follows.

HT-1

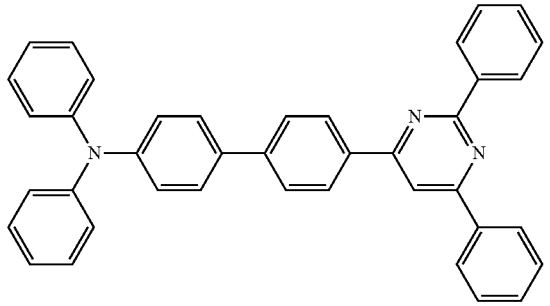

HT-2

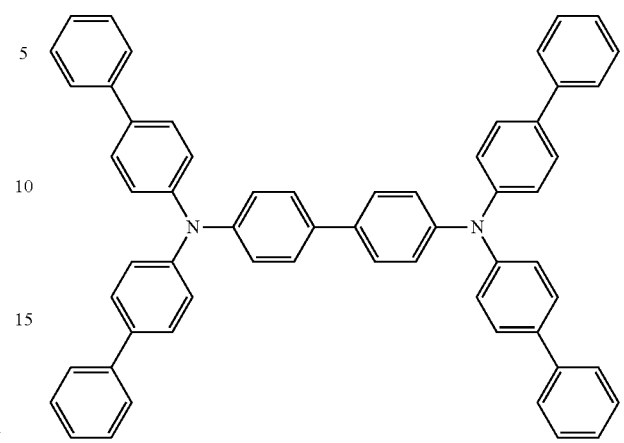

HT-3

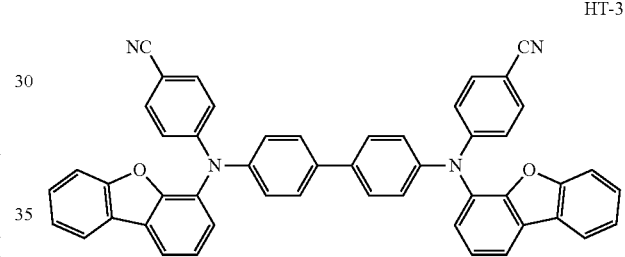

HT-4

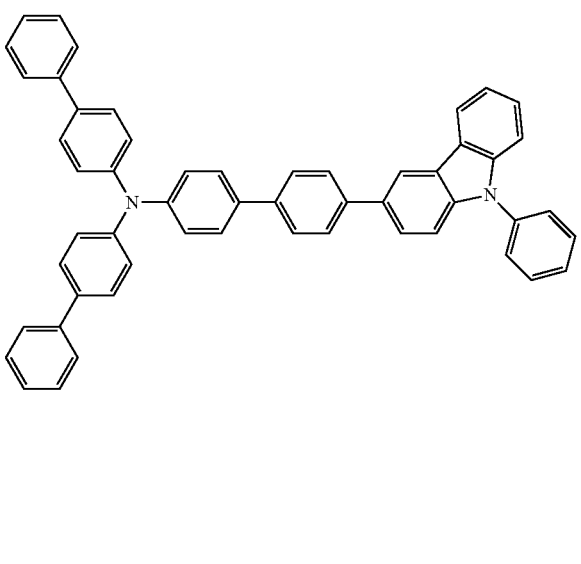

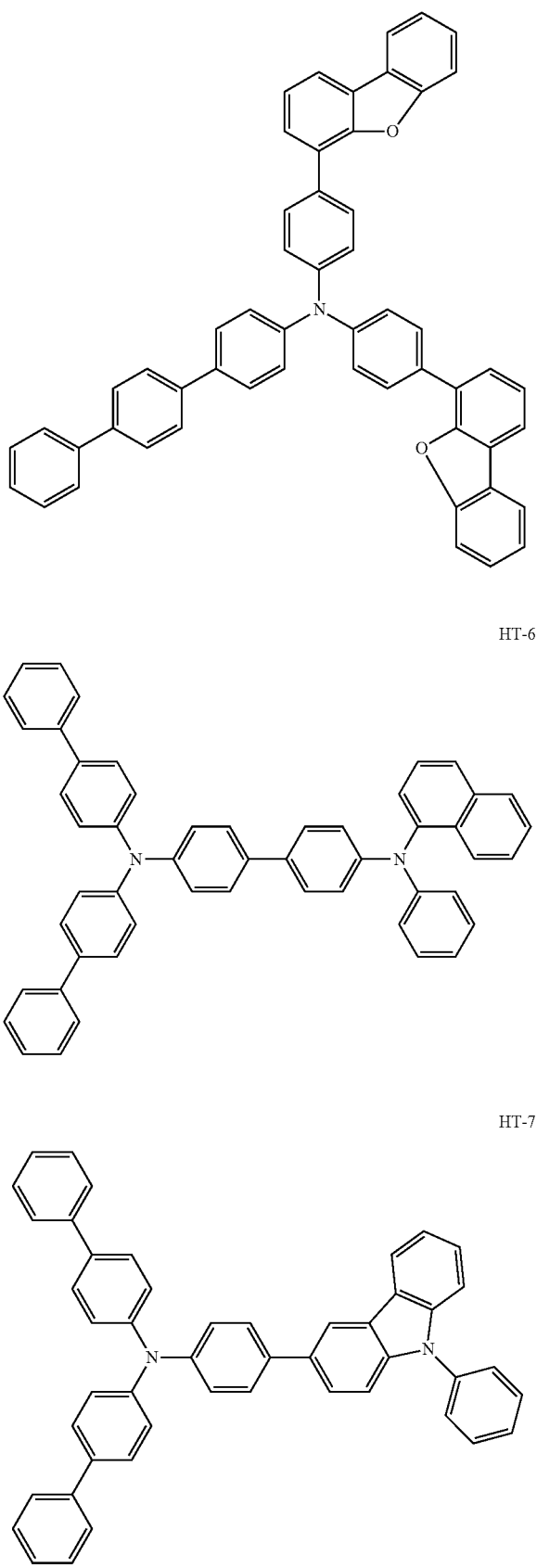

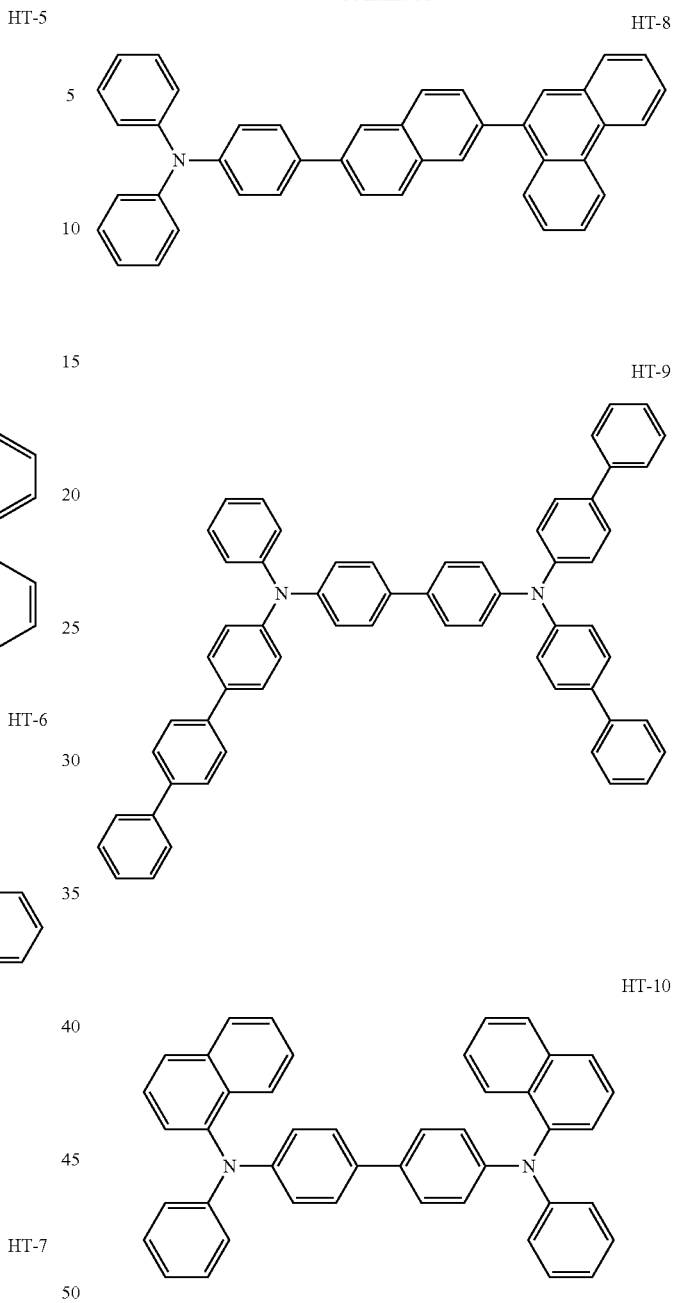

Seventh Exemplary Embodiment

An organic EL device according to a seventh exemplary embodiment preferably contains a metal complex as the second host material.

The metal complex is preferably represented by a formula (20) below.

$$L^{11}L^{12}L^{13}M^{11}{}_2Q^{11} \qquad (20)$$

In the formula: ligands $L^{11}$, $L^{12}$ and $L^{13}$ are independently selected from a structure represented by a formula (21) below; $M^{11}$ is a divalent metal; and $Q^{11}$ is a monovalent anion induced from inorganic or organic acids.

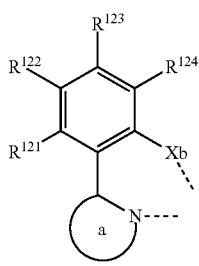

In the ligands: Xb is O, S or Se; a-ring is oxazole, thiazole, imidazoles, oxadiazole, thiadiazole, benzooxazole, benzothiazole, benzoimidazole, pyridine, or quinoline; $R^{121}$ to $R^{124}$ are independently hydrogen, an alkyl group having 1 to 5 carbon atoms, halogen, silyl group or aryl group having 6 to 20 carbon atoms, which may be bonded to an adjacent substituent via alkylene or alkenylene to form a fused ring. The pyridine and quinoline may be bonded to R1 to form a fused ring.

The a-ring and the aryl group for $R^{121}$ to $R^{124}$ may be further substituted by a C1-C5 alkyl group, halogen, C1-C5 alkyl group having a halogen substituent, phenyl group, naphthyl group, silyl group, or amino group.

The ligands $L^{11}$, $L^{12}$ and $L^{13}$ are independently selected from the following structures.

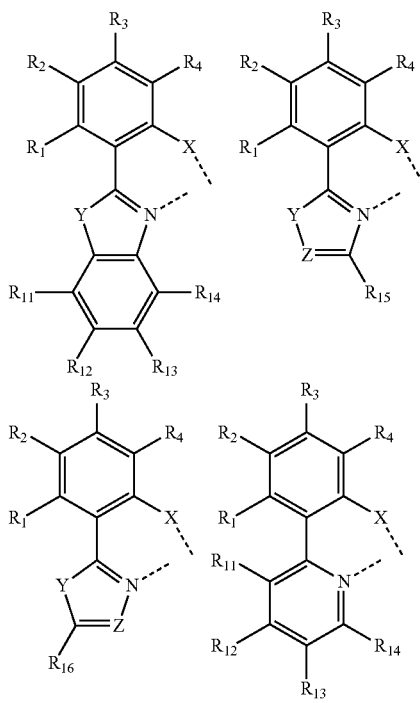

In the ligands: X and $R_1$ to $R_4$ represent the same as Xb and $R^{121}$ to $R^{124}$ in the formula (21); Y is O, S or $NR_{21}$; Z is CH or N; $R_{11}$ to $R_{16}$ are independently hydrogen, a C1-C5 alkyl group, halogen, C1-C5 alkyl group having a halogen substituent, phenyl group, naphthyl group, silyl group, or amino group; and $R_{11}$ to $R_{14}$ may be bonded to an adjacent substituent via alkylene or alkenylene to form a fused ring.

The ligands $L^{11}$, $L^{12}$ and $L^{13}$ of the compound may be the same and can be selected from the following structures.

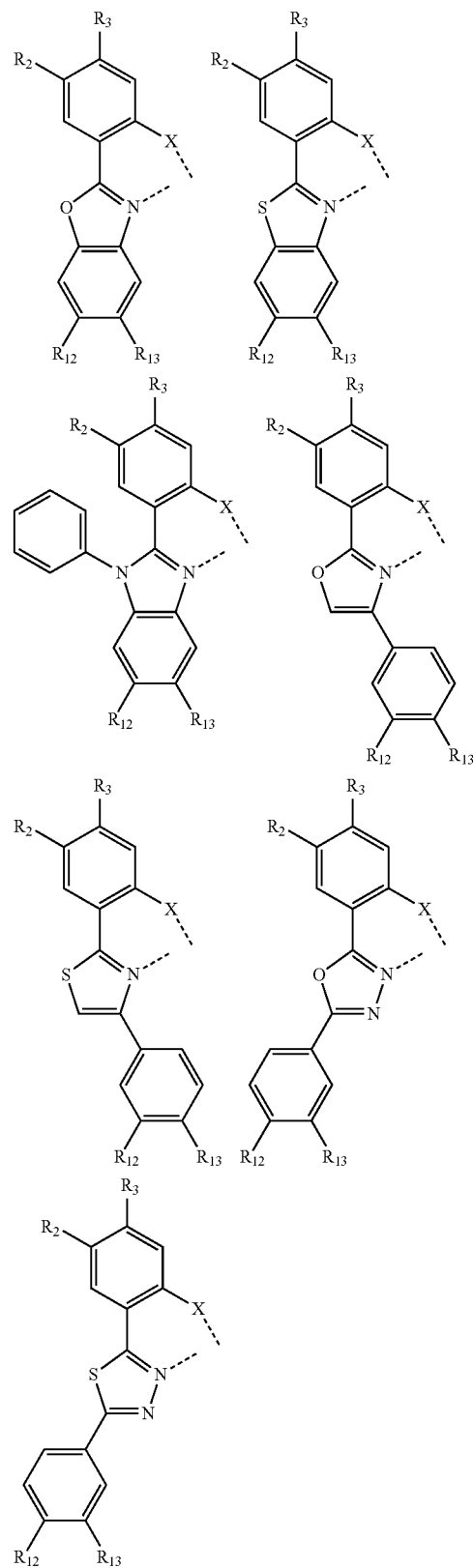

In the ligands: X is O, S or Se; $R_2$, $R_3$, $R_{12}$ and $R_{13}$ are independently hydrogen, methyl, ethyl, n-propyl, isopropyl, fluorine, chlorine, trifluoromethyl, phenyl, naphthyl, fluorenyl, trimethylsilyl, triphenylsilyl, t-butyldimethylsilyl, dimethylamine, diethylamine, or diphenylamine.

The phenyl, naphthyl, fluorenyl are further substituted by fluorine, chlorine, trimethylsilyl, triphenylsilyl, t-butyldimethylsilyl, dimethylamine, diethylamine, or diphenylamine.

Furthermore, in this exemplary embodiment, the metal complex is preferably a zinc complex. Examples of such a preferable zinc complex are shown below.

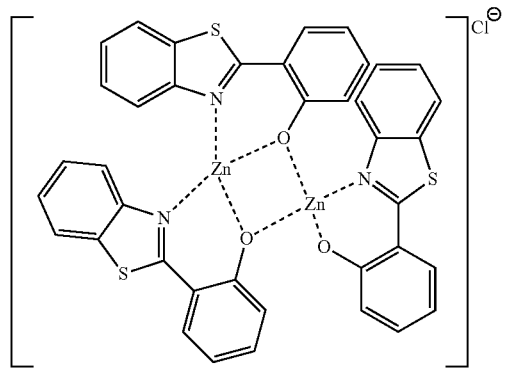

269
-continued
8
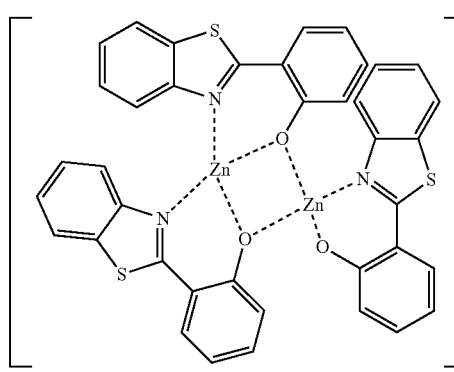
9
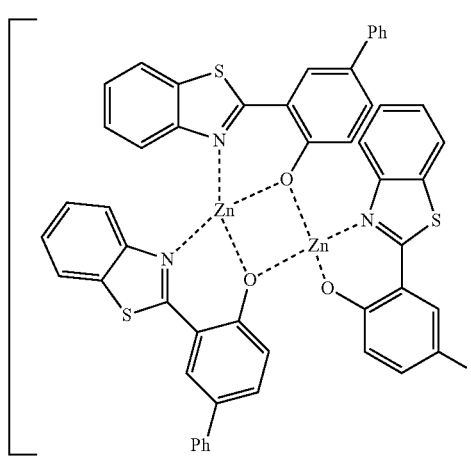
10
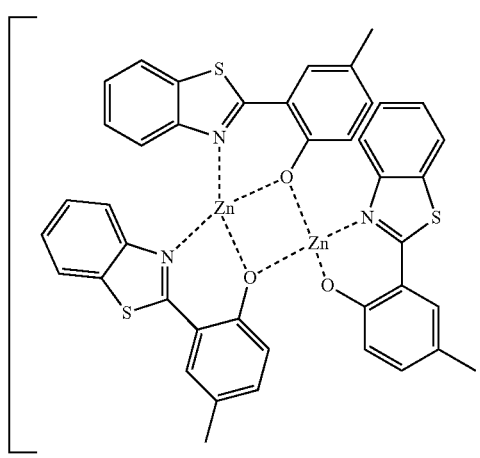
270
-continued
11
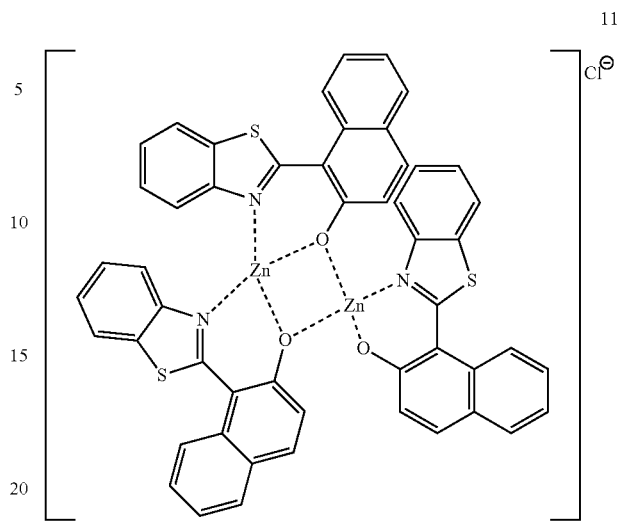
12
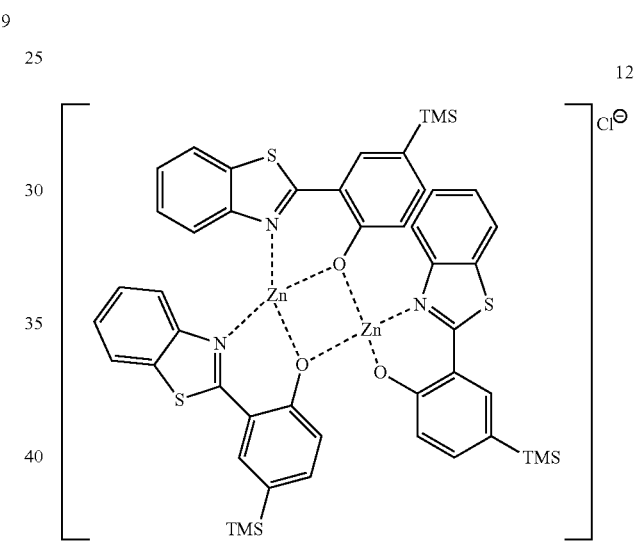
13
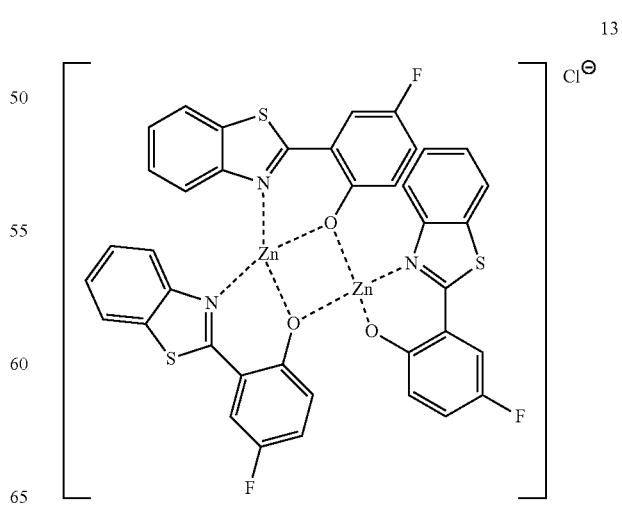

271
-continued
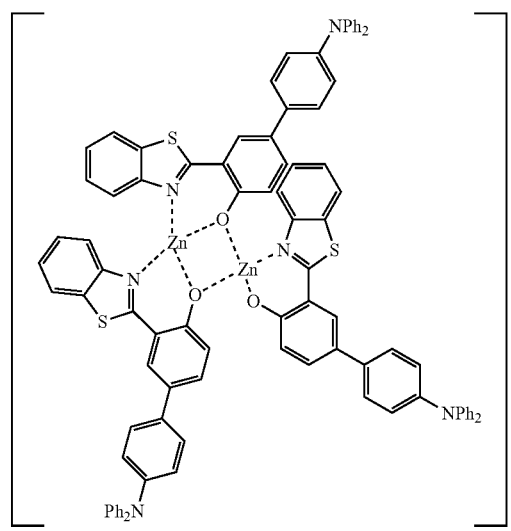
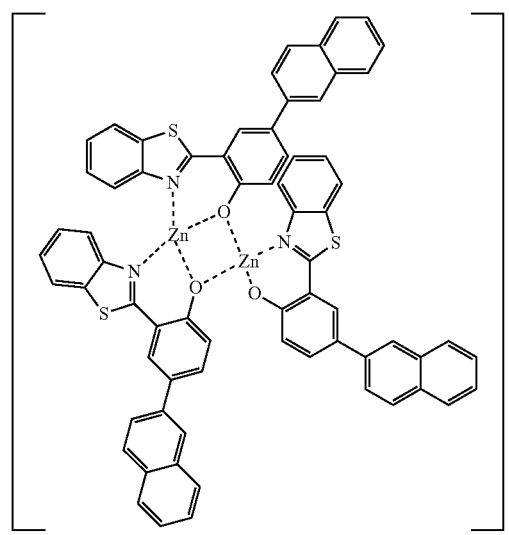
272
-continued
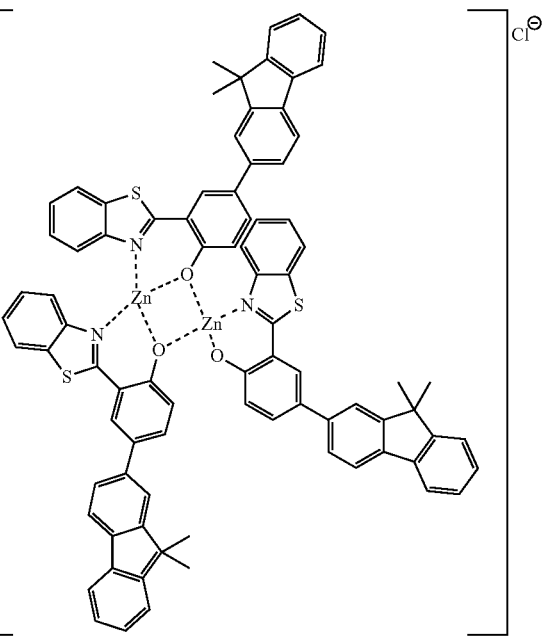
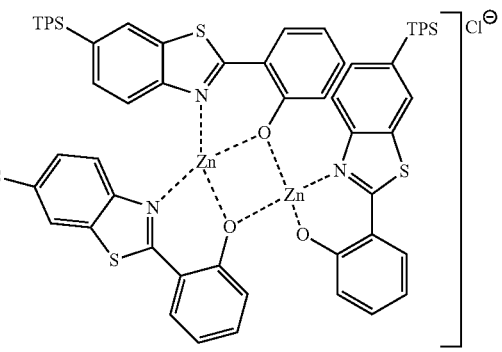
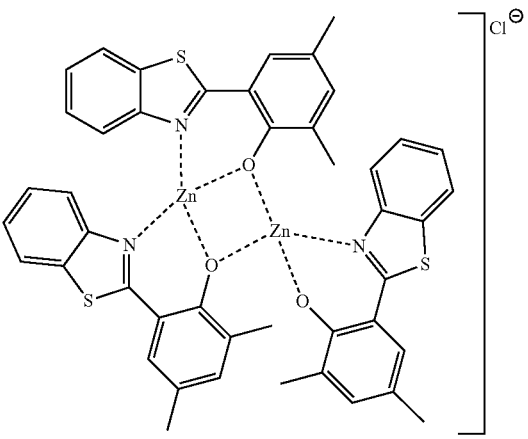

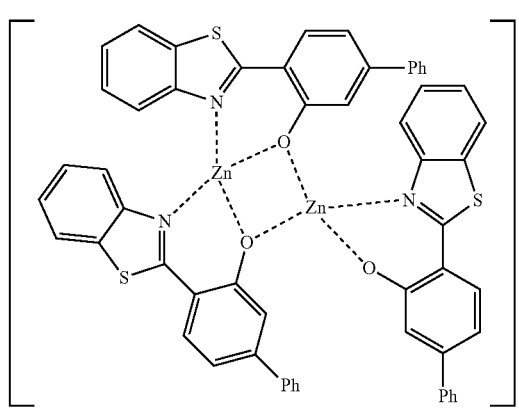
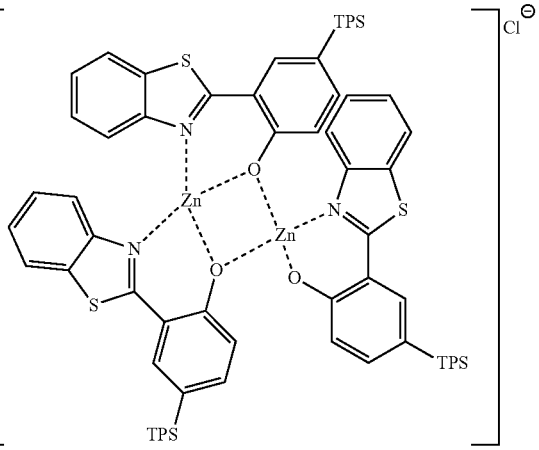
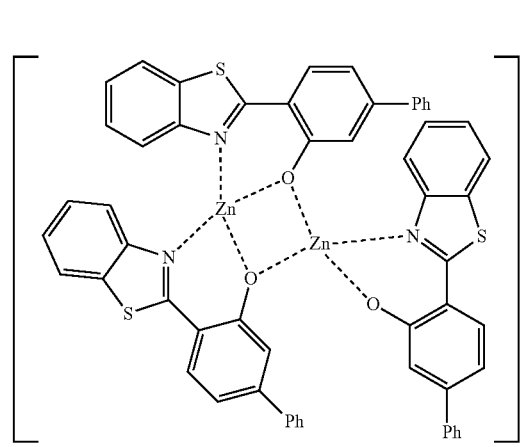
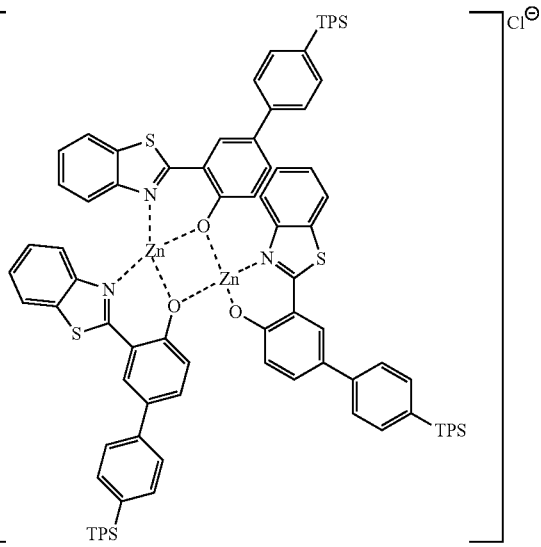
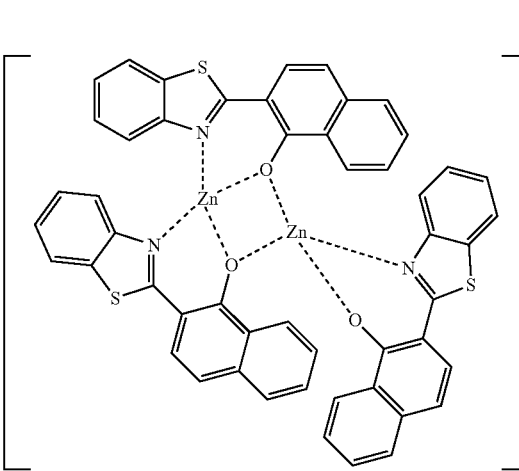
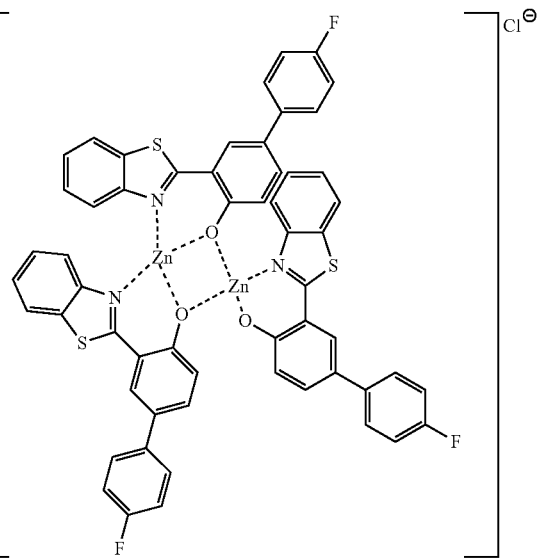

275
-continued
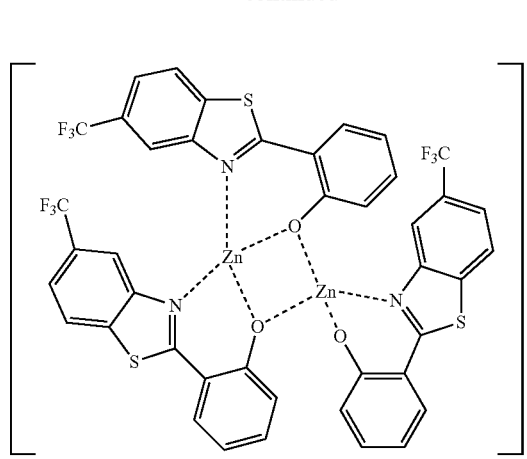
25
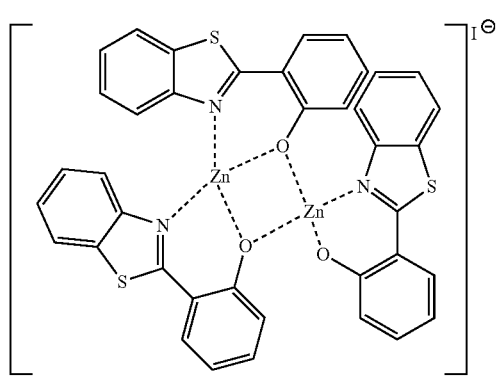
26
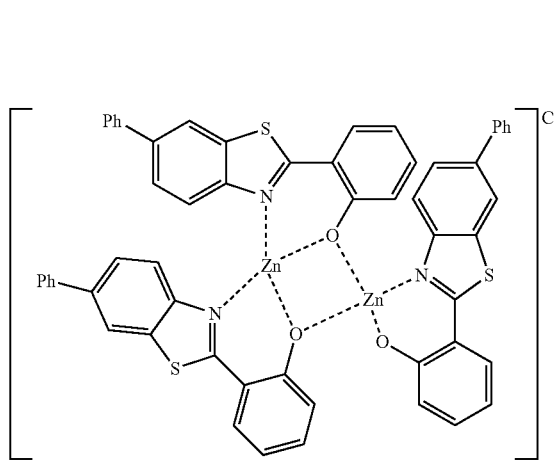
27
276
-continued
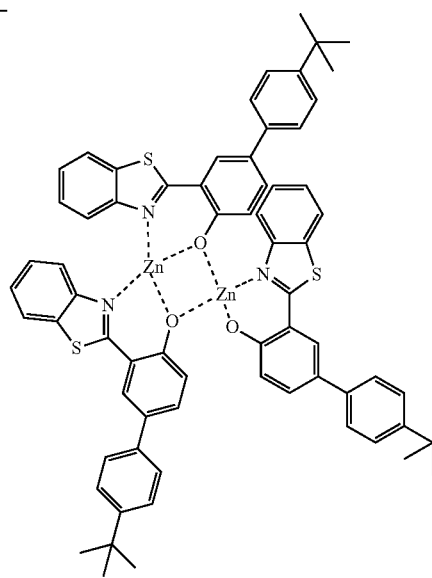
28
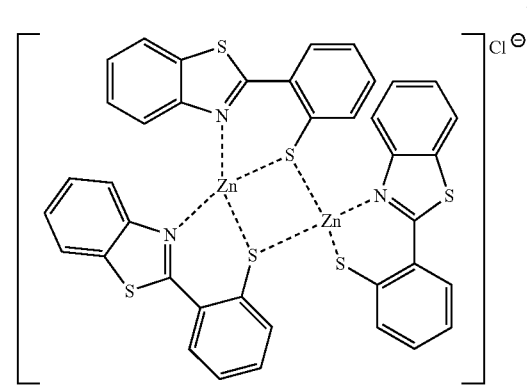
29
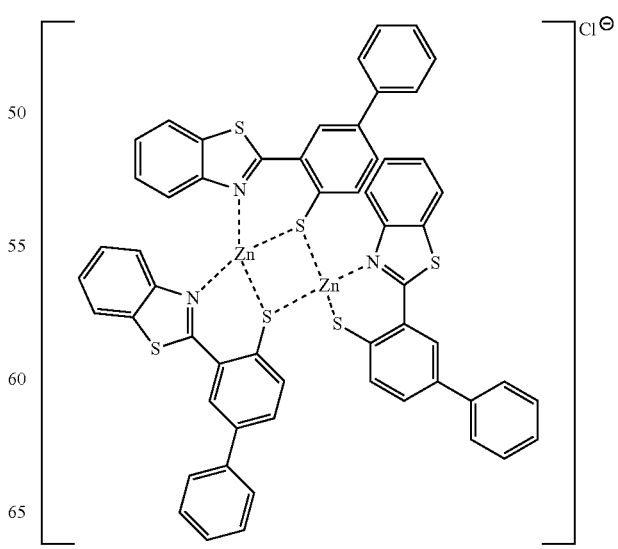
30

31
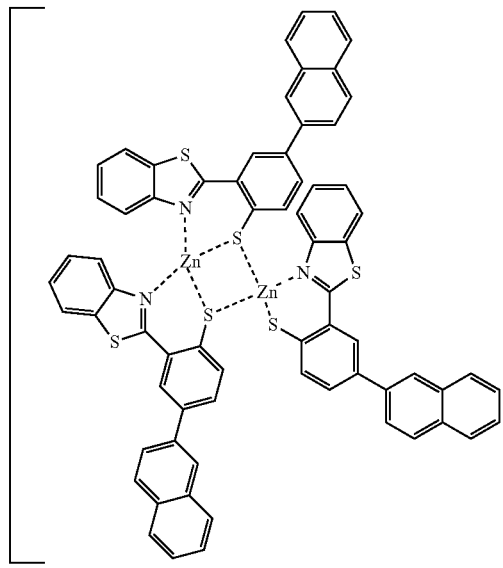
33
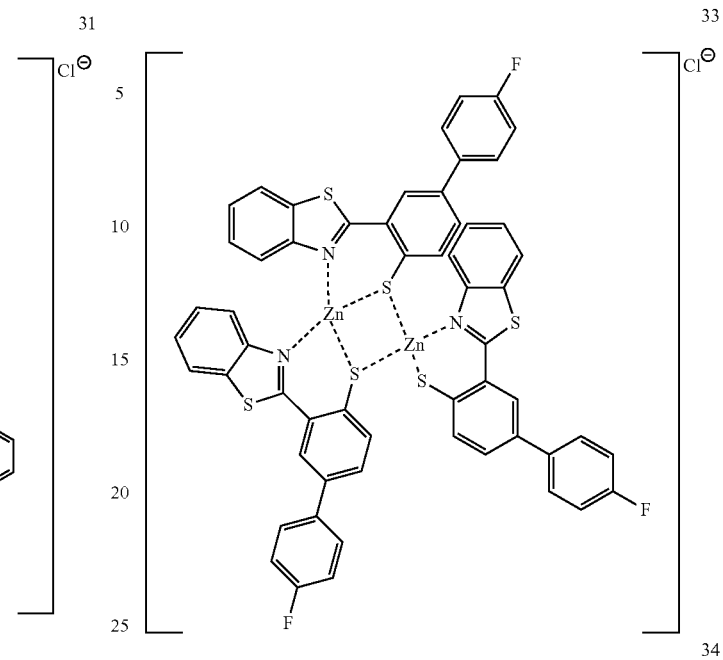
32
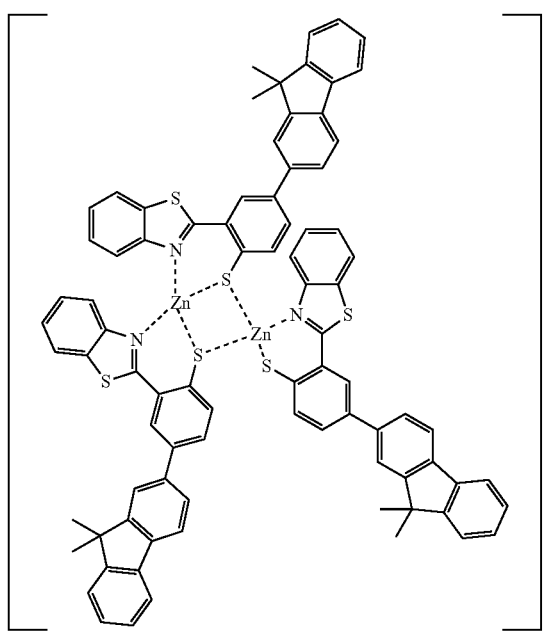
34
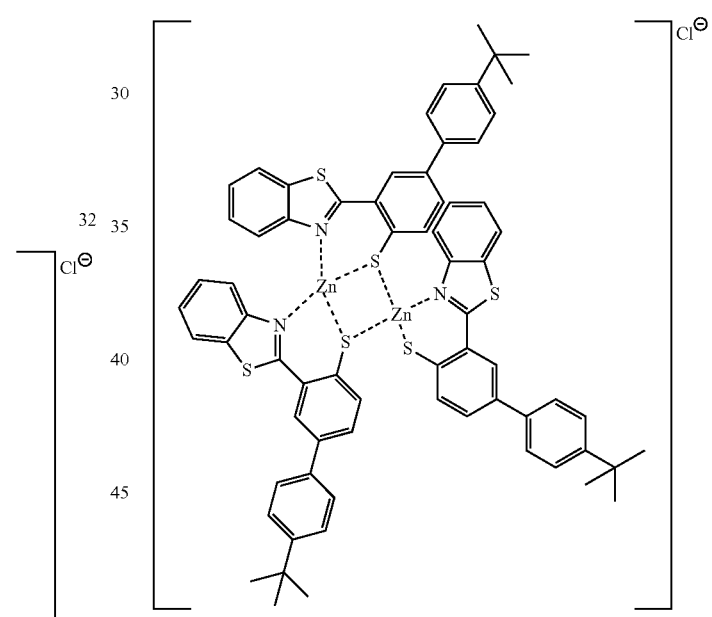
Eighth Exemplary Embodiment
The second host material may be compounds represented by formulae (22) to (24) below.
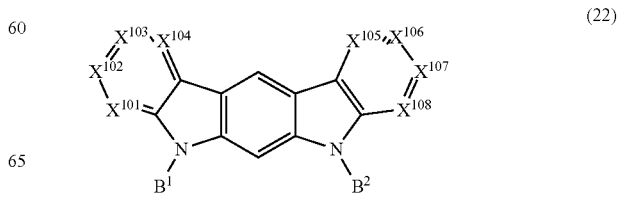
(22)

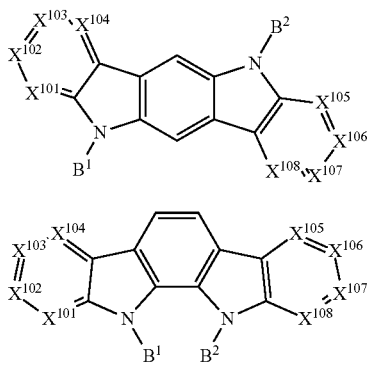

In the formulae (22) to (24): $X^{101}$ to $X^{108}$ are a nitrogen atom or C—$Ar^{131}$. $Ar^{131}$ represent a hydrogen atom, a fluorine atom, a cyano group, a substituted or unsubstituted alkyl group having 1 to 20 carbon atoms, substituted or unsubstituted alkoxy group having 1 to 20 carbon atoms, substituted or unsubstituted haloalkyl group having 1 to 20 carbon atoms, substituted or unsubstituted haloalkoxy group having 1 to 20 carbon atoms, substituted or unsubstituted alkylsilyl having 1 to 10 carbon atoms, substituted or unsubstituted arylsilyl having 6 to 30 carbon atoms, substituted or unsubstituted aromatic hydrocarbon group having 6 to 30 ring carbon atoms, substituted or unsubstituted fused aromatic hydrocarbon group having 6 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms.

Adjacent ones of $X^{101}$ to $X^{108}$ may be bonded to each other to form a ring structure.

$B^1$ and $B^2$ represent a group represented by a formula (25A) or (25B) below.

$$(M^1)_c\text{-}(L^5)_d\text{-}(M^2)_e \qquad (25A)$$

In the formula (25A): $M^1$ and $M^2$ each independently represent a substituted or unsubstituted nitrogen-containing aromatic heterocyclic ring or nitrogen-containing fused aromatic heterocyclic ring having 2 to 40 ring carbon atoms; $M^1$ and $M^2$ may be the same or different;

$L^5$ represents a single bond, substituted or unsubstituted aromatic hydrocarbon group having 6 to 30 carbon atoms, substituted or unsubstituted fused aromatic hydrocarbon group having 6 to 30 carbon atoms, substituted or unsubstituted cycloalkylene group having 5 to 30 carbon atoms, substituted or unsubstituted aromatic heterocyclic group having 2 to 30 carbon atoms, or substituted or unsubstituted fused aromatic heterocyclic group having 2 to 30 carbon atoms;

c represents an integer of 0 to 2; d represents an integer of 1 to 2; e represents an integer of 0 to 2; and c+e represents 1 or more.

$$(M^3)_c\text{-}(L^6)_d\text{-}(M^4)_e \qquad (25B)$$

In the formula (25B): $M^3$ and $M^4$ each independently represent a substituted or unsubstituted aromatic hydrocarbon group having 2 to 40 ring carbon atoms; $M^3$ and $M^4$ may be the same or different; $L^6$ represents a single bond, substituted or unsubstituted aromatic hydrocarbon group having 6 to 30 carbon atoms, substituted or unsubstituted fused aromatic hydrocarbon group having 6 to 30 carbon atoms, or substituted or unsubstituted cycloalkylene group having 5 to 30 carbon atoms;

c represents an integer of 0 to 2; d represents an integer of 1 to 2; e represents an integer of 0 to 2; and c+e represents 1 or more.

The formulae (25A) and (7A) are respectively the same as the formulae (25B) and (7B). $M^1$ to $M^4$ and $L^5$ to $L^6$ are the same as those described in relation to the formulae (7A) and (7B).

Specific examples of compounds represented by the formulae (22) to (24) are shown.

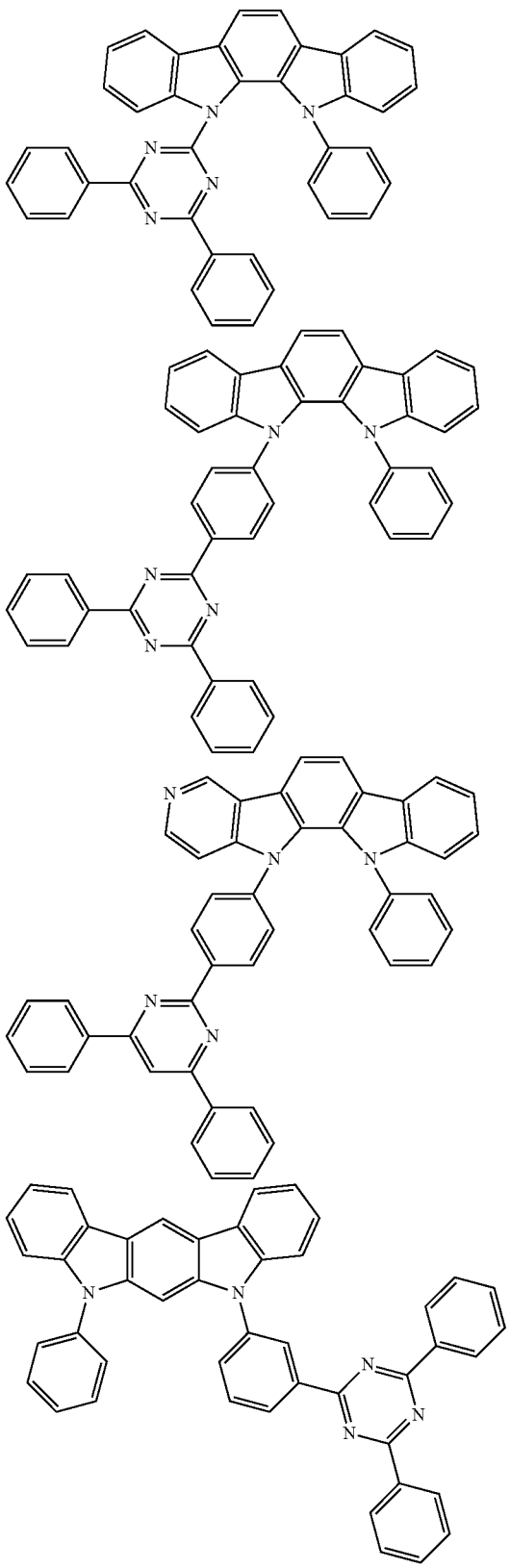

-continued

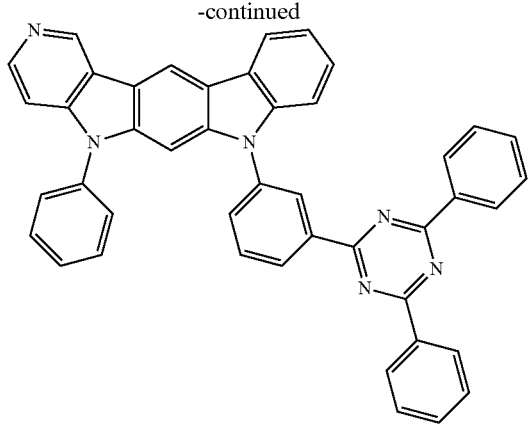

Ninth Exemplary Embodiment

The second host material may be compounds represented by the above formula (1) and having a different structure from that of the first host material.

It should be noted that the invention is not limited to the above description but may include any modification as long as such modification stays within a scope and a spirit of the invention.

For instance, the following is a preferable example of such modification made to the invention.

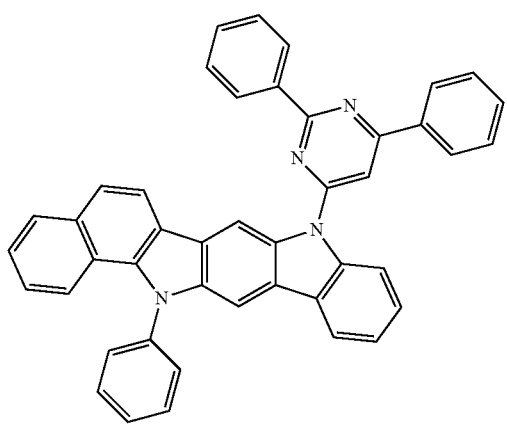

In the invention, the emitting layer may also preferably contain an assistance material for assisting injection of charges.

When the emitting layer is formed of a host material that exhibits a wide energy gap, a difference in ionization potential (Ip) between the host material and the hole injecting/transporting layer etc. becomes so large that injection of the holes into the emitting layer becomes difficult, which may cause a rise in a driving voltage required for providing sufficient luminance.

In the above instance, introducing a hole-injectable/transportable assistance material for assisting injection of charges in the emitting layer can contribute to facilitation of the injection of the holes into the emitting layer and to reduction of the driving voltage.

As the assistance material for assisting the injection of charges, for instance, a typical hole injecting/transporting material or the like can be used.

Specific examples of the assistance material for assisting the injection of charges are a triazole derivative, oxadiazole derivative, imidazoles derivative, polyarylalkane derivative, pyrazoline derivative, pyrazolone derivative, phenylenediamine derivative, arylamine derivative, amino-substituted chalcone derivative, oxazole derivative, styrylanthracene derivative, fluorenone derivative, hydrazone derivative, silazane derivative, polysilane copolymer, aniline copolymer, and conductive polymer oligomer (particularly, a thiophene oligomer).

The hole injecting material is exemplified by the above. The hole injecting material is preferably a porphyrin compound, aromatic tertiary amine compound and styryl amine compound, particularly preferably aromatic tertiary amine compound.

In addition, 4,4'-bis(N-(1-naphthyl)-N-phenylamino)biphenyl (hereinafter, abbreviated as NPD) having two fused aromatic rings in a molecule, or 4,4',4"-tris(N-(3-methylphenyl)-N-phenylamino)triphenylamine (hereinafter, abbreviated as MTDATA) in which three triphenylamine units are bonded in a starburst form as disclosed and the like may also be used.

Moreover, a hexaazatriphenylene derivative and the like may be also preferably used as the hole injecting material.

Alternatively, inorganic compounds such as p-type Si and p-type SiC can also be used as the hole-injecting material.

EXAMPLES

Next, the invention will be described in further detail by exemplifying Example(s) and Comparison(s). However, the invention is not limited by the description of Example(s).

Synthesis Example 1

Synthesis of Compound 1

A synthesis scheme is shown below.

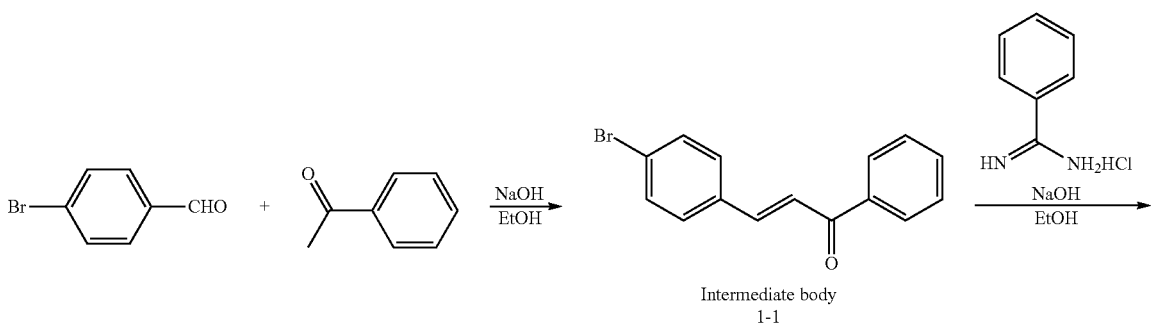

Intermediate body
1-1

-continued
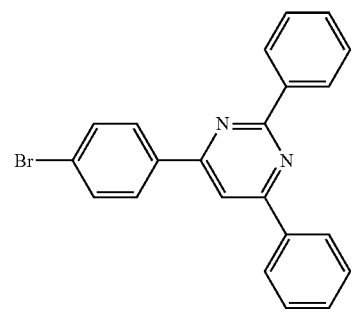
Intermediate body
1-2
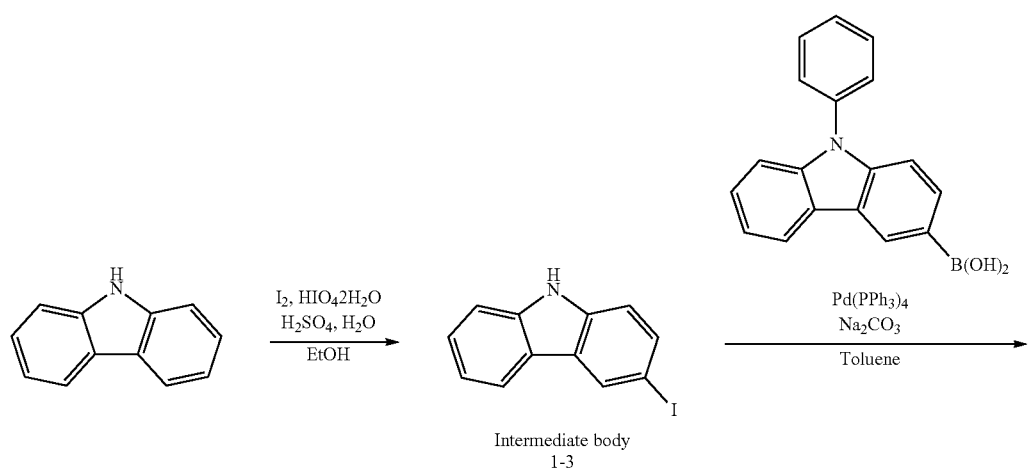
Intermediate body
1-3
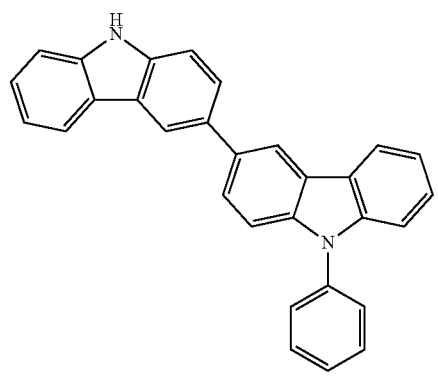
Intermediate body
1-4

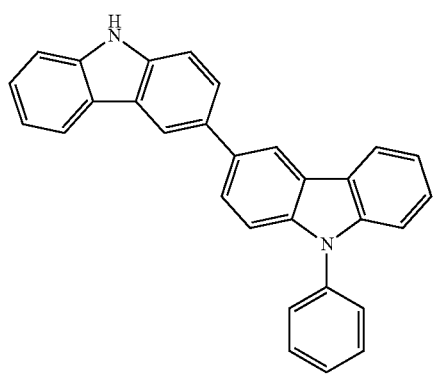

Intermediate body
1-4

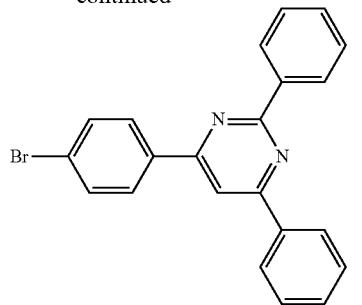

Intermediate body
1-2
CuI-cyclohexenediamine K₃PO₄
─────────────────────→
dioxane

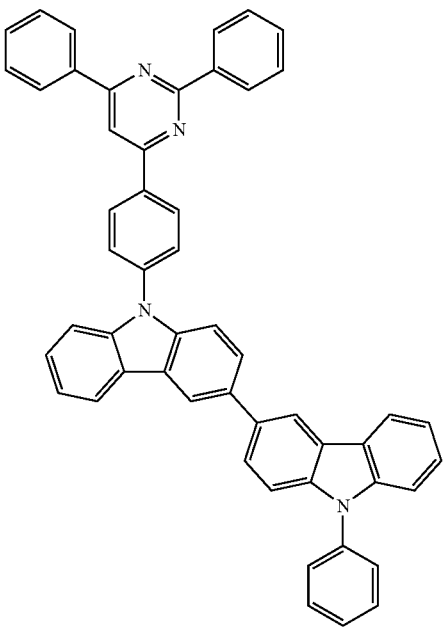

Compound 1

Synthesis of Intermediate Body 1-1

4-bromobenzaldehyde (25 g, 135 mmol) and acetophenone (16.2 g, 135 mmol) were added to ethanole (200 mL). An aqueous solution of 3M potassium hydrate (60 mL) was further added thereto and stirred at room temperature for 7 hours. A precipitated solid was separated by filtration. Then, the obtained solid was washed with methanol. A white solid intermediate body 1-1 (28.3 g, a yield rate 73%) was obtained. Synthesis of Intermediate Body 1-2

The intermediate body 1-1 (20 g, 69.7 mmol) and benzamidine hydrochloride (10.8 g, 69.7 mmol) were added to ethanole (300 mL). Sodium hydroxide (5.6 g, 140 mmol) was further added thereto and heated to reflux at room temperature for 8 hours. A precipitated solid was separated by filtration. Then, the obtained solid was washed with hexane. A white solid intermediate body 1-2 (10.3 g, a yield rate 38%) was obtained.

Synthesis of Intermediate Body 1-3

Carbazole (15 g, 92.6 mmol) was added to ethanol (70 mL). Sulfuric acid (6 mL), water (3 mL), $HIO_4 \cdot 2H_2O$ (8.2 g, 35.9 mmol) and $I_2$ (9.1 g, 35.9 mmol) were added thereto and stirred at room temperature for 4 hours. Water was added to the reaction solution and a precipitated solid was separated by filtration. Then, the obtained solid was washed with methanol. By dissolving the obtained solid in heated toluene for recrystallization, an intermediate body 1-3 (5.1 g, a yield rate 18.8%) was obtained.

Synthesis of Intermediate Body 1-4

Under an argon gas atmosphere, N-phenylcarbazolyl-3-boronic acid (2.0 g, 7.0 mmol), the intermediate body 1-3 (2.05 g, 7.0 mmol), $Pd(PPh_3)_4$ (0.15 g, 0.14 mmol), toluene (20 mL) and an aqueous solution of 2M sodium carbonate (10.5 mL) were added together, and stirred at 80 degrees C.

for 7 hours. Water was added to the reaction solution to precipitate solid. Then, the obtained solid was washed with methanol. By washing the obtained solid by heated toluene, an intermediate body 1-4 (2.43 g, a yield rate 84%) was obtained.

Synthesis of Compound 1

Under an argon gas atmosphere, to a three-necked flask, the intermediate body 1-2 (2.28 g, 5.88 mmol), the intermediate body 1-4 (2.4 g, 5.88 mmol), CuI (0.56 g, 2.9 mmol), tripotassium phosphate (2.5 g, 11.8 mmol), anhydrous dioxane (30 mL) and cyclohexane diamine (0.33 g, 2.9 mmol) were added together in sequential order, and stirred at 100 degrees C. for 8 hours.

Water was added to the reaction solution to precipitate solid. Then, the obtained solid was washed with hexane, followed by methanol. The obtained solid was refined by silica-gel column chromatography, whereby a white solid compound 1 (2.7 g, a yield rate 65%) was obtained.

FD-MS analysis consequently showed that m/e was equal to 714 while a calculated molecular weight was 714.

Synthesis Example 2

Synthesis of Compound 2

The intermediate body 1-1 (6.49 g, 22.6 mmol), phenacylpyridinium bromide (12.7 g, 45.6 mmol), ammonium acetate (45 g), acetic acid (200 mL), and N,N-dimethylformamide (200 mL) were heated to reflux and stirred for 8 hours. The reaction solution was put into an ice water and a precipitated solid was separated by filtration. Then, the obtained solid was washed with methanol. The obtained solid was refined by silica-gel column chromatography (dissolving solvent: hexane/methylene chloride), whereby an intermediate body 2-1 (3.7 g, a yield rate 42%) was obtained.

Subsequently, under an argon gas atmosphere, to a three-necked flask, the intermediate body 2-1 (2.81 g, 7.3 mmol), the intermediate body 1-4 (3.0 g, 7.3 mmol), CuI (1.4 g, 7.3 mmol), tripotassium phosphate (2.3 g, 11 mmol), anhydrous dioxane (30 mL) and cyclohexane diamine (0.84 g, 7.3 mmol) were added together in sequential order, and stirred at 100 degrees C. for 8 hours.

Water was added to the reaction solution to precipitate solid. Then, the obtained solid was washed with hexane, followed by methanol. The obtained solid was refined by silica-gel column chromatography, whereby a compound 2 (3.4 g, a yield rate 65%) was obtained.

FD-MS analysis consequently showed that m/e was equal to 713 while a calculated molecular weight was 713.

A synthesis scheme of the compound 2 is shown below.

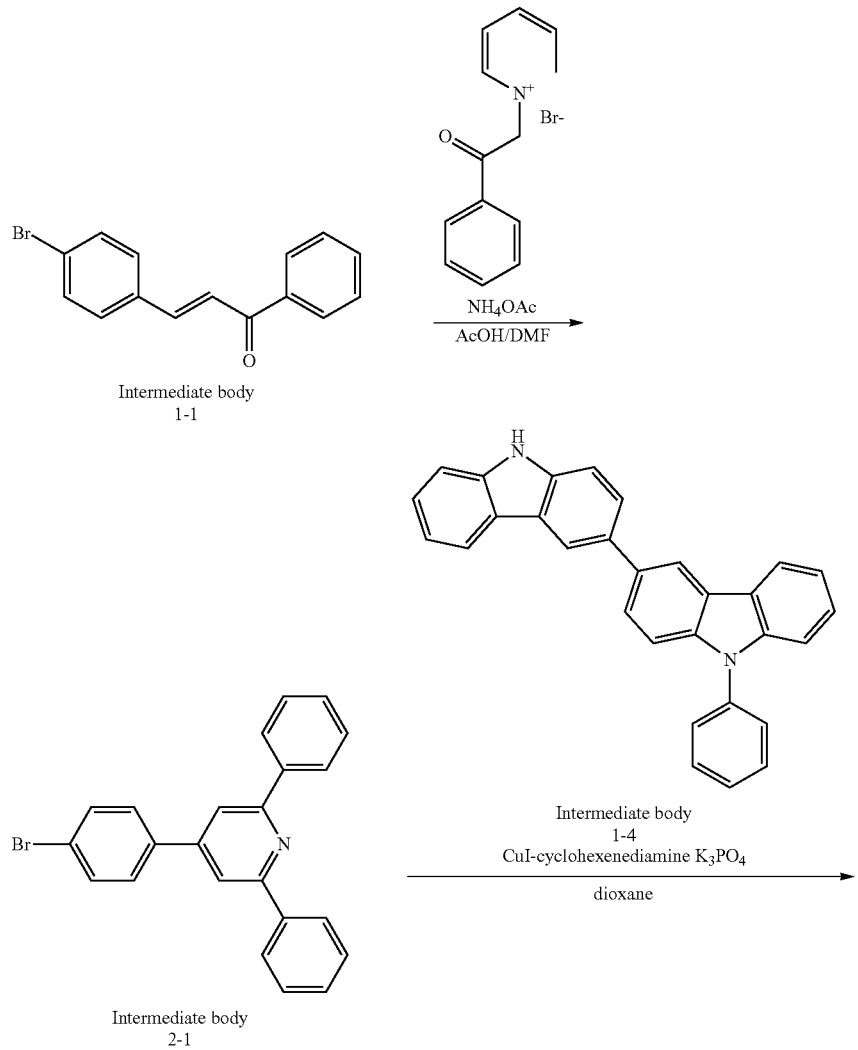

-continued

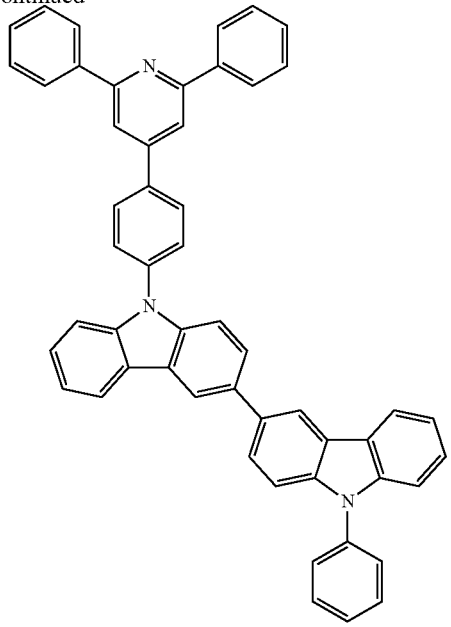

Compound 2

Synthesis Example 3

Synthesis of Compound 3

Under a nitrogen gas atmosphere, trichloropyrimidine (8 g, 43.4 mmol), phenylboronic acid (11.6 g, 95.4 mmol), tetrakis(triphenylphosphine)palladium (1.83 g, 1.74 mmol), toluene (300 mL) and an aqueous solution of 2M sodium carbonate (130 mL) were added together in sequential order, and heated to reflux for 8 hours. After the reaction solution was cooled down to the room temperature, an organic layer was removed and an organic solvent was distilled away under reduced pressure. The obtained residue was refined by silica-gel column chromatography, whereby an intermediate body 3-1 (8.2 g, a yield of 71%) was obtained.

Subsequently, under a nitrogen gas atmosphere, intermediate body 3-1 (8 g, 29.9 mmol), p-chlorophenylboronic acid (5.1 g, 32.9 mmol), tetrakis(triphenylphosphine)palladium (0.63 g, 0.6 mmol), toluene (60 mL) and an aqueous solution of 2M sodium carbonate (30 mL) were added together in sequential order, and heated to reflux for 8 hours.

After the reaction solution was cooled down to the room temperature, an organic layer was removed and an organic solvent was distilled away under reduced pressure. The obtained residue was refined by silica-gel column chromatography, whereby an intermediate body 3-2 (7.0 g, a yield of 68%) was obtained.

Under an argon gas atmosphere, the intermediate body 3-2 (6.5 g, 18.9 mmol), the intermediate body 1-4 (7.7 g, 18.9 mmol), palladium acetate (0.085 g, 0.38 mmol), sodium t-butoxide (2.72 g, 28.4 mmol), anhydrous toluene (60 mL), and tri-t-butyl phosphine (0.077 g, 0.38 mmol) were sequentially mixed, and stirred at 90 degrees C. for 8 hours.

After the reaction solution was cooled down to the room temperature, an organic layer was removed and an organic solvent was distilled away under reduced pressure. The obtained residue was refined by silica-gel column chromatography, whereby a compound 3 (7.8 g, a yield of 58%) was obtained.

FD-MS analysis consequently showed that m/e was equal to 715 while a calculated molecular weight was 715.

A synthesis scheme of the compound 3 is shown below.

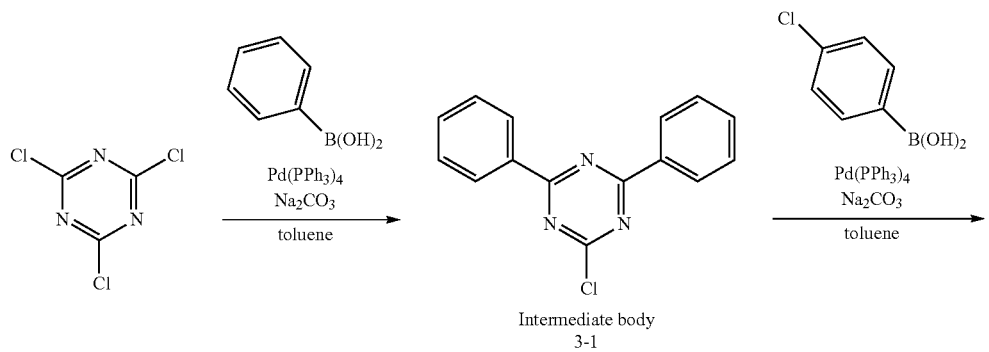

Intermediate body 3-1

-continued

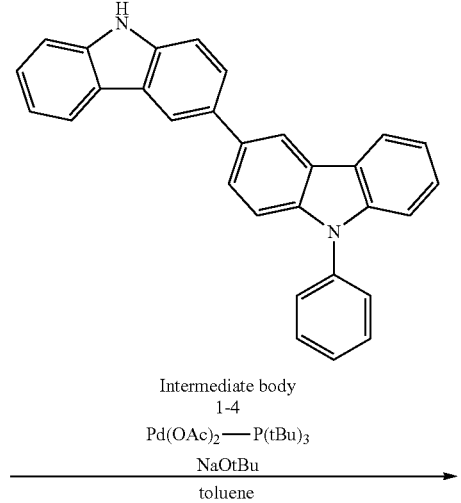

Intermediate body
1-4

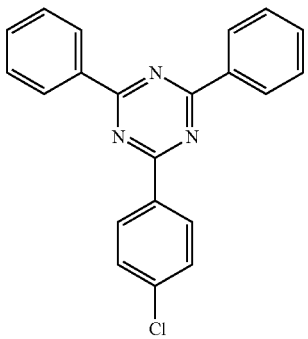

Intermediate body
3-2

$Pd(OAc)_2$ — $P(tBu)_3$
NaOtBu
toluene

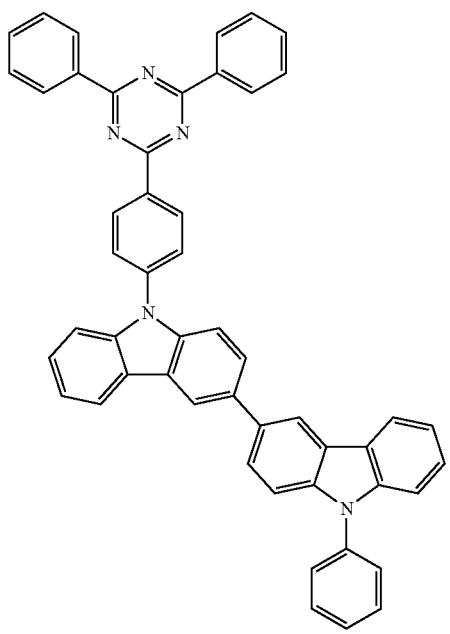

Compound 3

Synthesis Example 4

Synthesis of Compound 4

3,3'-dicarbazolyl was synthesized by a method disclosed in WO2006-25186.

Under an argon gas atmosphere, to a three-necked flask, 3,3'-dicarbazolyl (2.4 g, 7.3 mmol), the intermediate body 1-2 (5.6 g, 14.6 mmol), CuI (1.4 g, 7.3 mmol), tripotassium phosphate (6.4 g, 30 mmol), anhydrous dioxane (50 mL) and cyclohexane diamine (0.84 g, 7.3 mmol) were added together in sequential order, and stirred at 100 degrees C. for 8 hours.

Water was added to the reaction solution to precipitate solid. Then, the obtained solid was washed with hexane, followed by methanol. The obtained solid was refined by silica-gel column chromatography, whereby a compound 4 (3.1 g, a yield rate 45%) was obtained.

FD-MS analysis consequently showed that m/e was equal to 945 while a calculated molecular weight was 945.

A synthesis scheme of the compound 4 is shown below.

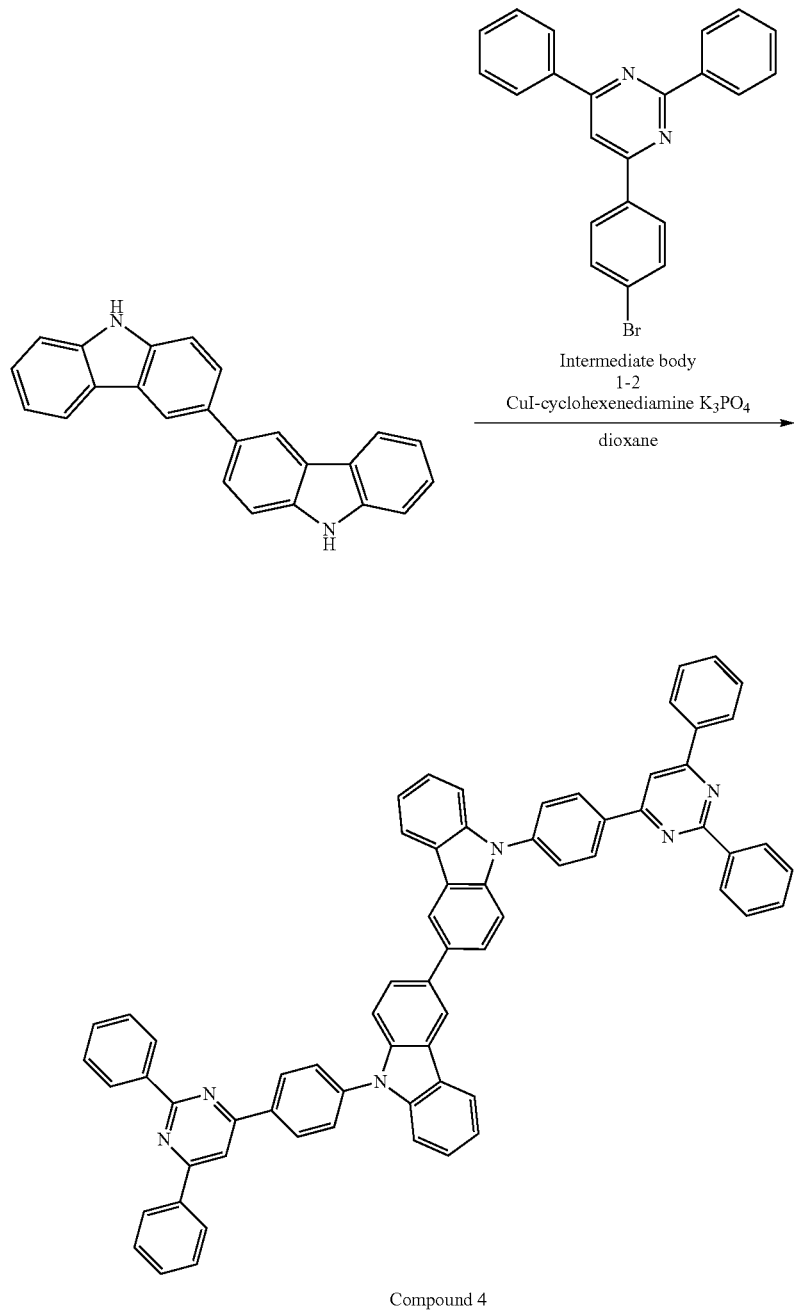

Compound 4

Synthesis Example 5

Synthesis of Compound 5

Under an argon gas atmosphere, the intermediate body 3-1 (1.0 g, 3.9 mmol), the intermediate body 1-4 (1.6 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for 8 hours.

After the reaction solution was cooled down to the room temperature, an organic layer was removed and an organic solvent was distilled away under reduced pressure. The obtained residue was refined by silica-gel column chromatography, whereby a compound 5 (1.8 g, a yield of 74%) was obtained.

FD-MS analysis consequently showed that m/e was equal to 639 while a calculated molecular weight was 639.

A synthesis scheme of the compound 5 is shown below.

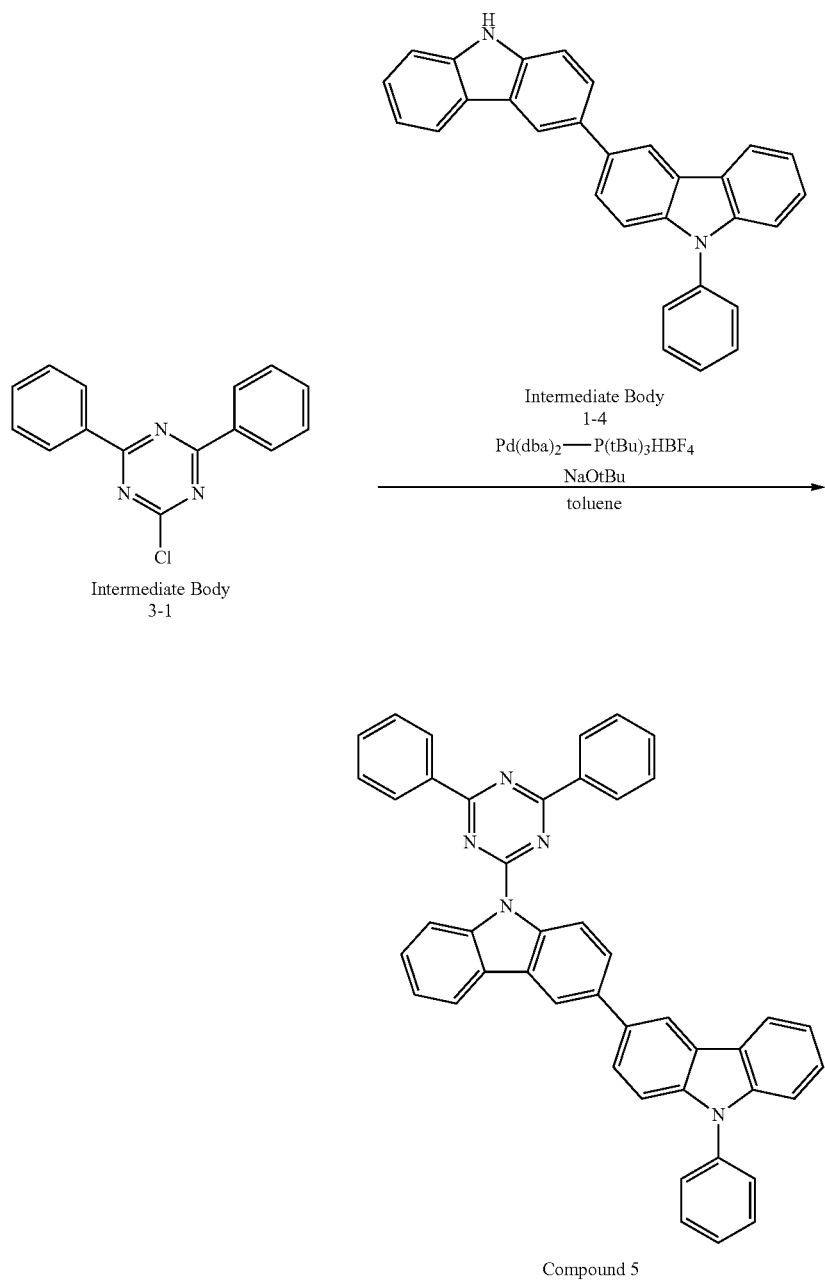

Compound 5

Synthesis Example 6

Synthesis of Compound 6

3-bromobenzaldehyde (18.4 g, 100 mmol) was dissolved in dimethylformamide (300 mL). Benzamidine hydrochloride (31.2 g, 200 mmol) and potassium carbonate (41 g, 300 mmol) were added thereto and heated to reflux at 80 degrees C. for 8 hours. After the reaction solution was cooled down to the room temperature, an organic layer was removed and an organic solvent was distilled away under reduced pressure. The obtained residue was refined by silica-gel column chromatography, whereby an intermediate body 6-1 (12 g, a yield of 32%) was obtained.

Under an argon gas atmosphere, the intermediate body 6-1 (1.5 g, 3.9 mmol), the intermediate body 1-4 (1.6 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for 8 hours.

After the reaction solution was cooled down to the room temperature, an organic layer was removed and an organic solvent was distilled away under reduced pressure. The obtained residue was refined by silica-gel column chromatography, whereby a compound 6 (2.3 g, a yield of 82%) was obtained.

FD-MS analysis consequently showed that m/e was equal to 715 while a calculated molecular weight was 715.

A synthesis scheme of the compound 6 is shown below.
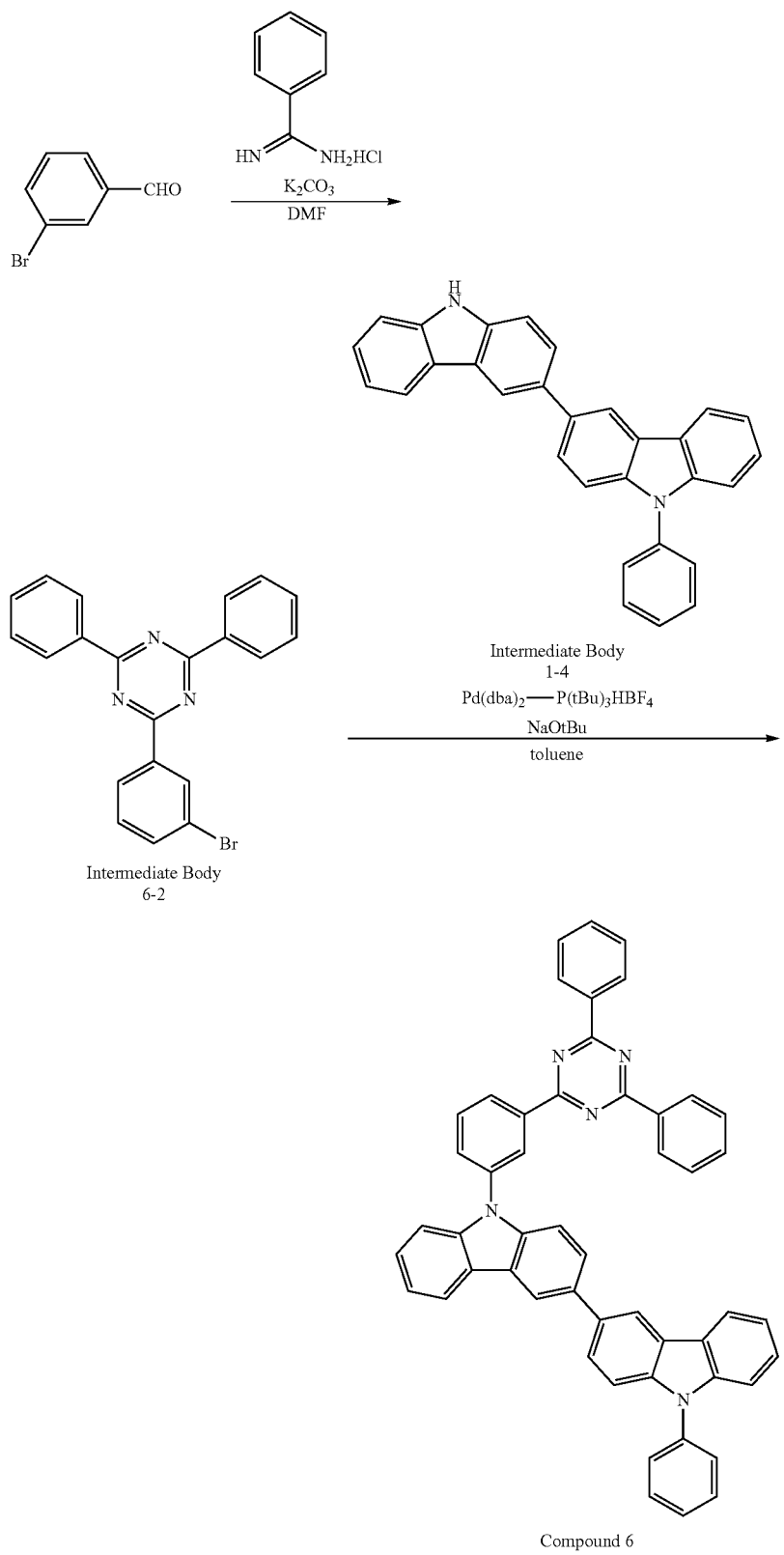
Compound 6

Synthesis Example 7

Synthesis of Compound 7

For synthesis of Compound 7, an intermediate body 7-1 was firstly synthesized by applying a method described in a document (J. Bergman, A. Brynolf, B. Elman and E. Vuorinen, *Tetrahedron*, 42, 3697-3706 (1986)). Specifically, to a three-necked flask (500 ml), 1M tetrahydrofuran solution of phenylmagnesium bromide (100 ml, 100 mmol) was added. Dry ether (100 ml) was further added and heated to reflux in an oil bath at 45 degrees C. A dry ether solution (50 ml) of 2-cyanoaniline (5.91 g, 50 mmol) was dropped in for 30 minutes After refluxed for another 1.5 hours, the reaction solution was cooled down to 0 degree C. in an ice water bath. Subsequently, a dry ether solution (100 ml) of 4-bromobenzoate chloride (13.2 g, 60 mmol) was dropped in the reaction solution for 10 minutes and heated to reflux for 2 hours in a 45-degree-C. oil bath. After reaction, the reaction solution was cooled down to 0 degree C. in an ice water bath. A saturated ammonium chloride aqueous solution was added. A precipitated solid was separated by filtration. Then, the obtained was washed with a small amount of methanol and vacuum-dried to obtain an intermediate body 7-1 (10.8 g, a yield of 60%).

Subsequently, under a nitrogen atmosphere, the intermediate body 7-1 (1.4 g, 3.9 mmol), the intermediate body 1-4 (1.6 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for 8 hours. After the reaction solution was cooled down to the room temperature, an organic layer was removed and an organic solvent was distilled away under reduced pressure. The obtained residue was refined by silica-gel column chromatography, whereby a compound 7 (2.0 g, a yield of 75%) was obtained.

FD-MS analysis consequently showed that m/e was equal to 688 while a calculated molecular weight was 688.

A synthesis scheme of the compound 7 is shown below.

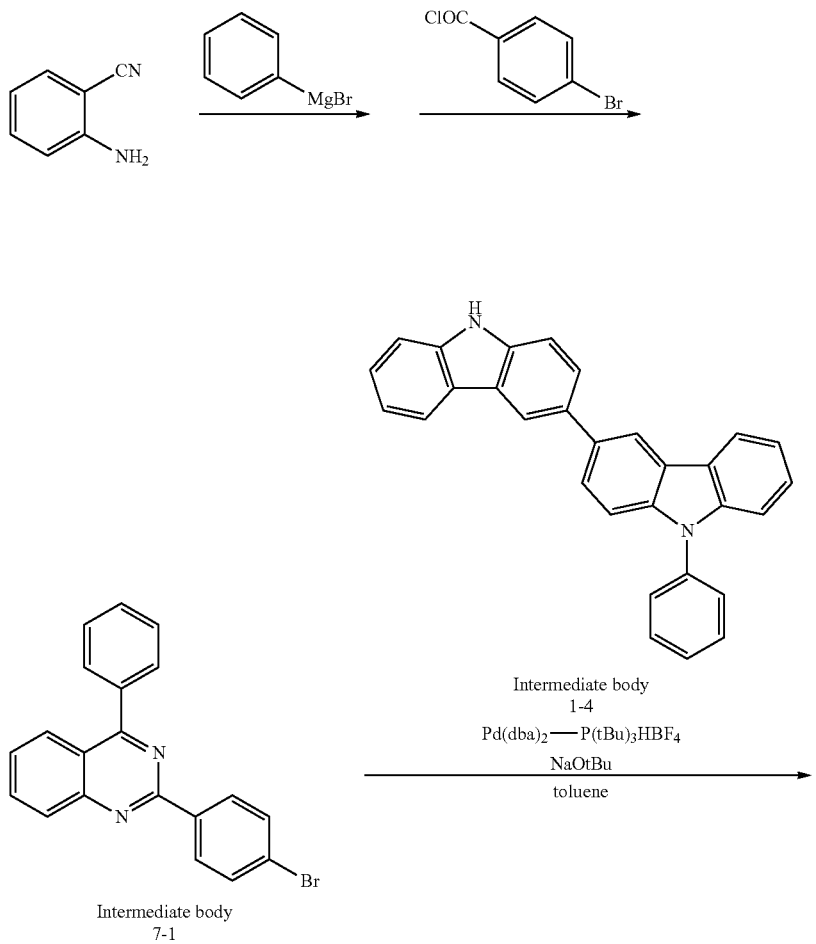

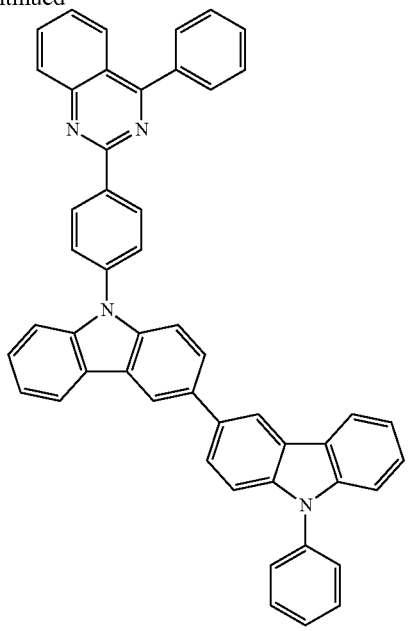

Compound 7

Synthesis Example 8

Synthesis of Compound 8

Specifically, to a three-necked flask (500 ml), 1M tetrahydrofuran solution of phenylmagnesium bromide (100 ml, 100 mmol) was added. Dry ether (100 ml) was further added and heated to reflux in an oil bath at 45 degrees C. A dry ether solution (50 ml) of 2-cyanoaniline (5.91 g, 50 mmol) was dropped in for 30 minutes After refluxed for another 1.5 hours, the reaction solution was cooled down to 0 degree C. in an ice water bath. Subsequently, a dry ether solution (100 ml) of 3-bromobenzoate chloride (13.2 g, 60 mmol) was dropped in the reaction solution for 10 minutes and heated to reflux for 2 hours in a 45-degree-C. oil bath. After reaction, the reaction solution was cooled down to 0 degree C. in an ice water bath. A saturated ammonium chloride aqueous solution was added. A precipitated solid was separated by filtration. Then, the obtained was washed with a small amount of methanol and vacuum-dried to obtain an intermediate body 8-1 (8.5 g, a yield of 47%).

Subsequently, under a nitrogen atmosphere, the intermediate body 8-1 (1.4 g, 3.9 mmol), the intermediate body 1-4 (1.6 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and anhydrous toluene (20 mL) were sequentially mixed, and heated to reflux for 8 hours. After the reaction solution was cooled down to the room temperature, an organic layer was removed and an organic solvent was distilled away under reduced pressure. The obtained residue was refined by silica-gel column chromatography, whereby a compound 8 (1.9 g, a yield of 71%) was obtained.

FD-MS analysis consequently showed that m/e was equal to 688 while a calculated molecular weight was 688.

A synthesis scheme of the compound 8 is shown below.

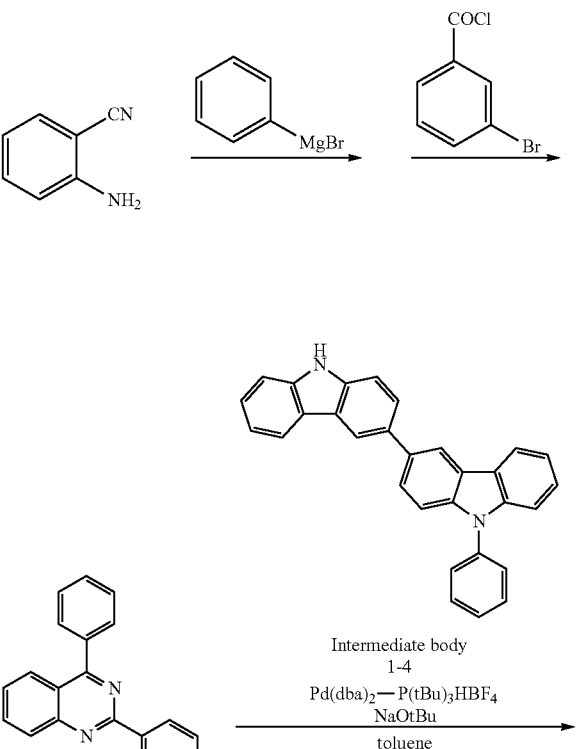

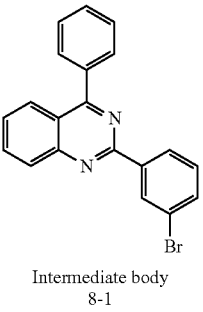

Intermediate body
8-1

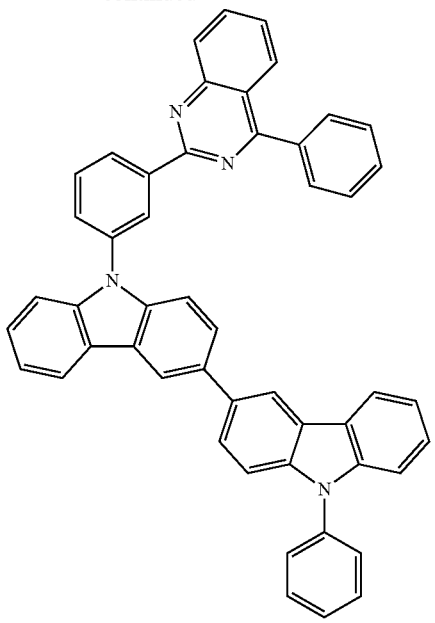

Compound 8

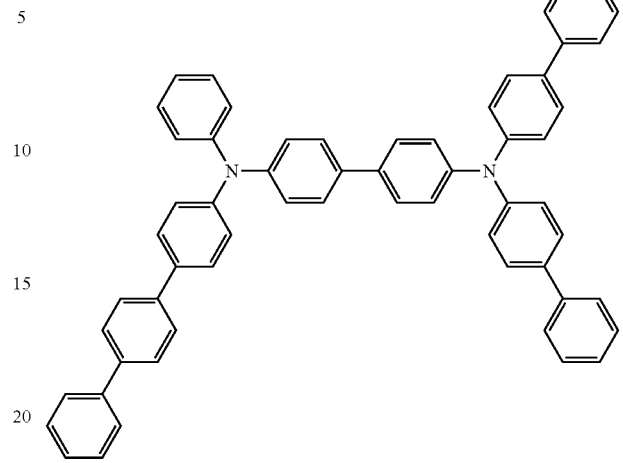

Compound A

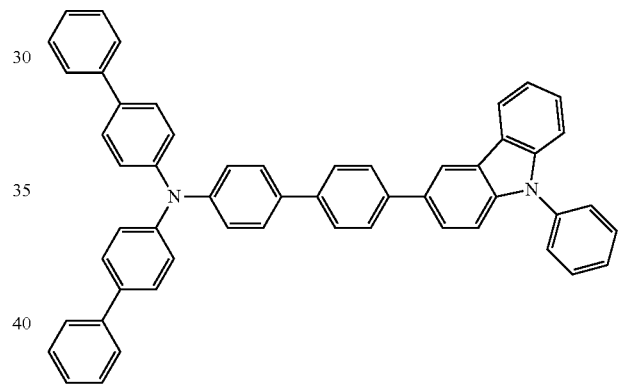

Compound B

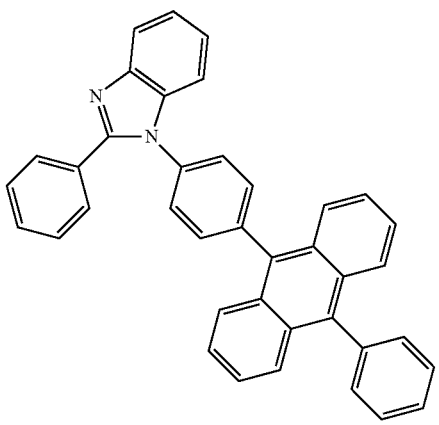

Compound C

Example 1

Manufacture of Organic EL Device

A glass substrate (size: 25 mm×75 mm×1.1 mm) having an ITO transparent electrode (manufactured by GEOMATEC Co., Ltd.) was ultrasonic-cleaned in isopropyl alcohol for five minutes, and then UV (Ultraviolet)/ozone-cleaned for 30 minutes.

After the glass substrate having the transparent electrode was cleaned, the glass substrate was mounted on a substrate holder of a vacuum deposition apparatus, and a hole injecting layer was initially formed by depositing a compound A onto the substrate to be 40 nm thick to cover a surface of the glass substrate where a transparent electrode line was provided. Next, a compound B was deposited onto the hole injecting layer to be 20 nm thick, and a hole transporting layer was obtained.

A phosphorescent-emitting layer was obtained by co-depositing the compound 1 used as a phosphorescent host material and Ir(Ph-ppy)$_3$ used as a phosphorescent dopant material onto the hole transporting layer to be 40 nm thick. The concentration of Ir(Ph-ppy)$_3$ was 20 mass %.

Subsequently, a 30-nm-thick compound C, 1-nm-thick LiF and 80-nm-thick metal Al are sequentially layered to obtain a cathode. LiF, which is an electron injectable electrode, was formed at a speed of 1 Å/min.

Compound 1
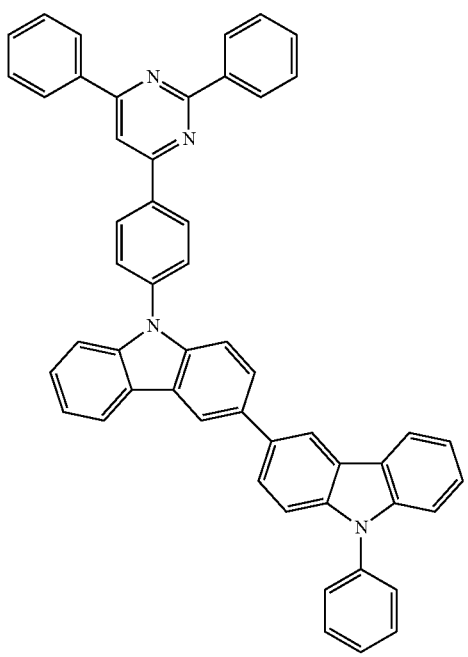
Compound 2
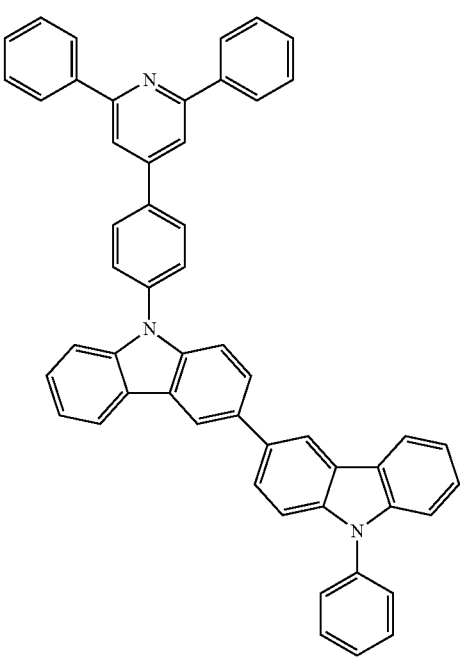
Ir(Ph-ppy)₃ (facial body)
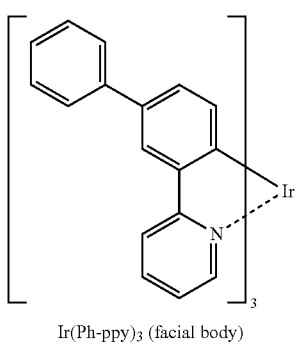
Compound 3
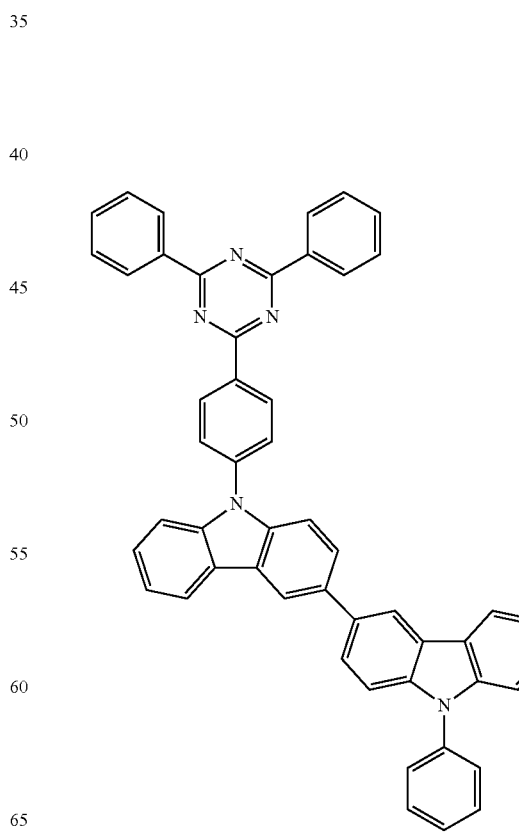
Examples 2 to 6
Manufacture of Organic EL Devices 2 to 6
In Example 1, the compounds 2 to 6 below were used in place of the compound 1 to manufacture organic EL devices 2 to 6.

Compound 4

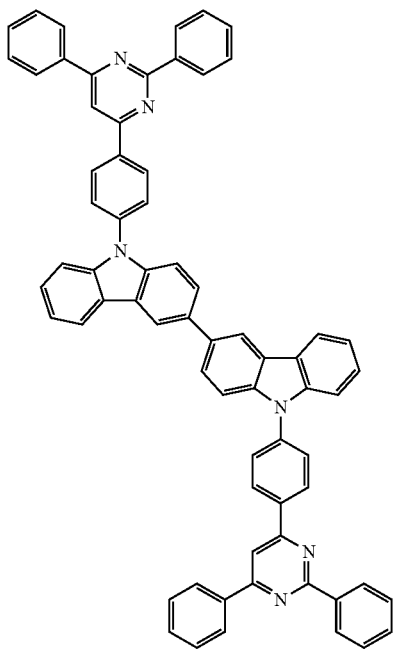

Compound 5

Compound 6

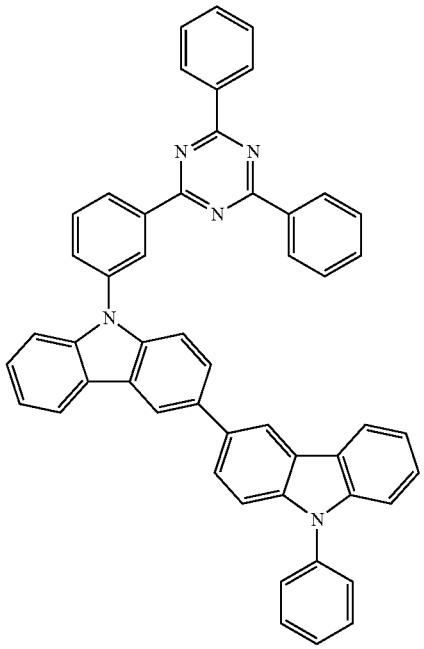

Comparisons 1 to 4

The organic EL devices according respectively to Comparisons 1 to 4 were formed in the same manner as in Example 1 except that the following comparative compounds D to G were respectively used as a host material in place of the compound 1 in Example 1.

Evaluation of Organic EL Device

The organic EL devices manufactured in Examples 1 to 6 and Comparisons 1 to 4 were driven by direct-current electricity to emit light, where luminescent performance was evaluated and time elapsed until an initial luminescence intensity of 20,000 cd/m² was reduced to the half was measured. The results are shown in Table 4.

Compound D

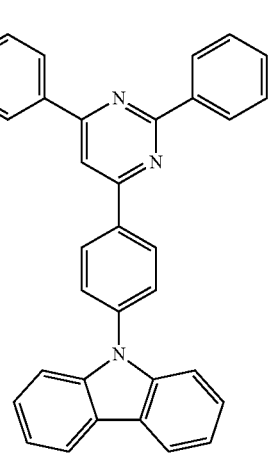

Compound E

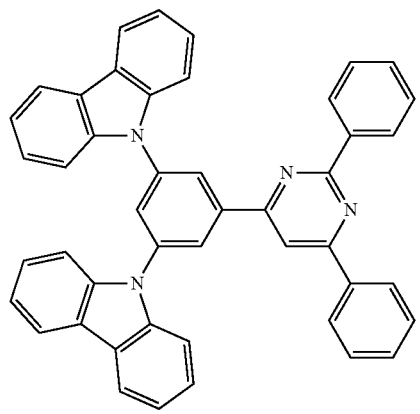

Compound F

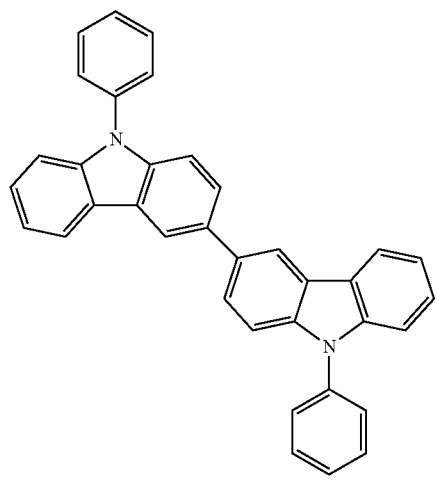

Compound G

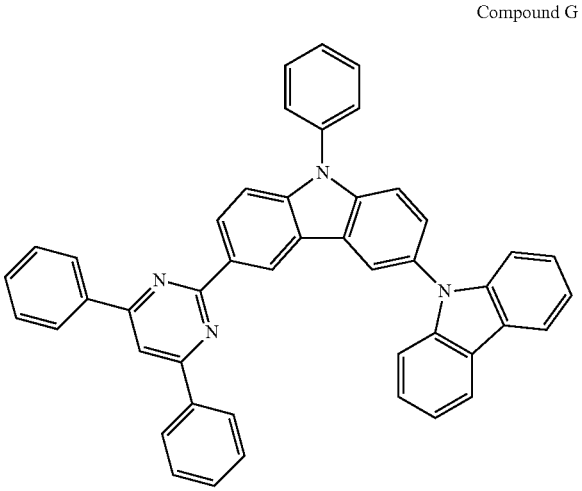 [SMILES: c1ccc(-c2cc(-c3ccccc3)nc(-c3ccc4c(c3)c3cc(-n5c6ccccc6c6ccccc65)ccc3n4-c3ccccc3)n2)cc1]

TABLE 4

| | Host Material | Voltage (V) @ 1 mA/cm² | Luminous Efficiency (cd/A) @ 1 mA/cm² | Luminance half-life (hrs) |
|---|---|---|---|---|
| Example 1 | Compound 1 | 4.0 | 61 | 950 |
| Example 2 | Compound 2 | 4.1 | 63 | 750 |
| Example 3 | Compound 3 | 4.0 | 65 | 730 |

TABLE 4-continued

| | Host Material | Voltage (V) @ 1 mA/cm² | Luminous Efficiency (cd/A) @ 1 mA/cm² | Luminance half-life (hrs) |
|---|---|---|---|---|
| Example 4 | Compound 4 | 4.3 | 62 | 670 |
| Example 5 | Compound 5 | 4.1 | 61 | 1100 |
| Example 6 | Compound 6 | 4.3 | 64 | 1000 |
| Comparison 1 | Compound D | 4.2 | 38 | 310 |
| Comparison 2 | Compound E | 4.5 | 54 | 450 |
| Comparison 3 | Compound F | 5.1 | 50 | 210 |
| Comparison 4 | Compound G | 4.6 | 48 | 350 |

Table 4 shows that the compounds of the invention used in Examples 1 to 6 have a significantly long luminance half-life and a high luminous efficiency while being capable of low-voltage drive compared with those of Comparisons 1 to 4.

In Comparison 1, since the compound D has a single carbazolyl group and is poor in hole transporting performance, luminance half-life is short. In Comparison 2, although having two carbazolyl groups, the compound E has a poor hole transporting performance and a short luminance half-life, presumably because of small overlapping margin between the molecules. In Comparison 3, since the compound F has a nitrogen-containing heterocyclic ring only in a carbazolyl group, electrons are difficult to be injected, so that the compound F has a low luminous efficiency and a short luminance half-life. In Comparison 4, although having two carbazolyl groups, the compound G has a poor hole transporting capability and a short luminance half-life, presumably because of small overlapping margin between the molecules.

Example 7

Manufacture of Organic EL Device 7

A glass substrate (size: 25 mm×75 mm×1.1 mm thick) having an ITO transparent electrode (manufactured by GEO-MATEC Co., Ltd.) was ultrasonic-cleaned in isopropyl alcohol for five minutes, and then UV/ozone-cleaned for 30 minutes.

After the glass substrate having the transparent electrode line was cleaned, the glass substrate was mounted on a substrate holder of a vacuum deposition apparatus, so that the following electron accepting compound (C-1) was deposited to form a 5-nm thick C-1 film on a surface of the glass substrate where the transparent electrode line was provided so as to cover the transparent electrode. On the C-1 film, the following aromatic amine derivative (X1) was deposited as a first hole transporting material to form a 50-nm thick first hole transporting layer. After film formation of the first hole transporting layer, the following aromatic amine derivative (X2) was deposited as a second hole transporting material to form a 60-nm thick second hole transporting layer.

Further on the second hole transporting layer, the compound 1 obtained in Synthesis Example 1 was deposited to form a 45-nm thick emitting layer. Simultaneously, the following compound (D3) was co-deposited as a phosphorescent material. A concentration of the compound D3 was 8.0 mass %. This co-deposited film serves as the emitting layer.

After the film formation of the emitting layer, a 30-nm thick film of the following compound (ET2) was formed. The ET1 film serves as the electron transporting layer.

Next, a 1-nm thick film of LiF was formed as an electron-injecting electrode (cathode) at a film-forming speed of 0.1

Å/min. Metal (Al) was deposited on the LiF film to form an 80-nm thick metal cathode, thereby providing an organic electroluminescence device.

For each of the obtained organic EL devices, luminous efficiency was measured when the device was driven by DC constant current at the initial luminescence of 2000 cd/m² at the room temperature, and the time elapsed until a half-life of emission was measured when the device was driven by DC constant current at the initial luminescence of 5000 cd/m² at the room temperature. The results are shown in Table 5.

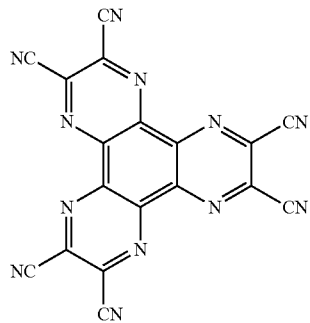

C-1

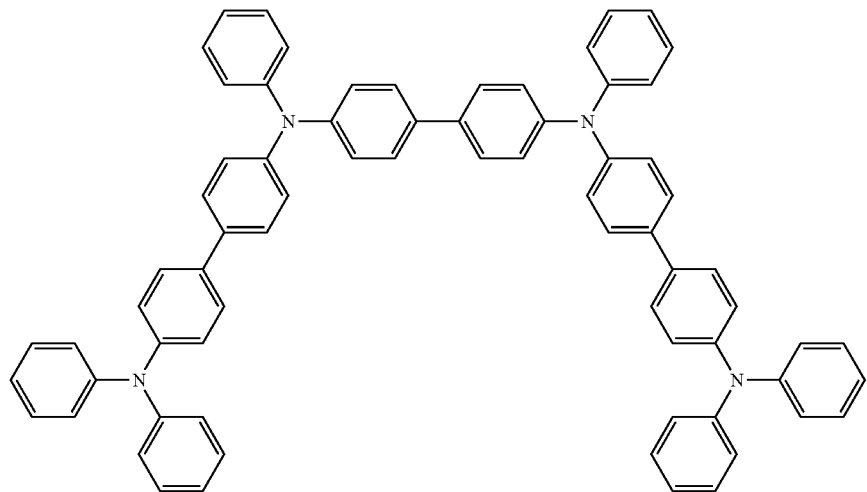

X1

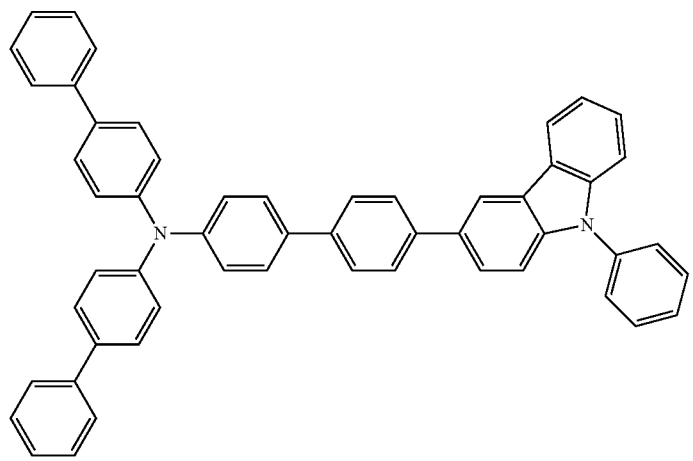

X2

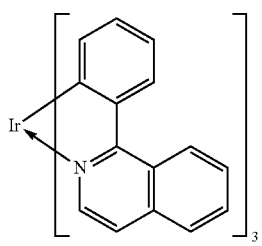

D3

-continued

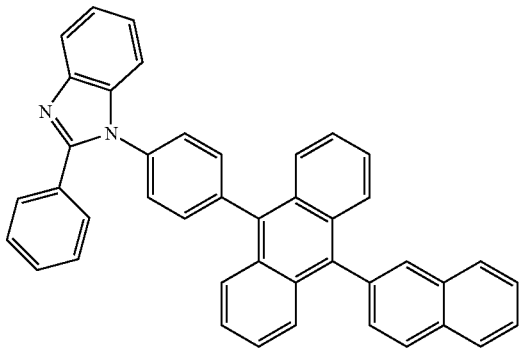

ET2

Examples 8 to 14

Manufacture of Organic EL Devices 8 to 14

The organic EL devices according to Examples 8 to 14 were manufactured in the same manner as that in Example 7 except that the compounds 2 to 8 were used in place of the compound 1 as materials for the emitting layer. For each of the obtained organic EL devices, luminous efficiency was measured when the device was driven by DC constant current at the initial luminescence of 2000 cd/m² at the room temperature, and the time elapsed until a half-life of emission was measured when the device was driven by DC constant current at the initial luminescence of 5000 cd/m² at the room temperature. The results are shown in Table 5.

Comparisons 5 and 6

The organic EL devices according to Comparisons 5 and 7 were manufactured in the same manner as that in Example 7 except that the comparative compounds D and F were used in place of the compound 1 as materials for the emitting layer. For each of the obtained organic EL devices, luminous efficiency was measured when the device was driven by DC constant current at the initial luminescence of 2000 cd/m² at the room temperature, and the time elapsed until a half-life of emission was measured when the device was driven by DC constant current at the initial luminescence of 5000 cd/m² at the room temperature.

The results are shown in Table 5.

TABLE 5

| | Host Material | Voltage (V) | Luminous Efficiency (cd/A) | Luminance half-life (hrs) |
|---|---|---|---|---|
| Example 7 | Compound 1 | 4.1 | 11 | 400 |
| Example 8 | Compound 2 | 4.3 | 10 | 350 |
| Example 9 | Compound 3 | 4.2 | 12 | 540 |
| Example 10 | Compound 4 | 4.4 | 12 | 350 |
| Example 11 | Compound 5 | 4.1 | 12 | 450 |
| Example 12 | Compound 6 | 4.2 | 12 | 450 |
| Example 13 | Compound 7 | 4.2 | 11 | 400 |
| Example 14 | Compound 8 | 4.1 | 10 | 350 |
| Comparison 5 | Compound D | 4.1 | 7 | 200 |
| Comparison 6 | Compound F | 5.2 | 6.5 | 220 |

The table 5 shows that the compounds of the invention also function as a red phosphorescent host material.

Examples 15 to 18 and Comparison 7

The organic EL devices according respectively to Examples 15 to 18 and Comparison 7 were formed in the same manner as in Example 1 except that the materials, a thickness of each of the layers and a concentration of each of the emitting materials were changed as shown in Table 6. In Table 6, figures in parentheses without a unit indicate a thickness of each of the layers (unit: nm). A structure of HT-7 is shown below.

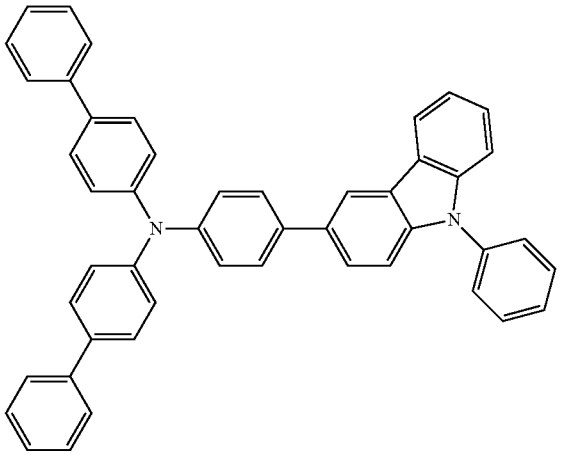

HT-7

Table 7 shows physical properties of the host materials used in Examples 15 to 18 and Comparison 7.

A method for measuring each of the physical properties is as follows.

(1) Ionization Potential (Ip)

Ionization potential was measured in the atmosphere by using a photoelectron spectrometer (AC-1 manufactured by Riken Keiki Co., Ltd.). Specifically, ionization potential was measured by irradiating the materials with light and measuring the amount of electrons generated by charge separation at that time.

(2) Affinity (Af)

Affinity was calculated based on measurement values of ionization potential Ip and energy gap Eg. A calculation equitation is as follows.

$$Af = Ip - Eg$$

The energy gap was measured from an absorption end of absorption spectrum of benzene. Specifically, the absorption spectrum is measured with a commercially available ultra-violet-visible spectrophotometer, and the energy gap is calculated from a wavelength at which the absorption spectrum appears.

(3) Singlet Energy (S1) and Triplet Energy (T1)

The optical energy gap S1 (also referred to as singlet energy) is a difference between a conduction level and a valence level. The optical energy gap was obtained by converting into energy a wavelength value at an intersection of a long-wavelength-side tangent line in an absorbing spectrum of a toluene-diluted solution of each material and a base line in the absorbing spectrum (zero absorption).

The triplet energy gap T1 of the material may be exemplarily defined based on the phosphorescence spectrum. The triplet energy gap T1 was defined as follows in Examples.

Specifically, each material was dissolved in an EPA solvent (diethylether:isopentane:ethanol=5:5:2 in volume ratio) with a concentration of 10 μmol/L, thereby forming a sample for phosphorescence measurement.

Then, the sample for phosphorescence measurement was put into a quartz cell, cooled to 77K and irradiated with exciting light, so that a wavelength of phosphorescence radiated therefrom was measured.

A tangent line is drawn to be tangent to a rising section adjacent to short-wavelength of the obtained phosphorescence spectrum, a wavelength value at an intersection of the tangent line and a base line is converted into energy value, and the converted energy value is defined as the triplet energy gap T1.

For the measurement, a measurement machine F-4500 (manufactured by Hitachi) was used.

Evaluation of Organic EL Device

Voltage was applied to the organic EL device so that a current density becomes 10 mA/cm$^2$, and a voltage value (V) at that time was measured. Moreover, current efficiency (L/J) (cd/A), power efficiency (lm/W) and life-time (hrs) were measured.

As for life-time, after the device was driven by constant current at the initial luminescence, an elapsed time when the luminescence reached 90% of the initial luminescence (LT90) or the luminescence reached 50% of the initial luminescence (LT50) was measured.

The results are shown in Table 8.

TABLE 6

| | Arrangement of Organic EL Device |
|---|---|
| Example 15 | ITO(70)/Compound A(30)/HT-7(20)/PH1 + Ir(ppy)$_3$(40, 90% + 10%)/ET2(30)/Liq(1)/Al(80) |
| Example 16 | ITO(70)/Compound A(30)/HT-7(20)/PH2 + Ir(ppy)$_3$(40, 90% + 10%)/ET2(30)/LiF(1)/Al(80) |
| Example 17 | ITO(70)/Compound A(30)/HT-7(20)/PH3 + Ir(ppy)$_3$(40, 90% + 10%)/ET2(30)/LiF(1)/Al(80) |
| Example 18 | ITO(130)/Compound A(50)/PH2 + Ir(piq)$_3$(30, 92% + 8%)/ET2(30)/LiF(1)/Al(80) |
| Comparison 7 | ITO(70)/Compound A(30)/HT-7(20)/PH5 + Ir(ppy)$_3$(40, 90% + 10%)/ET2(30)/Liq(1)/Al(80) |

TABLE 7

| Host Material | Ip(eV) | Af(eV) | S1(eV) | T1(eV) |
|---|---|---|---|---|
| PH1 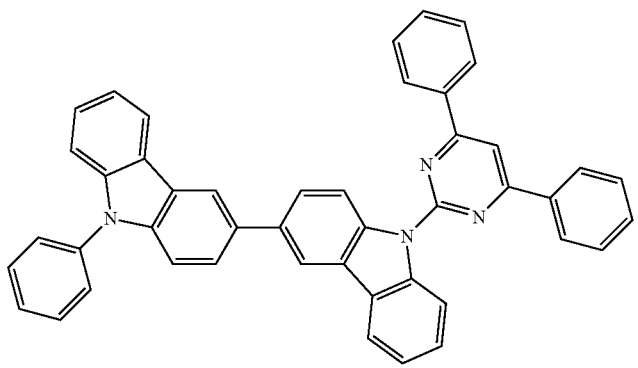 | 5.5 | 2.4 | 3.1 | 2.9 |
| PH2 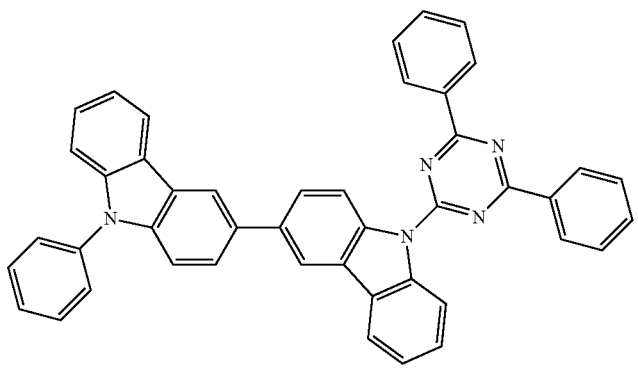 | 5.7 | 2.3 | 3.3 | 2.8 |

TABLE 7-continued
| Host Material | | Ip(eV) | Af(eV) | S1(eV) | T1(eV) |
|---|---|---|---|---|---|
| PH3 | 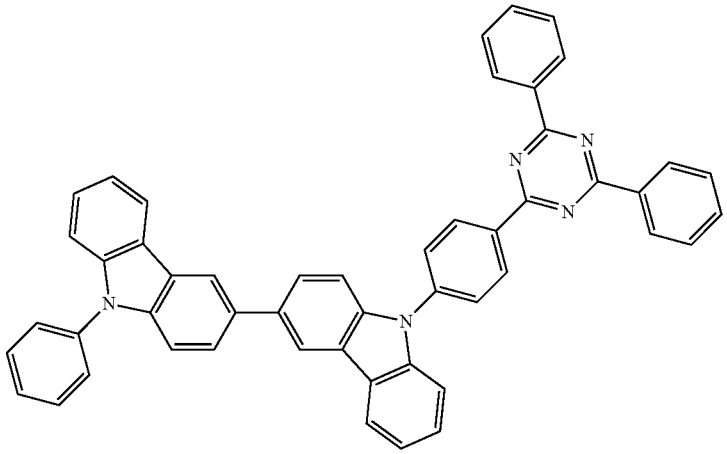 [SMILES: c1ccc(-c2nc(-c3ccccc3)nc(-c3ccc(-n4c5ccccc5c5cc(-c6ccc7c(c6)c6ccccc6n7-c6ccccc6)ccc54)cc3)n2)cc1] | 5.7 | 2.7 | 3.0 | 2.8 |
| PH5 | 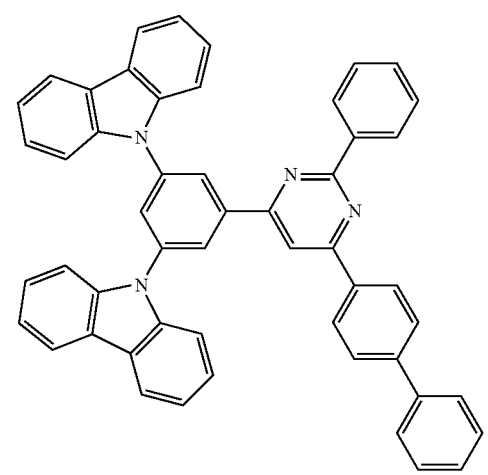 [SMILES: c1ccc(-c2ccc(-c3cc(-c4cc(-n5c6ccccc6c6ccccc65)cc(-n5c6ccccc6c6ccccc65)c4)nc(-c4ccccc4)n3)cc2)cc1] | 6.1 | 2.6 | 3.5 | 2.7 |
TABLE 8
| | Host material | Voltage (V) | Current density (mA/cm²) | luminescence (nit) | L/J (cd/A) | η (lm/W) | LT90 (hrs) | LT50 (hrs) |
|---|---|---|---|---|---|---|---|---|
| Example 15 | PH1 | 3.00 | 1 | 494 | 49.4 | 51.7 | 250 @3000 cd/m² | — |
| Example 16 | PH2 | 2.85 | 1 | 637 | 63.7 | 70.3 | — | 500 @10000 cd/m² |
| Example 17 | PH3 | 2.67 | 1 | 572 | 57.2 | 67.3 | — | 800 @10000 cd/m² |
| Example 18 | PH2 | 3.54 | 1 | 85 | 8.5 | 7.5 | — | 1000 @10000 cd/m² |
| Comparison 7 | PH5 | 2.72 | 1 | 492 | 49.2 | 56.7 | 90 @3000 cd/m² | — |

Example 19

Manufacture of Organic EL Device 19

A glass substrate (size: 25 mm×75 mm×1.1 mm) having an ITO transparent electrode (manufactured by GEOMATEC Co., Ltd.) was ultrasonic-cleaned in isopropyl alcohol for five minutes, and then UV (Ultraviolet)/ozone-cleaned for 30 minutes.

After the glass substrate having the transparent electrode was cleaned, the glass substrate was mounted on a substrate holder of a vacuum deposition apparatus, and a hole injecting layer was initially formed by depositing a compound A onto the substrate to be 40 nm thick to cover a surface of the glass substrate where a transparent electrode line was provided. Next, a compound B was deposited onto the hole injecting layer to be 20 nm thick, and a hole transporting layer was obtained.

A phosphorescent-emitting layer was obtained by co-depositing the compound 3 used as the first phosphorescent host material, $Ir(Ph-ppy)_3$ used as a phosphorescent dopant material, and HT-5 used as the following second host material onto the hole transporting layer to be 40 nm thick. The concentration of $Ir(Ph-ppy)_3$ was 20 mass % and the concentration of HT-5 was 10 mass %.

Subsequently, a 30-nm-thick compound C, 1-nm-thick LiF and 80-nm-thick metal Al are sequentially layered to obtain a cathode. LiF, which is an electron injectable electrode, was formed at a speed of 1 Å/min.

With respect to the organic EL devices 19, luminescent performance was evaluated in the same manner as in Example 1 and time elapsed until an initial luminescence intensity of 20,000 $cd/m^2$ was reduced to the half was measured. The results are shown in Table 9.

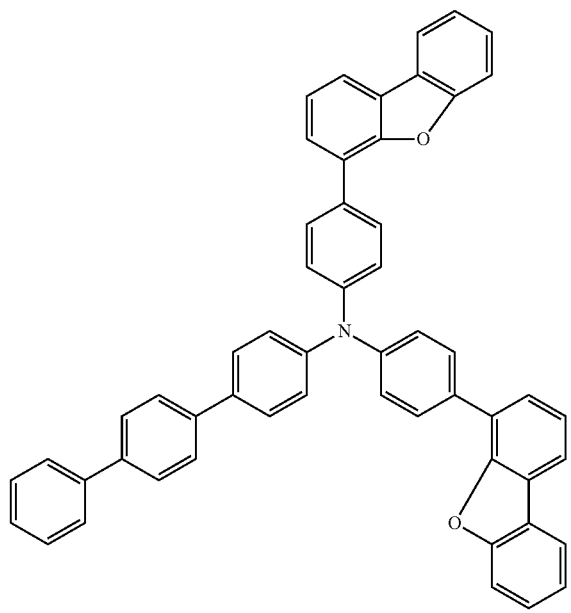

HT-5

Example 20

Manufacture of Organic EL Device 20

In Example 19, HT-9 was used in place of HT-5 to manufacture an organic EL device 6.

With respect to the organic EL devices 20, luminescent performance was evaluated in the same manner as in Example 1 and time elapsed until an initial luminescence intensity of 20,000 $cd/m^2$ was reduced to the half was measured. The results are shown in Table 9.

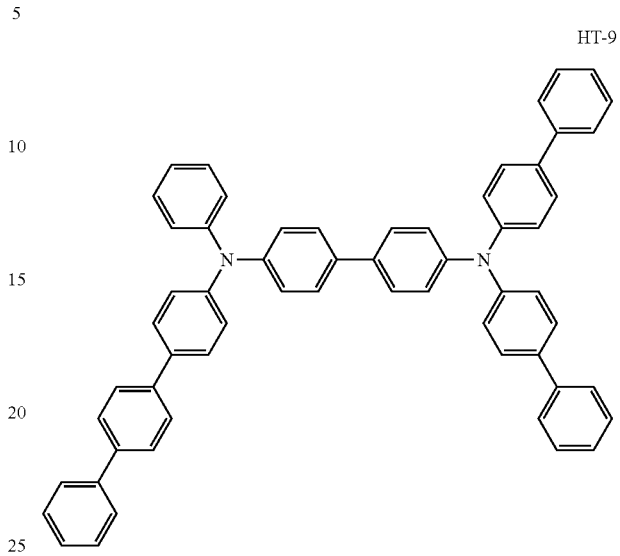

HT-9

Comparison 8

In Example 19, the compound D was used in place of the compound 3 to manufacture an organic EL device. With respect to the organic EL devices, luminescent performance was evaluated in the same manner as in Example 1 and time elapsed until an initial luminescence intensity of 20,000 $cd/m^2$ was reduced to the half was measured. The results are shown in Table 9.

Comparison 9

In Comparison 8, HT-9 was used in place of HT-5 to manufacture an organic EL device. With respect to the organic EL devices, luminescent performance was evaluated in the same manner as in Example 1 and time elapsed until an initial luminescence intensity of 20,000 $cd/m^2$ was reduced to the half was measured. The results are shown in Table 9.

TABLE 9

|  | First/Second host materials | Voltage (V) @ 1 mA/$cm^2$ | Luminous Efficiency (cd/A) @ 1 mA/$cm^2$ | Luminance half-life (hrs) |
| --- | --- | --- | --- | --- |
| Example 19 | Compound 3/HT-5 | 3.9 | 72 | 800 |
| Example 20 | Compound 3/HT-9 | 3.9 | 69 | 800 |
| Comparison 8 | Compound D/HT-5 | 4.0 | 40 | 400 |
| Comparison 9 | Compound D/HT-9 | 4.1 | 41 | 380 |

Table 9 shows that the compounds of the invention used in Examples 19 and 20 have a significantly long luminance half-life and a significantly high luminous efficiency as compared with those in Comparisons 8 and 9.

Examples 21 to 26

The organic EL devices according respectively to Examples 21 to 26 were formed in the same manner as in Example 19 except that the materials, a thickness of each of the layers and a concentration of each of the emitting materials were changed as shown in Table 10.

Table 7 above and Table 11 below show the chemical formulae and physical properties of the host material used in Examples 21 to 26.

TABLE 10

| | Arrangement of Organic EL Device |
|---|---|
| Example 21 | ITO(70)/Compound A(30)/HT-7(20)/PH1 + PH5 + Ir(ppy)$_3$(40, 45% + 45% + 10%)/ET2(30)/Liq(1)/Al(80) |
| Example 22 | ITO(70)/Compound A(30)/HT-7(20)/PH2 + PH6 + Ir(ppy)$_3$(40, 45% + 45% + 10%)/ET2(30)/LiF(1)/Al(80) |

TABLE 10-continued

| | Arrangement of Organic EL Device |
|---|---|
| Example 23 | ITO(70)/Compound A(30)/HT-7(20)/PH3 + PH6 + Ir(ppy)$_3$(40, 45% + 45% + 10%)/ET2(30)/LiF(1)/Al(80) |
| Example 24 | ITO(70)/Compound A(30)/HT-7(20)/PH3 + PH7 + Ir(ppy)$_3$(40, 45% + 45% + 10%)/ET2(30)/LiF(1)/Al(80) |
| Example 25 | ITO(130)/Compound A(50)/PH2 + PH10 + Ir(piq)$_3$(30, 50% + 42% + 8%)/ET2(30)/LiF(1)/Al(80) |
| Example 26 | ITO(70)/Compound A(30)/HT-7(20)/PH1 + PH3 + Ir(ppy)$_3$(40, 45% + 45% + 10%)/ET2(30)/LiF(1)/Al(80) |

TABLE 11

| Host Material | Ip(eV) | Af(eV) | S1(eV) | T1(eV) |
|---|---|---|---|---|
| PH6 | 6.0 | 2.5 | 3.5 | 3.0 |
| PH7 | 6.0 | 2.5 | 3.5 | 2.8 |
| PH10 | 6.2 | 3.1 | 3.1 | 2.3 |

Evaluation of Organic EL Device

The organic EL devices according to Examples 21 to 26 were evaluated in the same manner as in Examples 15 to 18. The results are shown in Table 12.

Figure 2A:
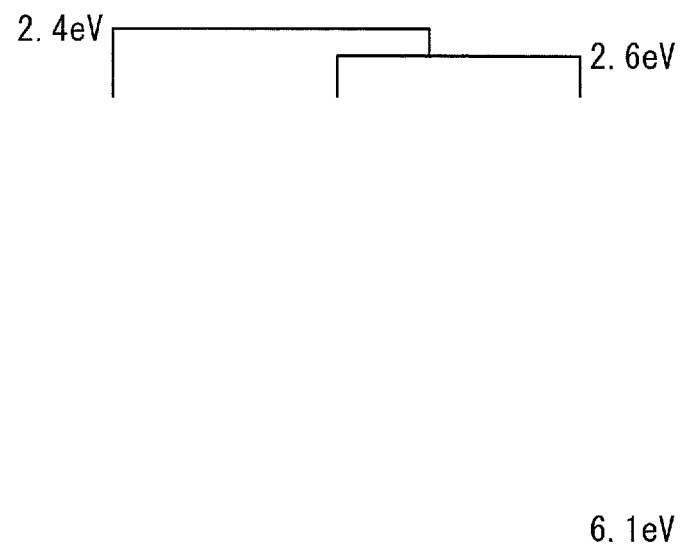
FIG. 2A shows an energy diagram of an emitting layer in an organic EL device according to Examples of the invention.
Figure 2B:
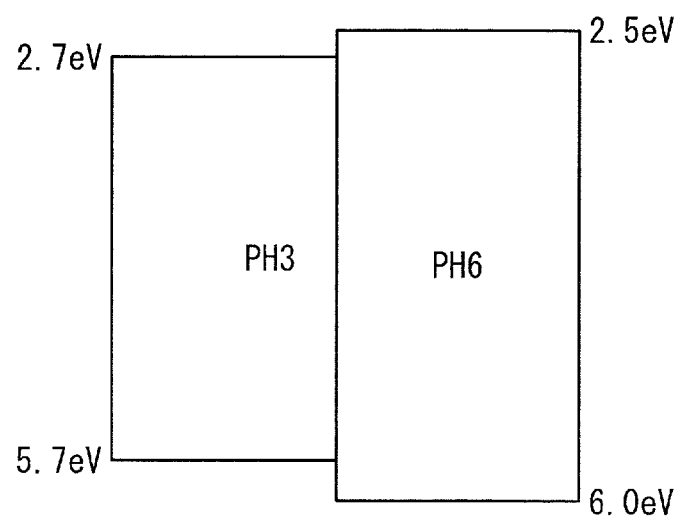
FIG. 2B shows an energy diagram of an emitting layer in an organic EL device according to Examples of the invention.

FIG. 2(A) shows an energy diagram in the emitting layer in Example 21. FIG. 2(B) shows an energy diagram in the emitting layer in Example 23.

TABLE 12

| | Host material | Voltage (V) | Current density (mA/cm$^2$) | luminescence (nit) | L/J (cd/A) | η (lm/W) | LT90 (hrs) | LT50 (hrs) |
|---|---|---|---|---|---|---|---|---|
| Example 21 | PH1/PH5 | 2.83 | 1 | 517 | 51.7 | 57.5 | 600 @3000 cd/m$^2$ | — |
| Example 22 | PH2/PH6 | 3.39 | 1 | 673 | 67.3 | 62.4 | — | 900 @10000 cd/m$^2$ |
| Example 23 | PH3/PH6 | 3.10 | 1 | 726 | 72.6 | 73.6 | — | 1000 @10000 cd/m$^2$ |
| Example 24 | PH3/PH7 | 3.08 | 1 | 888 | 88.8 | 90.6 | 40 @20000 cd/m$^2$ | — |
| Example 25 | PH2/PH10 | 3.88 | 1 | 92 | 9.2 | 7.4 | — | 1500 @10000 cd/m$^2$ |
| Example 26 | PH2/PH3 | 2.92 | 1 | 752 | 75.2 | 80.9 | — | 750 @10000 cd/m$^2$ |

In comparison between Table 8 and Table 12, it has been found that the organic EL devices according to Examples 21 to 26, in which the first and second host materials are used, have a long life-time and improved luminous efficiency as compared with the organic EL devices in which a single host material is used.

What is claimed is:

1. A biscarbazole derivative represented by a formula (1) below,

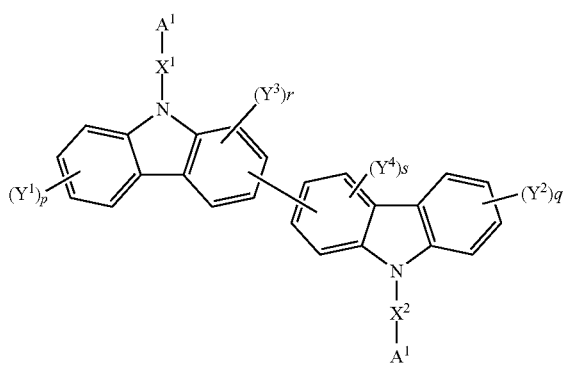

(1)

where: $A^1$ represents a substituted or unsubstituted quinazoline ring bound to $X^1$ through the nitrogen-containing ring of the quinazoline, when $A^1$ has a substituent, the substituent of $A^1$ is an alkyl group having 1 to 20 carbon atoms, alkoxy group having 1 to 20 carbon atoms, haloalkyl group having 1 to 20 carbon atoms, alkylsilyl group having 1 to 10 carbon atoms, arylsilyl group having 6 to 30 ring carbon atoms, cyano group, halogen atom, aromatic hydrocarbon group having 6 to 30 ring carbon atoms, substituted or unsubstituted fused aromatic hydrocarbon group having 10 to 30 ring carbon atoms, or monocyclic aromatic heterocyclic group having 2 to 30 ring carbon atoms;

$A^2$ represents a substituted or unsubstituted aromatic hydrocarbon group having 6 to 30 ring carbon atoms, when $A^2$ has a substituent, the substituent of $A^2$ is an alkyl group having 1 to 20 carbon atoms, alkoxy group having 1 to 20 carbon atoms, haloalkyl group having 1 to 20 carbon atoms, alkylsilyl group having 1 to 10 carbon atoms, arylsilyl group having 6 to 30 ring carbon atoms, cyano group, halogen atom, aromatic hydrocarbon group having 6 to 30 ring carbon atoms, substituted or an unsubstituted fused aromatic hydrocarbon group having 10 to 30 ring carbon atoms, or monocyclic aromatic heterocyclic group having 2 to 30 ring carbon atoms;

$X^1$ and $X^2$ each are a linking group and independently represent a single bond, substituted or unsubstituted aromatic hydrocarbon group having 6 to 30 ring carbon atoms, substituted or unsubstituted fused aromatic hydrocarbon group having 10 to 30 ring carbon atoms, when $X^1$ and $X^2$ each have a substituent, the substituent of $X^1$ and $X^2$ is an alkyl group having 1 to 20 carbon atoms, alkoxy group having 1 to 20 carbon atoms, haloalkyl group having 1 to 20 carbon atoms, alkylsilyl group having 1 to 10 carbon atoms, arylsilyl group having 6 to 30 ring carbon atoms, cyano group, halogen atom, aromatic hydrocarbon group having 6 to 30 ring carbon atoms, substituted or an unsubstituted fused aromatic hydrocarbon group having 10 to 30 ring carbon atoms, or monocyclic aromatic heterocyclic group having 2 to 30 ring carbon atoms:

$Y^1$, $Y^3$ and $Y^4$ independently represent a hydrogen atom, fluorine atom, cyano group, substituted or unsubstituted alkyl group having 1 to 20 carbon atoms, substituted or unsubstituted alkoxy group having 1 to 20 carbon atoms, substituted or unsubstituted haloalkyl group having 1 to 20 carbon atoms, substituted or unsubstituted haloalkoxy group having 1 to 20 carbon atoms, substituted or unsubstituted alkylsilyl having 1 to 10 carbon atoms, substituted or unsubstituted arylsilyl having 6 to 30 carbon atoms, substituted or unsubstituted aromatic hydrocarbon group having 6 to 30 ring carbon atoms, substituted or unsubstituted fused aromatic hydrocarbon group having 10 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms:

$Y^2$ represents a hydrogen atom, fluorine atom, cyano group, unsubstituted alkyl group having 1 to 20 carbon atoms, unsubstituted alkoxy group having 1 to 20 carbon atoms, unsubstituted haloalkyl group having 1 to 20 carbon atoms, unsubstituted haloalkoxy group having 1 to 20 carbon atoms unsubstituted alkylsilyl having 1 to 10 carbon atoms, unsubstituted arylsilyl having 6 to 30 carbon atoms, unsubstituted aromatic hydrocarbon group having 6 to 30 ring carbon atoms, unsubstituted fused aromatic hydrocarbon group having 10 to 30 ring carbon atoms unsubstituted monocyclic aromatic heterocyclic group having 2 to 30 ring carbon atoms, or unsubstituted fused aromatic heterocyclic group having 2 to 30 ring carbon atoms;

adjacent ones of $Y^1$ to $Y^4$ are allowed to be bonded to each other to form a ring structure;

p and q represent an integer of 1 to 4; r and s represent an integer of 1 to 3; and when p and q are an integer of 2 to 4 and r and s are an integer of 2 to 3, a plurality of $Y^1$ to $Y^4$ are allowed to be the same or different.

2. The biscarbazole derivative according to claim 1, wherein the biscarbazole derivative is represented by a formula (2) below,

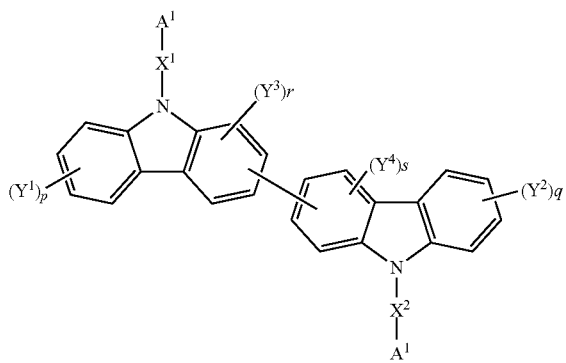

(2)

where: $A^1$, $A^2$, $X^1$, $X^2$, $Y^1$ to $Y^4$, p, q, r and s represent the same as $A^1$, $A^2$, $X^1$, $X^2$, $Y^1$ to $Y^4$, p, q, r and s of the formula (1).

3. The biscarbazole derivative according to claim 2, wherein in formula (2)

when $A^1$ has a substituent, the substituent of $A^1$ is an aromatic hydrocarbon group having 6 to 30 ring carbon atoms or a substituted or an unsubstituted fused aromatic hydrocarbon group having 10 to 30 ring carbon atoms;

$Y^1$ to $Y^4$ are a hydrogen atom; and when $A^2$ has a substituent, the substituent of $A^2$ is an aromatic hydrocarbon group having 6 to 30 ring carbon atoms or a substituted or an unsubstituted fused aromatic hydrocarbon group having 10 to 30 ring carbon atoms.

4. The biscarbazole derivative according to claim 2, wherein in formula (2)

when $A^1$ has a substituent, the substituent of $A^1$ is an aromatic hydrocarbon group having 6 to 30 ring carbon atoms or a substituted or an unsubstituted fused aromatic hydrocarbon group having 10 to 30 ring carbon atoms;

$Y^1$ to $Y^4$ are a hydrogen atom;

when $A^2$ has a substituent, the substituent of $A^2$ is an aromatic hydrocarbon group having 6 to 30 ring carbon atoms or a substituted or an unsubstituted fused aromatic hydrocarbon group having 10 to 30 ring carbon atoms; and $X^1$ is a single bond.

5. The biscarbazole derivative according to claim 2, wherein in formula (2)

when $A^1$ has a substituent, the substituent of $A^1$ is an aromatic hydrocarbon group having 6 to 30 ring carbon atoms or a substituted or an unsubstituted fused aromatic hydrocarbon group having 10 to 30 ring carbon atoms;

$Y^1$ to $Y^4$ are a hydrogen atom;

when $A^2$ has a substituent, the substituent of $A^2$ is an aromatic hydrocarbon group having 6 to 30 ring carbon atoms or a substituted or an unsubstituted fused aromatic hydrocarbon group having 10 to 30 ring carbon atoms; and $X^1$ is an unsubstituted aromatic hydrocarbon group having 6 to 30 ring carbon atoms or an unsubstituted fused aromatic hydrocarbon group having 10 to 30 ring carbon atoms.

6. An organic-EL-device material comprising the biscarbazole derivative according to claim 1.

7. An organic electroluminescence device comprising: a cathode: an anode; and a plurality of organic thin-film layers provided between the cathode and the anode, the organic thin-film layers comprising an emitting layer, wherein at least one of the organic thin-film layers comprises the organic-EL-device material according to claim 6.

8. The organic electroluminescence device according to claim 7, wherein the emitting layer comprises the organic-EL-device material as a host material.

9. The organic electroluminescence device according to claim 7, wherein the emitting layer comprises a phosphorescent material.

10. The organic electroluminescence device according to claim 9, wherein the phosphorescent material is an ortho-metalated complex of a metal atom selected from iridium (Ir), osmium (Os) and platinum (Pt).

11. The organic electroluminescence device according to claim 7, wherein an electron injecting layer is provided between the cathode and the emitting layer, the electron injecting layer comprising a nitrogen-containing cyclic derivative.

12. The organic electroluminescence device according to claim 7, wherein an electron transporting layer is provided between the cathode and the emitting layer, the electron transporting layer comprising the organic-EL-device material.

13. The organic electroluminescence device according to claim 7, wherein a reduction-causing dopant is present at an interfacial region between the cathode and at least one of the organic thin-film layers.

14. An organic electroluminescence device comprising: a cathode; an anode; and a plurality of organic thin-film layers provided between the cathode and the anode, the organic thin-film layers comprising an emitting layer, wherein at least one of the organic thin-film layers is the emitting layer comprising a first host material, a second host material and a phosphorescent material providing phosphorescence, the first host material being a compound represented by a formula (4) below,

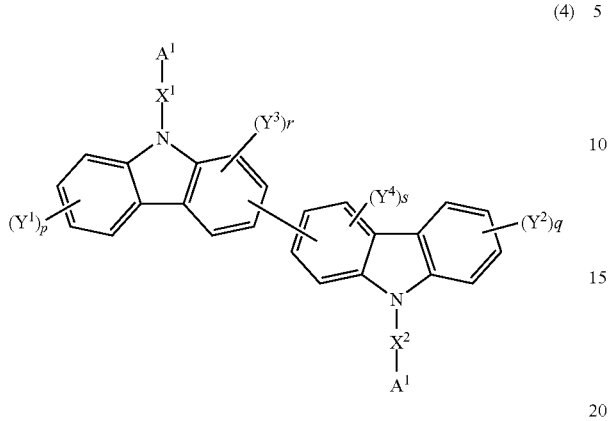 (4)

where: $A^1$ represents a substituted or unsubstituted quinazoline ring bound to $X^1$ through the nitrogen-containing ring of the quinazoline, when $A^1$ has a substituent, the substituent of $A^1$ is an alkyl group having 1 to 20 carbon atoms, alkoxy group having 1 to 20 carbon atoms, haloalkyl group having 1 to 20 carbon atoms, alkylsilyl group having 1 to 10 carbon atoms, arylsilyl group having 6 to 30 ring carbon atoms, cyano group, halogen atom, aromatic hydrocarbon group having 6 to 30 ring carbon atoms, substituted or unsubstituted fused aromatic hydrocarbon group having 10 to 30 ring carbon atoms, or monocyclic aromatic heterocyclic group having 2 to 30 ring carbon atoms;

$A^2$ represents a substituted or unsubstituted aromatic hydrocarbon group having 6 to 30 ring carbon atoms, when $A^2$ has a substituent, the substituent of $A^2$ is an alkyl group having 1 to 20 carbon atoms, alkoxy group having 1 to 20 carbon atoms, haloalkyl group having 1 to 20 carbon atoms, alkylsilyl group having 1 to 10 carbon atoms, arylsilyl group having 6 to 30 ring carbon atoms, cyano group, halogen atom, aromatic hydrocarbon group having 6 to 30 ring carbon atoms, substituted or an unsubstituted fused aromatic hydrocarbon group having 10 to 30 ring carbon atoms, or monocyclic aromatic heterocyclic group having 2 to 30 ring carbon atoms;

$X^1$ and $X^2$ each are a linking group and independently represent a single bond, substituted or unsubstituted aromatic hydrocarbon group having 6 to 30 ring carbon atoms, substituted or unsubstituted fused aromatic hydrocarbon group having 10 to 30 ring carbon atoms, when $X^1$ and $X^2$ each have a substituent, the substituent of $X^1$ and $X^2$ is an alkyl group having 1 to 20 carbon atoms, alkoxy group having 1 to 20 carbon atoms, haloalkyl group having 1 to 20 carbon atoms, alkylsilyl group having 1 to 10 carbon atoms, arylsilyl group having 6 to 30 ring carbon atoms, cyano group, halogen atom, aromatic hydrocarbon group having 6 to 30 ring carbon atoms, substituted or an unsubstituted fused aromatic hydrocarbon group having 10 to 30 ring carbon atoms, or monocyclic aromatic heterocyclic group having 2 to 30 ring carbon atoms;

$Y^1$, $Y^3$ and $Y^4$ independently represent a hydrogen atom, fluorine atom, cyano group, substituted or unsubstituted alkyl group having 1 to 20 carbon atoms, substituted or unsubstituted alkoxy group having 1 to 20 carbon atoms, substituted or unsubstituted haloalkyl group having 1 to 20 carbon atoms, substituted or unsubstituted haloalkoxy group having 1 to 20 carbon atoms, substituted or unsubstituted alkylsilyl having 1 to 10 carbon atoms, substituted or unsubstituted arylsilyl having 6 to 30 carbon atoms, substituted or unsubstituted aromatic hydrocarbon group having 6 to 30 ring carbon atoms, substituted or unsubstituted fused aromatic hydrocarbon group having 10 to 30 ring carbon atoms, substituted or unsubstituted aromatic heterocyclic group having 2 to 30 ring carbon atoms, or substituted or unsubstituted fused aromatic heterocyclic group having 2 to 30 ring carbon atoms;

$Y^2$ represents a hydrogen atom, fluorine atom, cyano group, unsubstituted alkyl group having 1 to 20 carbon atoms, unsubstituted alkoxy group having 1 to 20 carbon atoms, unsubstituted haloalkyl group having 1 to 20 carbon atoms, unsubstituted haloalkoxy group having 1 to 20 carbon atoms, unsubstituted alkylsilyl having 1 to 10 carbon atoms, unsubstituted arylsilyl having 6 to 30 carbon atoms, unsubstituted aromatic hydrocarbon group having 6 to 30 ring carbon atoms, unsubstituted fused aromatic hydrocarbon group having 10 to 30 ring carbon atoms, unsubstituted monocyclic aromatic heterocyclic group having 2 to 30 ring carbon atoms, or unsubstituted fused aromatic heterocyclic group having 2 to 30 ring carbon atoms;

adjacent ones of $Y^1$ to $Y^1$ are allowed to be bonded to each other to form a ring structure:

p and q represent an integer of 1 to 4; r and s represent an integer of 1 to 3; and when p and q are an integer of 2 to 4 and r and s are an integer of 2 to 3, a plurality of $Y^1$ to $Y^4$ are allowed to be the same or different.

15. The organic electroluminescence device according to claim 14, wherein the second host material is represented by either one of a formula (13) or (14) below,

 (13)

where: $X^3$ represents a substituted or unsubstituted arylene group having 10 to 40 ring carbon atoms; and $A^3$ to $A^6$ represent a substituted or unsubstituted aryl group having 6 to 60 ring carbon atoms, or heteroaryl group having 6 to 60 ring atoms,

 (14)

where: $A^7$ to $A^9$ represent a substituted or unsubstituted aryl group having 6 to 60 ring carbon atoms, or heteroaryl group having 6 to 60 ring atoms.

16. The organic electroluminescence device according to claim 15, wherein the second host material is represented by any one of formulae (15) to (19) below,

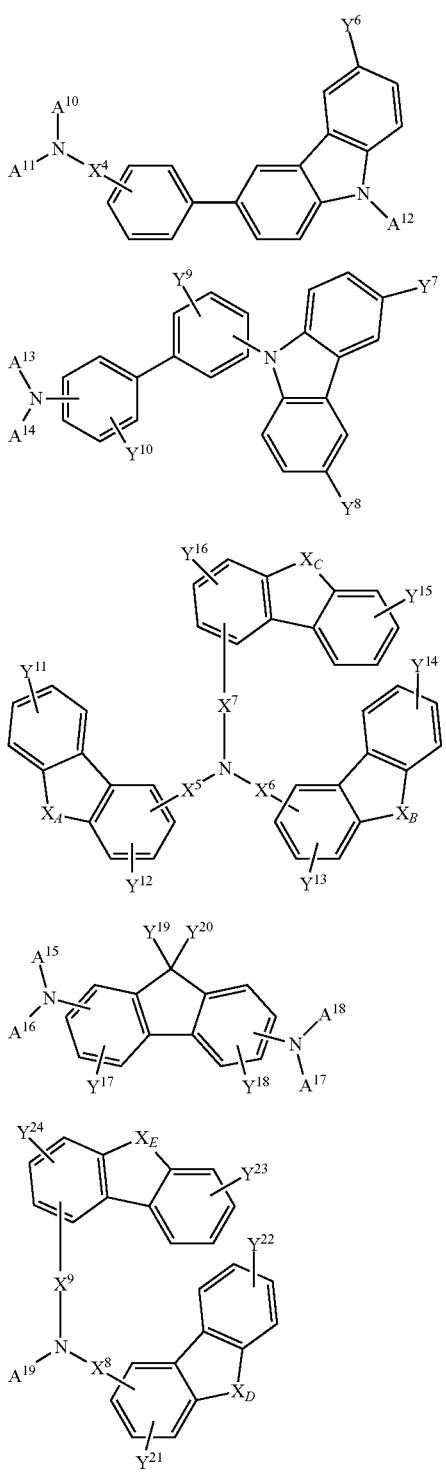

where: $A^{10}$ to $A^{19}$ each represent a substituted or unsubstituted aryl group having 6 to 40 carbon atoms, or substituted or unsubstituted aromatic heterocyclic group having 2 to 40 carbon atoms;

variable pairs $A^{10}$ and $A^{11}$; $A^{13}$ and $A^{14}$; $A^{15}$ and $A^{16}$; $A^{17}$ and $A^{18}$ together with the nitrogen to which they are bonded optionally form a ring;

$X^4$ to $X^9$ represent a single bond or a linking group having 1 to 30 carbon atoms;

$Y^6$ to $Y^{24}$ represent a hydrogen atom, halogen atom, substituted or unsubstituted alkyl group having 1 to 40 carbon atoms, substituted or unsubstituted heterocyclic group having 3 to 20 carbon atoms, substituted or unsubstituted aryl group having 6 to 40 carbon atoms, substituted or unsubstituted aralkyl group having 7 to 20 carbon atoms, substituted or unsubstituted alkenyl group having 2 to 40 carbon atoms, substituted or unsubstituted alkylamino group having 1 to 40 carbon atoms, substituted or unsubstituted aralkylamino group having 7 to 60 carbon atoms, substituted or unsubstituted alkylsilyl group having 3 to 20 carbon atoms, substituted or unsubstituted arylsilyl group having 8 to 40 carbon atoms, substituted or unsubstituted aralkylsilyl group having 8 to 40 carbon atoms, or substituted or unsubstituted halogenated alkyl group having 1 to 40 carbon atoms; and $X_A$, $X_B$, $X_C$, $X_D$, $X_E$ each represent a sulfur atom, an oxygen atom or a monoaryl-substituted nitrogen atom.

17. The organic electroluminescence device according to claim 14, wherein
the emitting layer comprises a host material and a phosphorescent material, the phosphorescent material being an ortho-metalated complex of a metal atom selected from iridium (Ir), osmium (Os) and platinum (Pt).

18. The organic electroluminescence device according to claim 14, wherein
an electron injecting layer is provided between the cathode and the emitting layer, the electron injecting layer comprising a nitrogen-containing cyclic derivative.

19. The organic electroluminescence device according to claim 14, wherein
an electron transporting layer is provided between the cathode and the emitting layer, the electron transporting layer comprising a compound represented by the formula (4).

20. The organic electroluminescence device according to claim 14, wherein
a reduction-causing dopant is present at an interfacial region between the cathode and at least one of the organic thin-film layers.

21. The biscarbazole derivative according to claim 1, wherein in formula (1)
when $A^1$ has a substituent, the substituent of $A^1$ is an aromatic hydrocarbon group having 6 to 30 ring carbon atoms or a substituted or an unsubstituted fused aromatic hydrocarbon group
having 10 to 30 ring carbon atoms;
$Y^1$ to $Y^4$ are a hydrogen atom; and
when $A^2$ has a substituent, the substituent of $A^2$ is an aromatic hydrocarbon group having 6 to 30 ring carbon atoms or a substituted or an unsubstituted fused aromatic hydrocarbon group having 10 to 30 ring carbon atoms.

22. The biscarbazole derivative according to claim 1, wherein in formula (1)
when $A^1$ has a substituent, the substituent of $A^1$ is an aromatic hydrocarbon group having 6 to 30 ring carbon atoms or a substituted or an unsubstituted fused aromatic hydrocarbon group having 10 to 30 ring carbon atoms;
$Y^1$ to $Y^4$ are a hydrogen atom;
when $A^2$ has a substituent, the substituent of $A^2$ is an aromatic hydrocarbon group having 6 to 30 ring carbon atoms or a substituted or an unsubstituted fused aromatic hydrocarbon group having 10 to 30 ring carbon atoms; and
$X^1$ is a single bond.

23. The biscarbazole derivative according to claim 1, wherein in formula (1)
- when $A^1$ has a substituent, the substituent of $A^1$ is an aromatic hydrocarbon group having 6 to 30 ring carbon atoms or a substituted or an unsubstituted fused aromatic hydrocarbon group having 10 to 30 ring carbon atoms; $Y^1$ to $Y^4$ are a hydrogen atom;
- when $A^2$ has a substituent, the substituent of $A^1$ is an aromatic hydrocarbon group having 6 to 30 ring carbon atoms or a substituted or an unsubstituted fused aromatic hydrocarbon group having 10 to 30 ring carbon atoms; and
- $X^1$ is an unsubstituted aromatic hydrocarbon group having 6 to 30 ring carbon atoms or an unsubstituted fused aromatic hydrocarbon group having 10 to 30 ring carbon atoms.

24. An organic electroluminescence device comprising: a cathode; an anode; and a plurality of organic thin-film layers provided between the cathode and the anode, the organic thin-film layers comprising an emitting layer, wherein
- the emitting layer comprises the biscarbazole derivative according to claim 1 and a phosphorescent material, wherein the biscarbazole derivative is represented by formula (1), and when $A^1$ has a substituent, the substituent of $A^1$ is an aromatic hydrocarbon group having 6 to 30 ring carbon atoms or a substituted or an unsubstituted fused aromatic hydrocarbon group having 10 to 30 ring carbon atoms;
- $Y^1$ to $Y^4$ are a hydrogen atom;
- when $A^2$ has a substituent, the substituent of $A^2$ is an aromatic hydrocarbon group having 6 to 30 ring carbon atoms or a substituted or an unsubstituted fused aromatic hydrocarbon group having 10 to 30 ring carbon atoms;
- $X^1$ is a single bond, an unsubstituted aromatic hydrocarbon group having 6 to 30 ring carbon atoms or an unsubstituted fused aromatic hydrocarbon group having 10 to 30 ring carbon atoms; and
- the phosphorescent material is an Ir complex.

25. The organic electroluminescence device according to claim 24, wherein $X^1$ is a single bond in formula (1).

26. The organic electroluminescence device according to claim 24, wherein $X^1$ is an unsubstituted aromatic hydrocarbon group having 6 to 30 ring carbon atoms or an unsubstituted fused aromatic hydrocarbon group having 10 to 30 ring carbon atoms in formula (1).

27. An organic electroluminescence device comprising: a cathode; an anode; and a plurality of organic thin-film layers provided between the cathode and the anode, the organic thin-film layers comprising an emitting layer, wherein
- the emitting layer comprises the biscarbazole derivative according to claim 2 and a phosphorescent material, the biscarbazole derivative being represented by the formula (2), and when $A^1$ has a substituent, the substituent of $A^1$ is an aromatic hydrocarbon group having 6 to 30 ring carbon atoms or a substituted or an unsubstituted fused aromatic hydrocarbon group having 10 to 30 ring carbon atoms;
- $Y^1$ to $Y^4$ are a hydrogen atom;
- when $A^2$ has a substituent, the substituent of $A^2$ is an aromatic hydrocarbon group having 6 to 30 ring carbon atoms Or a substituted or an unsubstituted aromatic hydrocarbon group having 10 to 30 ring carbon atoms;
- $X^1$ is a single bond, an unsubstituted aromatic hydrocarbon group having 6 to 30 ring carbon atoms or an unsubstituted fused aromatic hydrocarbon group having 10 to 30 ring carbon atoms; and
- the phosphorescent material is an Ir complex.

28. The organic electroluminescence device according to claim 27, wherein
- $X^1$ is a single bond in formula (2).

29. The organic electroluminescence device according to claim 27, wherein
- $X^1$ is an unsubstituted aromatic hydrocarbon group having 6 to 30 ring carbon atoms or an unsubstituted fused aromatic hydrocarbon group having 10 to 30 ring carbon atoms in formula (2).

* * * * *

UNITED STATES PATENT AND TRADEMARK OFFICE
CERTIFICATE OF CORRECTION

PATENT NO. : 8,652,654 B2  
APPLICATION NO. : 13/091036  
DATED : February 18, 2014  
INVENTOR(S) : Tetsuya Inoue et al.

Page 1 of 3

It is certified that error appears in the above-identified patent and that said Letters Patent is hereby corrected as shown below:

In The Claims

Column 323, Claim 1, line 35, replace formula (1)

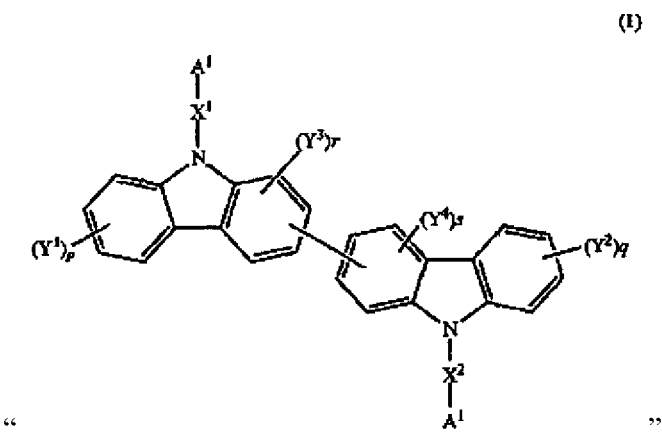

With:

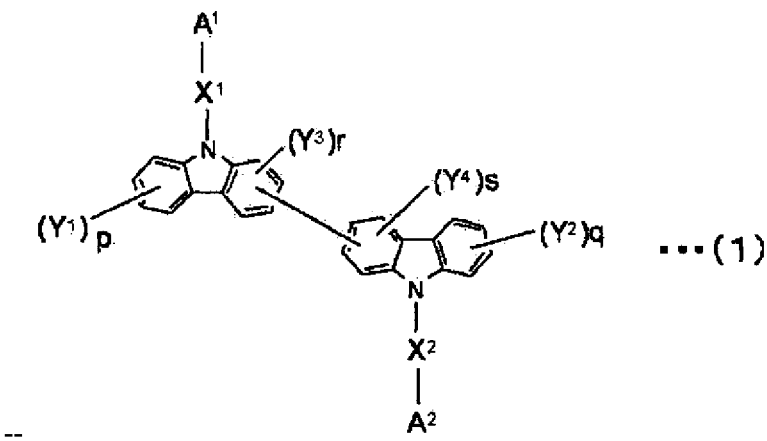

Signed and Sealed this  
Third Day of November, 2015

Michelle K. Lee  
*Director of the United States Patent and Trademark Office*

CERTIFICATE OF CORRECTION (continued)
U.S. Pat. No. 8,652,654 B2

In The Claims

Column 325, Claim 2, line 20, replace formula (2)

"
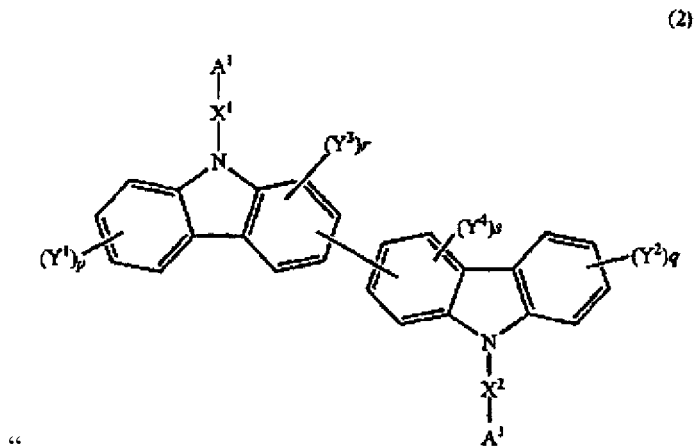
"

With:

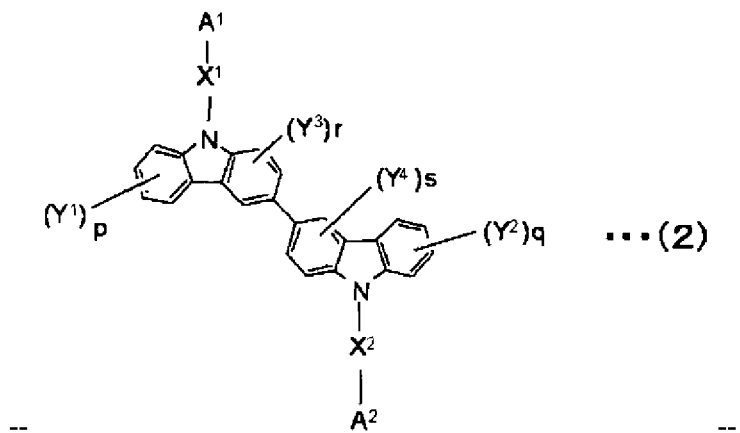

--

CERTIFICATE OF CORRECTION (continued)
U.S. Pat. No. 8,652,654 B2

In The Claims

Column 327, Claim 14, line 5, replace formula (4)

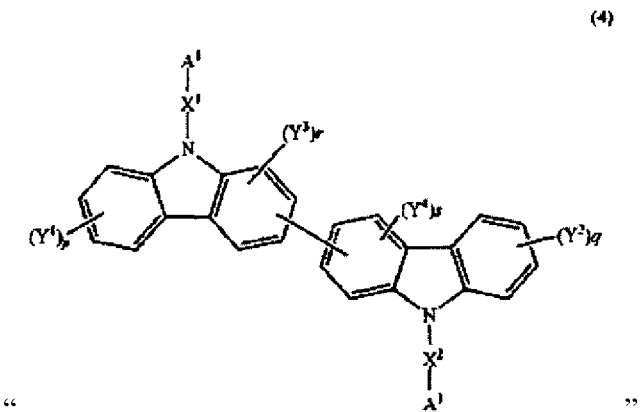

"

"

With:

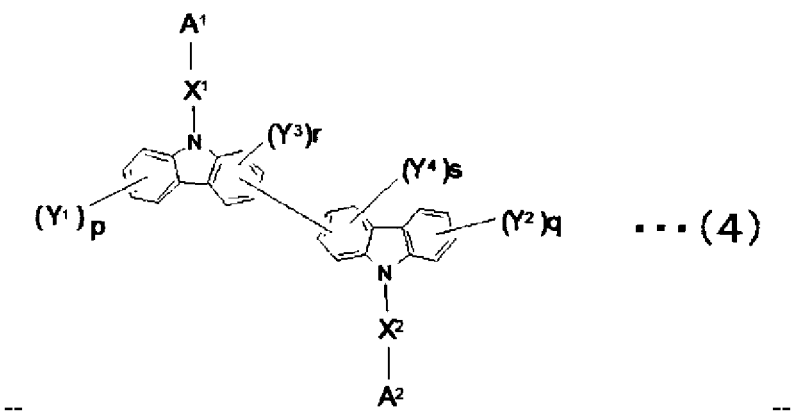

--  --